US012655214B2

(12) United States Patent
Wernig

(10) Patent No.: US 12,655,214 B2
(45) Date of Patent: Jun. 16, 2026

(54) TREATMENT OF FIBROSIS WITH COMBINED BLOCKADE OF IL-6 AND IMMUNE CHECKPOINT

(71) Applicant: The Board of Trustees of the Leland Stanford Junior University, Stanford, CA (US)

(72) Inventor: Gerlinde Wernig, Woodside, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 986 days.

(21) Appl. No.: 17/776,201

(22) PCT Filed: Nov. 18, 2020

(86) PCT No.: PCT/US2020/061015
§ 371 (c)(1),
(2) Date: May 11, 2022

(87) PCT Pub. No.: WO2021/101966
PCT Pub. Date: May 27, 2021

(65) Prior Publication Data
US 2022/0411500 A1     Dec. 29, 2022

Related U.S. Application Data

(60) Provisional application No. 62/936,952, filed on Nov. 18, 2019.

(51) Int. Cl.
| | |
|---|---|
| *C07K 16/28* | (2006.01) |
| *A61B 6/03* | (2006.01) |
| *A61K 38/17* | (2006.01) |
| *A61K 39/395* | (2006.01) |
| *A61P 1/04* | (2006.01) |
| *A61P 11/00* | (2006.01) |
| *A61P 17/00* | (2006.01) |
| *C07K 16/24* | (2006.01) |

(52) U.S. Cl.
CPC ............ *C07K 16/2803* (2013.01); *A61B 6/03* (2013.01); *A61P 1/04* (2018.01); *C07K 16/248* (2013.01)

(58) Field of Classification Search
None
See application file for complete search history.

(56) References Cited

U.S. PATENT DOCUMENTS

| | | | | |
|---|---|---|---|---|
| 2008/0220479 A1* | 9/2008 | Tocker | ..................... | A61P 1/12 |
| | | | | 435/348 |
| 2012/0301460 A1* | 11/2012 | Bao | ........................ | A61K 38/47 |
| | | | | 424/133.1 |

| | | | | |
|---|---|---|---|---|
| 2018/0064662 A1* | 3/2018 | Fukumura | ............ | A61K 31/401 |
| 2018/0125919 A1 | 5/2018 | Chojkier et al. | | |
| 2018/0155405 A1 | 6/2018 | Ring et al. | | |
| 2020/0262923 A1* | 8/2020 | Noble | ................ | A61K 31/5377 |
| 2021/0206850 A1* | 7/2021 | Lin | .................... | C07K 16/2803 |

OTHER PUBLICATIONS

Allard et al. Immunol Rev. Mar. 2017 ; 276(1): 121-144.*
Ohta A. (2016) Front. Immunol. 7: 109, 1-11.*
Chikuma et al. (2017) Cancer Sci 108: 574-580.*
Khair et al. (2019) Front. Immunol. 10: 453, 1-20.*
Qin et al. (2019) Molecular Cancer 18: 155, 1-14.*
Celada et al. PD-1 up-regulation on CD4+ T cells promotes pulmonary fibrosis through STAT3-mediated IL-17A and TGF-beta1 production. Sci. Transl. Med. 10, eaar8356 (2018), 1-14.*
Le et al. Blockade of IL-6 trans-signaling attenuates pulmonary fibrosis. J. Immunol. 193, 3755-3768 (2014).*
Habiel et al. Role of Immune Checkpoint Proteins in Idiopathic Pulmonary Fibrosis. bioRxiv, Aug. 8, 2017, p. 1-35.*
Ni et al. American Journal of Respiratory Cell and Molecular Biology, 58 (6):684-695, Jun. 2018.*
O'Donoghue et al., Genetic partitioning of interleukin-6 signaling in mice dissociates Stat3 from Smad3-mediated lung fibrosis. EMBO Mol. Med., 2012, vol. 4, pp. 939-951.*
Kobayashi et al., Bidirectional role of IL-6 signal in pathogenesis of lung fibrosis, Respiratory Research; 2015; vol. 16:99, pp. 1-14.*
Delaunay et al. Immune-checkpoint inhibitors associated with interstitial lung disease in cancer patients. Eur Respir J Aug. 2017; 50:1-13.*
Ahmed et al. Interleukin-17 pathways in systemic sclerosis-associated fibrosis. Rheumatology International (2019) 39: 1135-1143.*
Brown et al. (2019) "The immunopathogenesis of fibrosis in systemic sclerosis". Clin Exp Immunol. vol. 195(3), p. 310-321.
Duitman et al., (2019)"Immune Checkpoints as Promising Targets for the Treatment of Idiopathic alternative) Pulmonary Fibrosis?" J Clin Med, vol. 8(10): 1547.
Barratt et al., (2018) "Idiopathic Pulmonary Fibrosis (IPF): An Overview". J Clin Med. vol. 7(8): 201. PDF File: p. 1-21.
Le et al., (2014) "Blockade of IL-6 Trans Signaling Attenuates Pulmonary Fibrosis". J Immunol. vol. 193(7), p. 3755-3768.
Cui et al.. (2020) "Activation of JUN in fibroblasts promotes pro-fibrotic programmed and modulates protective immunity". Nat Commun. 2020, vol. 11(1):2795. PDF File: p. 1-14.

* cited by examiner

*Primary Examiner* — Ilia I Ouspenski
(74) *Attorney, Agent, or Firm* — Pamela J. Sherwood; Bozicevic, Field & Francis LLP

(57) ABSTRACT

Compositions and methods are provided for reducing fibrosis in a mammal by administering a therapeutic dose of a combination of agents to block interleukin-6 (IL-6), and an immune checkpoint inhibitor; wherein the checkpoint inhibitor comprising an agent that blocks programmed cell death protein 1 (PD1), blocks PD1 ligand 1 (PDL1), or blocks CD47/SIRPa pathway.

19 Claims, 64 Drawing Sheets

Specification includes a Sequence Listing.

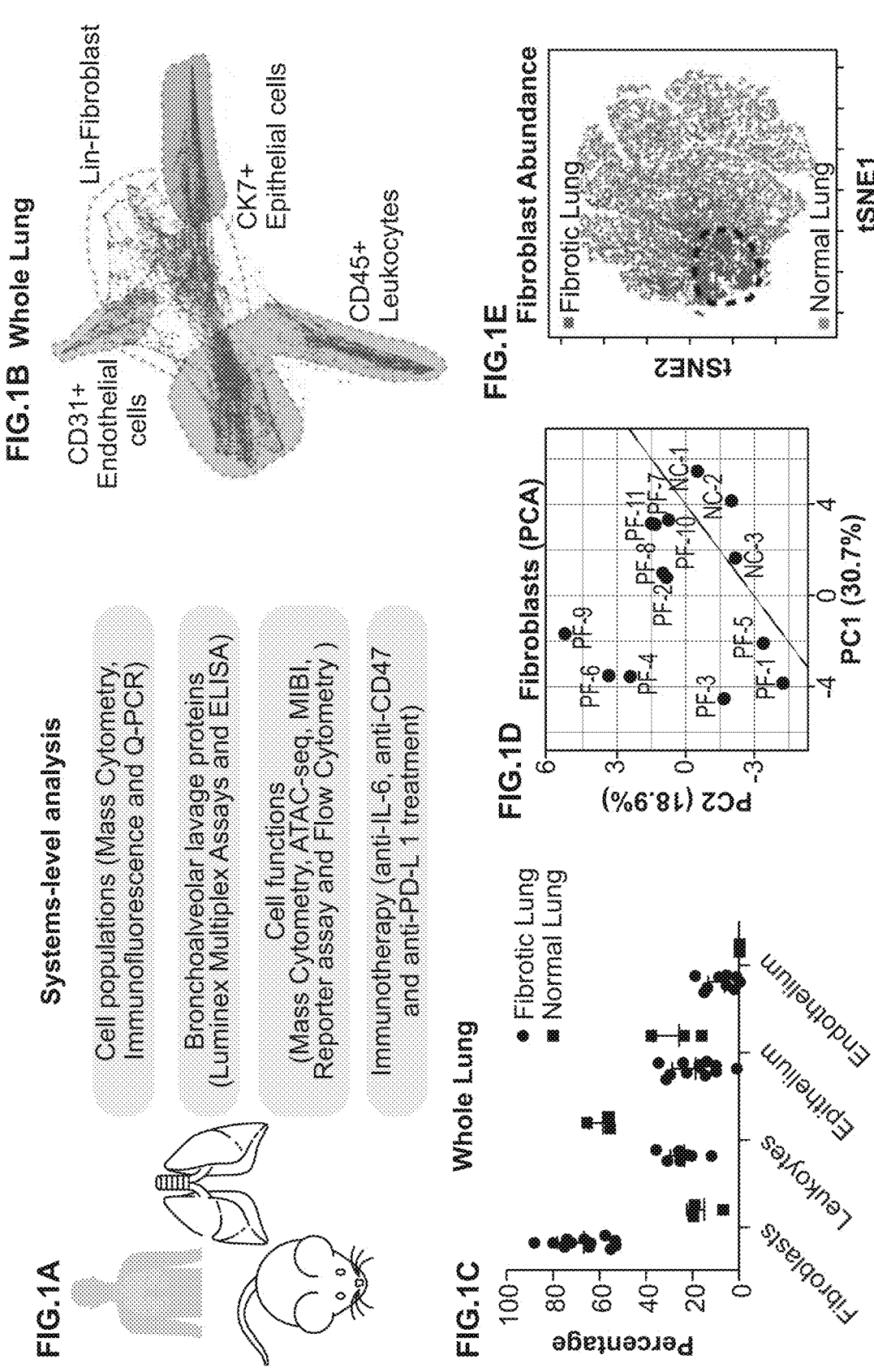

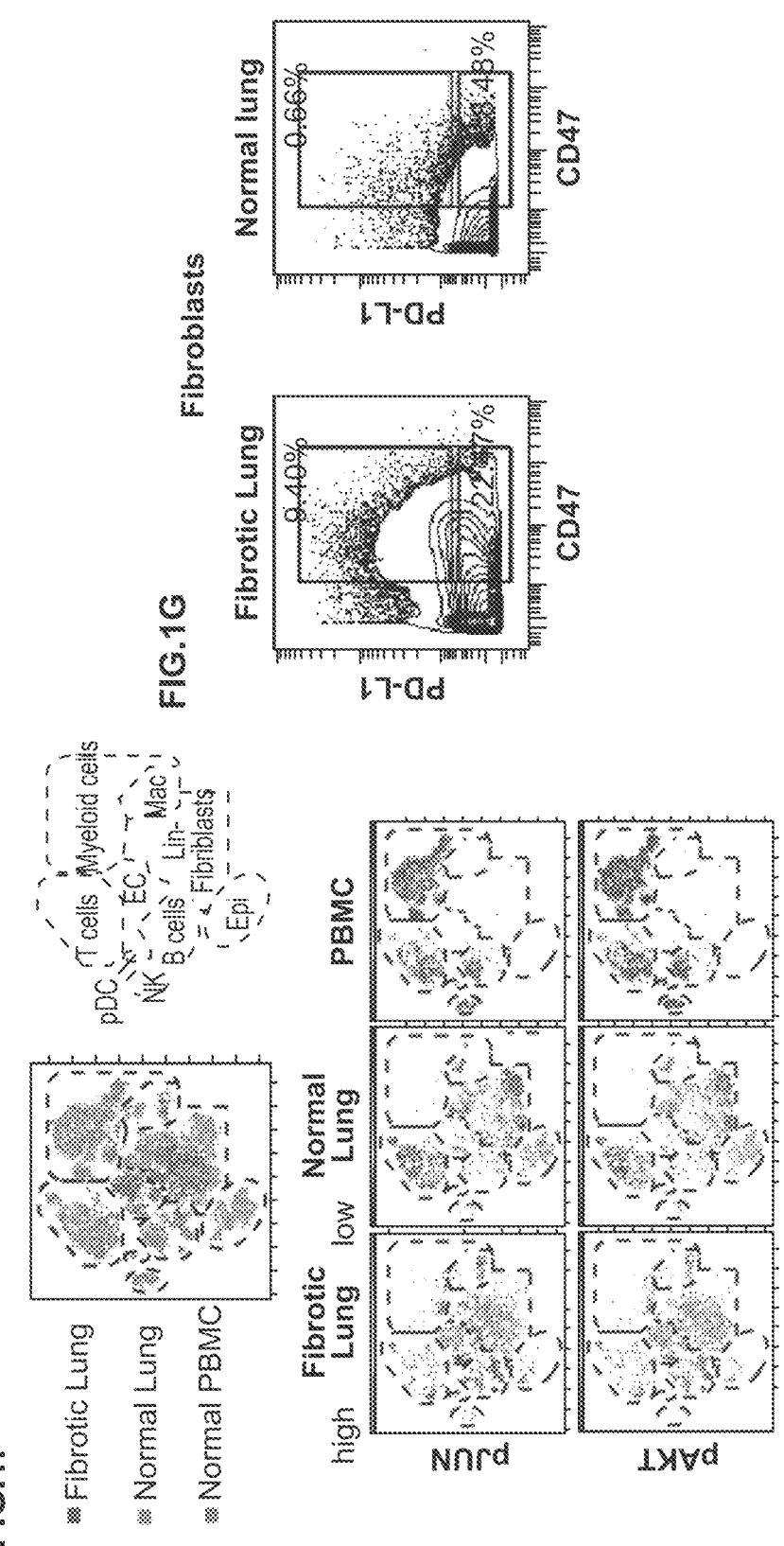

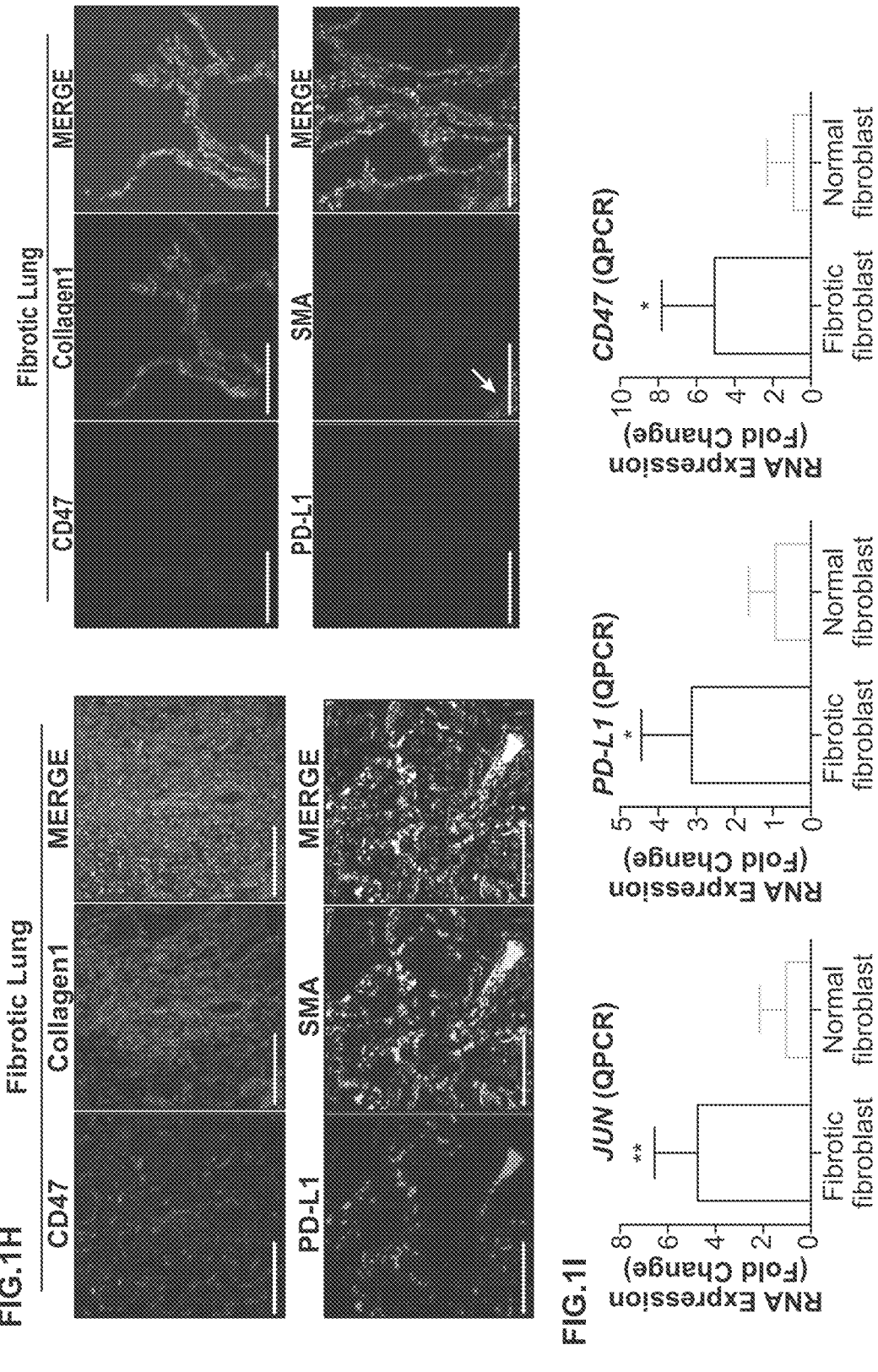

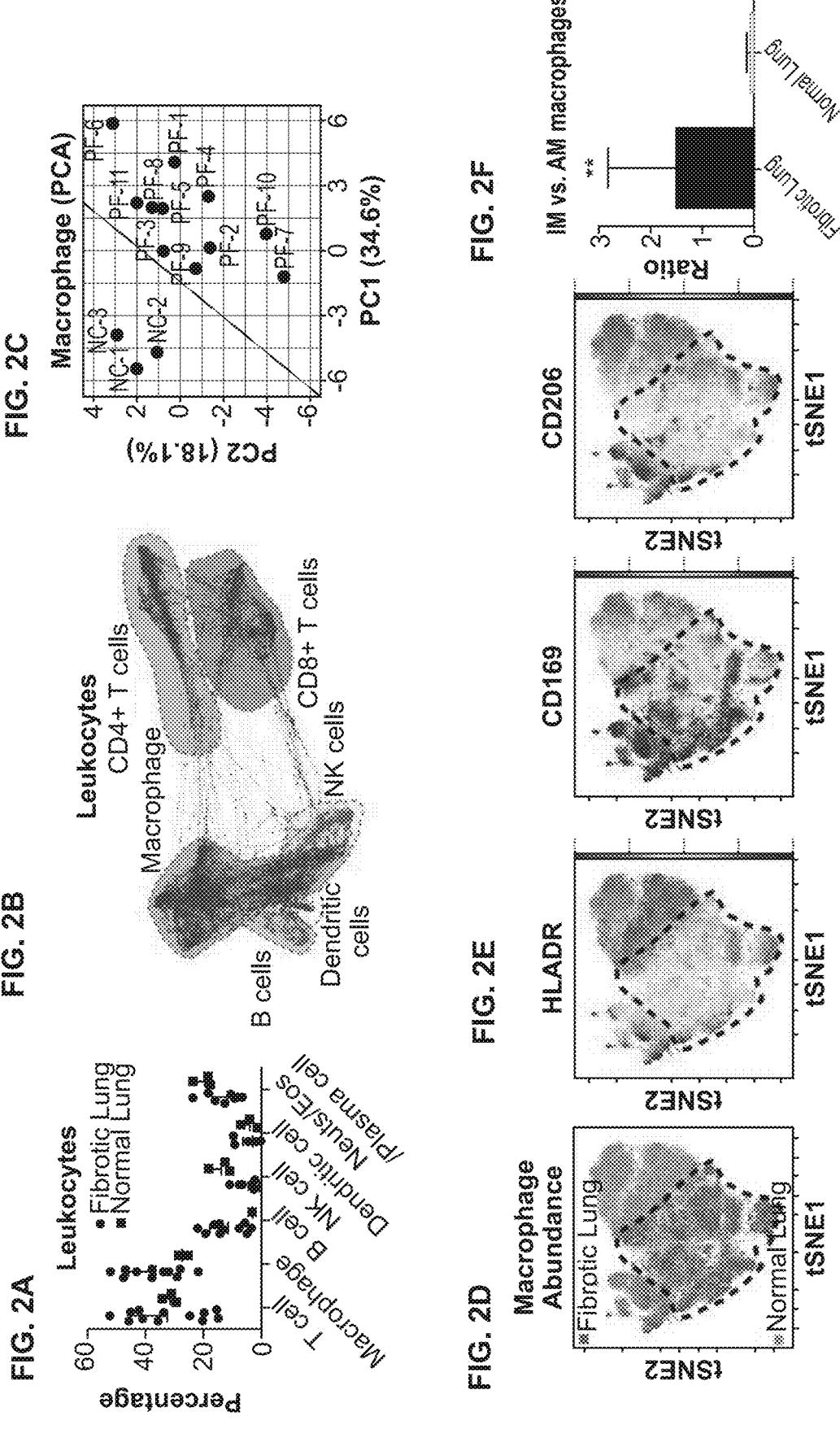

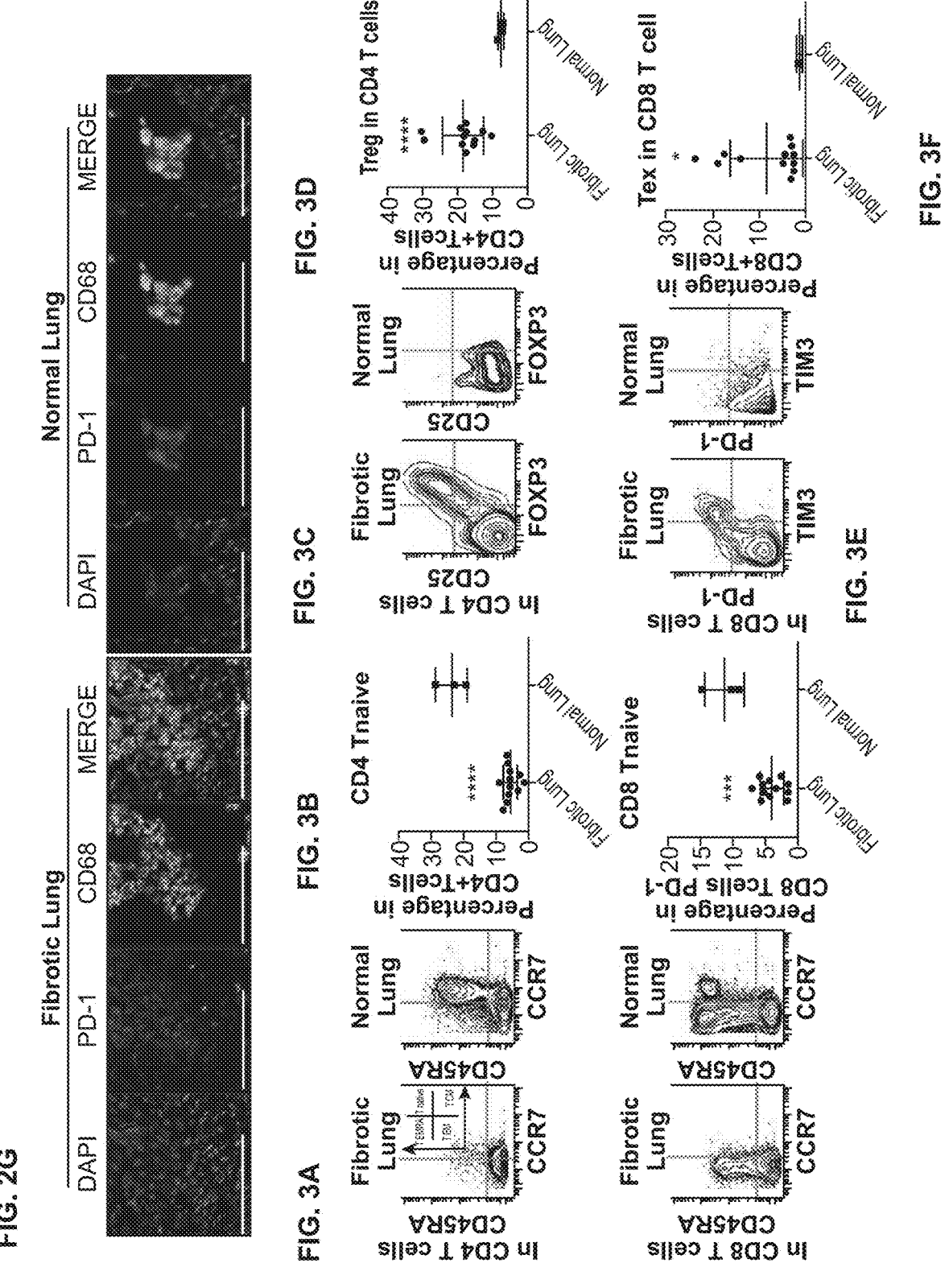

FIG.4E
Control reporter vector
CD47 Enhancer
reporter vector
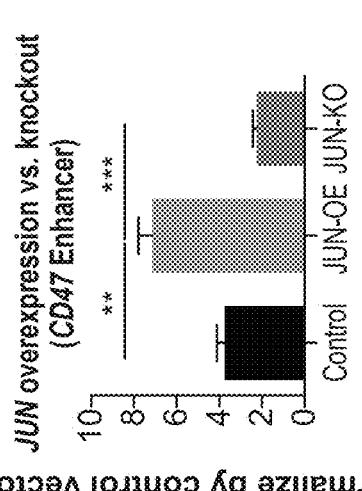
FIG.4G
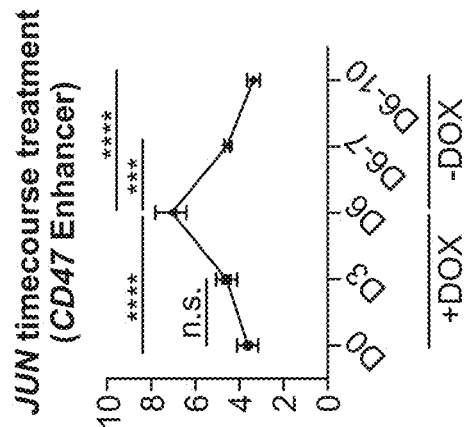
FIG.4F

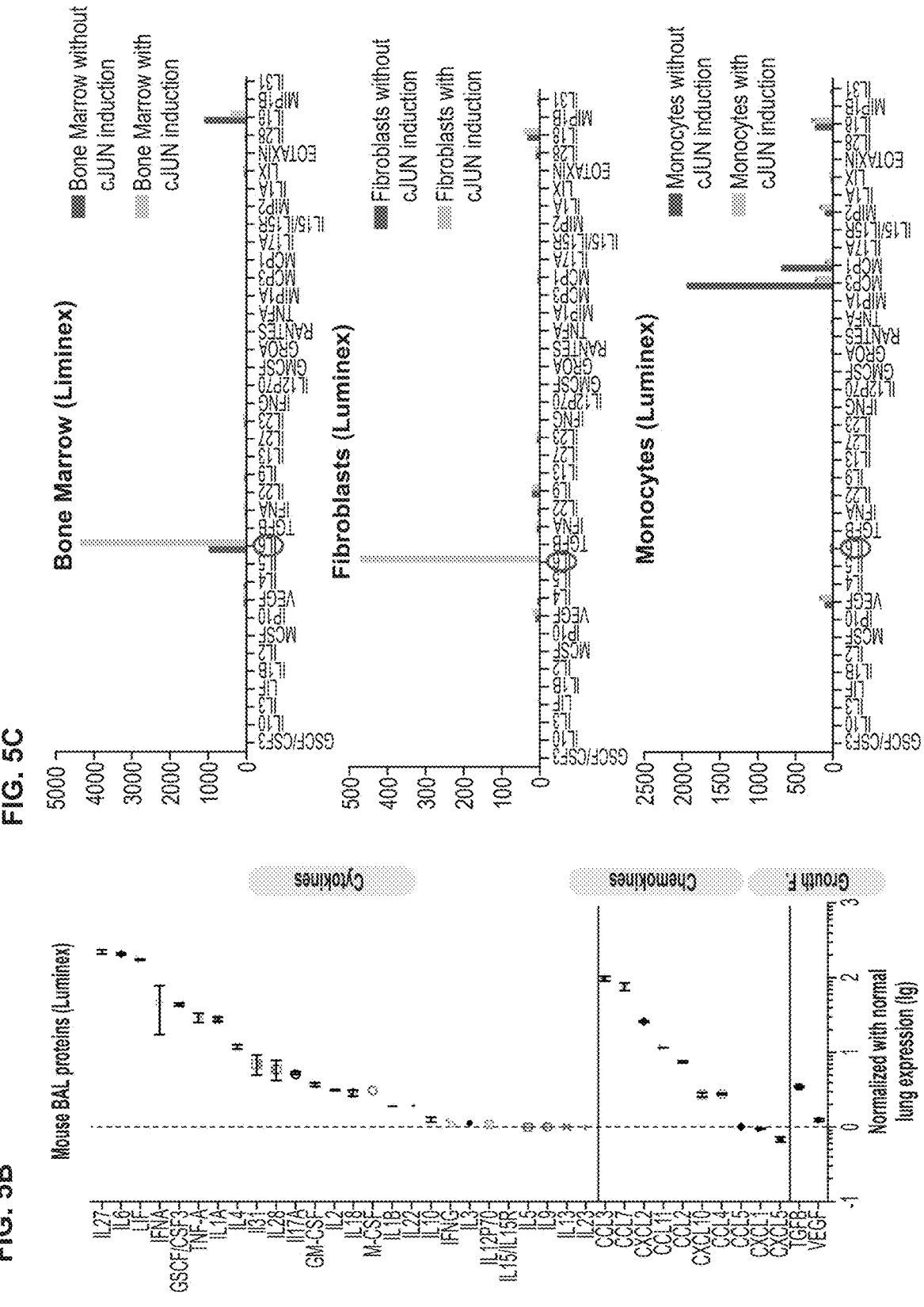

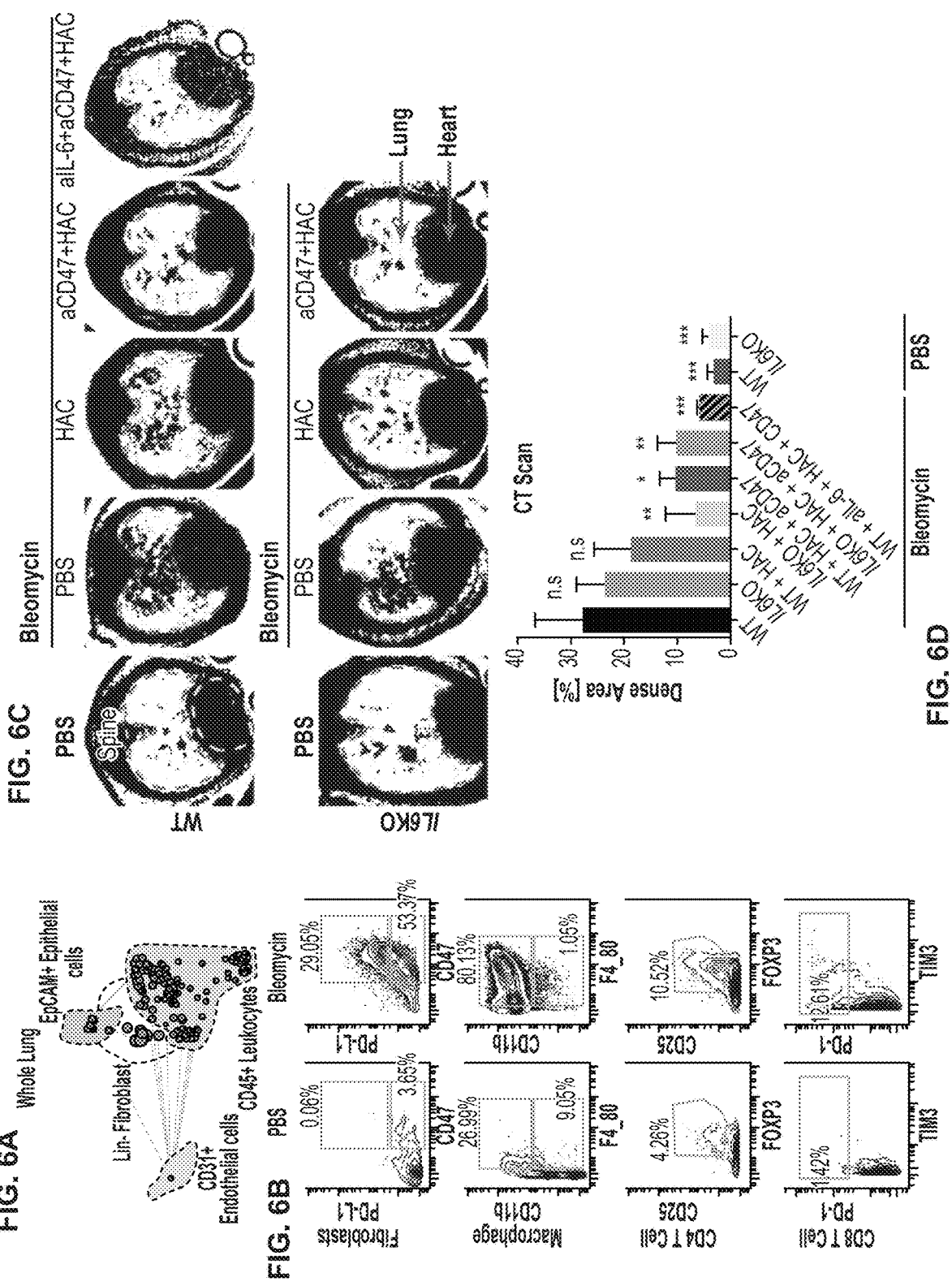

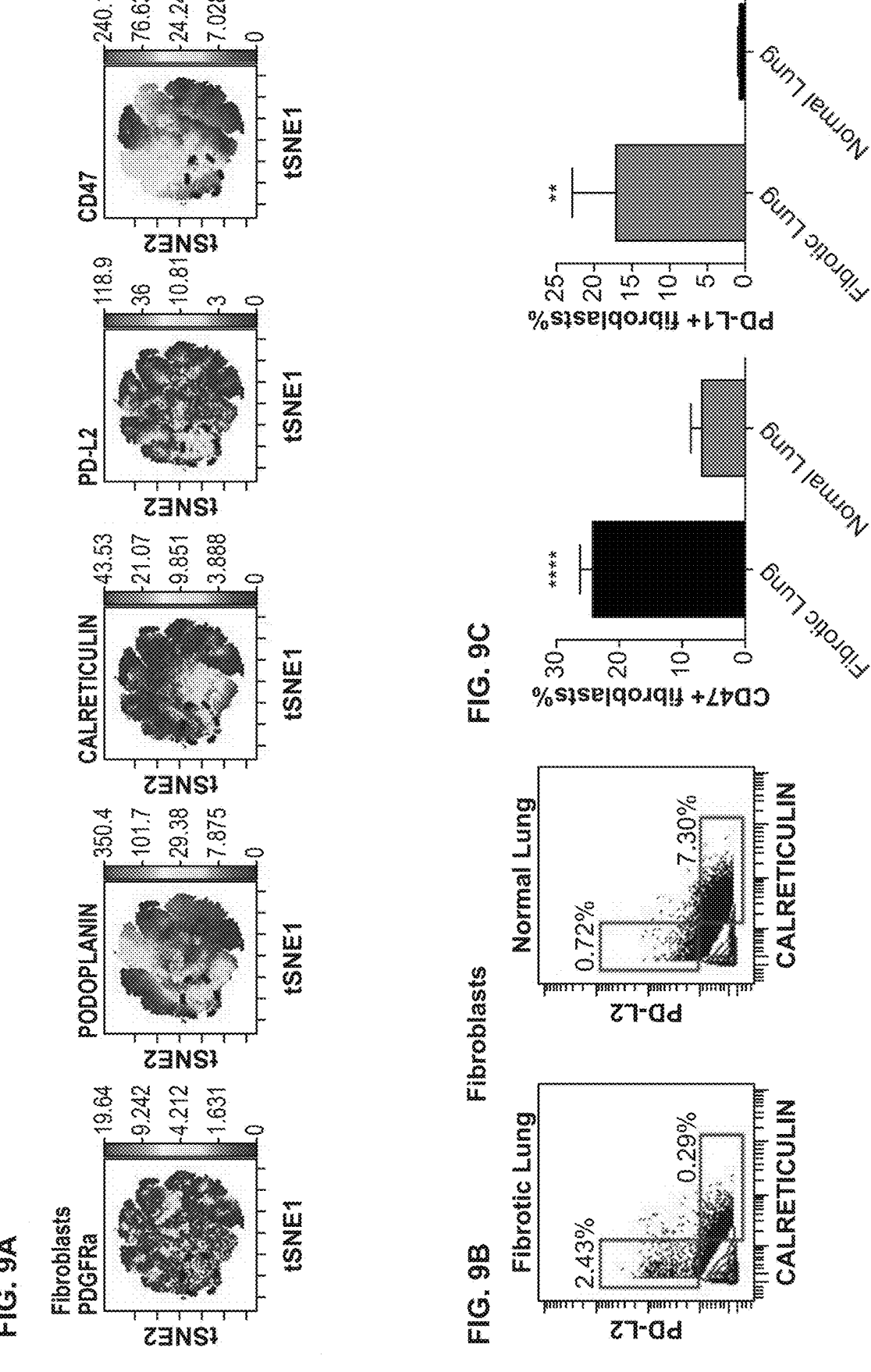

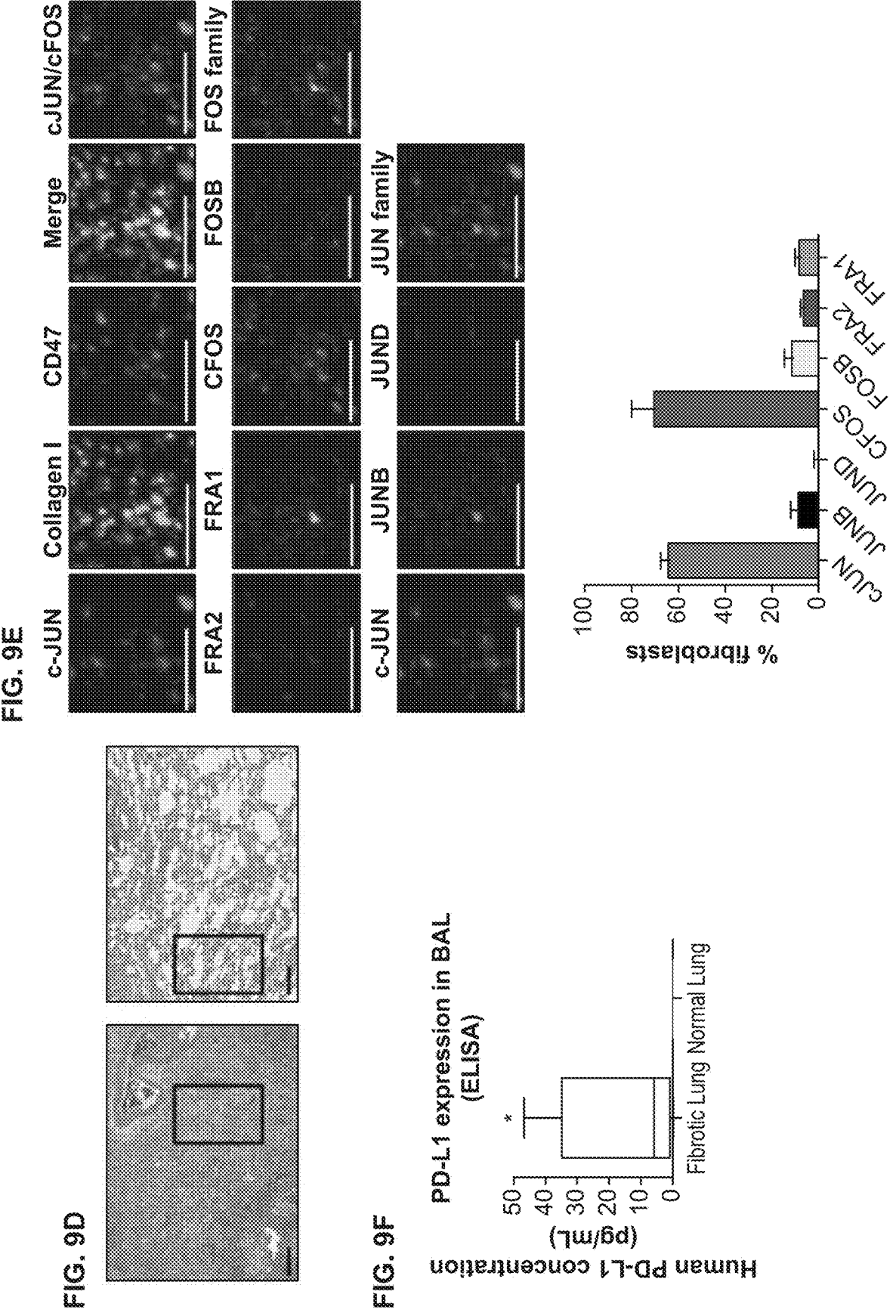

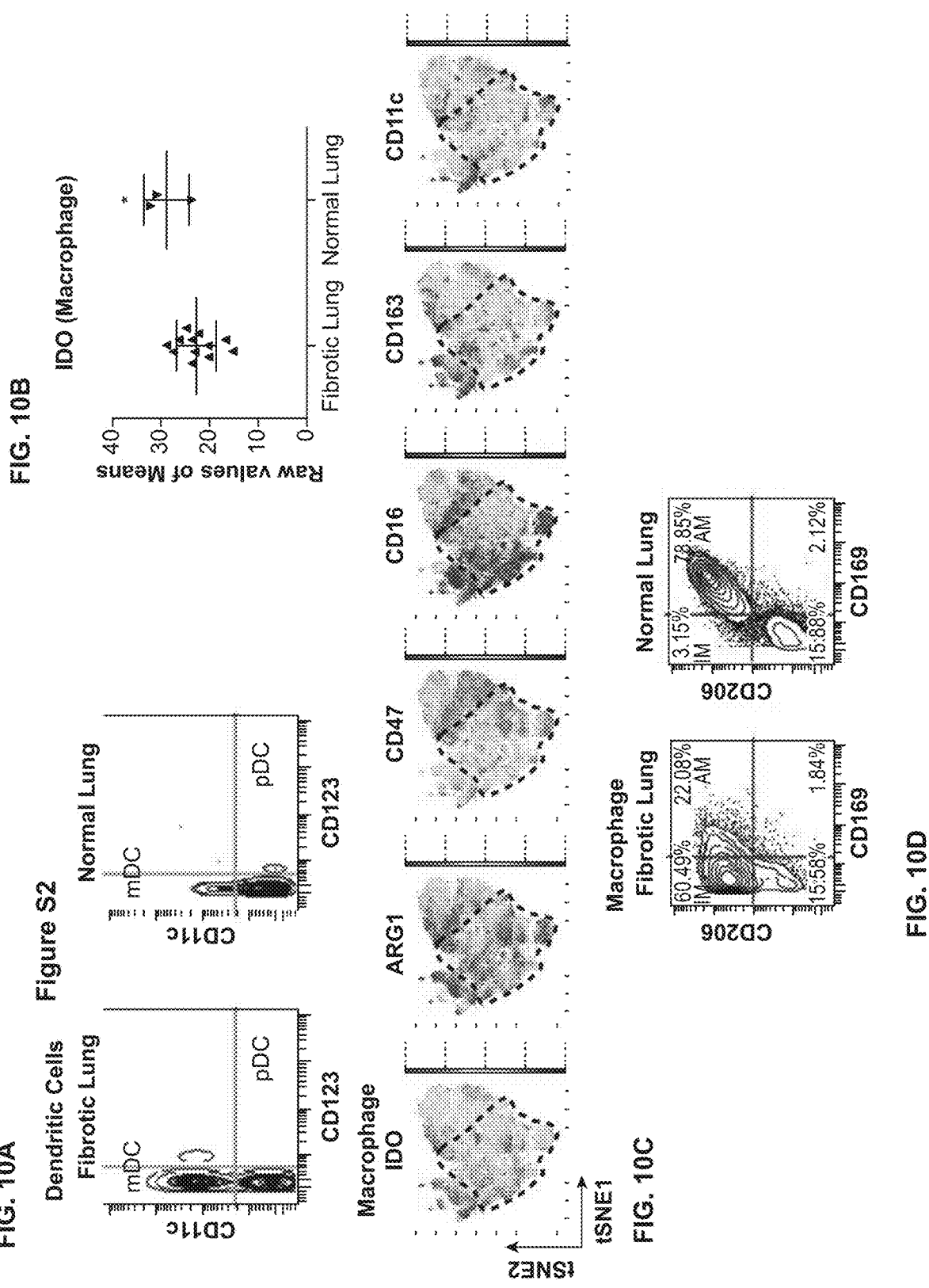

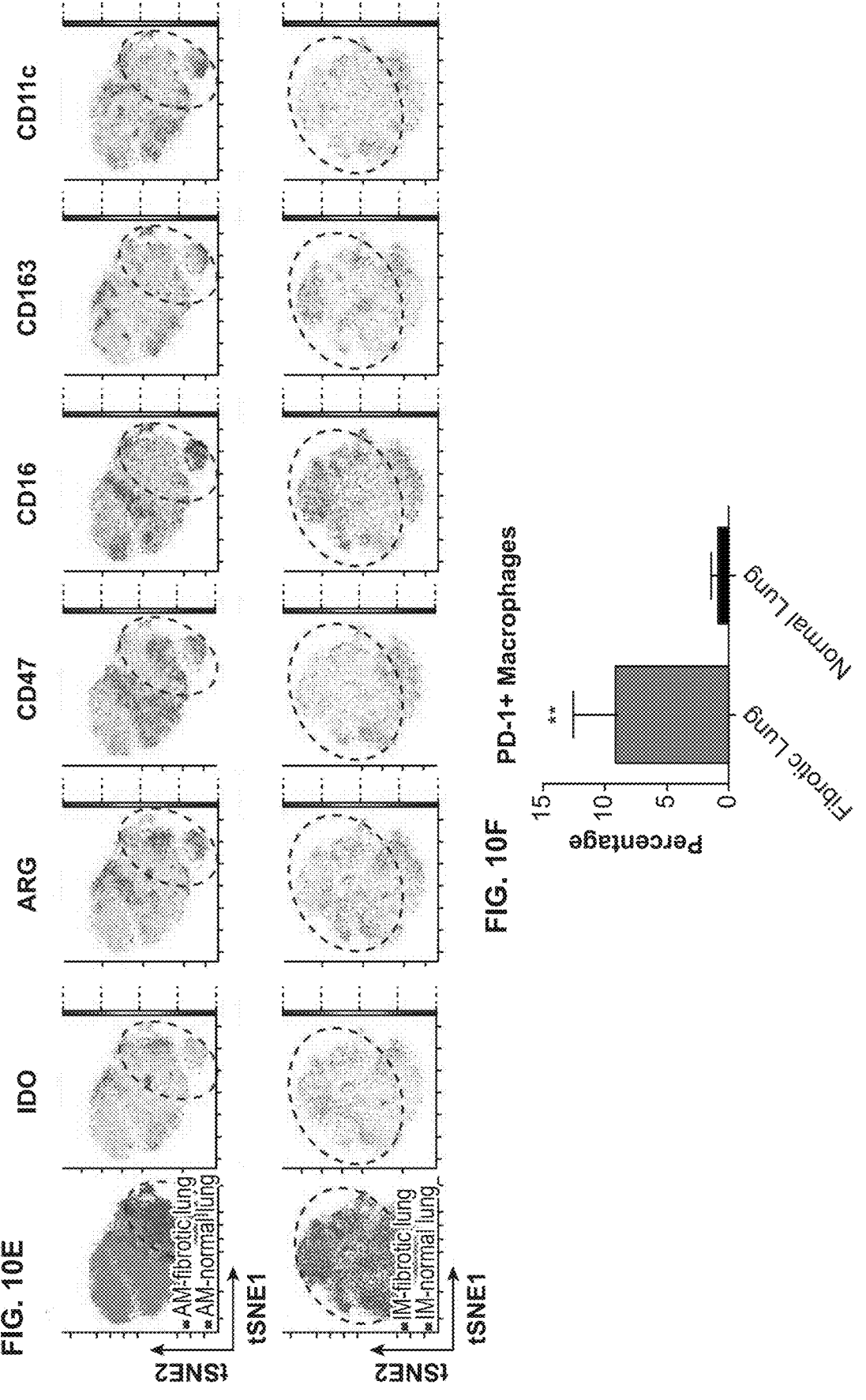

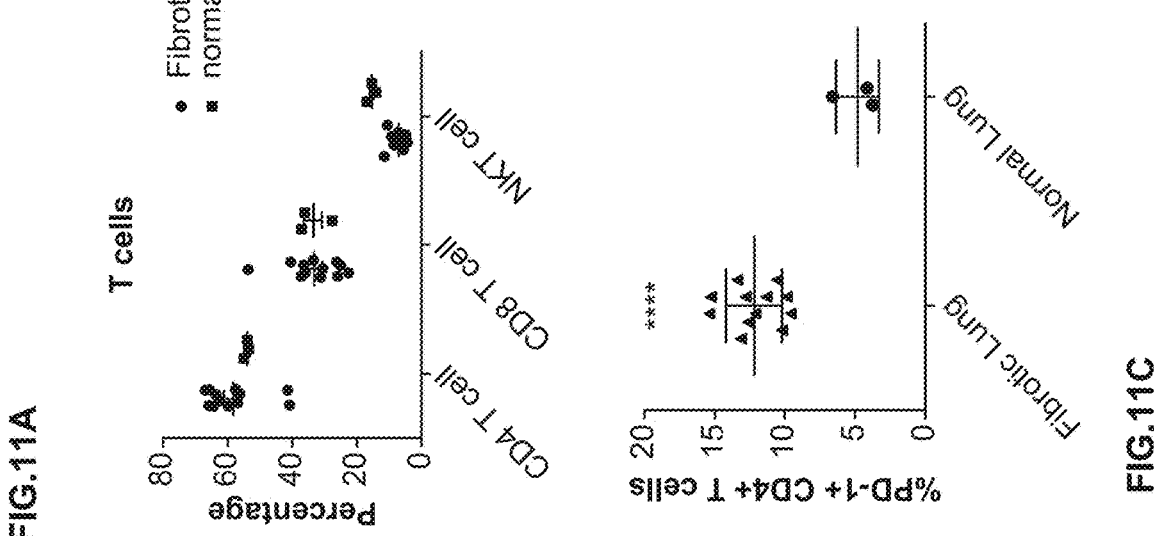

FIG.12B

Normal lung fibroblast over-expression vs untreated

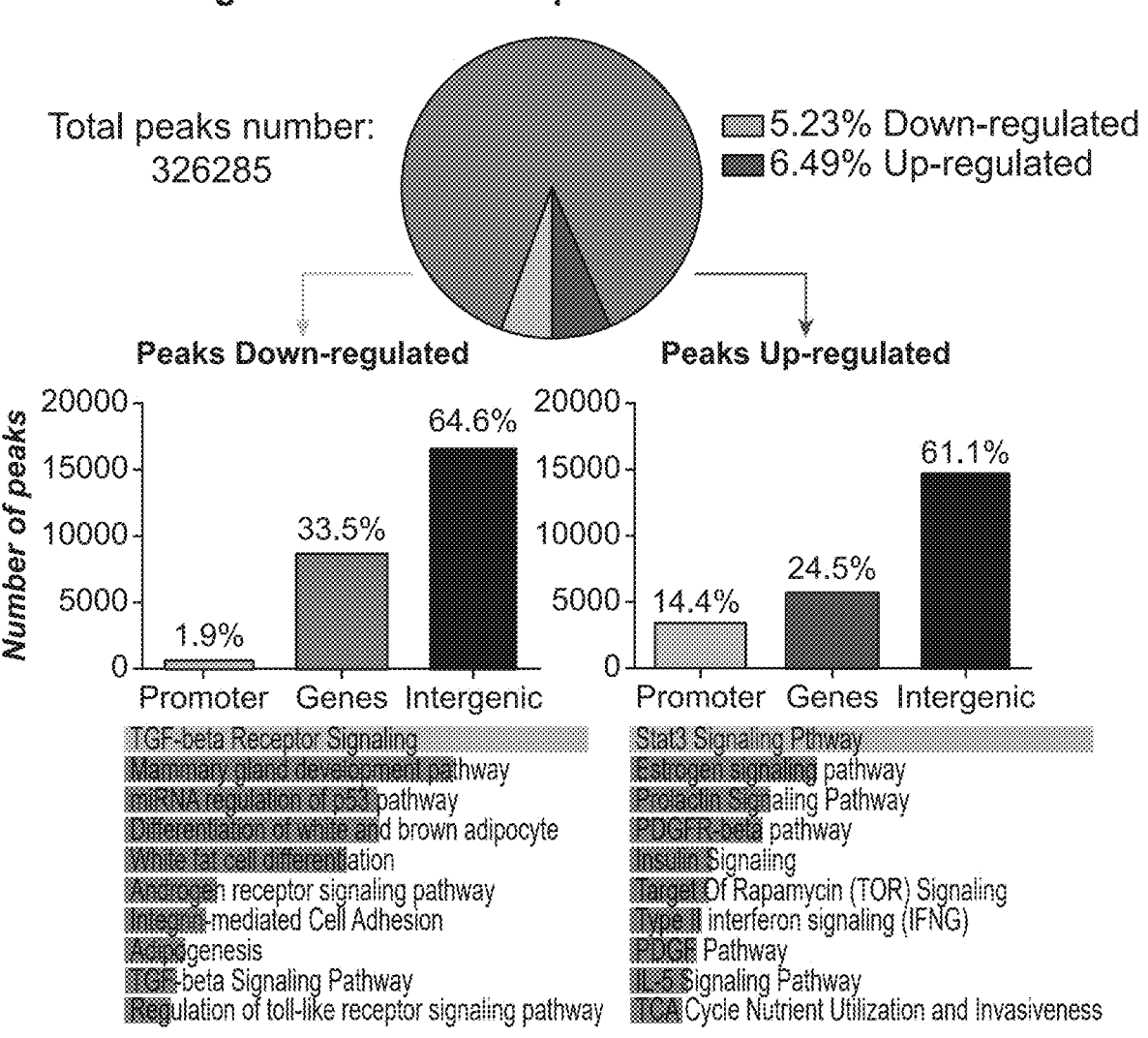

Total peaks number:
326285

5.23% Down-regulated
6.49% Up-regulated

Peaks Down-regulated 64.6%
33.5%
1.9%
Promoter   Genes   Intergenic

*Number of peaks*

TGF-beta Receptor Signaling
[...]hway
[...]pathway
[...]d brown adipocyte
[...]ation
[...]n receptor signaling pathway
[...]-mediated Cell Adhesion
[...]genesis
[...]-beta Signaling Pathway
[...]ulation of toll-like receptor signaling pathway Peaks Up-regulated 61.1%
24.5%
14.4%
Promoter   Genes   Intergenic Stat3 Signaling Pthway
[...] pathway
[...]aling Pathway
[...] pathway
[...]Signaling
[...]Of Rapamycin (TOR) Signaling
[...] interferon signaling (IFNG)
[...] Pathway
[...]Signaling Pathway
[...]Cycle Nutrient Utilization and Invasiveness

FIG.13A
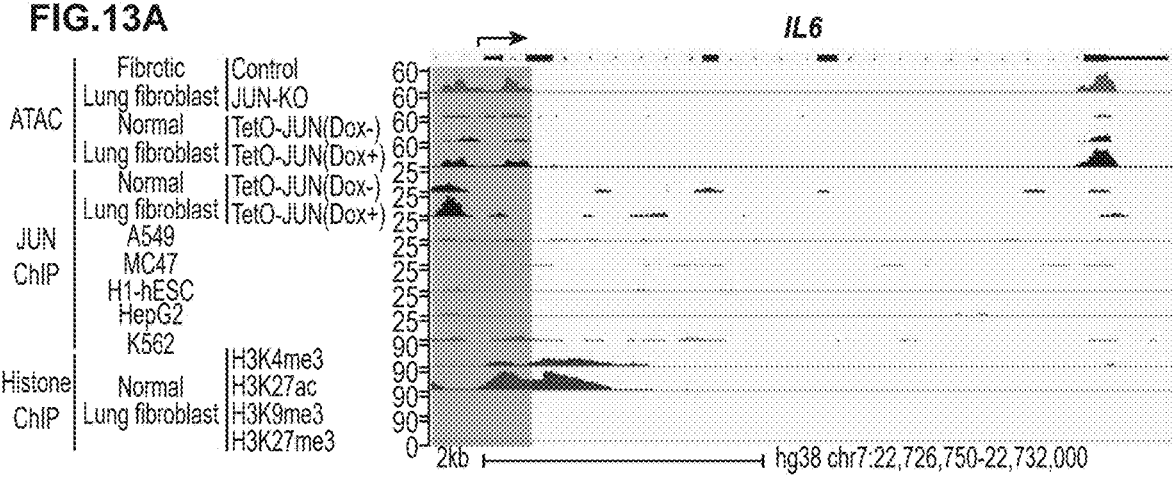
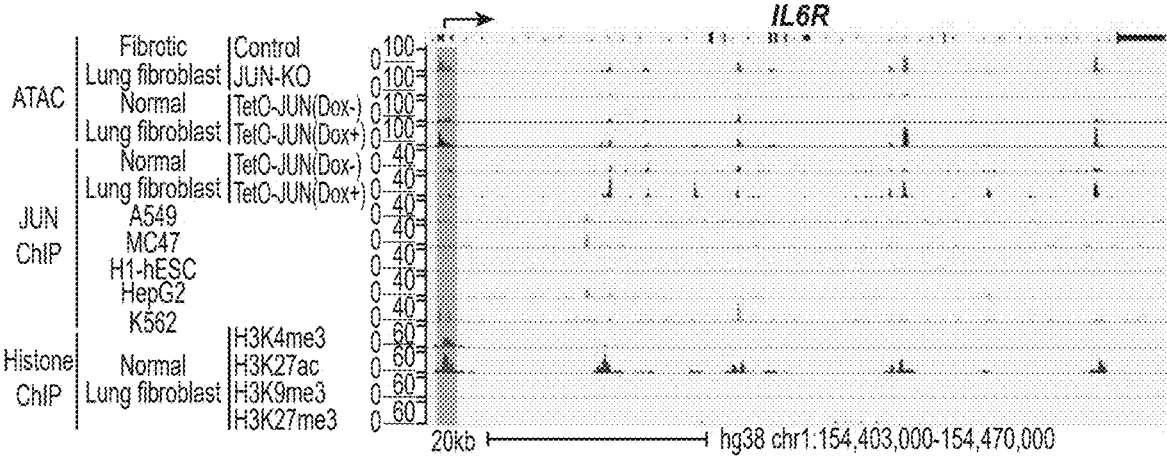
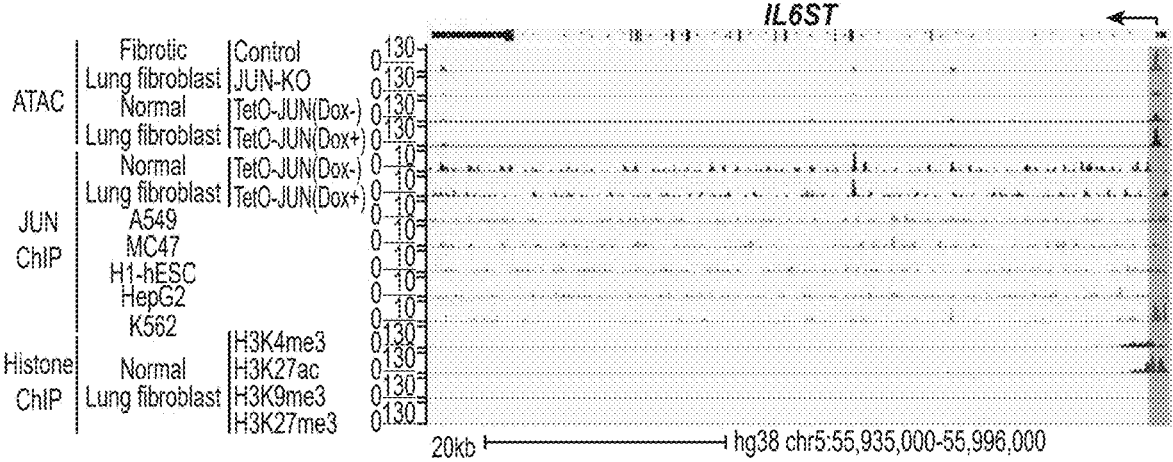

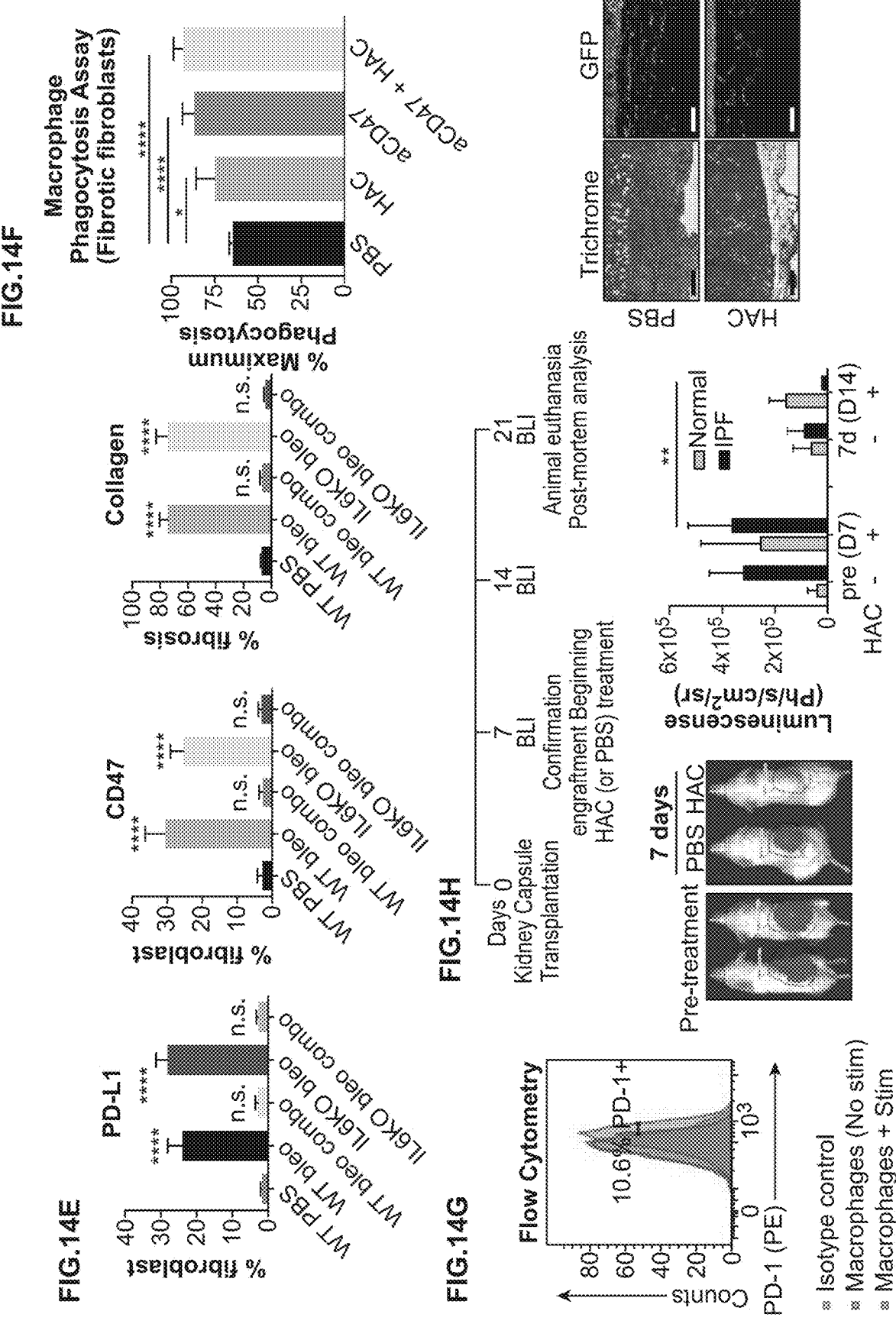

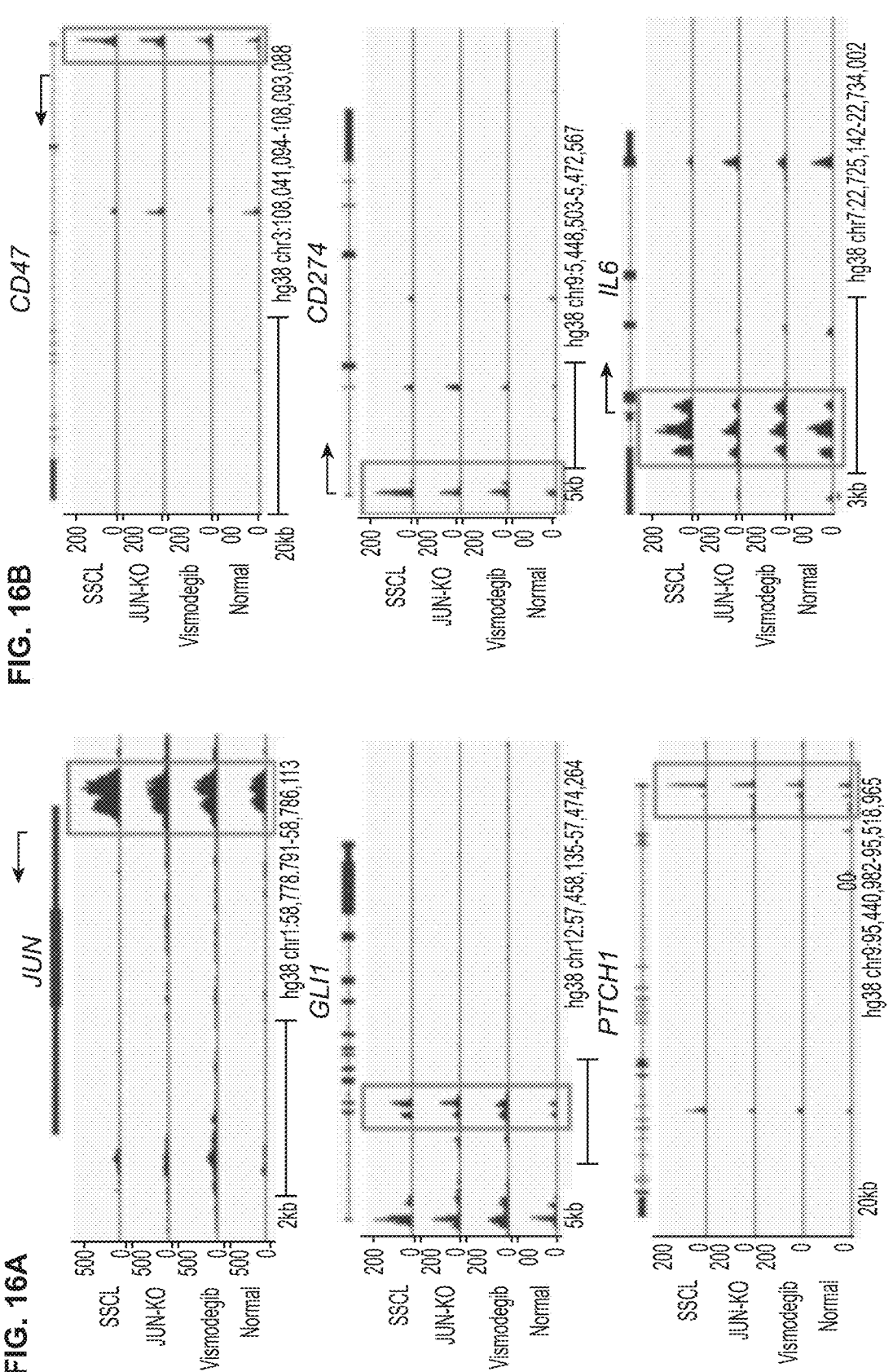

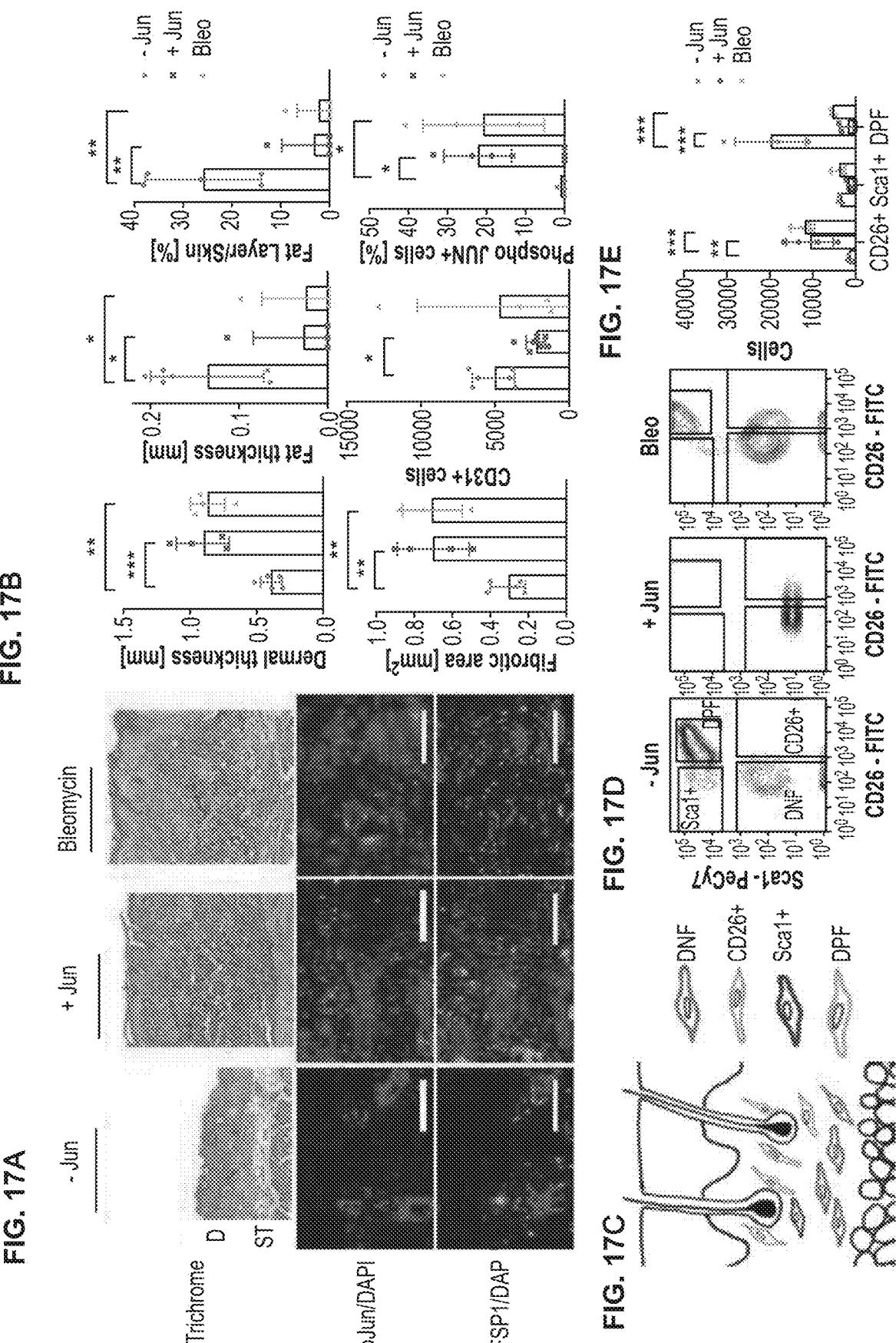

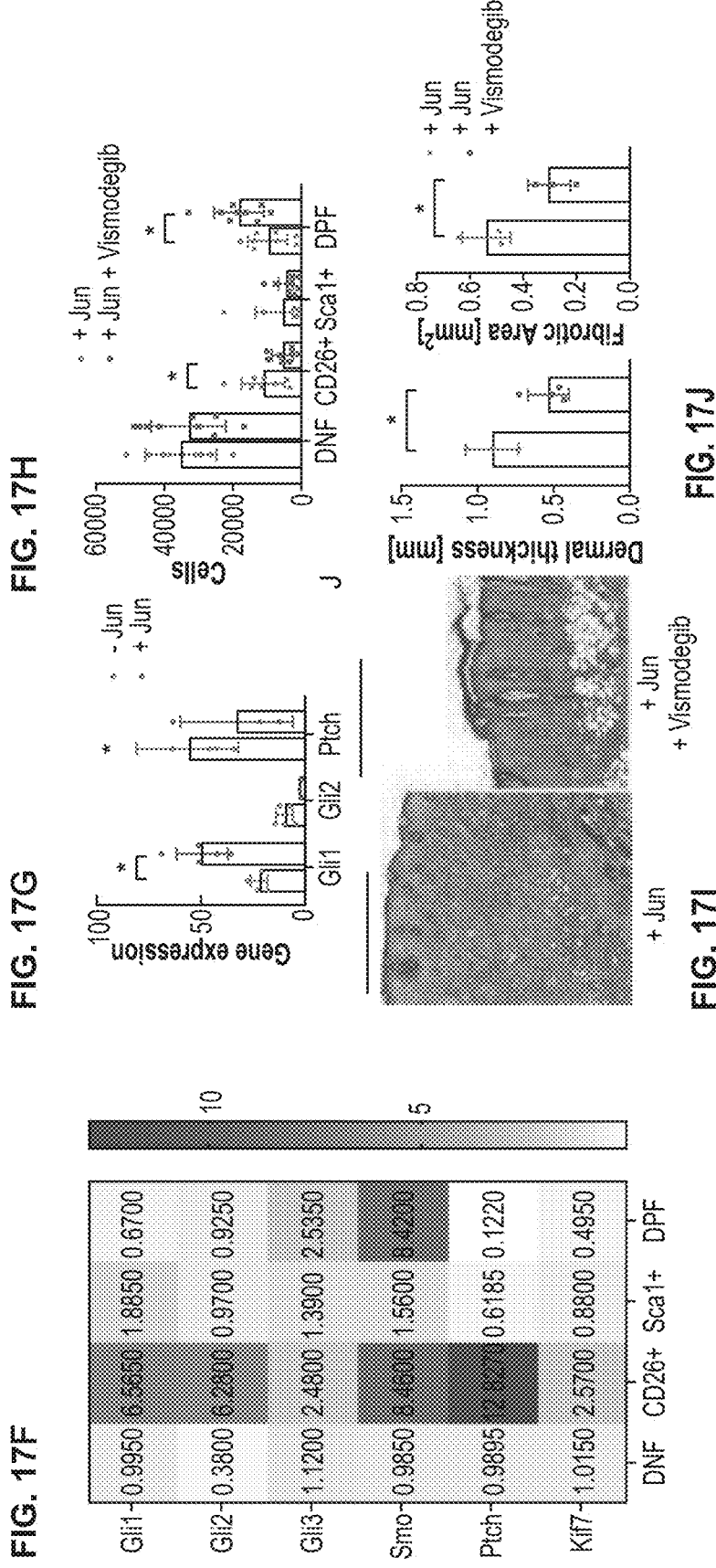

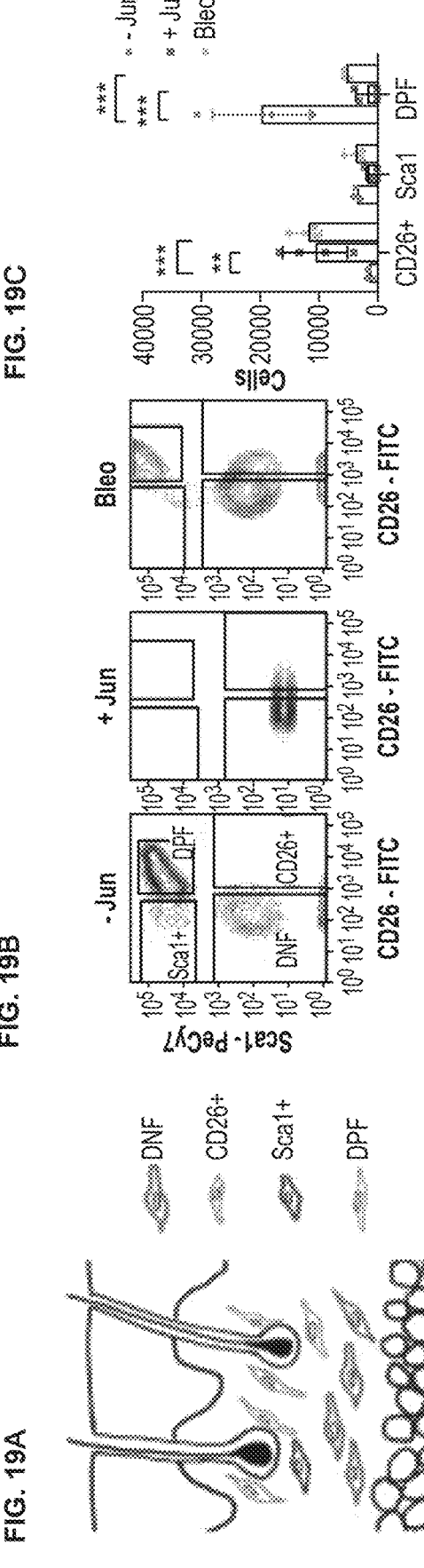

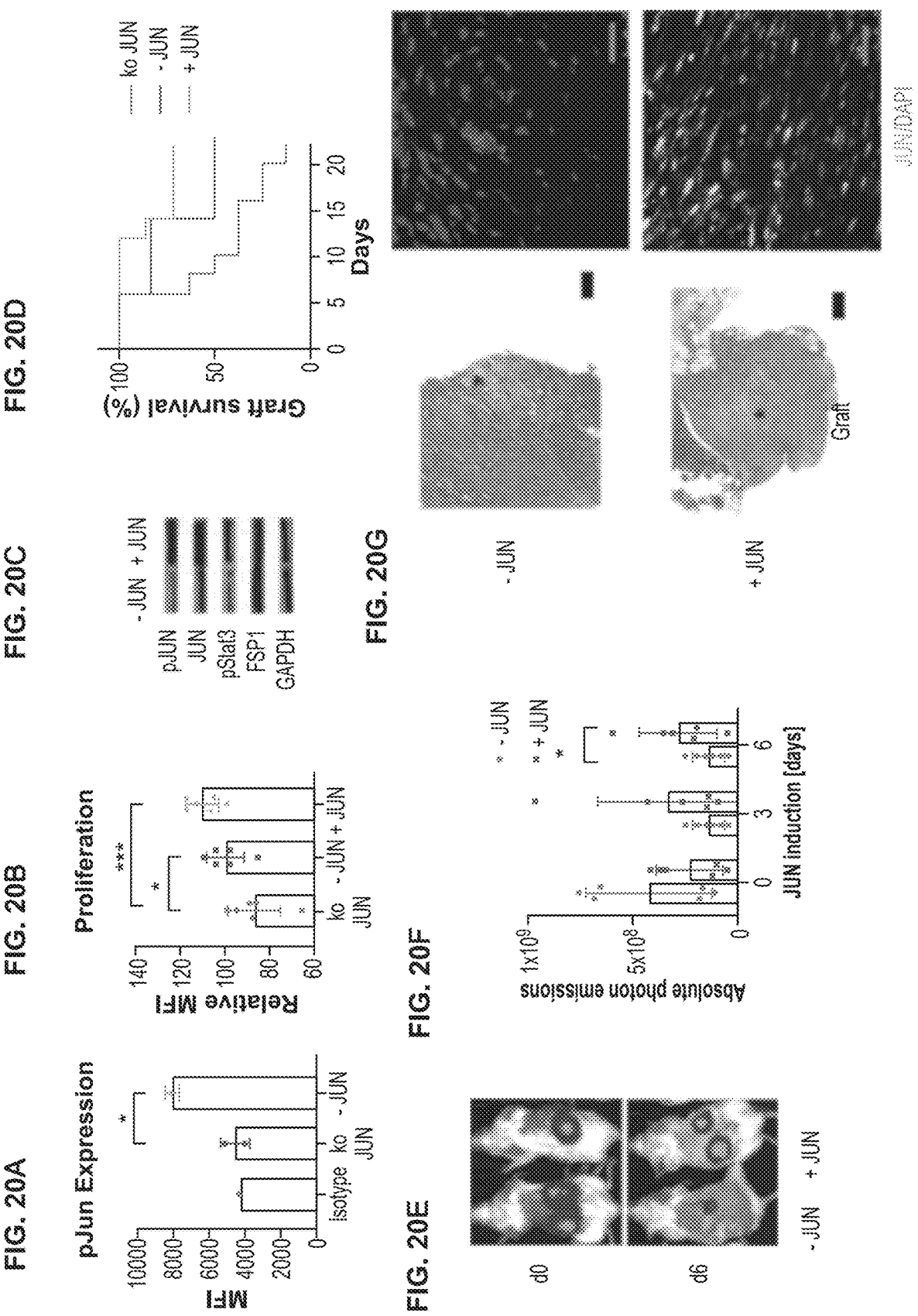

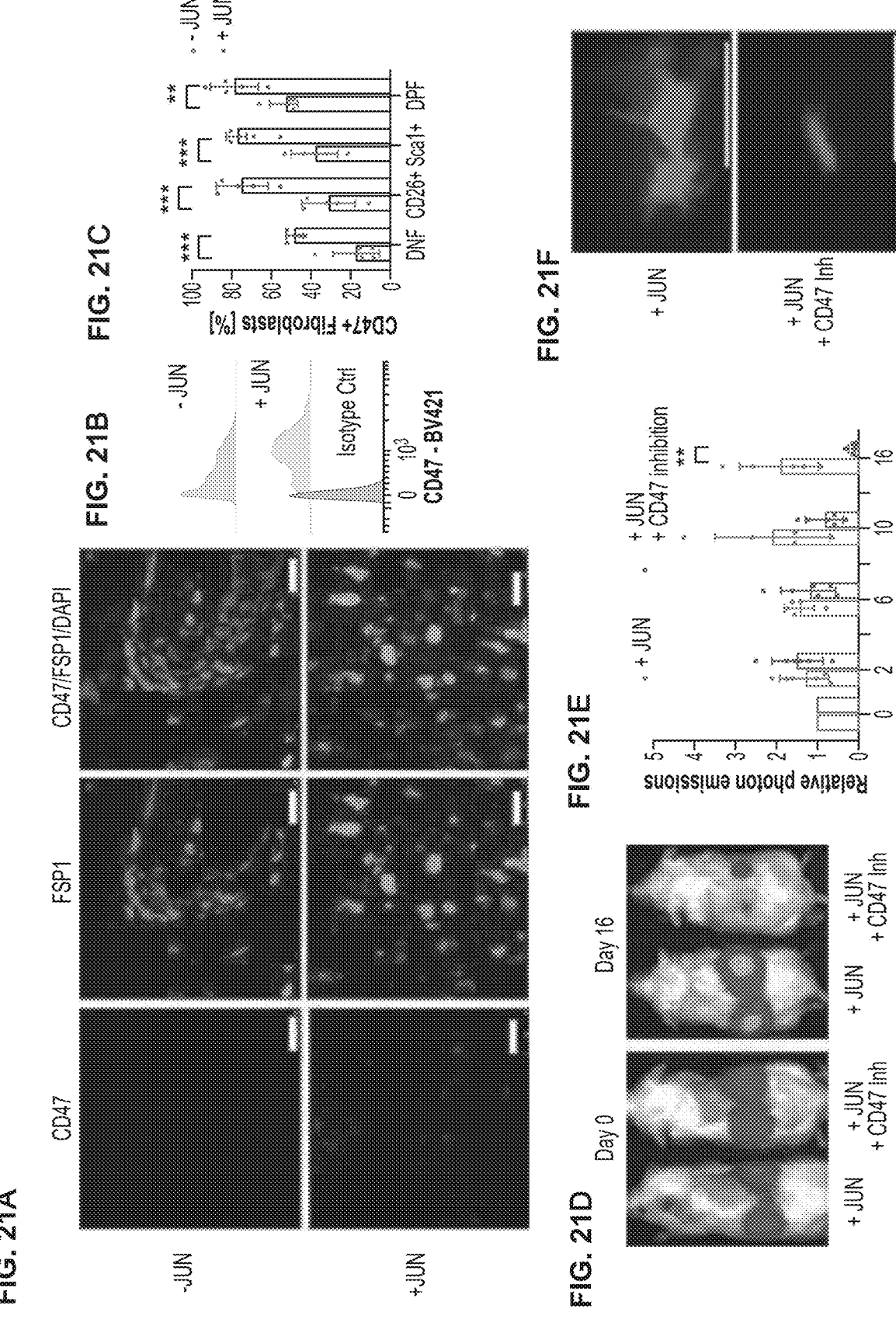

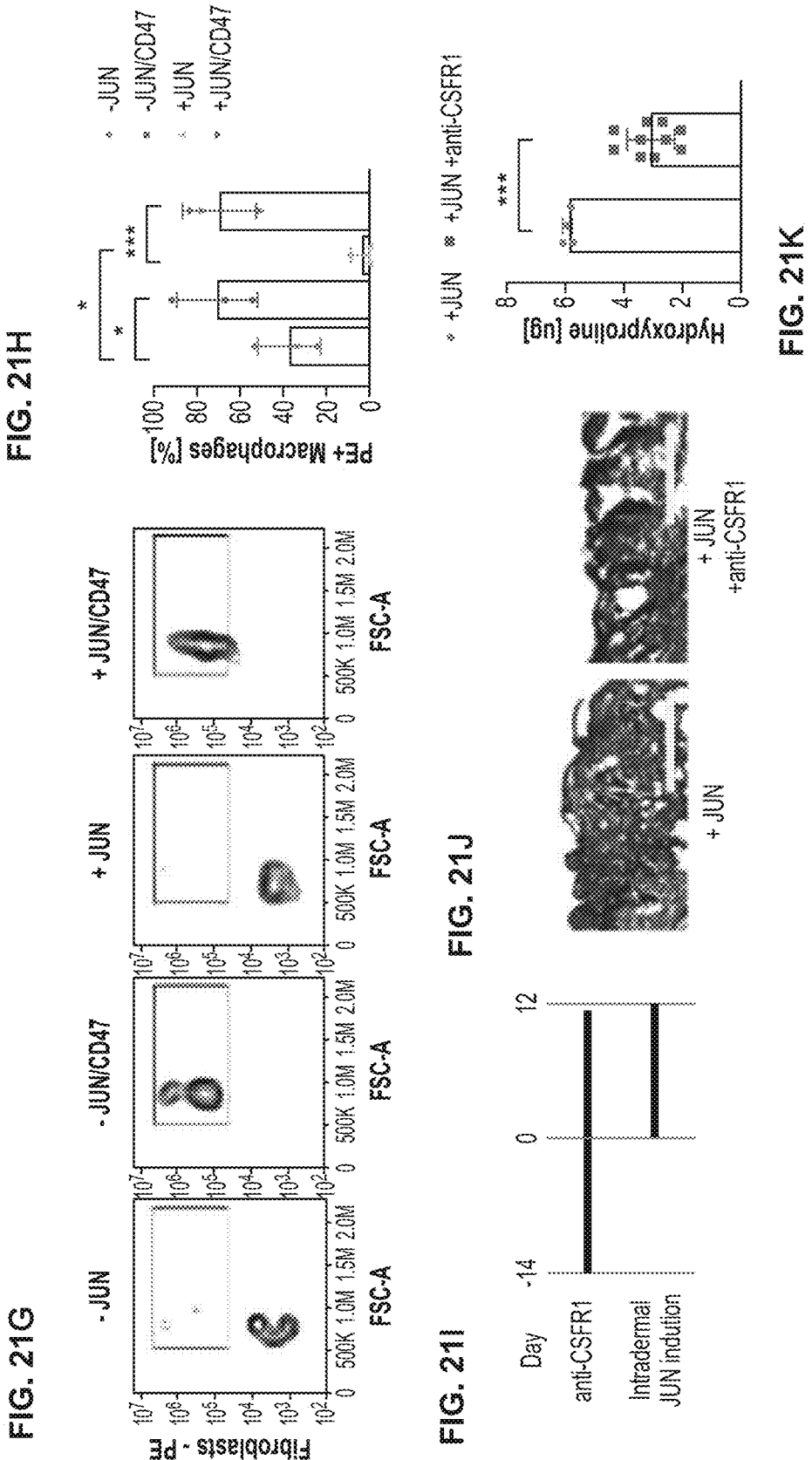

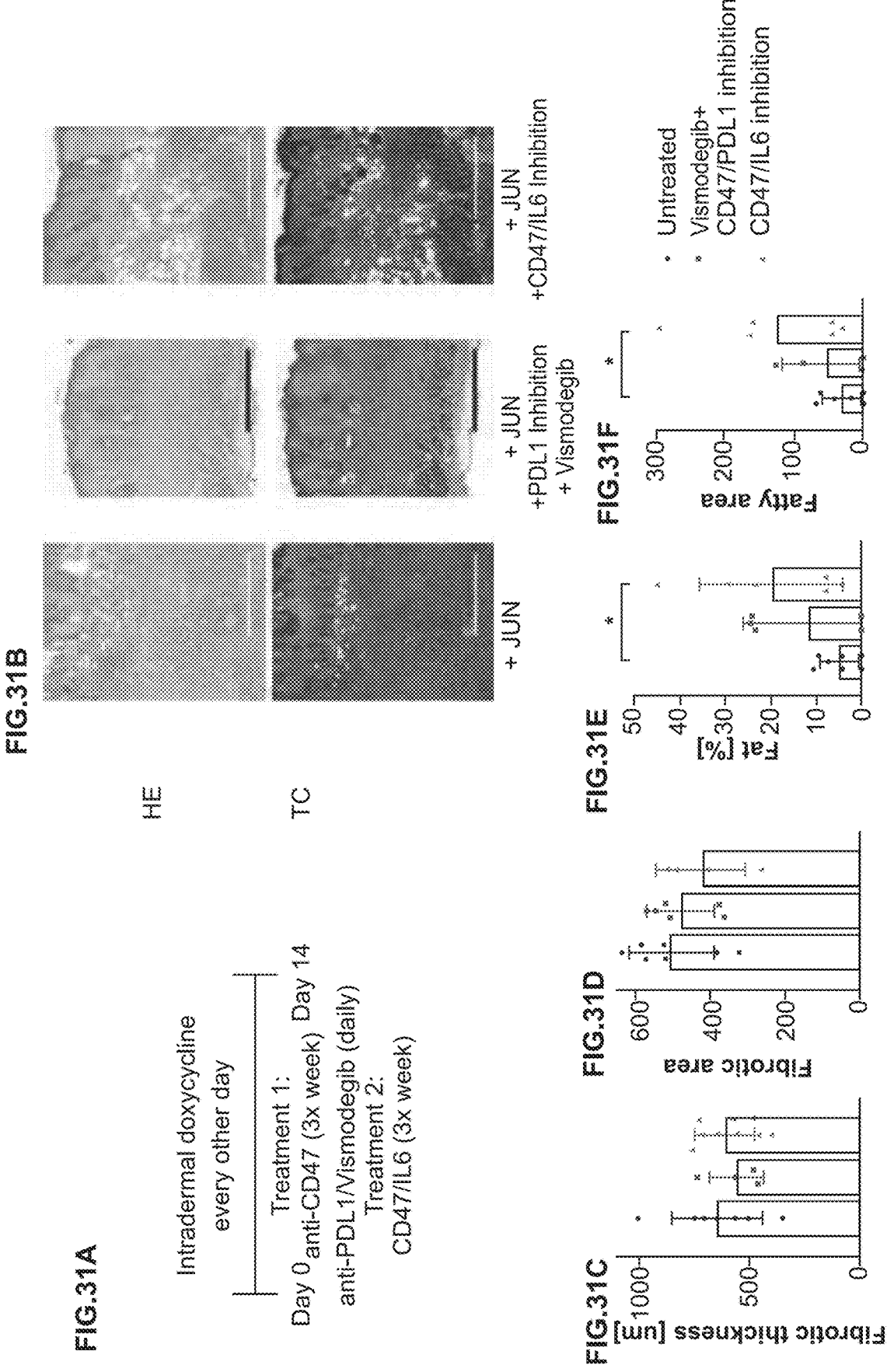

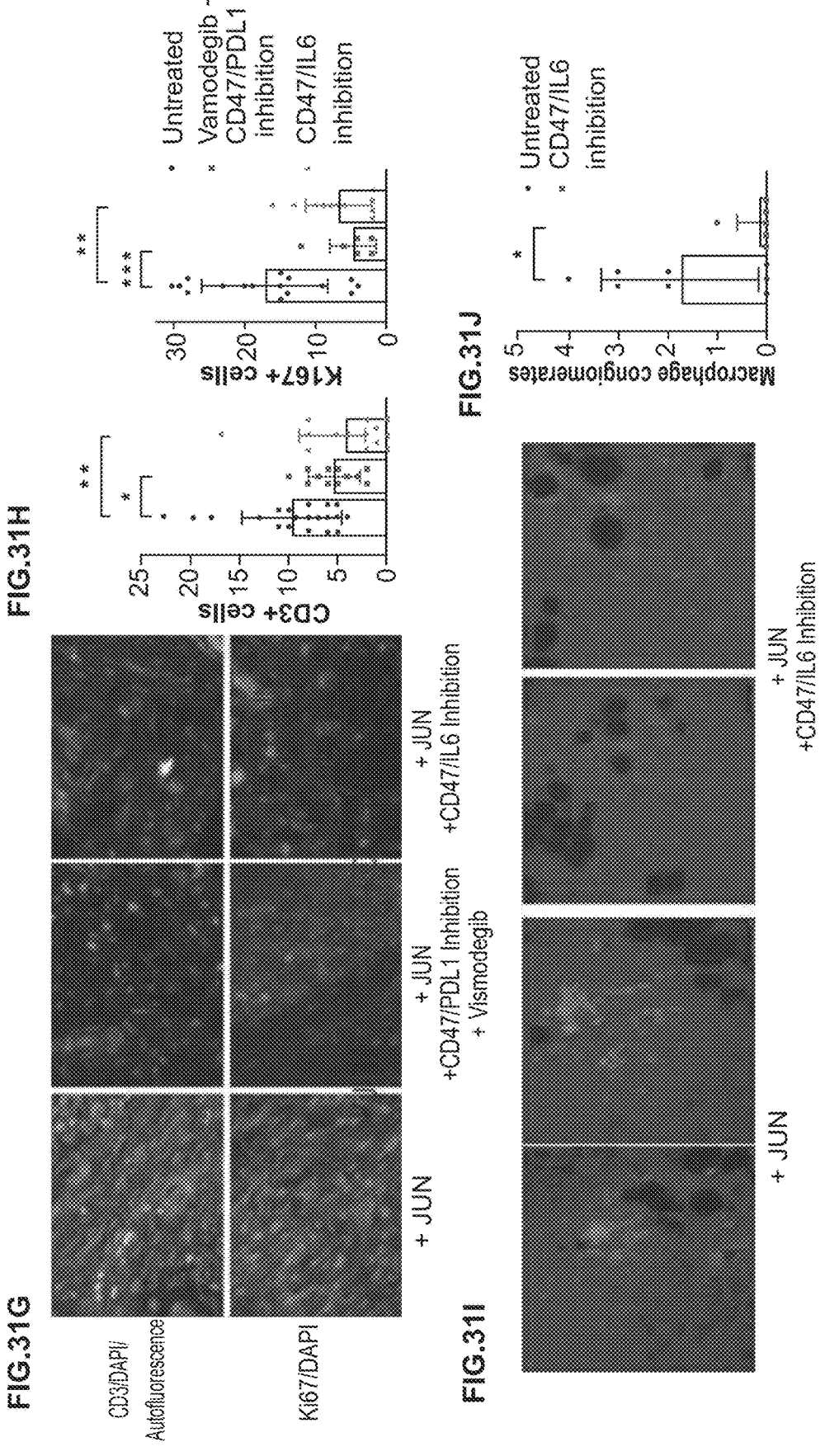

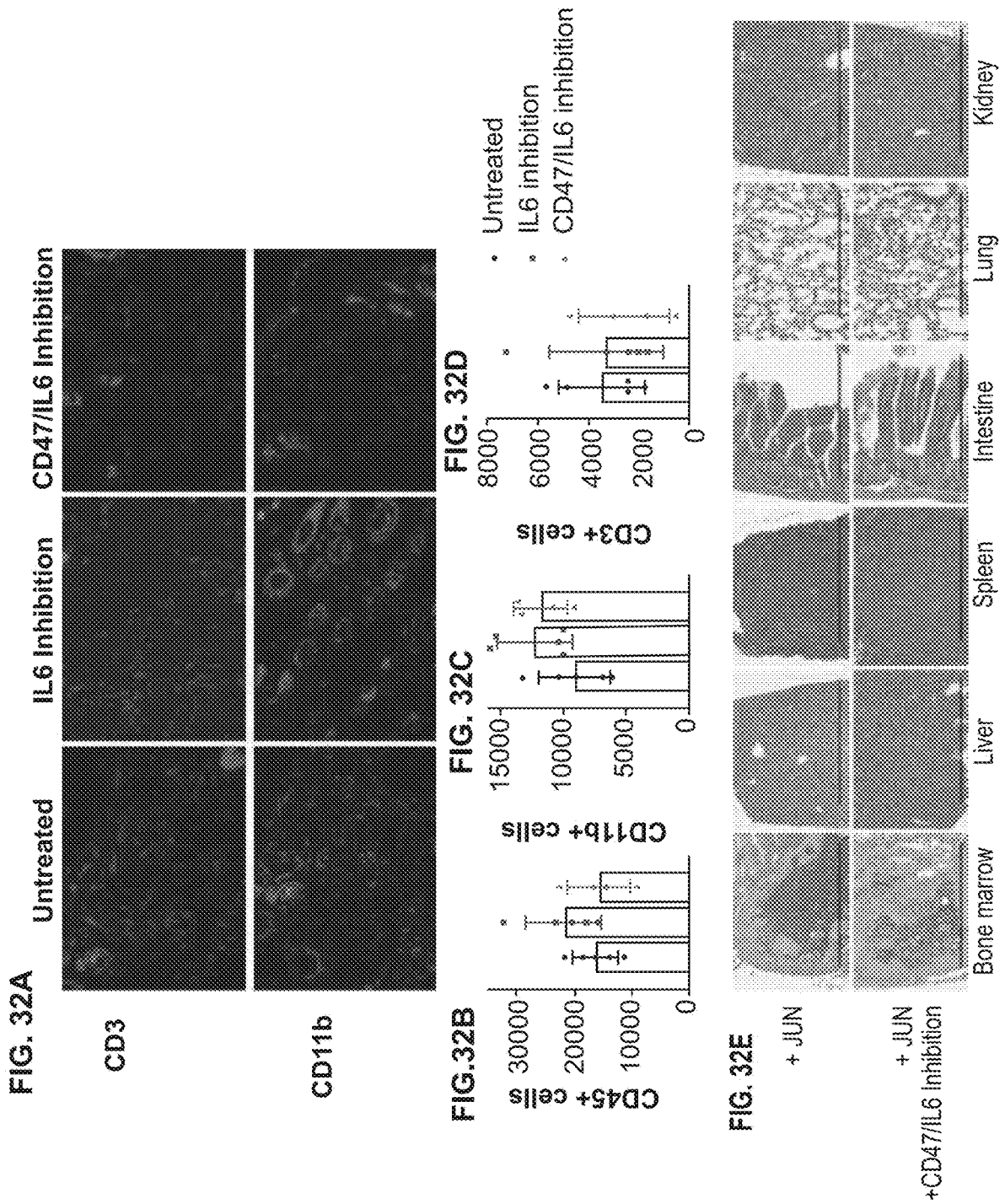

Fibroblasts in scl-GVHD upregulate JUN and CD47
FIG.33A
FIG.33B
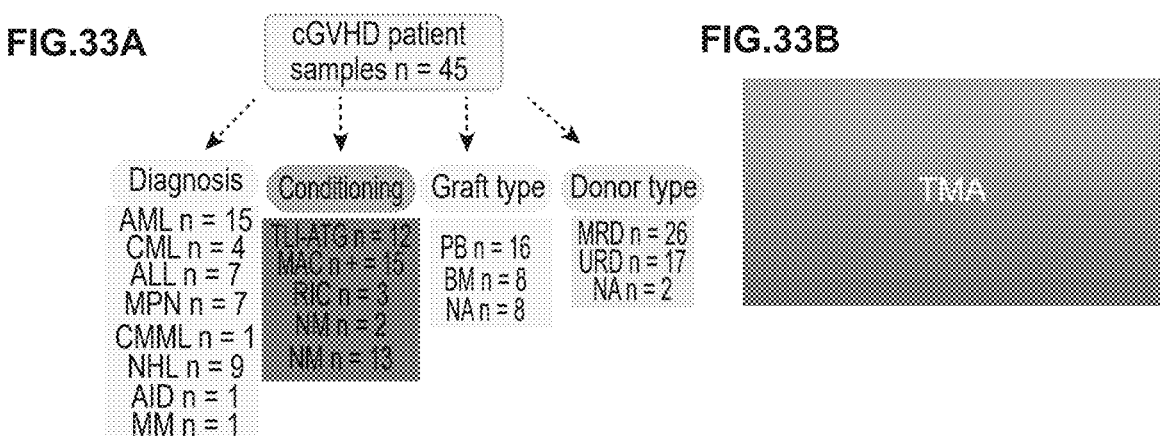
FIG.33C
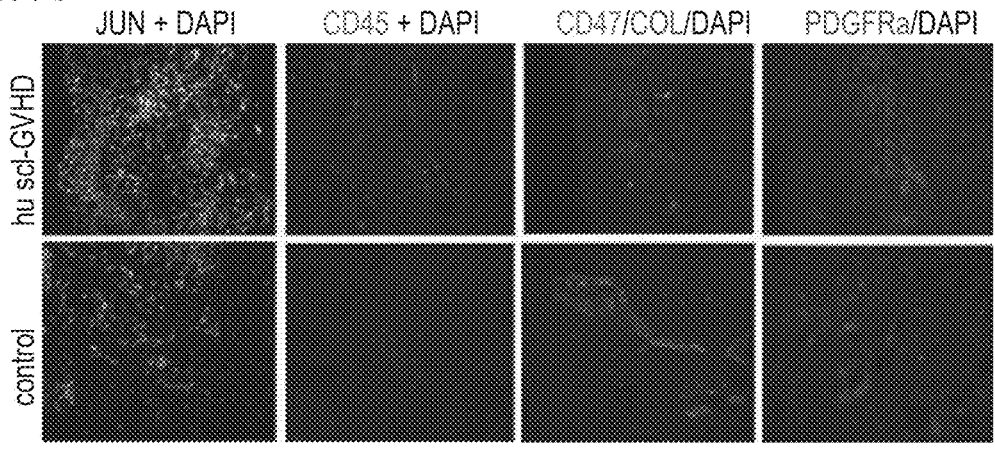

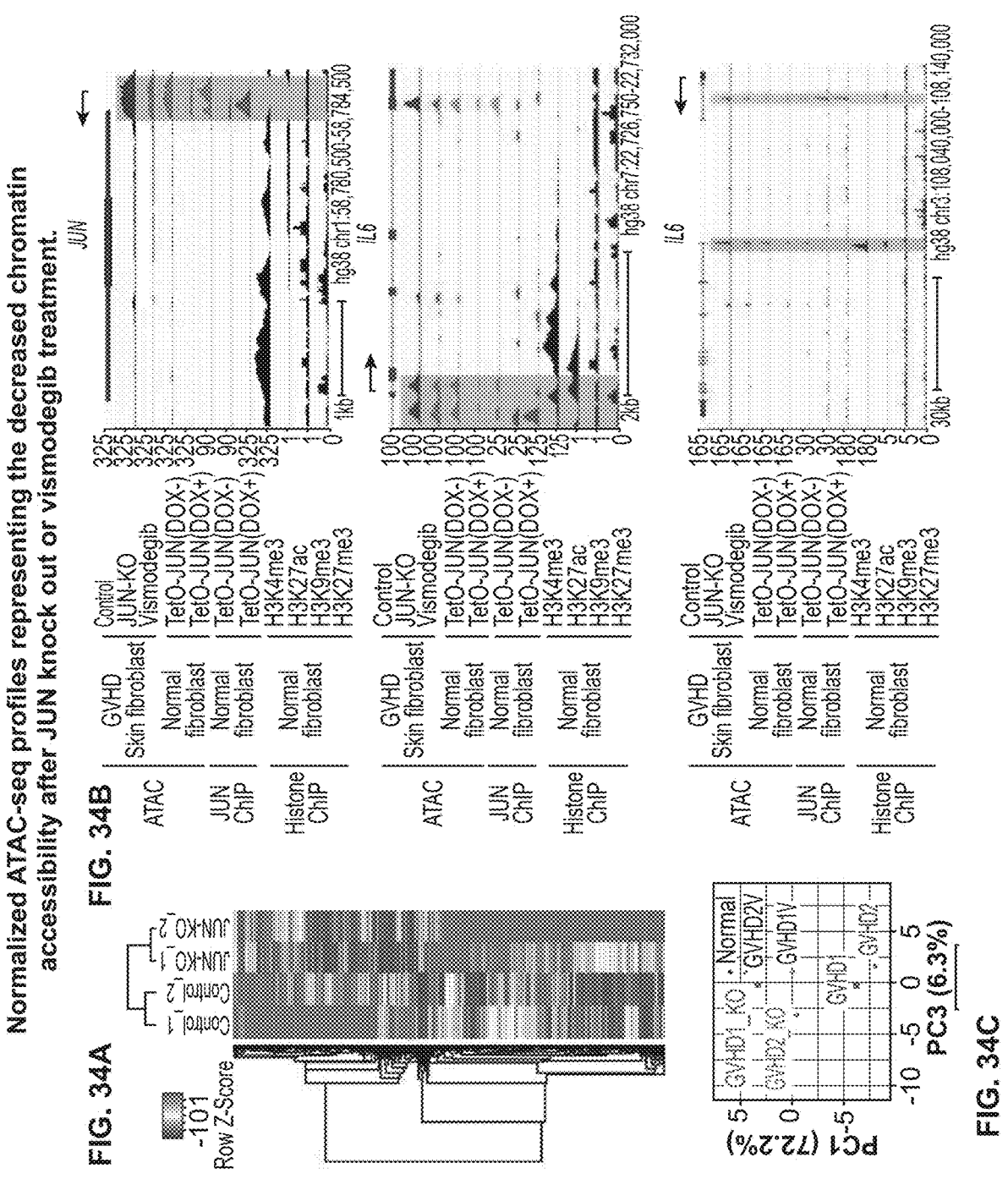
Normalized ATAC-seq profiles representing the decreased chromatin accessibility after JUN knock out or vismodegib treatment.

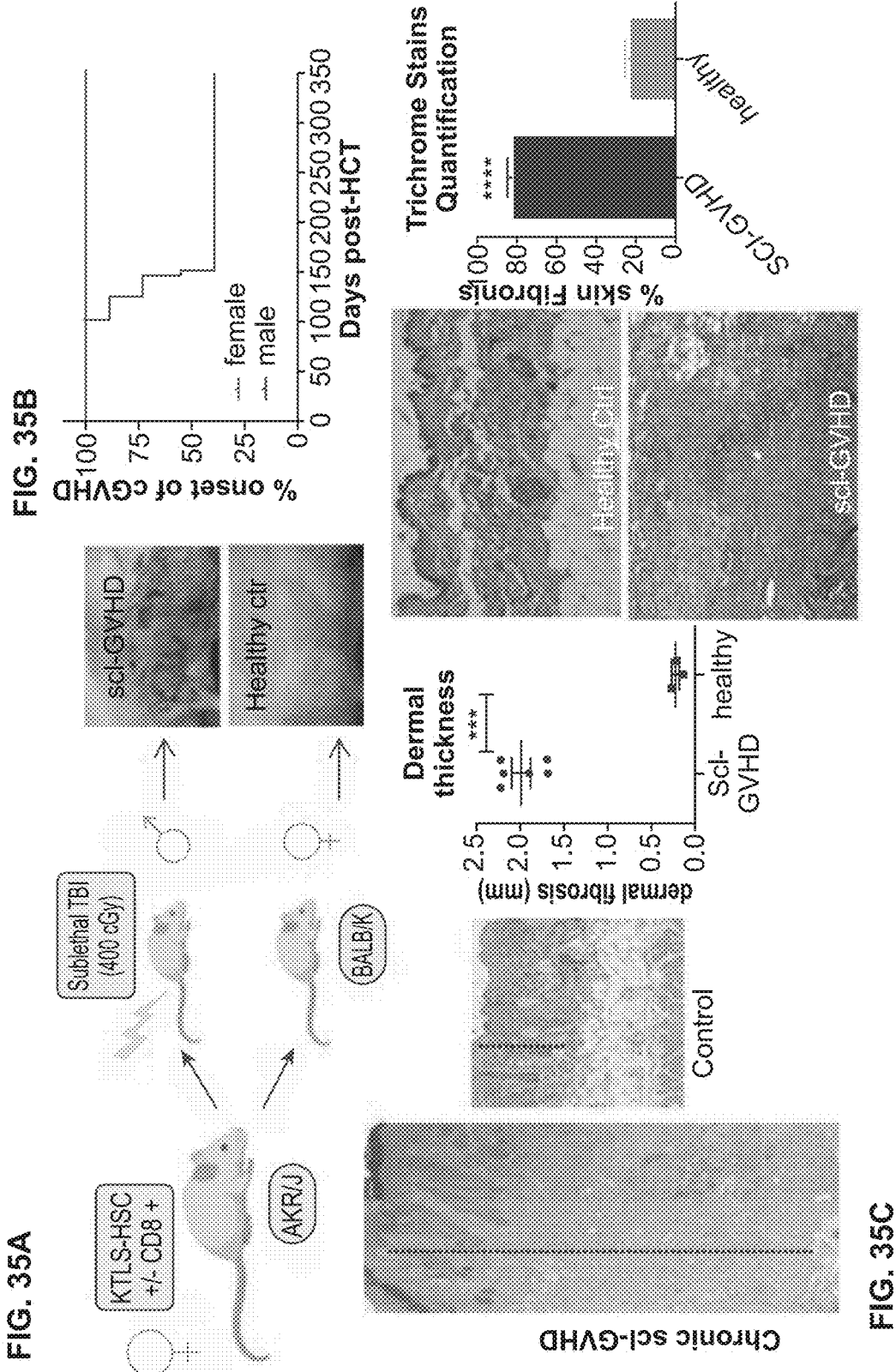

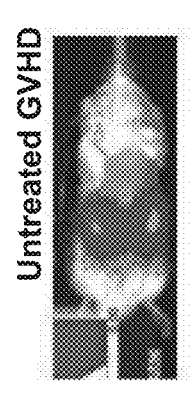
Untreated GVHD
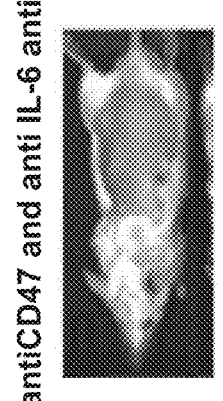
antiCD47 and anti IL-6 antibodies
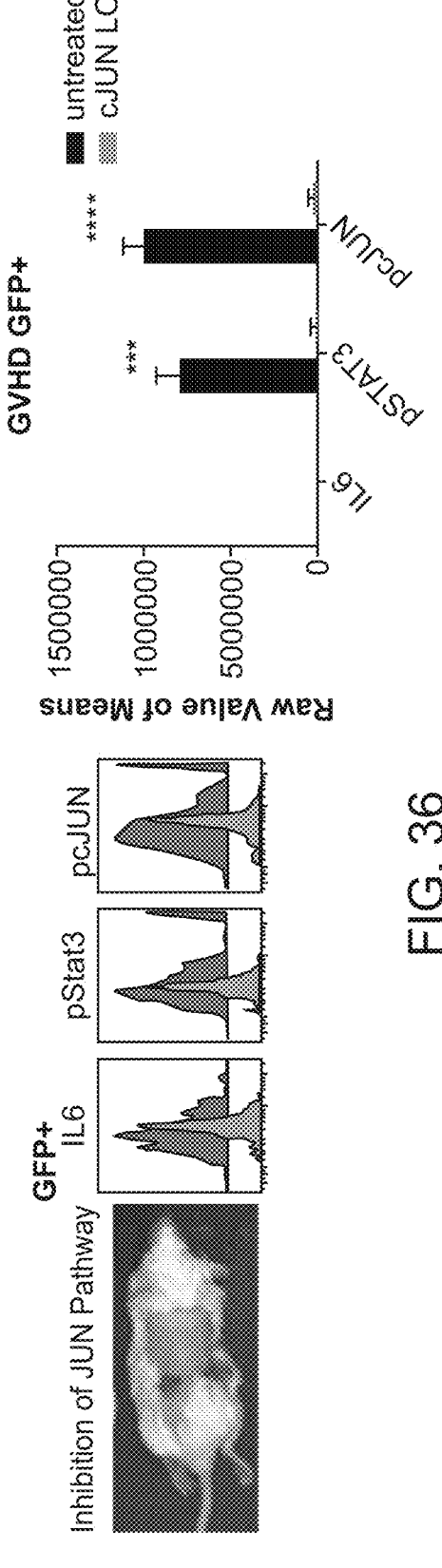
FIG. 36

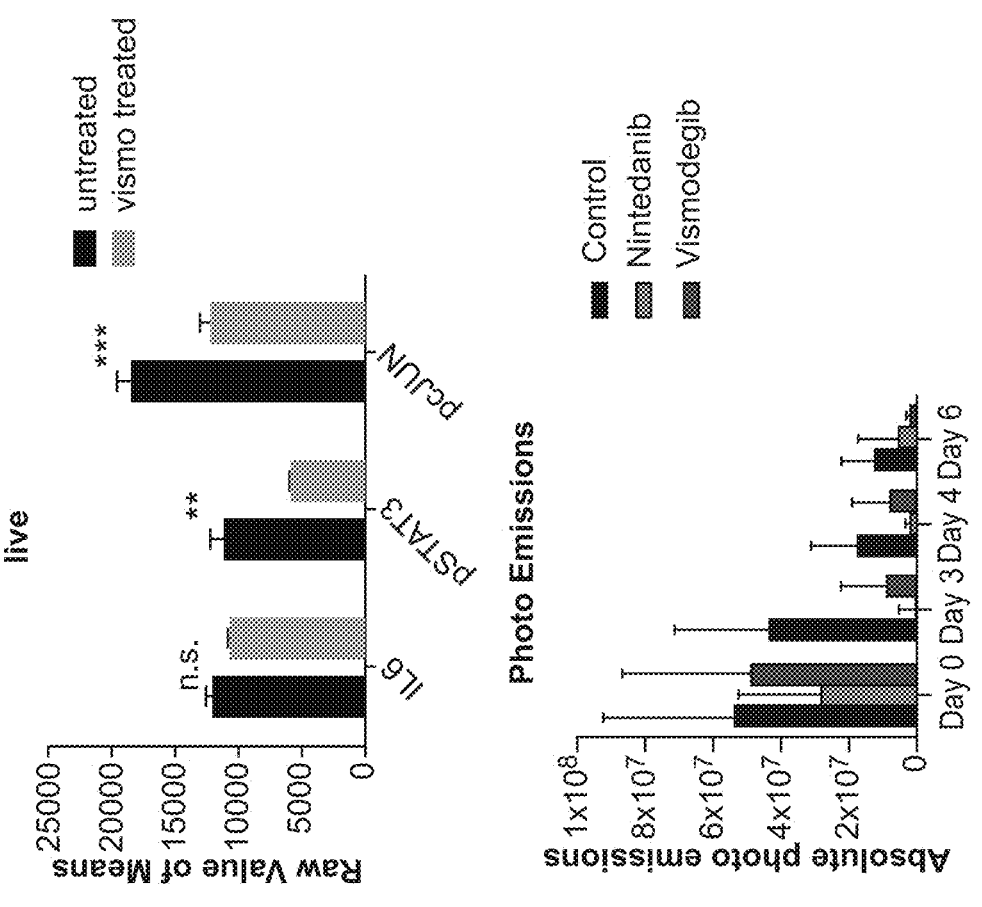
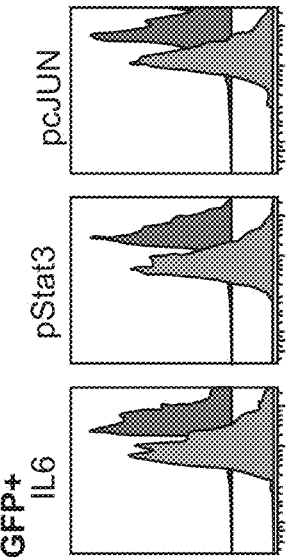
FIG. 39 (Cont.)

FIG. 40A
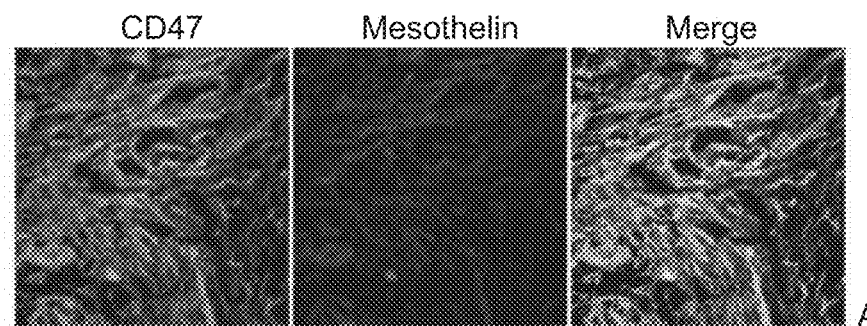
FIG. 40B
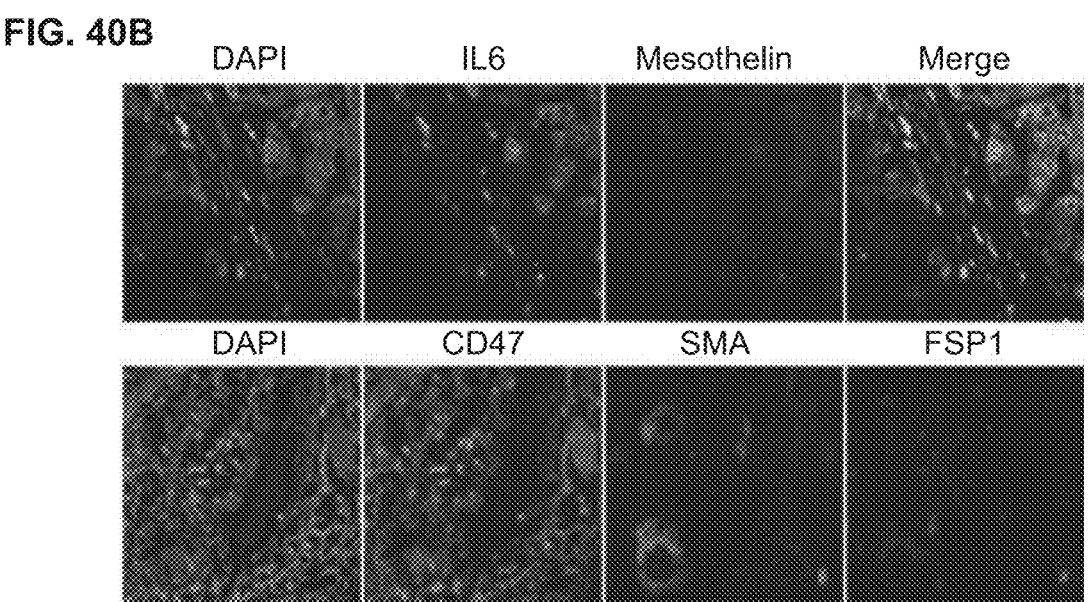
FIG. 40C

TREATMENT OF FIBROSIS WITH COMBINED BLOCKADE OF IL-6 AND IMMUNE CHECKPOINT

CROSS REFERENCE TO RELATED APPLICATION

This application is a U.S. National Stage of PCT Application No. PCT/US2020/061015, filed Nov. 18, 2020, which claims priority to U.S. Provisional Application No. 62/936, 652 filed Nov. 18, 2019, which applications are incorporated herein in their entirety for all purpose.

GOVERNMENT SUPPORT

This invention was made with Government support under contract HL143143 awarded by the National Institutes of Health. The Government has certain rights in the invention.

BACKGROUND OF THE INVENTION

Fibrosis is the excessive accumulation of extracellular matrix components (ECM) in and around inflamed or damaged tissue, often associated with chronic inflammation or cancer. The presence of fibrosis can be detected by means known in the art, for example by examination of tissue for excess scarring.

Pulmonary fibrosis is characterized by lung inflammation and abnormal tissue repair, resulting in the replacement of normal functional tissue with an abnormal accumulation of fibroblasts and deposition of collagen in the lung. This process involves cellular interactions via a complex cytokine-signaling mechanism and heightened collagen gene expression, ultimately resulting in its abnormal collagen deposition in the lung. In addition to inflammatory cells, the fibroblast and signaling events that mediate fibroblast proliferation and myofibroblasts play important roles in the fibrotic process. However, the most potent anti-inflammatory drugs that have been widely used in the treatment of pulmonary fibrosis do not seem to interfere with the fibrotic disease progression.

Interstitial lung disease, which may be referred to in the literature as idiopathic pulmonary fibrosis is a type of pulmonary fibrosis characterized by a progressive and irreversible decline in lung function. Symptoms typically include gradual onset of shortness of breath and a dry cough. The cause is unknown, although risk factors include cigarette smoking, certain viral infections, and a family history of the condition. About 5 million people are affected globally, most commonly with age.

With a three-year survival rate of only 50%, pulmonary fibrosis has a prognosis rivaling some of the worst malignancies. Pulmonary fibrosis is characterized by the spontaneous onset of progressive scarring of the lung in the absence of an infectious or autoimmune etiology. Despite the discovery that germline mutations of TERT are highly prevalent in these patients, the mechanism of pulmonary fibrosis disease remains incompletely understood.

There are no curative treatments for interstitial lung disease other than lung transplantation and novel therapies are desperately needed. Clinical trials for Nintedanib and Pirfenidon, two standard of care treatments targeting several growth factor receptors known to play a role in idiopathic pulmonary fibrosis, did not improve survival nor demonstrated long-term disease modifying effects for progressive pulmonary fibrosis, despite encouraging results for early pulmonary fibrosis. Other treatment strategies including but not limited to inhibiting toll-like receptors (TLR3, 4, 9) and metalloproteases, blocking macrophage activation and recruitment (mAbs TNFα and CCL2), targeting Th1 (=protective)/Th2 (=profibrotic) imbalance with INFγ and mAB IL-13, or immune modulatory treatments with CTLA4 and Azathioprine in pulmonary fibrosis patients treated for cancer failed to be effective in pulmonary fibrosis.

Scleroderma is the fibrotic skin manifestation of the autoimmune diseases morphea and systemic sclerosis, causing significant morbidity. Current treatments rely on immune suppression and primarily aim at stopping or slowing down the progression of scleroderma. Unfortunately, these treatments only bring temporary relief to most patients. Next to changes in the immune and vascular system, skin fibrosis represents one of scleroderma's clinical symptoms. Fibrosis is marked by an excessive amount of connective tissue primarily formed by fibroblasts. One of the genes that fibroblasts commonly upregulate in several fibrotic conditions, especially idiopathic pulmonary fibrosis, is the transcription factor JUN. JUN, that belongs to the family of the AP-1 transcription factors and that is activated through phosphorylation (pJUN), otherwise contributes to malignant diseases and plays a role in different developmental programs. To study the effects of Jun, our group uses a unique Jun-driven mouse model. In this model, Jun is inserted into the collagen locus and is under the control of a tetracycline-dependent promoter in the Rosa26 locus. Through doxycycline application, Jun can be induced either systemically through intraperitoneal injections or the drinking water, or locally through injections. Another characteristic feature of fibroblasts is their phenotypic and functional diversity. During development, they form different lineages. Lineages can be distinguished by specific surface markers and both CD26 and Sca1 are among these markers. While CD26+/Sca1− fibroblasts primarily reside in the upper dermis, CD26−/Sca1+ fibroblasts can be mainly found in the lower dermis. Though not specifically explored in these subsets of fibroblasts, hedgehog signaling with its main effector Gli1 has been shown to contribute to dermal fibrosis. Besides, hedgehog signaling plays a vital role in development and the maintenance of stem cell population.

Sclerodermatous chronic Graft-versus host disease (cGVHD) is a major complication of allogeneic hematopoietic stem-cell transplant (HCT) manifesting after 100 days. It is characterized by progressive scarring of the skin/organs leading to organ failure with an incidence ranging between 6-80%. Up to date, the pathomechanism of cGVHD is poorly understood. We recently reported that c-JUN is a central molecular mediator of severe fibrosis including Scleroderma (Wernig et al, PNAS 2017), and upregulated CD47, a critical immune checkpoint protein in fibroblasts. We subsequently demonstrated that αCD47 antibody treatment cured lung fibrosis in mice.

There remains a great need for therapies that impact the clinical course of patients with fibrosis, including interstitial lung disease (idiopathic pulmonary fibrosis) and scleroderma.

SUMMARY OF THE INVENTION

The present invention provides compositions and methods useful for reducing fibrosis, by administering an effective dose of (i) an immune checkpoint blocking agent; and (ii) an IL-6 blocking agent. In some embodiments the immune checkpoint blocking agent is selected from: an agent that blocks the CD47/SIRPα pathway; and an agent that blocks the PD-1/PD-L1 pathway. Blocking agents of interest include antibodies and variant proteins derived from an antibody that retains the complementarity determining regions of the antibody, e.g. an scFv, chimeric antigen receptor, FAb fragment, and the like. In certain embodiments a blocking agent is a soluble receptor, a dominant negative ligand, etc. Agents can inhibit a pathway by binding to and blocking either or both components of a pathway, for example a PD-1/PD-L1 blocking agent can bind to PD-1 or to PD-L1; a CD47/SIRPα blocking agent can bind to CD47 or to SIRPa, and an IL-6 blocking agent can bind to IL-6, or the IL-6 receptor, IL-6R.

In one embodiment, an effective dose of an IL-6 blocking agent and an effective dose of a CD47/SIRPα pathway blocking agent are concomitantly administered to an individual to block inflammation and to reduce abnormal accumulation of fibroblasts and collagen deposition in fibrotic tissue. In some embodiments the individual is human. In some embodiments the individual has been previously diagnosed with the fibrotic disease. In some embodiments the therapeutic method reverses pre-existing fibrosis.

In some embodiments the fibrotic tissue is lung tissue. In some embodiments the individual has been previously diagnosed with interstitial lung disease. In some embodiments pulmonary function is retained in an otherwise progressive form of the disease. In other embodiments the tissue is skin, e.g. in the treatment of skin fibrosis such as scleroderma and pathologic wound healing e.g. hypertrophic scarring. In some embodiments the individual has been previously diagnosed with scleroderma. In other embodiments, the tissue is liver, e.g. in the treatment of non-alcoholic steatohepatitis (NASH), liver cirrhosis, etc. Systemic sclerosis can also be treated.

Without being limited by the theory, the data herein indicate that IL-6 produced by pathologic fibroblasts in pulmonary fibrosis acts as an amplifier of JUN mediated immune suppressive signals, resulting in upregulation of CD47 and PD-L1 expression. Blocking IL-6 and the immune checkpoint concomitantly allows a normalization of immune responsiveness, for example by activation of macrophages; and results in a decrease in fibrosis, e.g. in existing fibrosis. In studies of established fibrosis, this combination therapy has a superior effect relative to standard of care in removal of cross-linked collagen. In some embodiments the combination provides for a synergistic effect compared to monotherapy blocking only IL-6 signaling or blocking only CD47 signaling. In addition, the IL-6-targeting approach provides for desensitization and prevention of immune-suppressive effects, e.g. reversion of T-cell exhaustion in interstitial lung disease. Blocking IL-6 is effective treatment when combined with other immune checkpoint therapies such as anti-CD47 or anti-PDL1 blockade.

An agent that blocks the CD47/SIRPα pathway, for use in the methods of the invention, interferes with binding between CD47 present on the fibrotic cell and SIRPα present on a phagocytic cell. Such methods increase macrophage activation and phagocytosis of the fibrotic cell. Suitable anti-CD47 agents include soluble SIRPα polypeptides; soluble CD47; anti-CD47 antibodies, anti-SIRPα antibodies, and the like. In some embodiments the anti-CD47 agent is an anti-CD47 antibody, including without limitation magrolimab. In some embodiments the anti-CD47 antibody is a non-hemolytic antibody. In some embodiments the antibody comprises a human IgG4 Fc region.

Compositions and kits for practicing the methods and/or for use with the systems of the disclosure are also provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1. Systems-level analysis of pulmonary fibrosis patients, from scleroderma, chronic graft-versus host disease, NASH and liver cirrhosis demonstrating a key role for immune-checkpoint proteins PD-L1 and CD47 in fibrotic lung fibroblasts as well as JUN. (a) Outline of our "Omics" approach in human fibrotic lung integrating proteomics, secretomics and genomics technology platforms to study the contribution of leukocytes and pathologic fibroblasts and to identify new therapeutic targets. (b) Single-cell force-directed layout of fibrotic lung tissues. Shaded regions indicate the location of manually gated cell populations: green-shaded area represents leukocytes (CD45+), pink area epithelial cells (CK7+), blue area endothelial cells (CD31+) and grey dotted circle highlights the fibroblasts (CD45−CK7−CD31−). (c) Frequencies of cell populations in the lung detected by mass cytometry (CyTOF). Data are displayed as mean±SD of 11 fibrotic and 3 normal control lung samples. (d) Principal component analysis (PCA) was computed on fibroblast clusters from 11 individual pulmonary fibrosis patients (PF) and 3 normal donors (NC) mass cytometry data sets demonstrating that fibrotic and the normal fibroblasts were distinct from each other. (e) ViSNE maps of fibroblast mass cytometry data demonstrating that the abundance of fibroblasts differed; while in normal controls the lung fibroblasts appeared heterogeneous, the fibroblasts cluster tightly together in fibrotic lungs (Blue: highlighted by the black dotted circle). The data demonstrate a representative example per group and each point in the viSNE map represents an individual cell. (f) VISNE analysis of mass cytometry data of fibrotic lung (blue dots), normal lung (orange dots) and normal peripheral blood mononuclear cells (PBMCs, green dots) revealed increased activation of the JUN and AKT pathways in fibrotic lung fibroblasts. Schematic diagram of the location of the indicated cell types on the viSNE map are based on the expression of lineage specific markers: epithelial cells (Epi), natural killer cells (NK), plasmacytoid dendritic cells (pDC), endothelial cells (EC), and macrophages (Mac). Red indicates high and blue low protein expression. (g) Representative mass cytometry plots of the pro-Fibrotic fibroblast population in fibrotic lung compared with normal Lung. (h) Immune fluorescent stains confirmed increased CD47 and PD-L1 co-expression in lung fibroblasts from fibrotic lungs but not in normal controls (activated fibroblasts expressing Collagen1+ and SMA+) (Scale bars, 100 μm). (i) RNA expression analysis of JUN, PD-L1 and CD47 in fibrotic and normal lung fibroblasts are detected by QPCR. Data are expressed as mean±SD of 5 fibrotic fibroblasts and 3 normal fibroblasts and is representative of at least three experiments. Data were analyzed by two-tailed unpaired t-test, *P<0.05; **P<0.01. See supplementary table 4 for statistical details.

FIG. 2. Lung fibrotic condition converts macrophages into an immunosuppressive phenotype. (a) Main cluster frequencies of CD45+ leukocytes (T cells, macrophages, B cells, NK cells, dendritic cells and other inflammatory cells such as neutrophils/eosinophils/plasma cells) contained in the lungs of pulmonary fibrosis patients and normal controls were quantified by mass cytometry. Data are expressed as mean±SD of 11 fibrotic and 3 normal lung samples. (b) Computational analysis of mass cytometry data of leuko- cytes derived from fibrotic lungs with a single-cell force- directed algorithm demonstrated that the different inflam- matory subsets segregated as indicated on the map: blue highlights CD4+ T cells, purple CD8+ T cells, green mac- rophages, orange B cells, yellow NK cells and white the dendritic cell subset. (c) Principal component analysis (PCA) of manually gated macrophages (CD45+CD68+nonB nonT nonNK Live cells) indicating that macrophages derived from the pulmonary fibrosis lungs (PF) cluster are distinct from normal lungs (NC). (d) A refined viSNE analysis of mass cytometry data demonstrating that macro- phages derived from normal lungs (orange) have a distinct profile from fibrotic lungs (blue: black dotted circle). (e) ViSNE analysis of macrophages isolated from normal lungs and fibrotic lungs demonstrating decreased activation of HLA-DR, CD169 and CD206 expression in fibrotic lungs relative to controls. Each point represents a single cell, and the samples are color coded as indicated: blue colors rep- resent low expression and yellow to red high protein expres- sion. (f) The corresponding ratio of interstitial macrophages (HLA-DR+CD206+CD169−, IM) versus alveolar macro- phages (HLA-DR++CD206++CD169+, AM) was displayed with mean±SD of 11 fibrotic and 3 normal lung samples, and analyzed by two-tailed unpaired t-test, **P<0.01. (g) Rep- resentative images of immune fluorescent stains highlighted increased PD-1 expression on macrophages from fibrotic lung tissues (Scale bars, 100 μm). See supplementary table 4 for statistical details.

FIG. 9. (a) ViSNE map of concatenated fibroblasts (CD45-CD31-CK7-population) from fibrotic lung (black dot circled) and normal lung demonstrating increased expression of PDGFRa, PODOPLANIN, CD47 and PD-L2 but not CALRETICULIN in subset of fibroblasts in fibrotic lungs. (b) Representative CyTOF plots of PD-L2 and Calreticulin protein in fibroblasts from fibrotic and normal lungs indicating increased PD-L2 and no difference in Calreticulin expression. (c) Quantitation of CD47 and PD-L1 immune stains in fibrotic and normal lung biopsies. Data are expressed as mean±SD, and analyzed by two-tailed unpaired t-test, P<0.01; **P<0.0001. The immune stains have been evaluated by a blinded pathologist, in addition to image J software. (d) The representative Haematoxylin and eosin staining of fibrotic and normal lung tissue. The inserted black frame highlighted the fibrotic and normal area. Scale bar, 100 μm. (e) Multiplexed ion beam imaging (MIBI) and relevant quantitation demonstrated the co-expression of JUN and FOS with CD47 in fibroblasts in fibrotic plaques in lungs of interstitial lung disease patients. Representative MIBI analysis of lung biopsy section out of 5 patients with interstitial lung disease were stained with metal-conjugated antibodies. In total, 10 different markers JUN, JUNB, JUND, FRA1, FRA2, FOS, FOSB, COLLAGEN1, CD47 and Hematoxylin were analyzed. 8 fields of view were acquired with ten repeat scans over a single area. Experiments were run multiple times, representative examples and related analysis are shown as mean±SD. Scale bar, 100 μm. (f) ELISA detected increased levels of secreted PD-L1 in fibrotic lung BAL compared to normal lungs. Data are expressed as mean±SD of 5 fibrotic and 3 normal samples. Data were analyzed by two-tailed unpaired t-test, *P<0.05.

FIG. 10. (a) We analyzed dendritic cells in fibrotic and normal lungs with mass cytometry and found increased numbers of myeloid dendritic cells (mDC: CD45+ nonB nonT nonNK nonmacrophage CD11c+CD123−) in fibrotic lung but no difference for plasmacytoid dendritic cells (pDC: CD45+ nonB nonT nonNK nonmacrophage CD11c−CD123+). (b) IDO protein expression in macrophages from fibrotic lungs is decreased compared to macrophages from normal control lungs. Raw values of means of CyTOF data are displayed on a per-patient basis with mean±SD of 11 fibrotic and 3 normal samples and analyzed by two-tailed unpaired t-test, *P<0.05. (c) The viSNE maps are colored by intensity of expression (red is high, and blue low) demonstrate the expression of IDO, ARG1, CD47, CD16, CD163 and CD11c in macrophages derived from fibrotic lungs which clustered spatially within the black circled area. (d) Representative histogram of mass cytometry data demonstrate decreased alveolar macrophages (AM) but increased interstitial macrophages (IM) in human fibrotic lungs. (e) Quantitation of PD-1+ expression on macrophages (CD68+) in fibrotic and normal lung biopsies. Data are expressed as mean±SD and analyzed by unpaired t test with Welch's correction (Two-tailed), **P<0.01. The immune stains have been evaluated by a blinded pathologist, in addition to image J software.

FIG. 11. (a) We quantified the frequencies of T cell and found no significant differences in total CD4 and CD3 T cells, but decreased numbers of NKT cells in individual samples plotted as a fraction of total T cells and displayed as mean±SD. (b) Representative plots of mass cytometry data showing no significant difference of CD4 T cell subsets, polarized Th1 (CD3+CD4+TBET+), Th2 (CD3+CD4+GATA3) and Th17 (CD3+CD4+RORgc) in fibrotic and normal lungs. (c) Percentage of PD-1+ expression on CD4+ T cells were displayed with mean±SD of 11 fibrotic and 3 normal lung samples. Data are expressed as mean±SD, and analyzed by two-way unpaired t-test, **P<0.0001. (d) Quantitation of PD-1+ expression on T cells (CD3+) in fibrotic and normal lung biopsies. Data are expressed as mean±SD and analyzed by unpaired t test with Welch's correction (Two-tailed), *P<0.001. The immune stains have been evaluated by a blinded pathologist, in addition to image J software.

FIG. 17. Human scleroderma increases promoter accessibilities of JUN and CD47. (A) ATAC Seq analysis for JUN and the hedgehog genes Glit and Ptch1 in scleroderma fibroblasts (SSCL), scleroderma fibroblasts after JUN knockout (JUN-KO) or under vismodegib, or normal skin fibroblasts. The promoter regions are highlighted with red boxes. n=2. (B) ATAC Seq analysis for the immune checkpoints CD47 and PDL1 and the interleukin IL6 in scleroderma fibroblasts (SSCL), scleroderma fibroblasts after JUN knockout (JUN-KO) or under vismodegib, or normal skin fibroblasts. The promoter regions are highlighted with red boxes. n=2. (C) Heatmap of differential open chromatin regulatory elements characterized from ATAC-seq. The color bar shows the relative ATAC-seq signal (Z score of normalized read counts) as indicated. Samples 1 and 2 in both groups are individual samples. n=2. (D) Fibrosis-linked genes with a fivefold decline in promoter accessibility after JUN knockout. n=2. (E) pJUN expression in pulmonary fibroblasts and scleroderma fibroblasts on a 70 kPa hydrogel or a regular polystyrene plastic dish. Two-sided t-test. p<0.01 *p<0.001. n=4. Turkey's multiple comparisons test. n=4. Bar graphs represent means with standard deviations.

FIG. 21. CD47 inhibition eliminates dermal fibroblasts in vivo and in vitro. (A) Immunofluorescence stains against CD47 and FSP1 with and without JUN induction. Scale bar=25 μm. n=5. (B) Histogram of CD47 expression in fibroblasts with and without JUN induction. n=5. (C) Percentage of CD47 positivity in different fibroblast populations with and without JUN induction. Fisher's multiple comparions test. *p<0.01. n=5. Bar graphs represent means with standard deviations. (D) Representative optical images of ectopically transplanted JUN inducible mouse dermal fibroblasts+/−CD47 inhibition. n=4. (E) Corresponding quantification of photon emissions. Values are normalized to day 0. Fisher's multiple comparions test. p<0.01. n=4. Bar graphs represent means with standard deviations. (F) Fluorescent graft visualization under the dissection microscope after seven days of CD47 inhibition. Scale bar=5 mm. n=2. (G) Facs Plot for PE/RFP+CD11b+ macrophages+/−JUN induction+/−CD47 inhibition in an in vitro phagocytosis assay. n=3. (H) Corresponding quantification of RFP+ macrophages. Turkey's multiple comparisons test. *p<0.05 *p<0.01. n=3. Bar graphs represent means with standard deviations. (I) Schema of a macrophage depletion trial with subsequent skin fibrosis induction. n=5. (J) Corresponding trichrome stains. Scale bar=500 μm. n=5. (K) Corresponding hydroxyproline assay. Two-sided t-test. *p<0.001. n=5. Bar graphs represent means with standard deviations.

μm. (C) Quantification of CD45+ cells under JUN induction over up to 5 days. Turkey's multiple comparisons test. *p<0.05. n=4-5. Bar graphs represent means with standard deviations. (D) Quantification of myeloid CD11b+ cells under JUN induction over up to 5 days. Fisher's multiple comparisons test. n=4-5. Bar graphs represent means with standard deviations. (E) Quantification of dendritic CD11b+ CD11c+ cells under JUN induction over up to 5 days. Turkey's multiple comparions test. *p<0.05. n=4-5. Bar graphs represent means with standard deviations. (F) Quantification of CD3+ T cells under JUN induction over up to 5 days. Turkey's multiple comparisons test. *p<0.05. n=4-5. Graph bars represent means with standard deviations. (G) Quantification of hematopoietic Cx3cr1+ cells under JUN induction over up to 5 days. Fisher's multiple comparisons test. n=4-5. Graph bars represent means with standard deviations. (H) In vitro collagen 1 secretion of fibroblasts and macrophages+/−JUN induction. One-way ANVOA * p<0.05 ***p<0.001 (n=4). Bar graphs represent means with standard deviations.

Figure 26:
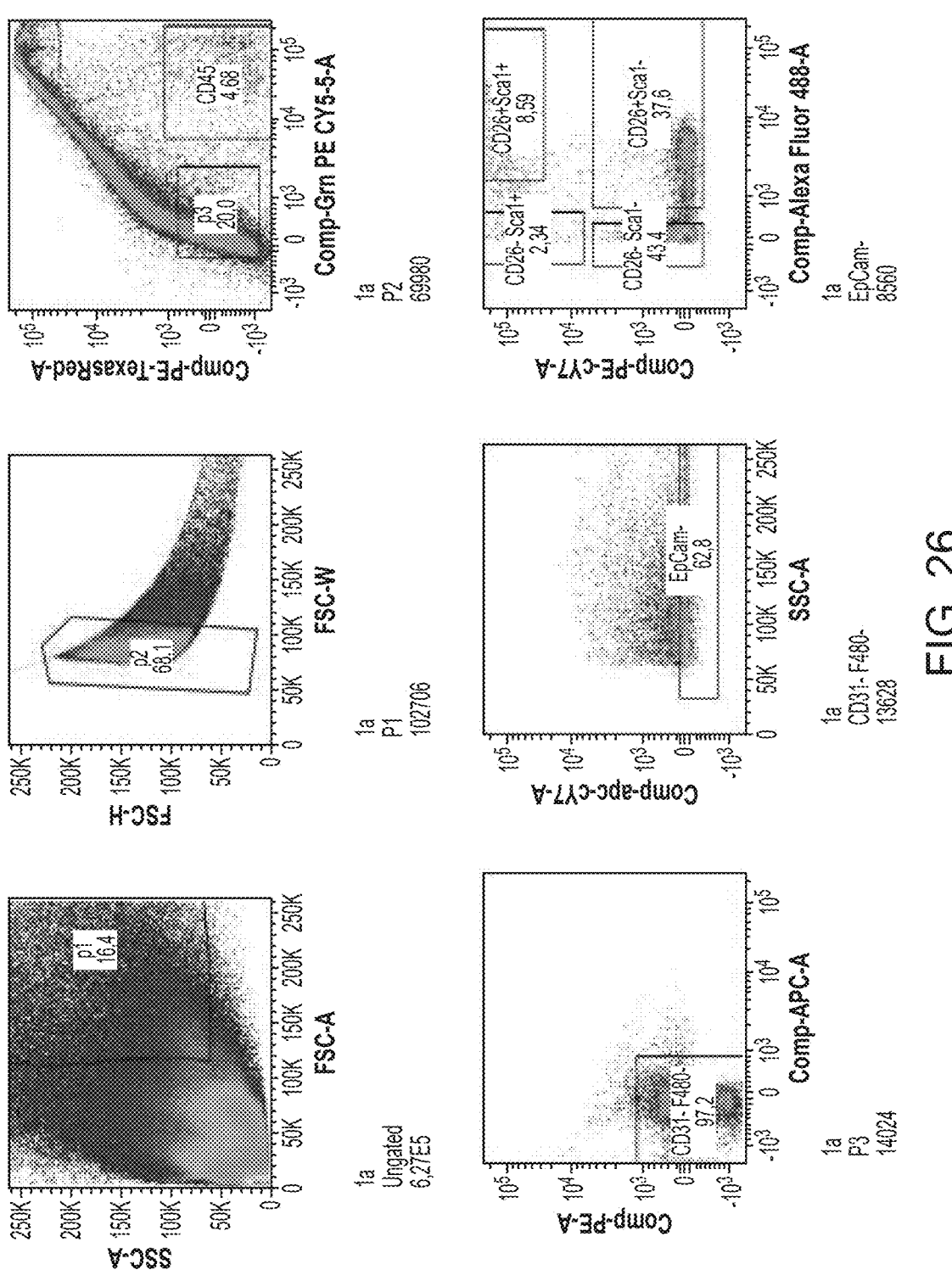

FIG. 26. Fibroblast gating strategy. After identifying cells and then single cells, hematopoietic (CD45+) and dead cells (PI) are excluded. In a next step, macrophages (F4/80+) and endothelial (CD31+) cells are excluded. After removing epithelial (CD326+) cells, fibroblasts are divided, based on their expression of CD26 and Sca1.

Figure 27:
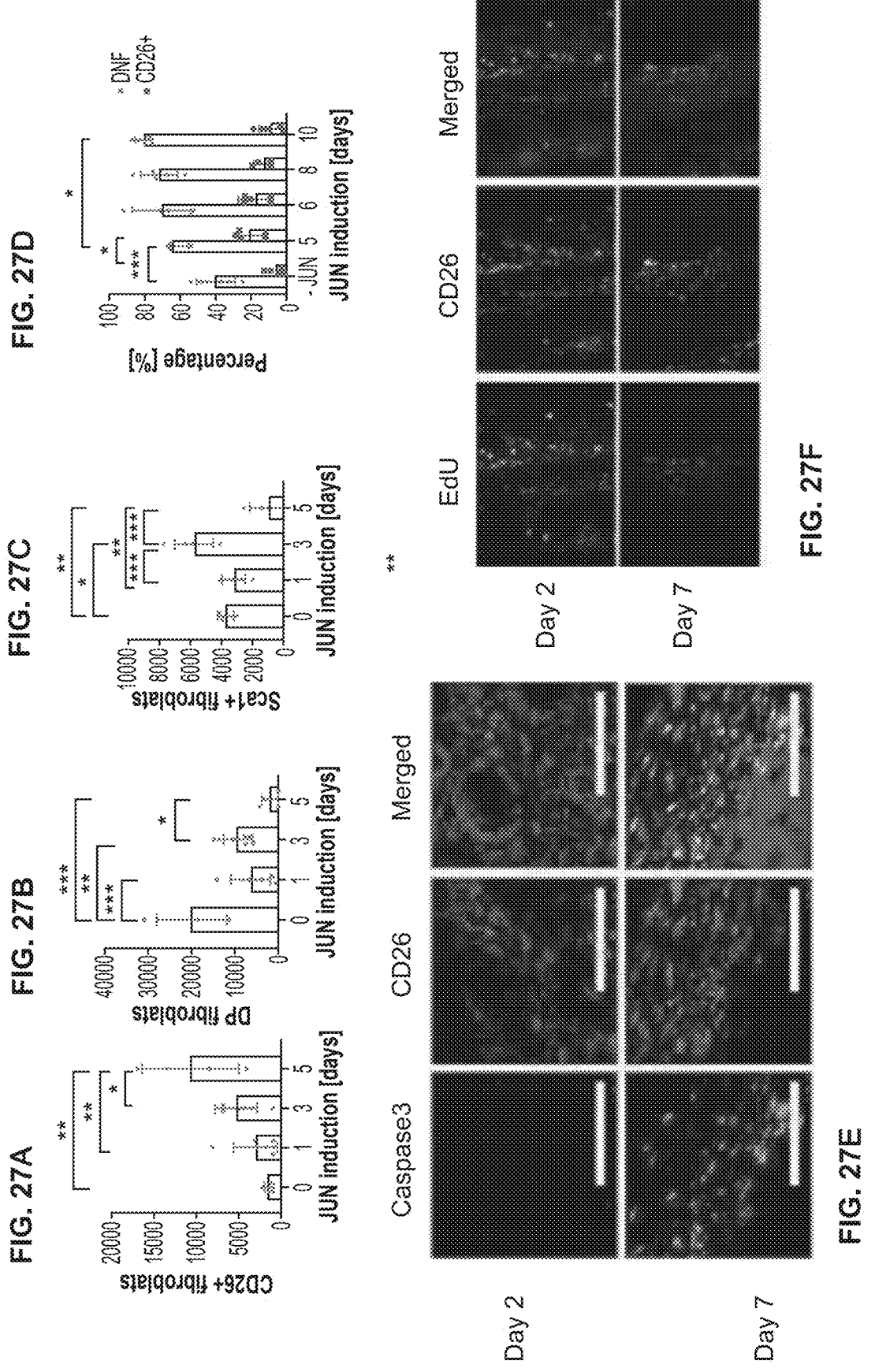

FIG. 27. JUN initially expands CD26+ fibroblasts. (A) Quantification of CD26+ fibroblasts, over five days of JUN induction. Turkey's multiple comparisons test. *p<0.05 p<0.01. n=4-5. Bar graphs represent means with standard deviations. (B) Quantification of DPF over five days of JUN induction. Turkey's multiple comparisons test. *p<0.001. n=5. Bar graphs represent means with standard deviations. (C) Quantification of Sca1+ fibroblasts over five days of JUN induction. Turkey's multiple comparisons test. p<0.01 *p<0.001. n=5. Bar graphs represent means with standard deviations. (D) Quantification of CD26+ fibroblasts and DP fibroblasts (DPF) over up to 10 days of JUN induction. Fisher's multiple comparisons test. *p<0.05 p<0.01 *p<0.001. n=4-6. Bar graphs represent means with standard deviations. (E) Representative immunofluorescence stains against Caspase3 and CD26 two and seven days after JUN induction. Scale bar=100 μm. (F) Representative immunofluorescence stain against CD26 and corresponding EdU visualization two and seven days after JUN induction.

Figure 28:
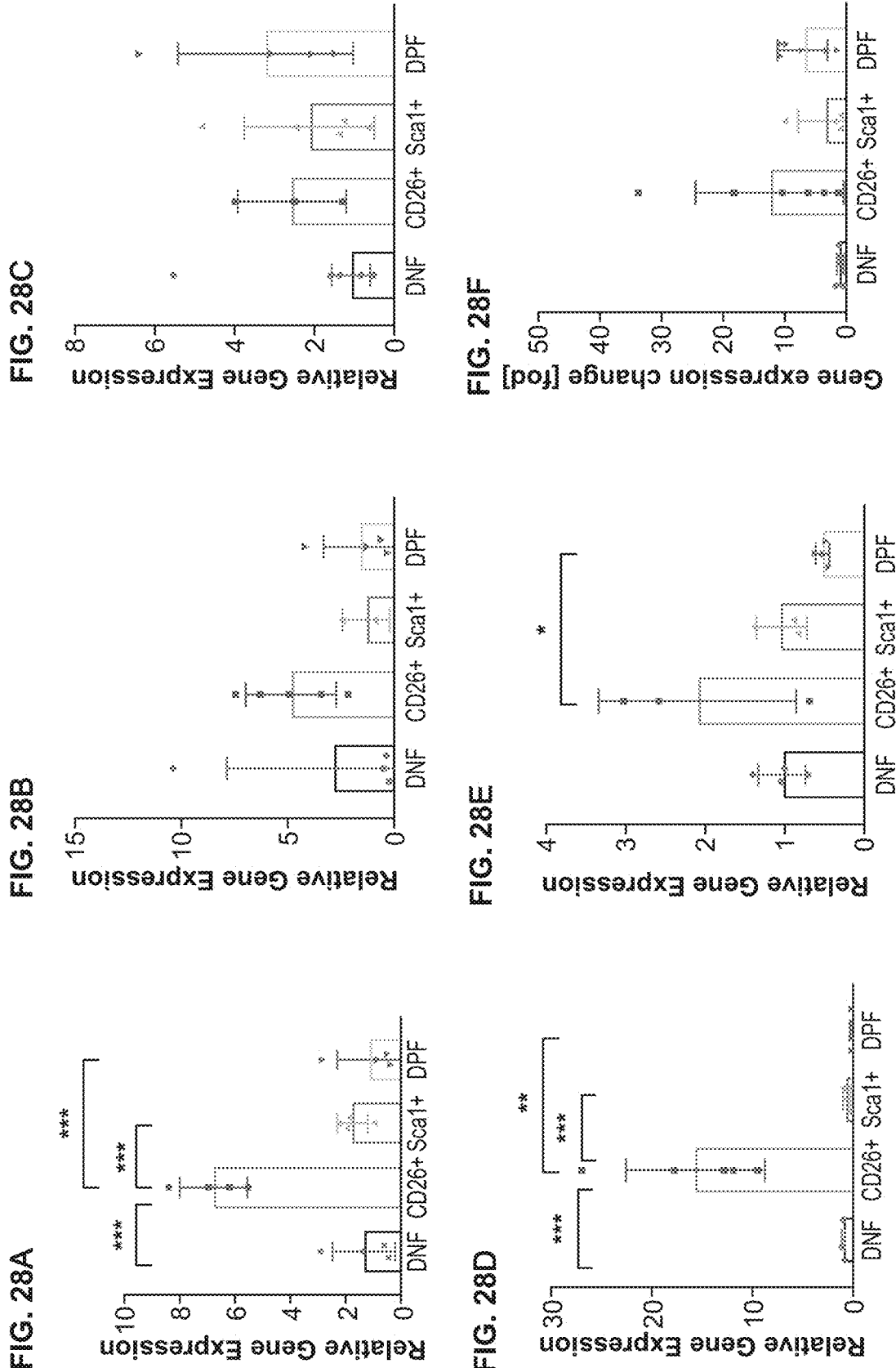

FIG. 28. CD26+ fibroblasts activate hedgehog signaling. Normalized qPCR data from facs purified fibroblast populations from non JUN-induced JUN mice. The values for each gene are compared to the mean value of the DN fibroblasts. (A) Gli1. Turkey's multiple comparisons test. *p<0.001. n=4. Bar graphs represent means with standard deviations. (B) Gli2. Turkey's multiple comparisons test. n=3-5. Bar graphs represent means with standard deviations. (C) Gli3. Turkey's multiple comparisons test. n=3-5. Bar graphs represent means with standard deviations. (D) Ptch1. Turkey's multiple comparisons test. p<0.01 ***p<0.001. n=3-5. Bar graphs represent means with standard deviations. (E) Kif7. Turkey's multiple comparisons test. *p<0.05. n=3-4. Bar graphs represent means with standard deviations. (F) Smo. Turkey's multiple comparisons test. n=4-6. Bar graphs represent means with standard deviations.

Figure 29:
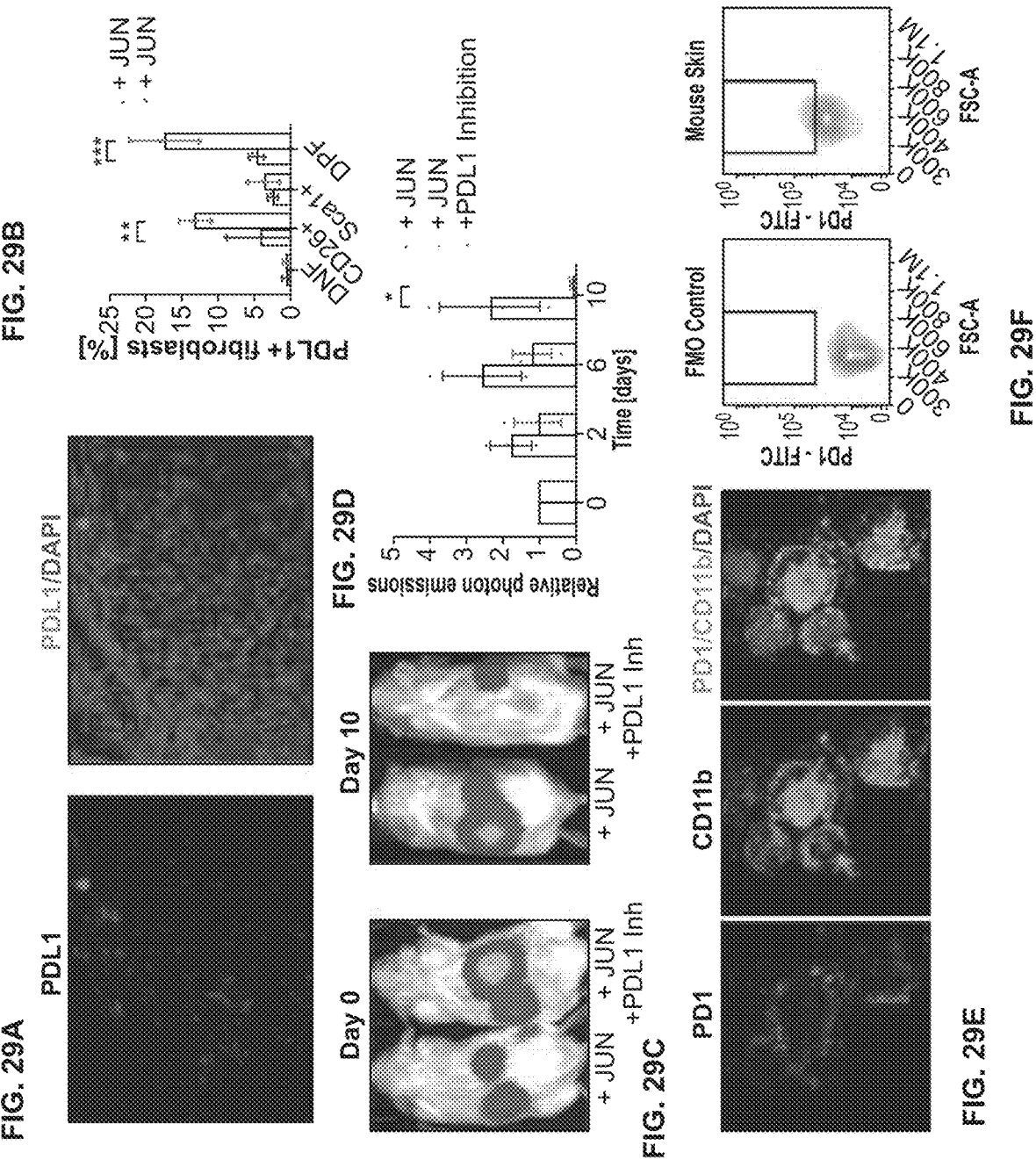

FIG. 29. PDL1 inhibition eliminates ectopic fibroblasts. (A) Immunofluorescence stains against PDL1 after local JUN induction in skin after 14 days. (B) PDL1 expression in different subsets of fibroblasts with and without JUN induction. Turkey's multiple comparisons test. **p<0.01

***p<0.001. n=3. Bar graphs represent means with standard deviations. (C) Representative optical images of ectopically transplanted JUN inducible fibroblasts+/−PDL1 inhibition. n=4. (D) Corresponding quantification of photon emissions. Turkey's multiple comparisons test. *p<0.05. n=4. Bar graphs represent means with standard deviations. (E) Immunofluorescence stains against PD1 and CD11b on macrophages harvested from the peritoneum. (F) FACS plots of PD1 expression in CD45+CD11b+ blood cells. n=2. Graph bars represent means with standard deviations.

Figure 30:
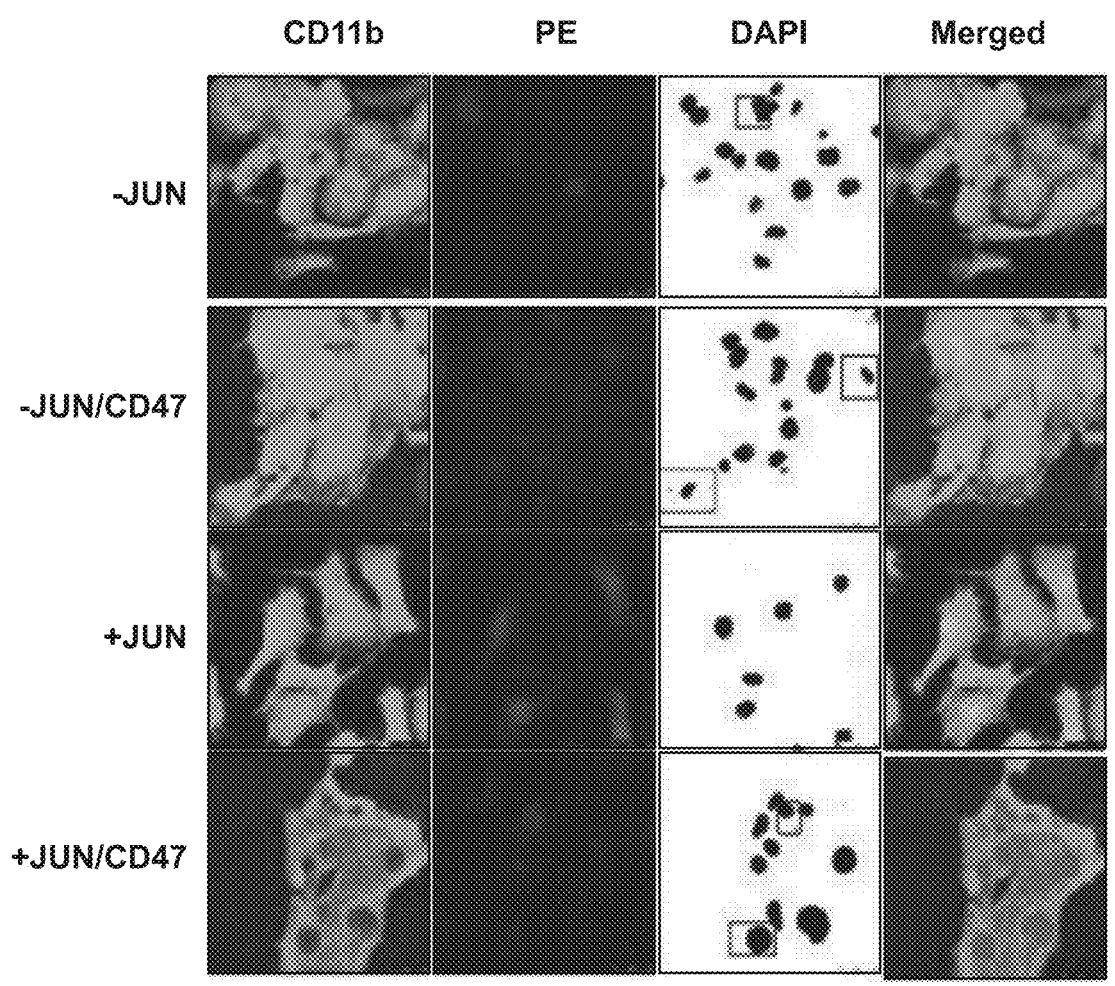

FIG. 30. CD47 inhibition increases phagocytosis of dermal fibroblasts in vitro. Images are taken with a confocal microscope. RFP+ target cells are detected in the PE channel. Macrophages who have fully digested target cells are marked by small isolated DNA pieces. Boxes in the DAPI represent macrophages with additional DNA pieces as signs of advanced phagocytosis.

FIG. 31. Combining CD47 and IL6 inhibition prevents loss in subcutaneous fat tissue. (A) Experimental outline (B) Representative H&E and Trichrome skin stains of untreated mice, mice under CD47/PDL1 inhibition and vismodegib, and mice under CD47/IL6 inhibition. Scale=500 μm. Bar graphs represent means with standard deviations. (C) Thickness of the dermal fibrotic/connective tissue in μm. Fisher's multiple comparisons test. n=4-7. Bar graphs represent means with standard deviations. (D) Area of the fibrotic tissue in untreated and treated samples, values indicate μm2/μm skin width. Fisher's multiple comparisons test. n=4-7. Bar graphs represent means with standard deviations. (E) Percentage of dermal fat, compared to the overall dermal area, in treated and untreated samples. Turkey's multiple comparisons test. *p<0.05. n=4-7. Bar graphs represent means with standard deviations. (F) Area of dermal fat tissue in untreated and treated samples, values indicate μm2/μm skin width. Turkey's multiple comparisons test. *p<0.05. n=4-7. Bar graphs represent means with standard deviations. (G) Representative stains against Ki67 and CD3. Counterstains with DAPI. (H) Quantification of CD3+ and Ki67+ stains. Indicated are the number of positive cells/high power view (63×). Turkey's multiple comparisons test. *p<0.05 p<0.01 *p<0.001. n=8-20. Bar graphs represent means with standard deviations. (I) Representative pictures of CD11b+ cells in skin fibrosis+/−CD47/IL6 inhibition. (J) Quantification of macrophage agglomerates determined by more than 20 macrophages/High power view in each sections. Two-sided t-test *p<0.05. n=8. Bar graphs represent means with standard deviations.

FIG. 32. Immune infiltrate in the therapeutic study. (A) Representative immunofluorescence stains against CD3 and CD11b in the three groups (Untreated, IL6 inhibition only and CD47/IL6 inhibition) (B) Quantification through flow cytometry for CD45+ cells. Turkey's multiple comparisons test. n=4. Bar graphs represent means with standard deviations. (C) Quantification through flow cytometry for myeloid CD11b+ cells. Turkey's multiple comparisons test. n=4. Bar graphs represent means with standard deviations. (D) Quantification for CD3+ T cells. Turkey's multiple comparisons test. n=4. Bar graphs represent means with standard deviations. (E) Corresponding organ sections from the untreated and the CD47/IL6 inhibition group. Flow cytometry numbers represent number of cells/100,000 live cells.

FIG. 33. Upregulation of JUN and CD47 in fibroblasts from patients with scl-GVHD (A) Schematic describing the strategy used for cGVHD patient data procurement and analysis. Patients were stratified based on diagnosis, conditioning, graft type and donor type. (B) Tissue Microarray schematic describing the preparation and analysis of patient skin samples. (C) Immunostaining of patient skin samples of human scl-GVHD. Skin specimens were stained for markers CD45, CD47 and PDGFRa using DAPI as a counterstain. All statistical analyses were performed using the Wilcoxon signed ranked test *p≤0.05, p≤0.01, *p≤0.001, ****p≤0.0001.

FIG. 34. JUN knockout alters chromatin accessibility and nucleosome positioning of fibrosis genes and immune regulatory proteins. (A) A heatmap of differential open chromatin regulatory elements characterized from ATAC-seq analysis. The color bar indicates relative ATAC-seq signal (Z score of normalized read counts). (B) Annotation genome tracks displaying promoter occupancy peaks for samples with JUN pulled down and analysed for occupancy at CD47 and IL6. Samples were analysed using CHIP-seq and ATAC-seq. Overlapping promoter regions with relative occupancies are displayed. ATAC-seq tracks show decreased chromatin accessibility at JUN, GLI1, CD47 and PDL1 loci upon JUN knock out or vismotigib treatment. (C) PCA plot describing percent variance between cell lines derived from patient tissue with GVHD and KO samples.

Figure 35D:
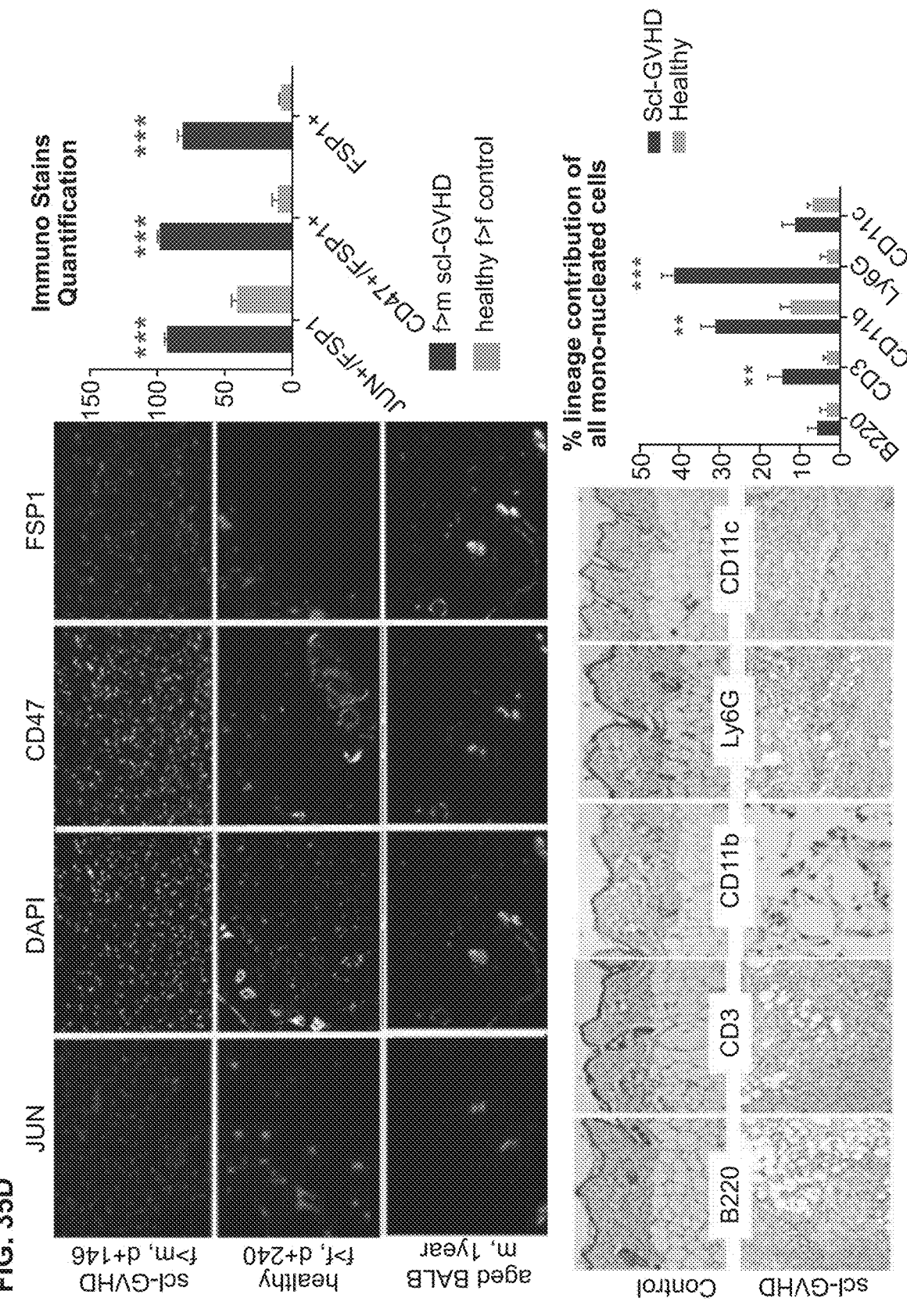

FIG. 35. JUN, CD47 and FSP1 are upregulated in a novel mouse model of sclGVHD (A) Schematic describing the procedure for generating our mouse model. (B) KM curves describing the difference between percent onset of cGVHD observed in female mice versus male mice post HCT. (C) Trichome stains displaying staining of percent fibrosis in patient samples versus control samples. Representative images are shown. All images are available in extended data. Quantification of dermal fibrosis described by a percentage of dermal thickness in tissue sample is graphically described. Percentage of skin fibrosis is also described as a measure of trichome staining in scl-GVHD mouse samples relative to healthy samples. (D) Immunostaining of mouse tissue specimens for JUN, CD47 and FSP1 is shown in diseased animals using healthy and aged BALB mice as controls. Quantification of each of the markers is also graphically provided. (D) Percentage of mononucleated cells in isolated tissue samples is also displayed with images and quantitative analysis. All statistical analyses were performed using the Students unpaired t-test *p≤0.05, p≤0.01, *p≤0.001, ****p≤0.0001.

FIG. 36. Human chronic GVHD patient derived dermal fibroblasts (GFP+) engrafted in NSG mice—In vivo treated with anti-CD47 and anti IL-6, or JUN-KO, or/and Vismodegib, Nintedanib.

Figure 37:
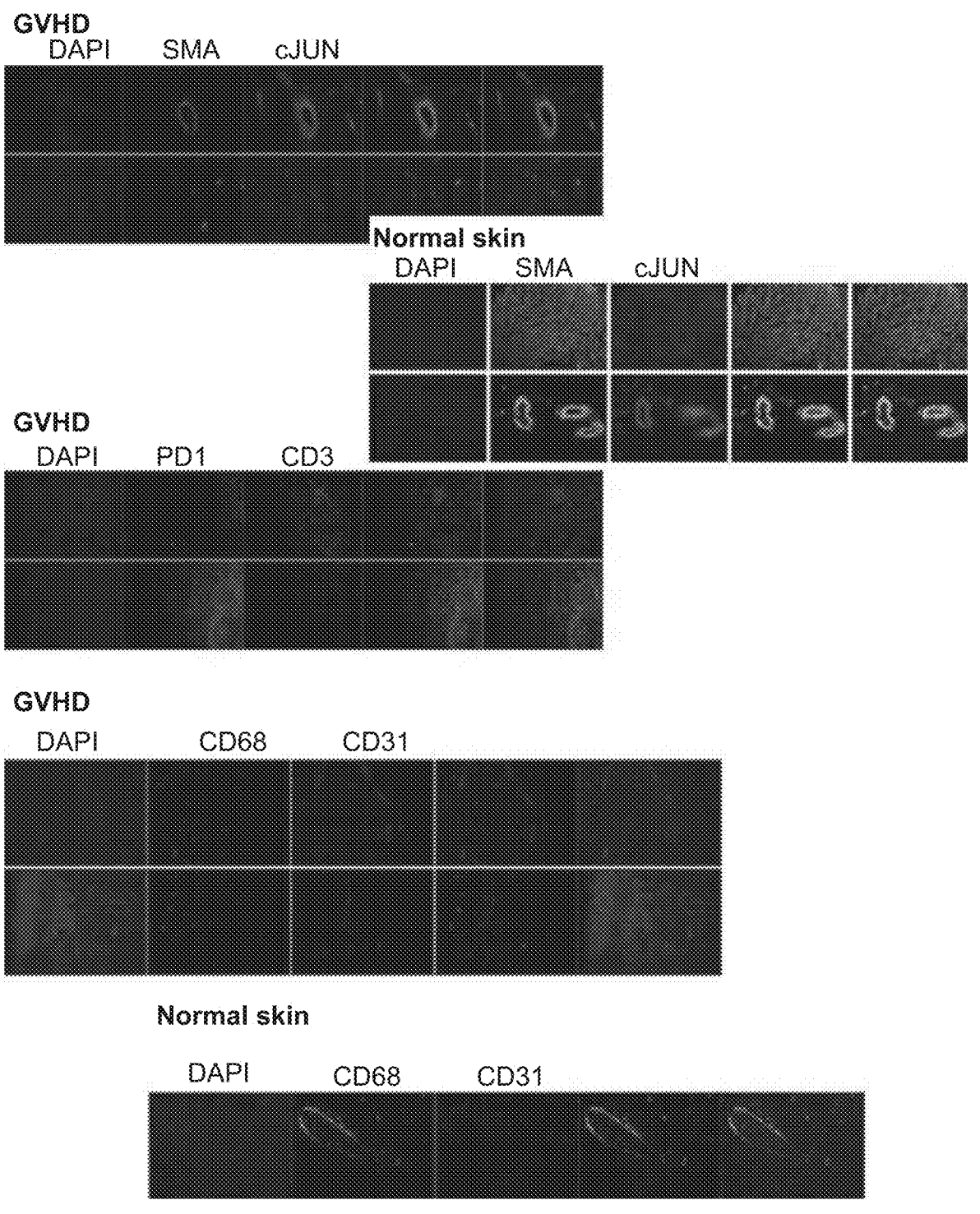

FIG. 37. Stained tissue slides.

Figure 38:
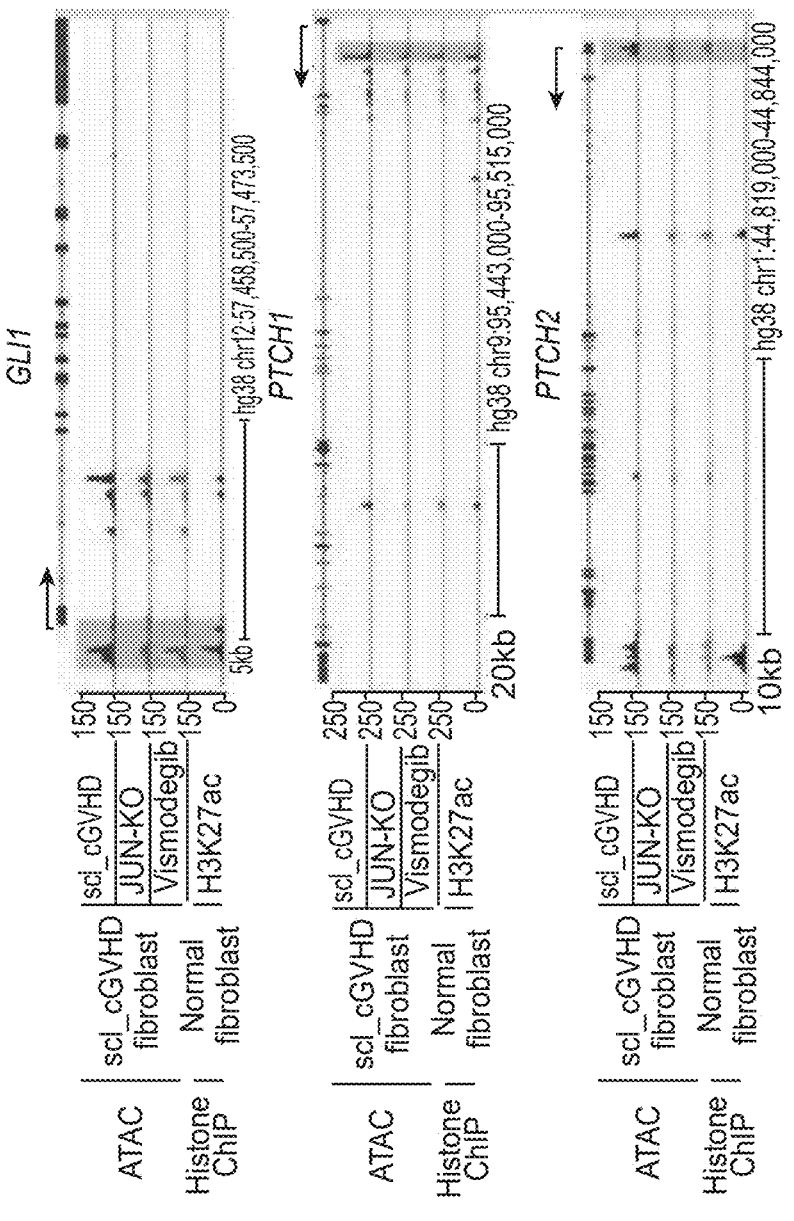

FIG. 38. Hedgehog pathway inhibition mimics JUN suppression in human cGVHD after JUN.

Figure 39:
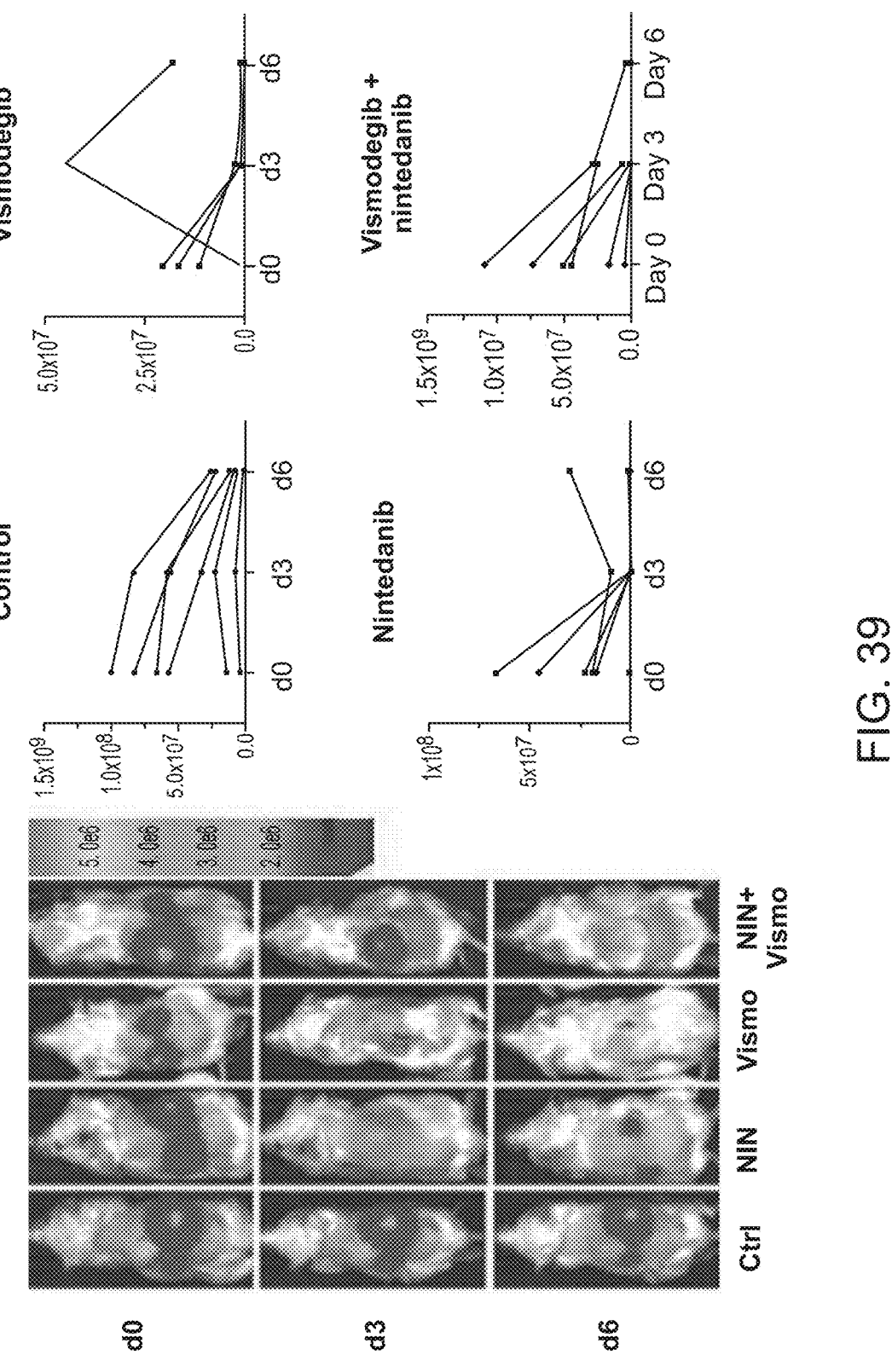

FIG. 39. Human chronic GVHD xenograft: patient derived dermal fibroblasts (GFP+)—In vivo treated with Hedgehog Inhibitor (left), untreated (right) Subsets of human sclerodermatous chronic Graft-versus host disease is also responsive to hedgehog pathway inhibition and anti-fibrotic treatment nintedanib.

FIG. 40 A-C. A representative section of human liver tissue microarrays (>60 patient samples of liver cirrhosis) demonstrating co-expression of CD47, SMA, Mesothelin and IL6 in fibrotic bands in liver cirrhosis. Magnification shown is 100×. B. Representative section of human liver cell cancer (HCC) demonstrating co-expression of IL6, Mesothelin, CD47, SMA and FSP1 in tumor stroma in liver cell cancer. Dapi highlights nuclear staining. Magnification shown is 63×. C. JUN lslrtTA Albumin CRE mouse with pronounced liver fibrosis/cirrhosis and HCC. Magnification shown is 63×.

DEFINITIONS

It is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Fibrosis is the excessive accumulation of extracellular matrix components (ECM) in and around inflamed or damaged tissue, often associated with chronic inflammation or cancer. The presence of fibrosis can be detected by means known in the art, for example by examination of tissue for excess scarring. Physiologically, fibrosis acts to deposit connective tissue, which can interfere with or totally inhibit the normal architecture and function of the underlying organ or tissue. Fibrosis can be used to describe the pathological state of excess deposition of fibrous tissue, as well as the process of connective tissue deposition in healing. Defined by the pathological accumulation of extracellular matrix (ECM) proteins, including collagen, fibrosis results in scarring and thickening of the affected tissue.

Prior to fibrosis, an individual may be determined to be susceptible based on undesirable increase in inflammatory mediators that can exacerbate tissue injury, such as IL-1β, TNF-α and reactive oxygen and nitrogen species. Profibrotic mediators such as TGF-β1 may be present. Also present are activated myofibroblasts, which may be resistant to induction of apoptosis.

Exemplary forms of fibrosis include, but are not limited to, tumor fibrosis, cardiac fibrosis, liver fibrosis, kidney and bladder fibrosis, lung fibrosis, dermal scarring and keloids, wound healing and adhesions, post-irradiation fibrosis, fibrosis related to chronic graft v host disease (GvHD), systemic sclerosis, and Alzheimer's disease. In still further embodiments, cardiac fibrosis is associated with hypertension, hypertensive heart disease (HHD), myocardial infarction (MI), cardiac scarring related to ischemia congestive heart failure, cardiomyopathy, post-myocardial infarction defects in heart function, atherosclerosis, and restenosis. Kidney fibrosis may include, but not be limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN. Liver fibrosis may include, but not be limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis). Lung fibrosis may include interstitial lung disease (idiopathic pulmonary fibrosis) or cryptogenic fibrosing alveolitis, chronic fibrosing interstitial pneumonia, interstitial lung disease (ILD), and diffuse parenchymal lung disease (DPLD)), lung scarring including without limitation damage from bacterial viral or fungal infection, emphysema, chronic obstructive pulmonary disease (COPD); and chronic asthma may also be prevented, treated, or ameliorated with compositions of described herein. Also included is fibrosis of the eye and lens, for example glaucoma; age-related macular degeneration (wet AMD and dry AMD), fibrosis of the lens, periorbital fibrosis as in IgG4-related disease, hyperthyroidism, etc. Uterine fibroids are also if interest for treatment.

Interstitial lung disease, the most common form of idiopathic interstitial pneumonia, causes progressive pulmonary fibrosis. Symptoms and signs develop over months to years and include exertional dyspnea, cough, and fine (Velcro) crackles. Diagnosis is based on history, physical examination, high-resolution CT, and/or lung biopsy, if necessary. Treatment may include antifibrotic drugs and oxygen therapy. Most patients deteriorate; median survival is about 3 years from diagnosis. Interstitial lung disease affects men and women >50 in a ratio of 2:1, with a markedly increased incidence with each decade of age. Current or former cigarette smoking is most strongly associated with the disorder. There is some genetic predisposition; familial clustering occurs in up to 20% of cases.

The key histologic findings of interstitial lung disease are subpleural fibrosis with sites of fibroblast proliferation (fibroblast foci) and dense scarring, alternating with areas of normal lung tissue (heterogeneity). Scattered interstitial inflammation occurs with lymphocyte, plasma cell, and histiocyte infiltration. Cystic abnormality (honeycombing) occurs in all patients and increases with advanced disease. A similar histologic pattern uncommonly occurs in cases of interstitial lung diseases of known etiology. Chest x-ray typically shows diffuse reticular opacities in the lower and peripheral lung zones. Small cystic lesions (honeycombing) and dilated airways due to traction bronchiectasis are additional findings. HRCT shows diffuse, patchy, subpleural, reticular opacities with irregularly thickened interlobular septa and intralobular lines; subpleural honeycombing; and traction bronchiectasis.

A variety of drugs have been tried in various fibroses, particularly lung fibrosis, with very little success. Anti-inflammatory drugs including prednisolone and azathioprine have little effect on fibrosis suggesting that inflammation is only the initiator, but not the driver of the disease. The use of non-specific anti-proliferatives like colchicine and cyclophosphamide will also prevent repair of the fibrotic tissue by impairing e.g. epithelial growth. Treatment with IFN-γ has shown some utility but is limited by severe side effects. Pirfenidone and nintedanib are standard of care for IPF, but have not been shown to extend survival.

By the time a typical patient presents with fibrosis-related symptoms (e.g. difficulty breathing for lung fibrosis, etc.), the fibrosis in the target organ is often quite severe, with much of the target organ architecture having been replaced with extracellular matrix. Stopping this ongoing fibrosis can extend lifespan and improve quality of life. Areas of the target organ where the fibrosis is not extensive may be restored to normal architecture with suitable treatment.

The efficacy of the methods described herein can be monitored in clinical and pre-clinical trials following treatment according to the methods as claimed. Analysis of fibrosis may be made by obtaining a biological sample and examining molecular or pathological state, disease or condition, and the like. For pre-clinical and in vitro models, analysis may comprise direct detection of collagen, extracellular matrix proteins, and scar tissue in the affected tissue, where effective treatment can prevent increase in ECM deposition over time, decrease the rate of ECM deposition, or may decrease the presence of ECM deposition. For example, extracellular cross-linked collagen can be measured in affected tissues.

For clinical use, efficacy is monitored with less invasive methods. One measurement is through detection of scar tissue in x-rays and other imaging systems. With the advent of high-resolution computed tomography (CT) scanners and sophisticated software programs, there are endeavors to now include objective CT-based scoring systems as endpoints for clinical trials in interstitial lung disease.

Common endpoints for evaluating efficacy of interstitial lung disease treatment include, for example an improvement or stabilization of forced vital capacity (FVC). It has many advantages that include being relatively easy to measure and reproduce. It is also commonly regarded as reflecting the burden of the fibrotic disease process. The change in the FVC over time is the outcome measure of interest. Typically, it has been the mean change in FVC for the patient cohorts that have been reported as an absolute change or relative change. Alternatively a method for evaluating the change in the FVC is to measure the slope of change, which incorporates all FVC measurements obtained for the duration of the study, rather than evaluating change between two predefined time points. Measurements may be taken at 1, 2, 3, 4, month intervals, and the like. The methods described herein may improve FVC by at least 5%, at least 10%, at least 20%, or more.

An alternative endpoint is the single breath diffusing capacity for carbon monoxide (DLco), or the Kco value (transfer coefficient for carbon monoxide), which is the DLco adjusted for the alveolar volume.

The 6-min walk test (6MWT) is commonly employed to provide a measure of a patient's functional status. Therefore, similar to the change in the FVC, multiple time points may be assessed. Apart from the distance walked, the oxygen saturation profile, Borg dyspnea score and pulse rate recovery (PRR) also provide useful ancillary information. The PRR is defined as the difference between the pulse rate at the end of the walk period and after 1 min of rest during the recovery phase. The smaller the pulse rate change, the worse the prognosis, with a cut point of 13 beats per minute proposed as best discriminating outcomes. The methods described herein may improve PRR by at least 5%, at least 10%, at least 20%, or more; and/or may stabilize PRR in patients with progressive interstitial lung disease.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having fibrosis, including without limitation, tumor fibrosis, cardiac fibrosis, liver fibrosis, kidney fibrosis, lung fibrosis, dermal scarring and keloids, Alzheimer's disease, etc. Subjects may be human, but also include other mammals, particularly those mammals useful as laboratory models for human disease, e.g. mouse, rat, etc.

The definition of an appropriate patient sample encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents; washed; or enrichment for certain cell populations, such as endometrial cells, etc. A sample if interest in bronchial lavage sample. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's sample cell, e.g., a sample comprising polynucleotides and/or polypeptides that is obtained from a patient's sample cell (e.g., a cell lysate or other cell extract comprising polynucleotides and/or polypeptides); and a sample comprising sample cells from a patient. A biological sample comprising a sample cell from a patient can also include normal, non-diseased cells.

The term "diagnosis" is used herein to refer to the identification of a molecular or pathological state, disease or condition, such as the identification of fibrosis.

IL-6 is a small polypeptide of approximately 26 kD molecular weight that is involved in the differentiation and growth of a variety of cells. IL-6 signals via glycoprotein 130 (gp130) and the membrane-bound or soluble IL-6 receptor (IL-6R), referred to as classic or trans-signaling, respectively. Inflammation triggers IL-6 expression, eventually rising to nanogram per mL serum levels, while soluble IL-6R (sIL-6R) and soluble gp130 (sgp130) are constitutively present in the upper nanogram per mL range. The soluble form of IL-6R facilitates and induces the signal rather than serving as an inhibitor. Soluble IL-6R binds IL-6 and this complex further binds membranal gp130, which, unlike IL-6R, is expressed in all cell types. This trans-signaling allows IL-6 to mediate its response on cells that lack IL-6R; among these are embryonic stem cells, endothelial cells, hematopoietic progenitor cells, osteoclasts, and neuronal cells.

In the early phases of inflammation, IL6 is produced by monocytes and macrophages, in particular though the stimulation of Toll-like receptors. A deregulated and persistent IL6 production has been observed in various chronic inflammatory and/or autoimmune diseases, including in animal models.

Anti-IL-6 agent. As used herein, the term "anti-IL-6 agent" or "IL-6 blocking agent" refers to any agent that inhibits IL-6 signaling pathway. Agents for this purpose known and used in the art include antibodies and proteins comprising antibody CDR regions, that bind to and inhibit the activity of IL-6 or IL-6R.

Compounds that target IL-6 pathways include antibodies against the IL-6 receptor, including, as non-limiting examples, tocilizumab and sarilumab. Tocilizumab is a humanised monoclonal antibody against the $\alpha$-subunit of the IL-6 receptor. Sarilumab is a human monoclonal antibody against the IL-6 receptor. Vobarilizumab is a nanobody that binds to and blocks IL-6R.

Antibodies against the IL-6 ligand have also been developed for clinical use, including olokizumab and clazakizumab, which are both humanized monoclonal antibodies against IL-6. Sirukumab is a human anti-IL-6 monoclonal antibody. Elsilimomab is a mouse monoclonal antibody that targets and blocks IL-6. Siltuximab is a chimeric monoclonal antibody that binds to interleukin-6. WBP216 (MEDI5117) is a fully humanized monoclonal IgG antibody that depletes IL-6. Gerilimzumab is a human anti-IL-6 antibody. FM101 is a recombinant humanized monoclonal antibody directed against a neutralizing epitope on human IL-6.

Blocking agents also include, for example, modified IL-6 ligand. Sant7, a potent antagonist of the IL6 receptor, was engineered through targeted amino acid substitutions in key residues of the human IL6 molecule. Sant7 shows higher affinity than IL6 for the gp80 receptor subunit, but completely lacks binding capacity to the gp130 receptor signaling subunit.

In addition, there are art-recognized inhibitors of IL-6 signal transduction such as the Janus kinase (JAK) inhibitors baricitinib and tofacitinib.

Immune checkpoint proteins are immune inhibitory molecules that act to decrease immune responsiveness toward a target cell. Endogenous responses by T cells or macrophages can be dysregulated by cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals.

Anti-CD47 agent. CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31 (2): 266-77; Hatherley et al. (2007) J. B. C. 282:14567-75; and the role of SIRPα cis dimerization in CD47 binding is discussed by Lee et al. (2010) J. B. C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent and in the presence of an effector cell, e.g. a macrophage or other phagocytic cell. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036 Feb. 1, 2004). Thus, in some embodiments, the anti-CD47 agent does not directly induce cell death of a CD47-expressing cell.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα-derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In a preferred embodiment the IgG Fc region is an IgG4 constant region. The IgG4 hinge may be stabilized by the amino acid substitution S241P (see Angal et al. (1993) Mol. Immunol. 30 (1): 105-108, herein specifically incorporated by reference).

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Examples include the antibodies disclosed in WO2019023347A1, herein specifically incorporated by reference. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

An immune-checkpoint receptor that has been actively studied in the clinic is the inhibitory receptor programmed cell death protein 1 (PD1; also known as CD279). The major role of PD1 is to limit the activity of T cells in peripheral tissues at the time of an inflammatory response to infection and to limit autoimmunity. PD1 expression is induced when T cells become activated. When engaged by one of its ligands, PD1 inhibits kinases that are involved in T cell activation. PD1 is highly expressed on $T_{Reg}$ cells, where it may enhance their proliferation in the presence of ligand. The two ligands for PD1 are PD1 ligand 1 (PDL1; also known as B7-H1 and CD274) and PDL2 (also known as B7-DC and CD273). The PD1 ligands are commonly upregulated on the tumor cell surface from many different human tumors. On cells from solid tumors, the major PD1 ligand that is expressed is PDL1. PDL1 is expressed on cancer cells and through binding to its receptor PD1 on T cells it inhibits T cell activation/function. Therefore, PD1 and PDL1 blocking agents can overcome this inhibitory signaling and maintain or restore anti-tumor T cell function.

Antibodies in clinical trials against PD-1 include, for example, Pembrolizumab (Keytruda), Nivolumab (Opdivo), Cemiplimab (Libtayo), Spartalizumab (PDR001); Camrelizumab (SHR1210); Sintilimab (IBI308); Tislelizumab (BGB-A317); Toripalimab (JS 001); AMP-224, by GlaxoSmithKline; and AMP-514, by GlaxoSmithKline. Antibodies in clinical trials against PD-L1 include, for example, Atezolizumab (Tecentriq); Avelumab (Bavencio); and Durvalumab (Imfinzi).

Antibodies targeting mesothelin, e.g. for liver cirrhosis may be used included in combination therapies, e.g. with anti-CD47, anti-IL6 and anti-PD1/PDL1.

As used herein, the terms "treatment," "treating," and the like, refer to administering an agent, or carrying out a procedure for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of fibrosis in a mammal, particularly in a human, and includes: (a) preventing the development of fibrosis; (b) inhibiting ongoing fibrosis, i.e., arresting its development; and (c) relieving fibrosis, i.e., causing regression of fibrosis.

Treating may refer to any indicia of success in the treatment or amelioration or prevention of fibrosis, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with fibrosis. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic (i.e., first therapeutic agent) and the compounds as used herein. When administered in combination, each component can be administered at the same time or sequentially in any order at different points in time. Thus, each component can be administered separately but sufficiently closely in time so as to provide the desired therapeutic effect. First therapeutic agents contemplated for use with the methods of the present invention include any other agent for use in the treatment of fibrosis. Examples of such therapeutic agents include but are not limited anti-fibrotic agents.

"Concomitant administration" of a known therapeutic agent with a pharmaceutical composition of the present invention means administration of the therapeutic agent and inhibitor agent at such time that both the known therapeutic agent and the composition of the present invention will have a therapeutic effect. Such concomitant administration may involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention. Therapeutic agents contemplated for concomitant administration according to the methods of the present invention include any other agent for use in the treatment of fibrosis.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The phrase "determining the treatment efficacy" and variants thereof can include any methods for determining that a treatment is providing a benefit to a subject. The term "treatment efficacy" and variants thereof are generally indicated by alleviation of one or more signs or symptoms associated with the disease and can be readily determined by one skilled in the art. "Treatment efficacy" may also refer to the prevention or amelioration of signs and symptoms of toxicities typically associated with standard or non-standard treatments of a disease. Determination of treatment efficacy is usually indication and disease specific and can include any methods known or available in the art for determining that a treatment is providing a beneficial effect to a patient. For example, evidence of treatment efficacy can include but is not limited to remission of the disease or indication. Further, treatment efficacy can also include general improvements in the overall health of the subject, such as but not limited to enhancement of patient life quality, increase in predicted subject survival rate, decrease in depression or decrease in rate of recurrence of the indication (increase in remission time). (See, e.g., Physicians' Desk Reference (2010).)

DETAILED DESCRIPTION OF THE EMBODIMENTS

Individuals diagnosed or at risk of developing a fibrotic disease, such as interstitial lung disease; scleroderma; nonalcoholic steatohepatitis (NASH); liver cirrhosis, etc., including pulmonary fibrosis, such as interstitial lung disease, are treated by administering an effective dose of (i) an immune checkpoint blocking agent; and (ii) an IL-6 blocking agent. In some embodiments the immune checkpoint blocking agent is selected from an agent that blocks the CD47/SIRPα pathway; and an agent that blocks the PD-1/PD-L1 pathway.

In one embodiment, an effective dose of an IL-6 blocking agent and an effective dose of a CD47/SIRPα pathway blocking agent are concomitantly administered to an individual to reduce abnormal accumulation of fibroblasts and collagen deposition in fibrotic tissue. In some embodiments the tissue is lung tissue. In some embodiments the individual is human. In some embodiments the individual has been previously diagnosed with interstitial lung disease. In some embodiments pulmonary function is retained in an otherwise progressive form of the disease.

Methods include administering to a subject in need of treatment a therapeutically effective amount or an effective dose of a therapeutic entity (e.g., blocking agent) of CD47 and IL-6. In some embodiments, effective doses of the therapeutic entity of the present invention described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. Reduction in fibrosis may be monitored for decrease in fibrotic cells, decrease in fatty infiltrating cells, etc.

In some embodiments CD47 blockade is accomplished by administering a soluble SIRPα polypeptide, which may be a high affinity SIRPα variant polypeptide. In other embodiments, antibodies specific for one or both of SIRPα and CD47 are administered.

The effective dose of an anti-CD47 agent can vary with the agent, but will generally range from up to about 50 mg/kg, up to about 40 mg/kg, up to about 30 mg/kg, up to about 20 mg/kg, up to about 10 mg/kg, up to about 5 mg/kg; up to about 1 mg/kg, up to about 0.5 mg/kg; up to about 0.1 mg/kg; up to about 0.05 mg/kg; where the dose may vary with the specific antibody and recipient. Agents that bind to CD47, e.g. soluble SIRPa polypeptides and anti-CD47 antibodies, may be administered at higher doses due to the larger number of CD47 expressing cells in the body.

The effective dose of an IL-6 agent can vary with the agent and may be within the prescribed dosage range for other conditions. As a non-limiting example, treatment of rheumatoid arthritis with anti-IL-6 or anti-IL-6R antibodies may deliver an intravenous (IV) dose of 0.1 to 10 mg/kg every 2-4 weeks. The effective dose for treatment of fibrosis may range up to about 30 mg/kg, up to about 20 mg/kg, up to about 10 mg/kg, up to about 5 mg/kg; up to about 1 mg/kg, up to about 0.5 mg/kg; up to about 0.1 mg/kg; up to about 0.05 mg/kg; where the dose may vary with the specific antibody and recipient.

The blocking agents may be administered one or a plurality of days, and in some embodiments is administered daily, every two days, semi-weekly, weekly, etc. for a period of from about 1, about 2, about 3, about 4, about 5, about 6, about 7 or more weeks, up to a chronic maintenance level of dosing. Therapeutic entities of the present invention are usually administered on multiple occasions. Intervals between single dosages can be weekly, monthly or yearly.

Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still yet some other embodiments, for prophylactic applications, pharmaceutical compositions or medicaments are administered to a patient susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In still yet some other embodiments, for therapeutic applications, therapeutic entities of the present invention are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved.

According to the present invention, compositions can be administered by parenteral, topical, intravenous, oral, subcutaneous, intraarterial, intracranial, intraperitoneal, intranasal, aerosol, or intramuscular means. The most typical route of administration is intravenous although other routes can be equally effective.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies and/or polypeptides can be administered in the form of a depot injection or implant preparation which can be formulated in such a manner as to permit a sustained release of the active ingredient. An exemplary composition comprises polypeptide at 1 mg/mL, formulated in aqueous buffer consisting of 10 mM Tris, 210 mM sucrose, 51 mM L-arginine, 0.01% polysorbate 20, adjusted to pH 7.4 with HCl or NaOH.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249:1527, 1990 and Hanes, Advanced Drug Delivery Reviews 28:97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

The pharmaceutical compositions are generally formulated as sterile, substantially isotonic and in full compliance with all Good Manufacturing Practice (GMP) regulations of the U.S. Food and Drug Administration. Preferably, a therapeutically effective dose will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1).

Also within the scope of the invention are kits comprising the compositions of the invention and instructions for use. The kit can further contain a least one additional reagent. Kits typically include a label indicating the intended use of the contents of the kit. The term label includes any writing, or recorded material supplied on or with the kit, or which otherwise accompanies the kit.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. It is also understood that the terminology used herein is for the purposes of describing particular embodiments Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

EXPERIMENTAL

Example 1

High-dimensional mass cytometry is used to profile protein expression and the secretome of individual fibroblasts and leukocytes from pulmonary fibrosis patients. JUN is activated in the fibroblasts derived from fibrotic lungs, which also had increased CD47 and PD-L1 expression. Using ATAC-seq and ChIP-seq, it is shown that activation of JUN in fibroblasts increased accessibility of enhancers of CD47, and PD-L1, which reporter assays corroborated. Increased IL-6 signaling is also shown, which amplified JUN-mediated CD47 enhancer activity and protein expression in fibrotic lung fibroblasts. Using an in vivo mouse model of fibrosis, we found two distinct mechanisms by which blocking IL-6, CD47 and PD-L1 reversed fibrosis, both by increasing phagocytosis of profibrotic fibroblasts and by eliminating suppressive effects on adaptive immunity. These results identify specific immune mechanisms that promote fibrotic process and provide a therapeutic approach for pulmonary fibrosis diseases.

Fibroblasts are known to be at the core of the fibrotic response, however quite surprisingly they represent a poorly characterized cell type. Fibroblasts are quite heterogeneous, and no common consensus exists on their subtypes, their biological properties such as signaling and plasticity. No comprehensive single cell data focusing on fibroblasts are yet available for pulmonary fibrosis patients. We tested reported canonical fibroblast markers and found that each only labeled a subset of fibroblasts—there were no universal fibroblast specific markers. We took the approach to define fibroblasts by only excluding leukocytes (CD45), epithelial cells (CK7), and endothelial cells (CD31). This strategy not only helped us to enrich but also to further characterize the heterogeneity of fibroblasts in pulmonary fibrosis.

Monocytes and macrophages, as part of the innate immune response, are thought to play a critical role to regulate both injury and repair in various models of fibrosis. Macrophage heterogeneity has emerged as an important area of study in fibrotic lungs. Adaptive immune processes have been shown to orchestrate existing fibrotic responses and various subsets of T cells have been shown to be enriched in fibrotic lung; and increased activated regulatory T cells correlate with the severity of fibrotic lung. Mass cytometry enables measurements of over 40 parameters simultaneously at the single cell level by using mass tagged antibodies to label proteins of interest on cells which are subsequently analyzed by a time-of-flight mass spectrometer. Here, we used mass cytometry to characterize over millions of primary lung cells from 11 pulmonary fibrosis patients and 3 normal donors. This allowed at the single cell level identification and functional aspects of various cell subsets in fibrotic lungs from a single experiment, in order to systematically monitor interactions between cells within the microenvironment.

We previously showed that JUN caused severe lung fibrosis when induced in adult mice. This represents a purely genetic model of lung fibrosis and highlights one critical transcription factor at the core of a general fibrotic response. JUN induction in mice resulted in upregulation of the CD47 protein in fibroblasts within less than 24 hours. CD47 is a key anti-phagocytic molecule that is known to render malignant cells resistant to programmed cell removal, or efferocytosis, and a key driver of impaired cell removal. Fibrosis in mice was prevented with anti-CD47 immune treatment. Importantly, it is now shown that anti-CD47 immune therapy reverses the fibrotic reaction.

Our single cell protein screening approach in fibrotic lung patients highlighted two immune regulatory pathways dysregulated in fibrotic lung, CD47 and PD-1/PD-L1. Antibody therapies against both are currently being tested in clinical trials for cancer, and have been demonstrated to prevent atherosclerosis. In addition, we identify the cytokine IL-6 at the core of progressive fibrosis in the lungs. IL-6 is known to mediate its broad effects on immune cells via a complicated signaling cascade in an almost hormone-like fashion. A clinically tested blocking antibody against IL-6R is available and FDA approved for rheumatoid arthritis.

Results

Figure 15:
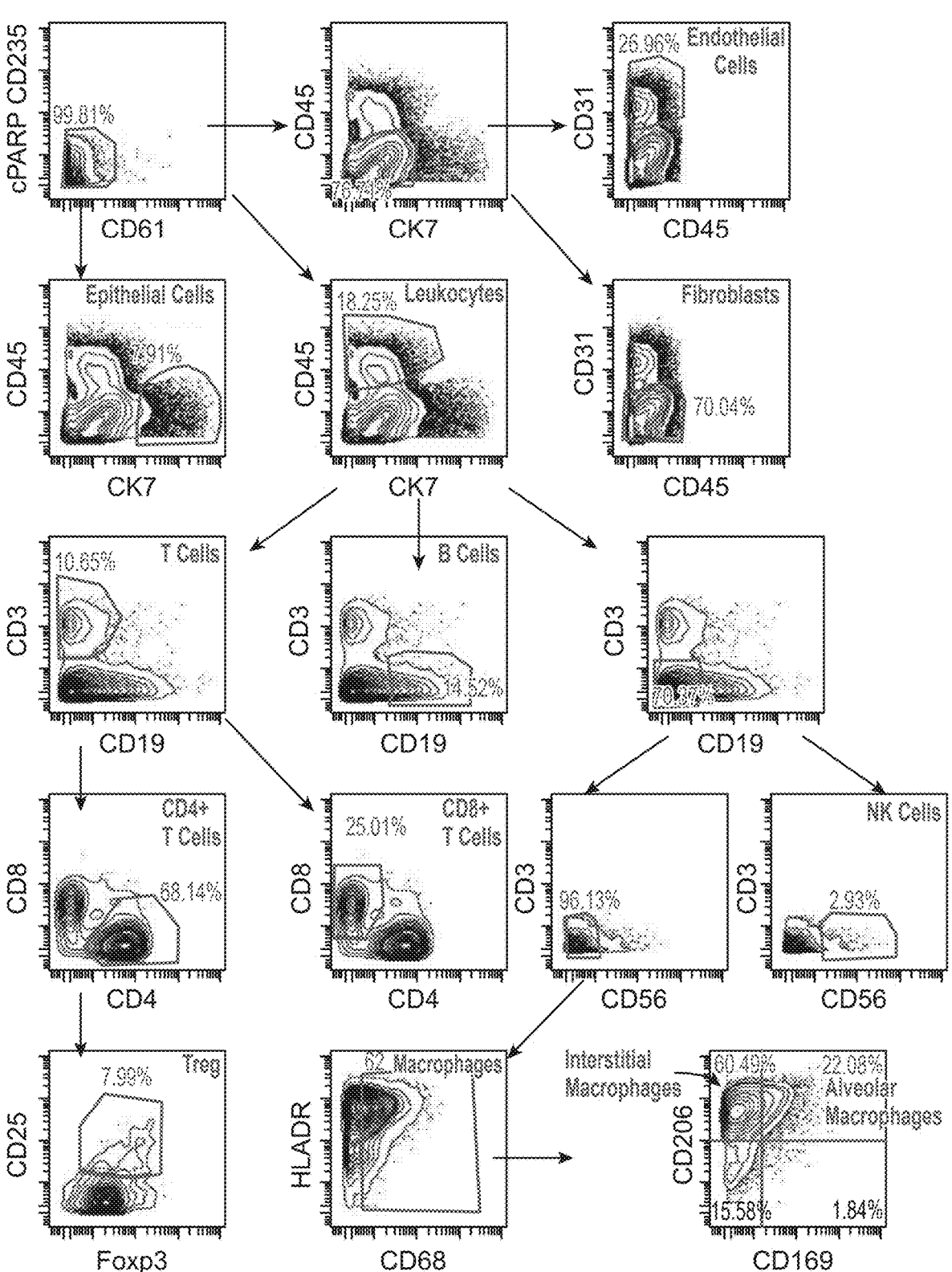
FIG. 15. Representative contour plots showing gating strategy for all the populations involved in this paper.

The immune checkpoint proteins PD-L1 and CD47 are upregulated in fibroblasts in pulmonary fibrosis. To systematically profile the pathophysiology of human pulmonary fibrosis, we applied an -omics approach combining multiparameter single cell mass cytometry, genome-wide chromatin accessibility assays together with a multiplexed luminex secretome analysis as outlined in FIG. 1. First, for profiling with mass cytometry, single cell suspensions of 14 representative lung samples, 11 fibrotic and 3 normal, were stained with a panel of 41 metal conjugated antibodies (Table 2) including 3 antibodies (CD45, CD31 and CK7) to allow for manual gating of four distinct cell lineages: CD45+ leukocytes, CK7+ broncho epithelial cells, CD31+ endothelial cells, and CD45−CK7−CD31− fibroblasts (FIG. 1b, gating strategy in FIG. 15 and live cells counts in Table 3). With this approach, we detected the frequency of fibroblasts was 5-fold-higher in fibrotic lungs (15% in normal lungs to 80% in fibrotic lungs), a 3-fold-lower in leukocytes (60% normal to 20% in fibrotic lung), a mild but not significant decrease in epithelial cells and a negligible increase in endothelial cells (FIG. 1c).

In addition to the increased abundance of fibroblasts, we performed a principal component analysis (PCA) of the expression level of all the markers (except the lineage markers CD45, CK7, CD31, CD61 and CD235a) on fibroblasts and demonstrated that fibrotic lung fibroblasts from 11 fibrotic lung patients clustered together and were distinct from lung fibroblasts derived from normal lungs (FIG. 1d), suggesting fibroblasts in fibrotic lungs are not only increased in numbers but also differ phenotypically from control lung fibroblasts. Consistent with principal component analysis results, viSNE plots showed enrichment of a distinct fibrotic lung specific fibroblast subpopulation (FIG. 1e).

Mass cytometry also demonstrated co-activation of phospho JUN and AKT in 50% of fibroblasts in un-manipulated human fibrotic lungs (FIG. 1f). The fibrotic lung-specific fibroblast subpopulation expressed high levels of CD47 and PODOPLANIN, whereas PDGFRa, CALRETICULIN and PD-L2 were moderately expressed (FIG. 9a, b). As shown in (FIG. 1g), >20% of the fibroblasts from fibrotic lungs expressed CD47 and a subset ~10% co-expressed PD-L1 and Mesothelin. To assess the expression and distribution of these two immune checkpoint proteins in intact lung tissues, we performed immune stains of fibrotic and normal control lungs. We detected abundant co-expression of CD47, Collagen 1, and PD-L1 with smooth muscle actin (SMA) in fibroblasts of fibrotic lung but not in normal lungs (FIG. 1h and FIG. 9c showing the statistical analysis, FIG. 9d showing the H.E. stains of the same fibrotic lung and normal lung) by immune fluorescent stains and 9-color multiplexed ion beam imaging (MIBI), a technology which allows concomitant staining of paraffin embedded tissues with multiple antibodies and provides histologic resolution (FIG. 9e).

We confirmed the upregulation of immune checkpoint regulators at the gene expression level with qPCR, where we detected increased JUN, PD-L1 and CD47 RNA expression in fibrotic over normal lungs (FIG. 1i). We also observed that secreted PD-L1 protein was increased in the broncho alveolar lavages of fibrotic lungs but not normal lungs (FIG. 9f). In conclusion, we found that lung fibroblasts in fibrotic lung are distinct from normal lung fibroblasts by abundance and molecular phenotype, and a third of them upregulate two immune checkpoint proteins: CD47 and PD-L1.

Macrophages and T cell derived from pulmonary fibrosis exhibit an immunosuppressive phenotype. While many different inflammatory subsets have been described to play a role in fibrotic lung, their individual contributions to pulmonary fibrosis progression are unclear. Here we used the unbiased comprehensive single cell characterization method mass cytometry to investigate leukocyte types contained in fibrotic and normal lungs. Among all CD45+ leukocytes contained in the lungs, while we found quantitative differences of B, NK and dendritic cells (FIG. 10a) in fibrotic compared to normal lung controls, we observed no significant differences in T cell and macrophage numbers (FIG. 2a, b).

In the lung myeloid compartment there are complex mixture of subpopulations, including dendritic cells, tissue monocytes and nonalveolar macrophages, called interstitial macrophages. By using all the markers in the CYTOF panel (except the lineage markers CD45, CD31, CK7, CD61, CD235a, cPARP, CD3, CD4, CD8, CD19, CD56 and CD68), we determined that macrophages from fibrotic lungs were phenotypically differed from normal lungs, as demonstrated by principal component analysis (PCA) (FIG. 2c). Consistently, viSNE plots also showed a distinct distribution of macrophages from fibrotic lung patients (black circle) (FIG. 2d). Macrophage markers, such as HLADR, CD169 and CD206 (FIG. 2e), as well as Indoleamine 2,3-dioxygenase (IDO) which is a rate-limiting enzyme in the metabolism of tryptophan and plays a critical role in immune regulation (FIG. 10b, c) were down regulated in the fibrotic lung macrophages.

We compared the ratio of interstitial macrophage (HLA-DR+CD206+CD169−, IM) to alveolar macrophage (HLA-DR++CD206++CD169+, AM) between fibrotic and normal lungs and found it was severely perturbed in fibrotic lungs (FIG. 2f, and FIG. 10d). The macrophages in fibrotic lung tissues co-expressed PD-1 (FIG. 2g and FIG. 10e showing the statistical analysis), a marker profile described for tumor-associated macrophages. These results suggest that during the fibrotic process, interstitial macrophages, rather than alveolar macrophages, have taken the pivotal part role to perform immune functions.

Figure 3G:
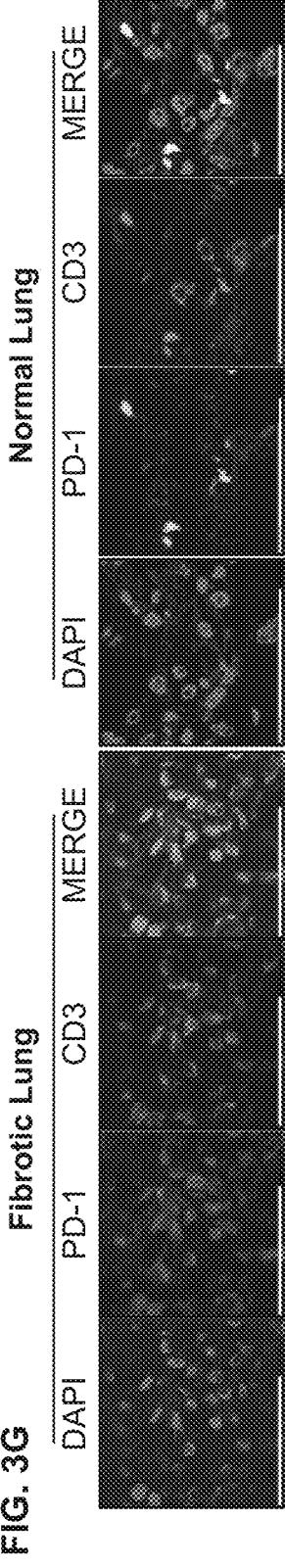
FIG. 3. T cells present in fibrotic lungs. (a, b) Represen- tative CyTOF plots and quantification of CD4+ (top) and CD8+ (bottom) naïve T cells (CCR7+ CD45RA+) demon- strating decreased naive T cells in fibrotic lungs. Data represent mean±SD of 11 fibrotic and 3 normal samples and are analyzed by two-tailed unpaired t-test, *P<0.001; *P<0.0001. (c, d) Representative CyTOF analysis showing increased frequency of regulatory CD4 T cells (Treg: CD4+ Foxp3+CD25+) in fibrotic lungs. Data represent mean±SD of 11 fibrotic and 3 normal samples, and are analyzed by two-tailed unpaired t-test, ****P<0.0001. (e, f) Represen- tative CyTOF plots and quantitative analysis indicating increased numbers of exhausted T cell (Tex: CD8+PD-1+ TIM3+) in fibrotic lungs. Data represent mean±SD of 11 fibrotic and 3 normal samples, and analyzed by two-tailed unpaired t-test, *P<0.05. (g) Representative images of immune fluorescent stains for PD-1 on T cells (CD3) high- lighting increased numbers of PD-1+ T cells in fibrotic lung samples. (Scale bars, 100 μm).

We performed a thorough characterization of T cells (FIG. 11a). Additional analysis of T cells in pulmonary fibrosis showed that specific subsets, such as naïve CD4 and naïve CD8, were decreased (FIG. 3a, b), but no difference was detected for Th1, Th2 and Th17 T cells (FIG. 11b). The most dramatic findings in fibrotic lung samples was increased numbers of regulatory T cells (Treg) and PD-1+CD4+ T cells (FIG. 3c, d and FIG. 11c), as well as increased numbers of exhausted T cells (FIG. 3e, f), which is suggestive of an immunosuppressive microenvironment. We confirmed these findings with immune stains and found increased PD-1+ expression on T cells (FIG. 3g and FIG. 11d showing the statistical analysis). We conclude that suppressive leukocyte types predominate in pulmonary fibrosis lungs.

JUN transcriptionally controls profibrotic and immune checkpoint pathway genes. Given the tight correlation between JUN activation and immune checkpoint protein expression on the single cell level, we hypothesized that JUN might directly regulate CD47 and PD-L1 at the transcriptional level in fibrosis. JUN, as part of the AP-1 (FOS/JUN) complex, can function as a pioneer transcription factor and acts as an enhancer selector to modulate the accessibility of DNA in fibroblasts.

We introduced doxycycline (Dox)-inducible overexpression to investigate ectopic expression and CRISPR-editing to assay loss-of-function phenotypes, with the goal of determining the chromatin configuration in response to JUN expression by ATAC-seq (Assay for Transposase-Accessible Chromatin using sequencing). This is a highly sensitive way to measure the chromatin accessibility of transposase with base pair resolution genome wide. We generated and performed ATAC-seq on primary fibrotic lung fibroblasts with (JUN-KO) or without (Control) genetic inactivation of JUN by CRISPR Cas9, then following ATAC-seq and ChIP-seq on primary normal lung fibroblasts with (TetO-JUN Dox+, JUN-OE) or without (TetO-JUN Dox−) JUN overexpression.

Figure 4A:
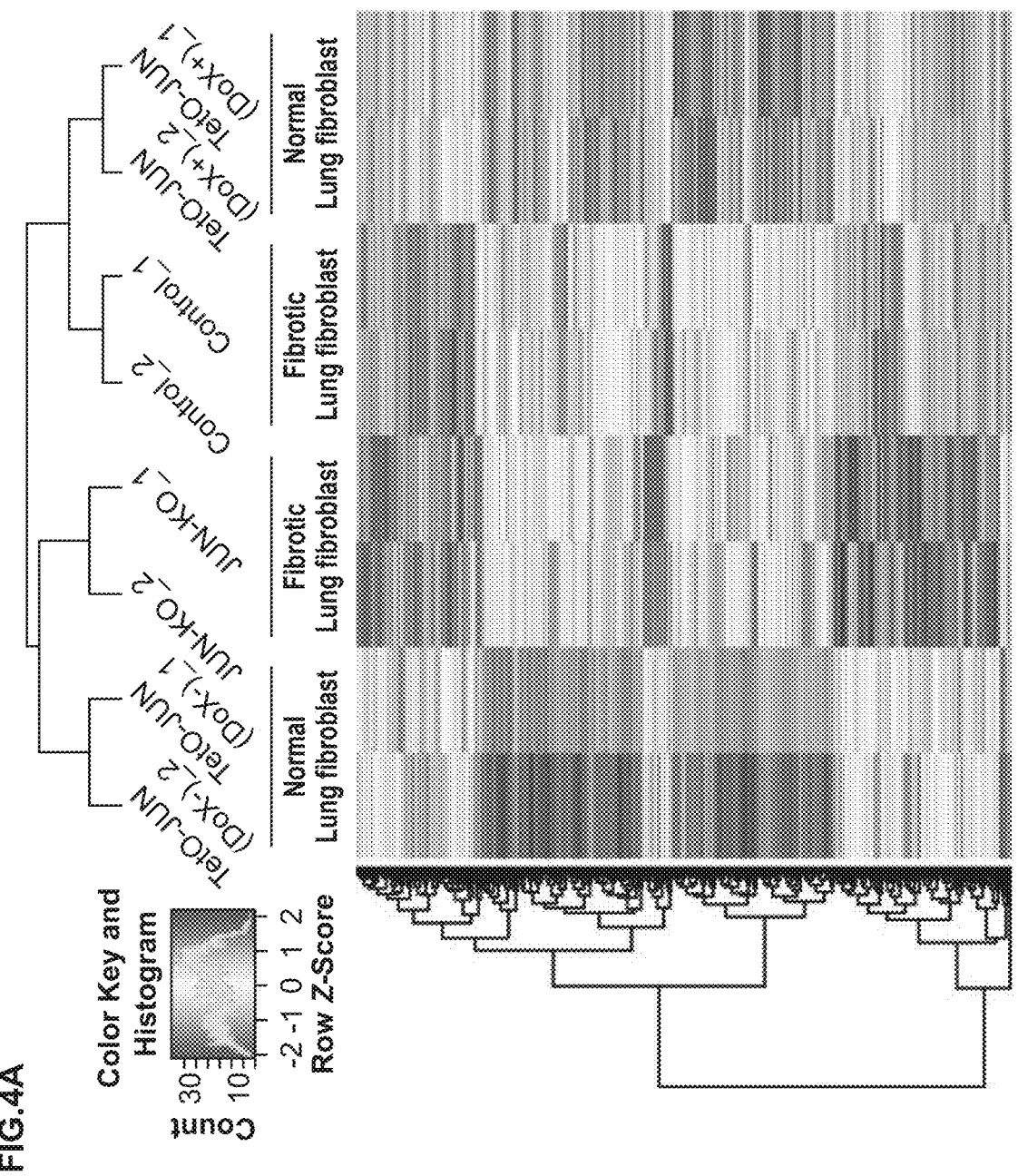
FIG. 4. Promoter accessibility of PD-L1 (CD274) and CD47 in fibrotic lung fibroblasts depends on JUN and directly appears to regulate the enhancer of CD47. (a) Heatmap demonstrating dynamic chromatin changes in fibrotic lung fibroblasts with (JUN-KO) or without (Control) JUN deletion, and normal lung fibroblasts with (TetO-JUN Dox+) or without (TetO-JUN Dox−) JUN activation. (b) Representative genome browser tracks comparing ATAC- seq signal in fibrotic lung fibroblasts (with (JUN-KO) or without (Control) JUN-knock out) and also ChIP-seq signal in Normal lung fibroblasts (with (TetO-JUN Dox+) or with- out (TetO-JUN Dox−) JUN overexpression) with A549, MCF7, h1-hESC, HepG2 and K562 from published data at JUN, CD47 and CD274 loci. The red boxes highlight ATAC-seq and ChIP-seq peaks in the promoter sites of JUN, CD47 and CD274 (and enhancer shows in Green). We also compared our peaks with H3K4me3 or H3K27Ac (=histone mark for open chromatin), H3K9me3 or H3K27me3 (=his- tone mark for close chromatin), ChIP-seq data generated from normal human lung fibroblast from published data, which highlighted the same areas respectively. (c) Gene expression changes in primary lung fibroblasts by compar- ing JUN knock-out (KO) or overexpression (OE). QPCR values were normalized to the value in JUN knock-out. Four experimental repeats. Ratio paired t test, P<0.01; *P<0.001. (d) Representative flow cytometry histograms showing reduced expression of pJUN, PD-L1 and CD47 after JUN overexpression (OE) or knock-out (KO). Yellow plot: JUN overexpression; Black plot: JUN knock-out. (e) Vector maps of the control and CD47 enhancer constructs used to engineer reporter cell lines. (f, g) CD47 enhancer reporter assays demonstrating that doxycycline induced JUN expression initiated CD47 enhancer expression which disappeared when JUN expression was turned off (f) or JUN was knocked out (g). Data are expressed as mean±SD, Ordinary one-way ANOVA (Tukey's multiple comparisons test), n.s., non-significant; P<0.01; *P<0.001; ****P<0.0001.

Hierarchical clustering of ATAC-seq signals revealed that the chromatin landscape of primary fibrotic lung fibroblasts is close to that of primary normal lung fibroblasts with JUN activation and clustered with fibrotic fibroblasts with JUN deactivation. Out of the total open chromatin cis-regulatory elements across all samples, we found the top differentially peaks enriched pro-inflammatory genes such as CD47, CD274 (PD-L1), GLI1 and NFKB1 appeared to be regulated and downstream of JUN as their chromatin accessibilities decreased in JUN-KO fibrotic fibroblasts and increased in JUN-OE normal fibroblasts (FIG. 4a). JUN ChIP-seq data coupled with the ATAC data confirms enrichment of bound JUN to the JUN promoter region (shaded in red), which correlates with accessible chromatin state in overexpressed JUN lung fibroblasts when compared to normal cells. This demonstrates that knock out JUN decreases accessibility to its own promoter in a negative regulatory feedback fashion, while overexpression of JUN is the opposite.

Figure 4B:
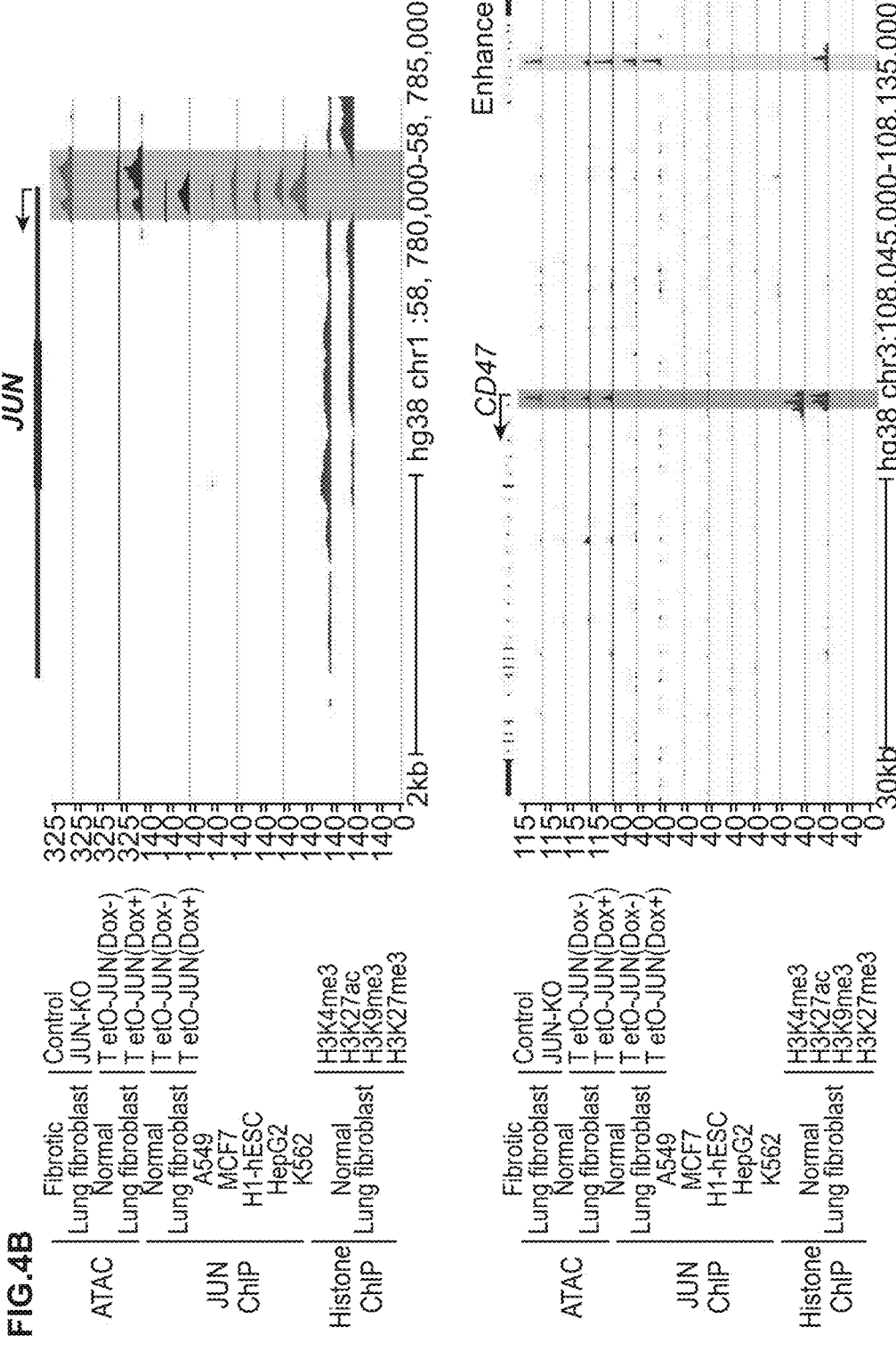

When we analyzed the DNA bound-JUN effects on chromatin structure of CD47 or PD-L1, we noticed that JUN enrichment (by JUN ChIP-seq) occurs preferentially in a distal genomic region (shaded in green, which previously had been shown to be a super-enhancer of CD47 in cancer) for CD47 and in first intronic genomic region (shaded in green, which has been reported as PD-L1 active enhancer) for PD-L1, rather than in the corresponding promoters for these genes (shaded in red). JUN enrichment observed in these two cases correlated with an increase in chromatin accessibility (detected by ATAC-seq) in lung fibroblast cells when compared to normal. This is particularly interesting as these changes are only present in our primary lung fibroblasts, but not in any of the other previously published data on JUN ChIP-seq performed on cancer cell lines such as A549, MCF7, H1-hESC, HepG2 or K562. These results suggest that the binding of JUN to specific CD47 and PDL1 regions can modulate accessibility to DNA in regulatory regions specific to fibrotic disease (FIG. 4b).

Figure 12A:
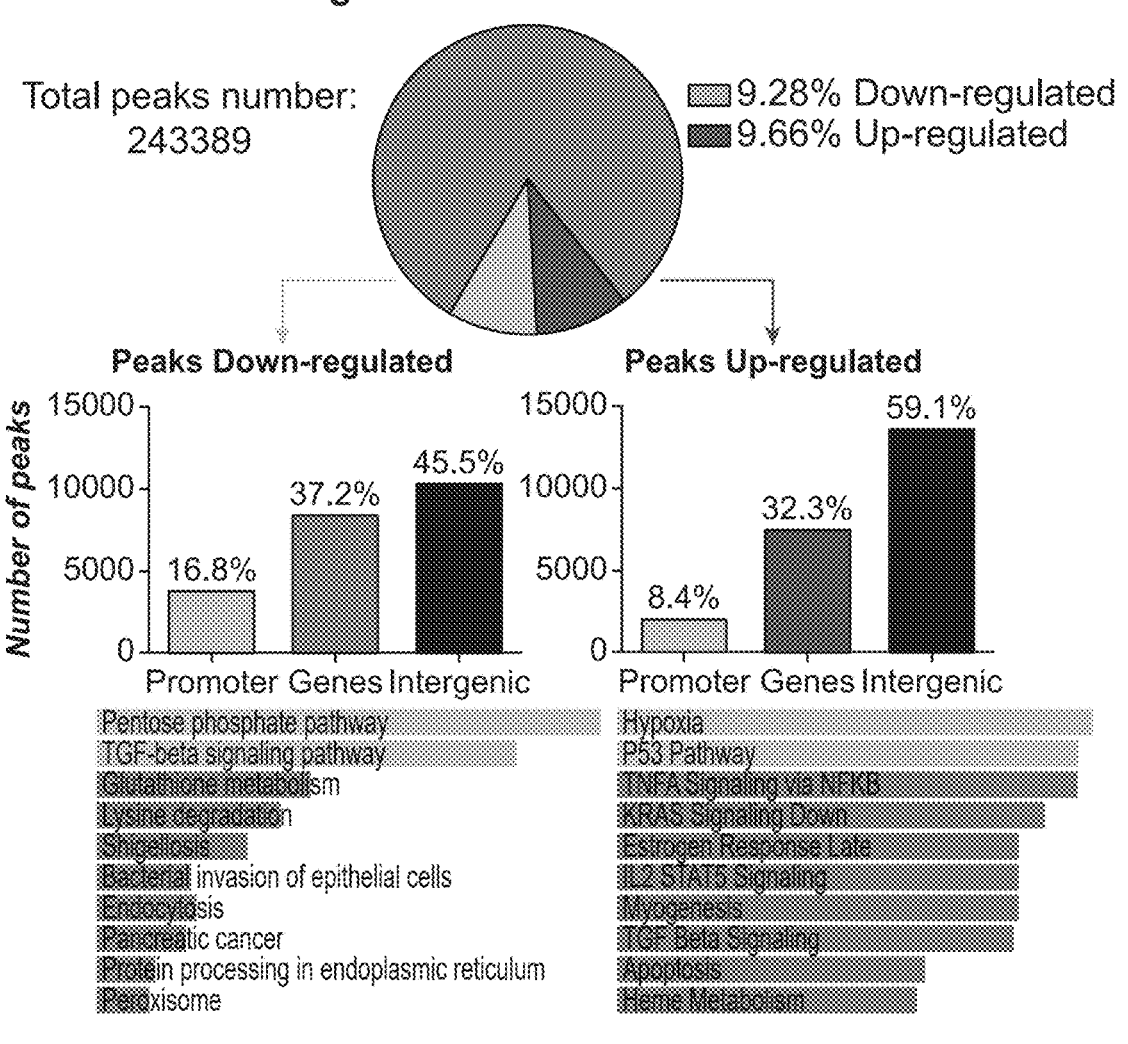
FIG. 12. (a, b) Quantitative comparative analysis of ATAC-seq peaks obtained from fibrotic lung fibroblasts with JUN deletion or not as well as Normal lung fibroblasts with JUN overexpression or not. The top ten significant pathways which were associated with down regulation (labeled as Promoter Down in red) or up regulation (labeled as Promoter Up in blue) of the promoters were shown. (c) Venn Diagram generated by comparing downregulated promoters in fibrotic lung fibroblasts after JUN deletion with published RNA-seq data of bulk fibrotic lung samples demonstrating that 1.6% or 70 of the gene which overlapped between these two distinct data sets encoded profibrotic pathways (red) and pathways which encoded T-cell exhaustion (green). (d) Reporter assays for the CD47 enhancer demonstrating continuously increasing activation of the CD47 enhancer (E7TK) reflected by increased EGFP expression with increased JUN expression (JUN-OE) while the CD47 enhancer activity decreased with doxycycline removal (turns JUN off) in a timely dependent manner and JUN deletion with CRISPR-Cas9 knock-out (JUN-KO) abolished the enhancer activity. Meanwhile the control TK vector showing no differences with JUN modification. Scale bar, 100 μm.
Figure 12C:
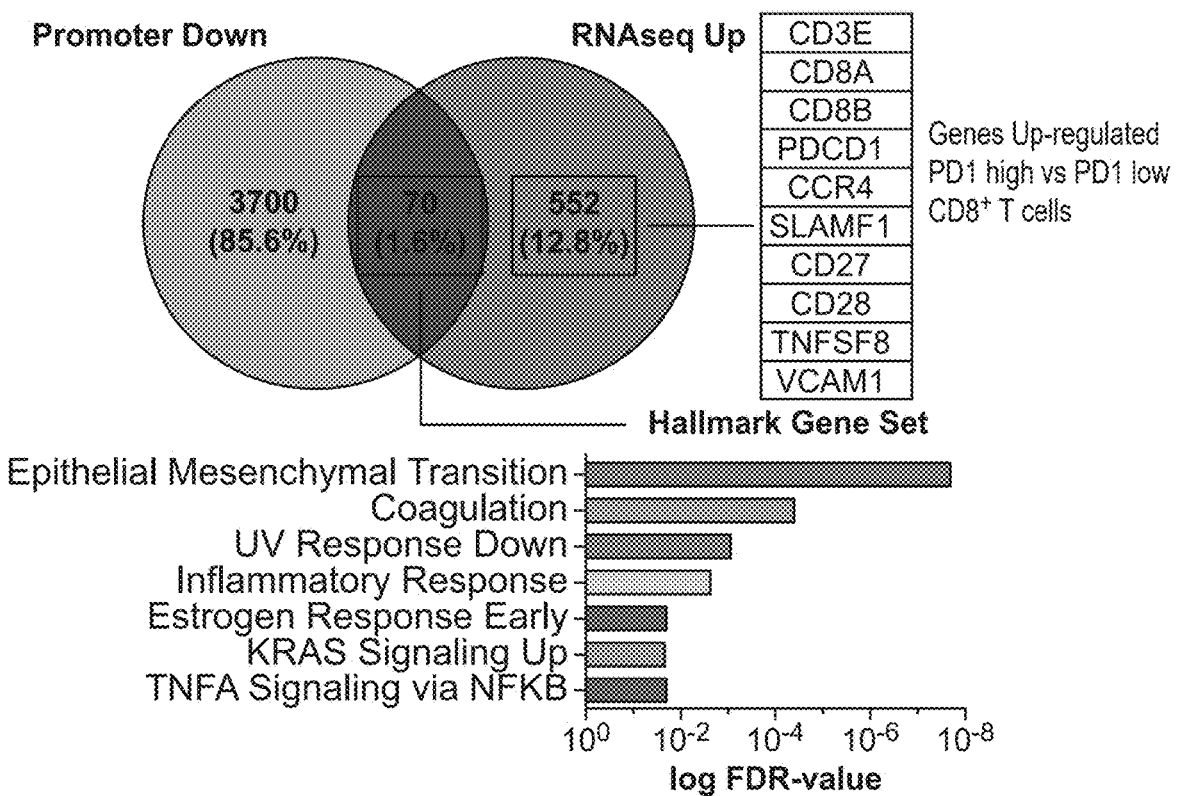

We also compared the JUN KO against control and JUN-OE (TetO-JUN Dox+) against control (TetO-JUN Dox−) and found that chromatin peaks from promoters involved in pro-fibrotic epithelial-mesenchymal transition pathway, TGF-beta receptor signaling and Stat3 signaling pathway which were most significantly with JUN modification (FIG. 12a, b). In addition, to demonstrate the physiological relevance of these findings, we compare our ATAC-seq data with published gene expression profiling from fibrotic and normal lungs, we found an overlap of 70 genes between these two datasets. Among the most significant were genes encoding the profibrotic epithelial-mesenchymal transition pathway, indicating that the JUN pathway could be a driver to promote fibrotic progression in pulmonary fibrosis (FIG. 12c).

Figures 4B, 4C, 4D:
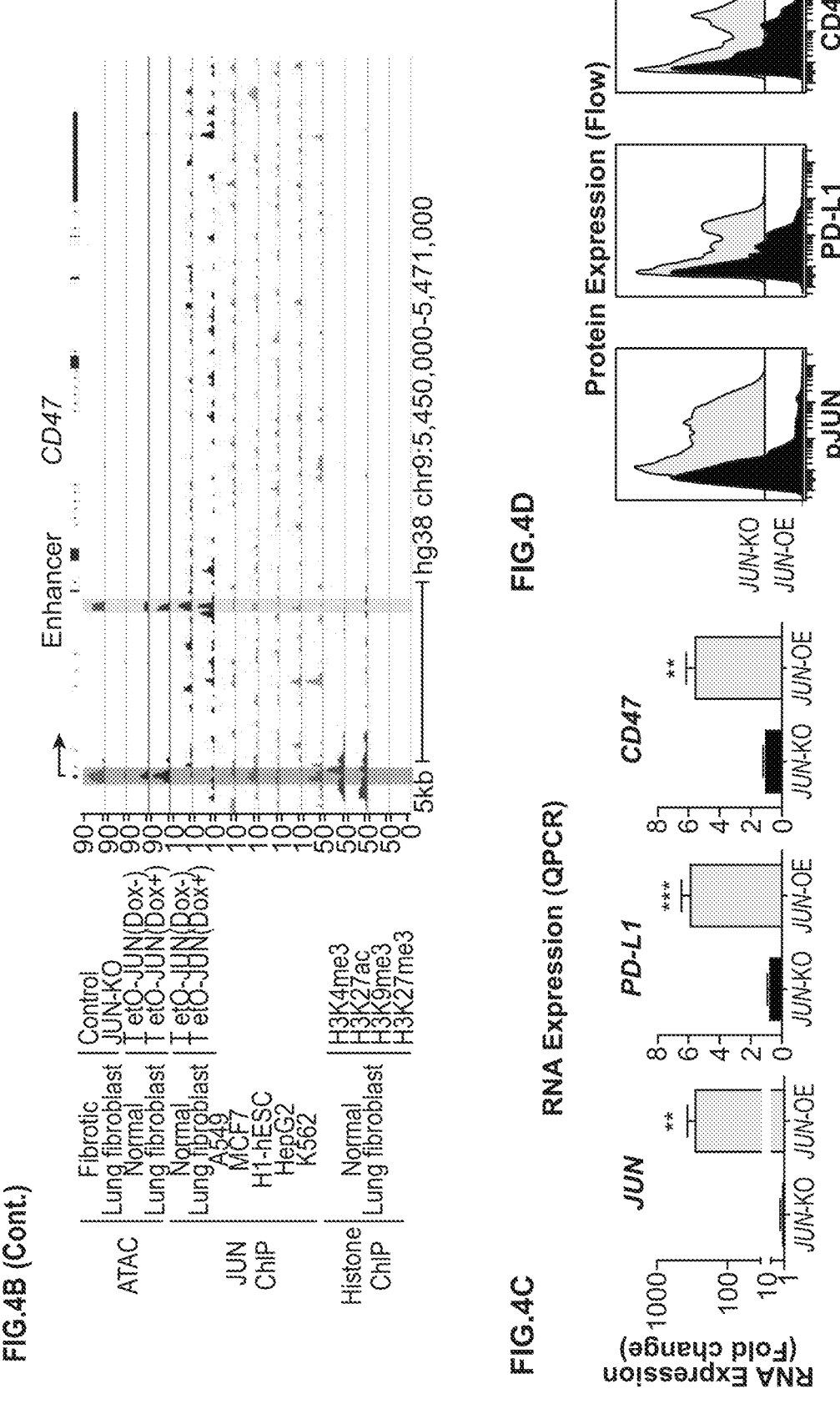
Figure 12D:
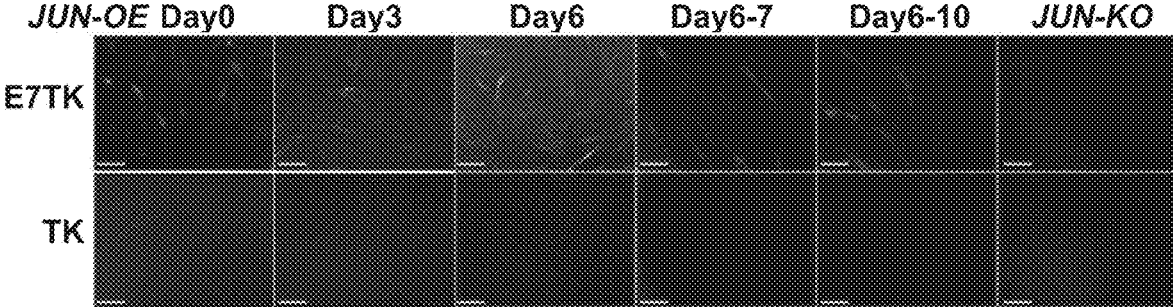

To demonstrate JUN regulation on CD47 and PD-L1, we investigated expression in fibroblasts following JUN modification after 4 days (FIG. 4c, d) and found that JUN-OE possessed a higher expression of in both RNA and protein levels. To confirm that changes in chromatin accessibility are pronounced in the enhancer region of CD47, we transduced fibrotic fibroblast cultures from patients with a construct containing CD47-enhancer followed by a GFP reporter such that the enhancer activity can be monitored by GFP expression (FIG. 4e). To study whether JUN pathway regulates CD47 through this enhancer, we serially measured GFP expression after JUN induction with a doxycycline inducible system over a time course of 6 days and found that the CD47 enhancer was active with JUN expression. When we removed JUN from the culture by doxycycline withdrawal, we almost immediately lost CD47 enhancer activity (FIG. 4f and FIG. 12d). GFP expression was further down-regulated in JUN KO cells (FIG. 4g and FIG. 12d). These findings demonstrated JUN is one of the key factors that can remodel chromatin, and increase DNA accessibility to regulate the expression of genes of fibrosis.

Figure 5A:
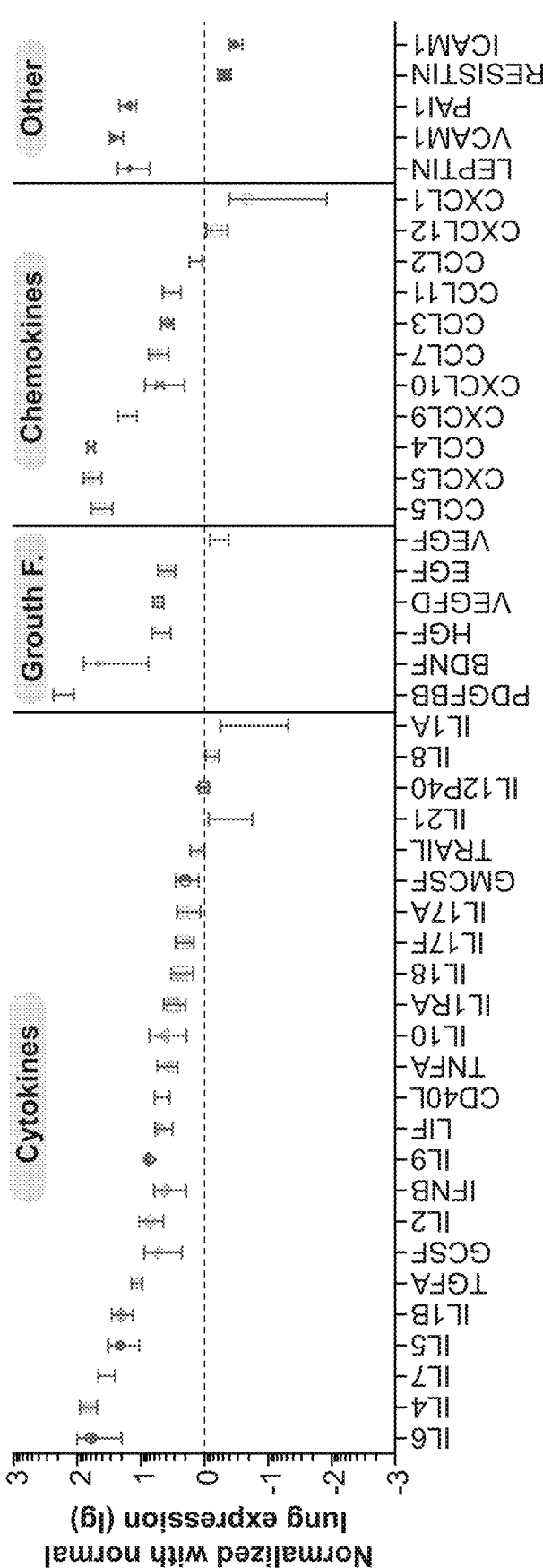
FIG. 5. IL6 mediates the pro-fibrotic response of JUN involvement. (a) Secreted proteins in lung bronchoalveolar lavage (BAL) of fibrotic lung patients were quantified by Luminex assay, showing IL-6 as the highest expressed cytokine across all fibrotic patient BAL samples. Data were normalized by protein levels of the BAL of normal lung, and presented as mean±SD. (b) Cytokines and chemokines in fibrotic mouse bronchoalveolar lavage (BAL) after JUN induction were quantified by Luminex assay. IL-6 was consistently detected amongst the most highly expressed cytokines in JUN-mouse fibrotic lungs indicative of IL-6- JAK-STAT pathway activation. Data were normalized by normal lung expression, and presented as mean±SD. (c) The cytokines/chemokines released from JUN induced lung fibrotic mice derived whole bone marrow, fibroblasts and monocytes/macrophages in the medium after 48 h of Dox- initiated JUN induction were quantified by Luminex assay, demonstrating that whole bone marrow and fibroblasts are secreting increased IL-6 in response to JUN. Data were presented as mean±SD. (d) Increased IL-6 expression level were detected by QPCR and Flow cytometry in primary lung fibroblast with JUN knock-out (KO) or overexpression (OE). Four experimental repeats. Ratio paired t test, *P<0.001. (e, f) IL-6 increased CD47 enhancer activity at concentrations as low as 1 ng/ml (e) and protein expression at 10 ng/ml (f) in a dose-dependent fashion. Data are expressed as mean±SD, Ordinary one-way ANOVA with multiple comparisons test, n.s., non-significant; P<0.01; ****P<0.0001.

Human fibrotic and mouse pro-fibrotic lung fibroblasts secrete IL-6 in a JUN-dependent manner and IL-6 signaling amplifies JUN-mediated pro-fibrotic effect via CD47. To identify the cytokine pathways that cooperate with JUN, we profiled chemokines using a multiplex assay in the same bronchoalveolar lavage (BAL) human fibrotic lung samples that we were analyzed with mass cytometry. Remarkably, we discovered that IL-6 was among the most highly upregulated cytokines, compared to BALs from normal donors, along with the PDGF-BB growth factor and CCL5/CXCL5, both critical factors shown to be involved in connective tissue remodeling (FIG. 5a). Additionally, we detected increased IL-6 and family members in our JUN induced pulmonary fibrosis mouse lung washings (FIG. 5b). To determine which cells were responsible for IL-6 secretion, we quantified IL-6 in the supernatant of cultures of lung fibroblasts, whole bone marrow and stroma and monocyte/macrophage cultures. We detected JUN-dependent IL-6 secretion only in the explanted lung fibroblast and marrow stroma cultures, but not in bone marrow derived monocytes/macrophage cultures which produced baseline IL-6 independent of JUN (FIG. 5c). These data indicated that IL-6 could be a critical downstream cytokine pathway involved in the JUN-mediated pro-fibrotic response.

Figures 5D, 5E, 5F:
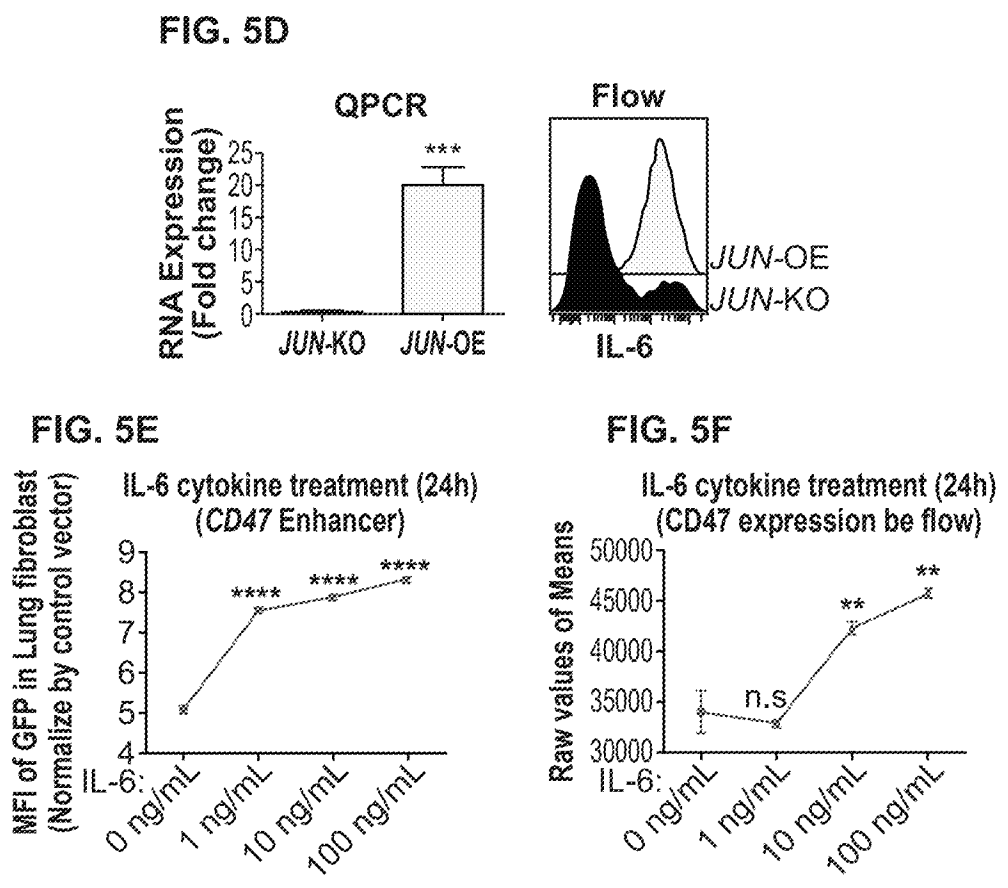

We evaluated the dependency of IL-6 on JUN in primary human lung fibroblast cultures in which JUN was inducible expressed or deleted JUN with CRISPR Cas9. We found that promoter accessibility of IL-6 and IL-6R and IL-6ST depended on JUN, since their accessibility (shaded in red) was lost with JUN deletion. JUN's binding is highly enriched in the overexpressed JUN lung fibroblast cells, thus, increasing IL6 promoter accessibility in these cells (FIG. 13a). IL-6 expression also confirmed to correlate with JUN protein expression and activation was lost with JUN deletion (FIG. 5d).

Figure 13B:
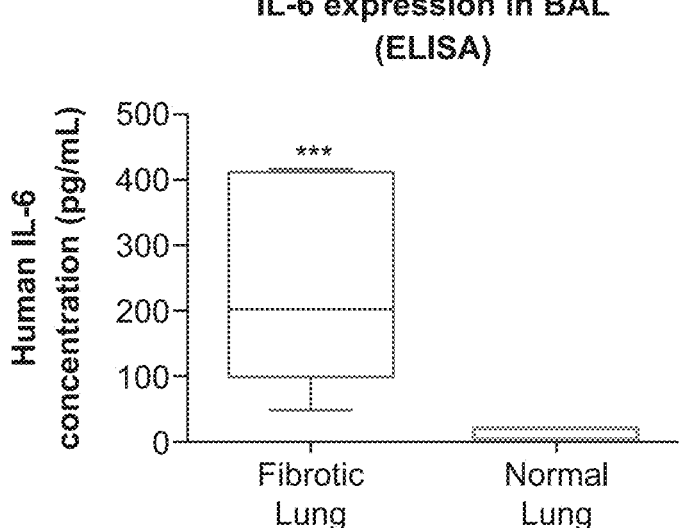
FIG. 13. (a) Schematic maps showing that the promoter sites (highlighted in red) for IL-6, IL-6R, and IL-6ST depended on JUN expression in Normal lung fibroblasts with (TetO-JUN Dox+) or without (TetO-JUN Dox−) JUN overexpression and fibrotic lung fibroblasts with (JUN-KO) or without (Control) JUN knockout with CRISPR-Cas9 but not in other cell lines like A549, MCF7, h1-hESC, HepG2 and K562. We also compared our data to publicly available H3K4me3 or H3K27Ac (=histone mark for open chromatin), H3K9me3 or H3K27me3 (=histone mark for close chromatin), ChIP-seq data generated from normal human lung fibroblast from published data to confirm the regions of open chromatin for the IL-6 family members. (b) IL-6 expression in the bronchoalveolar lavages (BAL) of fibrotic and normal lungs were measured by ELISA showing dramatically increased secreted IL-6 protein. Data are expressed as min to max of 5 fibrotic and 3 normal samples. Data were analyzed by unpaired t test with Welch's correction (Two-tailed), ***P<0.001. (c) CD47 constituent enhancer driven EGFP reporter (E7TK) expression was activated and increased in lung fibroblast cells treated with IL-6 in a dose dependent manner. Control cells were transduced with the lentiviral cassette containing the thymidine kinase (TK) minimal promoter only. Scale bar, 100 μm.
Figure 13C:
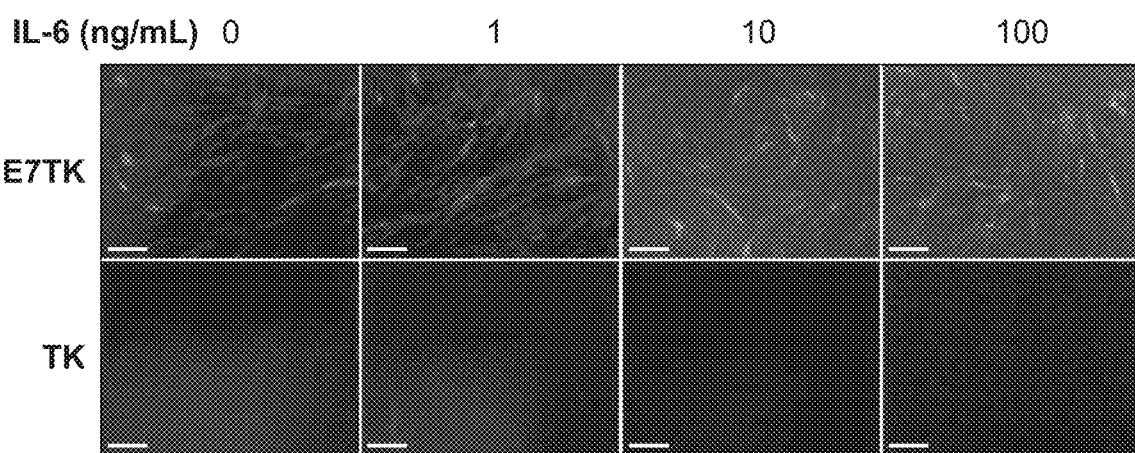

ELISA results demonstrate IL-6 concentrations around 200 μg/mL in BAL of fibrotic lung patients (FIG. 13b). Based on reported literature and our own quantitative IL-6 measurements in normal lung BAL, the baseline levels of IL-6 in healthy men are around 2-10 pg/mL. Hence, we used 1, 10, 100 ng/ml of IL-6 for stimulation, to investigate the influence of IL-6 on CD47 enhancer in normal lung fibroblasts. We found that increasing concentrations of IL-6 mimic JUN-mediated CD47 enhancer activity (FIG. 5e and FIG. 13c) and also increased CD47 protein expression (FIG. 5f). IL-6 addition to JUN KO fibroblasts had no effect on CD47 enhancer activity. Thus, IL-6 signaling cooperates with JUN to amplify JUN-mediated activation of the CD47 enhancer in a synergistic manner.

Figure 6E:
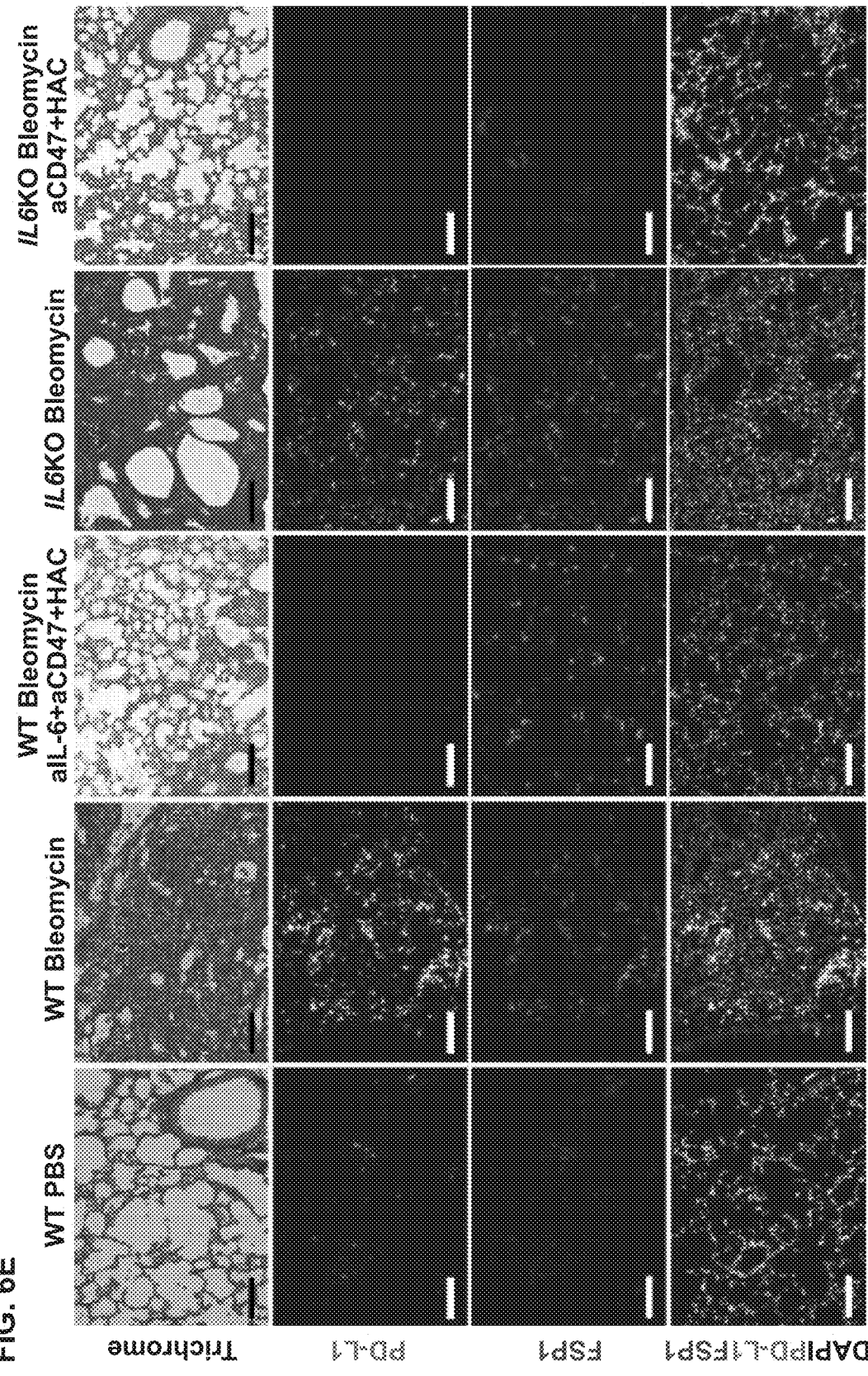
FIG. 6. Inhibition of immune checkpoints together with IL-6 resolves lung fibrosis. (a) Whole lung scaffold map for Bleomycin-induced lung fibrosis in mice. Each node repre- sents unsupervised cell clusters. (b) Representative mass cytometry plot demonstrating increased expression of immune checkpoint proteins CD47 and PD-L1 in fibro- blasts, an expansion of CD11b+F4/80+ macrophages, regu- latory T cells (CD3+CD4+CD25+FOXP3+) and exhausted T cells (CD3+CD8+PD-1+TIM3+) in mouse model after fibrosis induction with bleomycin for 2 weeks. (c, d) Rep- resentative images of Micro CT scans of wildtype and B6.129S2−//6$^{tm1Kopf}$/J (IL-6KO) mice highlighting increased fibrosis in the lung after fibrosis induction (wild- type and IL-6KO mice) and much improved fibrosis after treatment with HAC (anti-PD-L1) alone or combined with a blocking antibody against CD47 or/and IL-6. Data are expressed as mean±SD of 5 animals and analyzed by using one-way ANOVA followed by Tukey's multiple comparisons test for multiple comparison. n.s., non-significant; *P<0.05; P<0.01; *P<0.001. (e) Trichrome of lung sections of control mice, mice after fibrosis induction with bleomycin (wildtype and IL-6KO mice) and mice after treatment with a blocking antibody against IL-6, CD47 and HAC (the blocking reagent against PD-L1) demonstrating dramatically improved fibrosis (significantly decreased blue stained areas on Masson's trichrome stain which correspond to cross-linked collagen) and diminished PD-L1 expression in FSP1+ fibroblasts after treatment. Scale bar, 100 μm.

JUN induction in mouse lungs recapitulates the key molecular events found in human pulmonary fibrosis. It is shown herein that two critical immune check point proteins—CD47 and PD-L1—are not only induced in two mouse models of lung fibrosis (JUN and bleomycin mediated), but also in lung fibroblasts of human pulmonary fibrosis. Given these observations, we sought to determine whether blocking PD-1/PD-L1 would activate the immune system, both the innate and the adaptive, to eliminate overgrown fibroblasts in fibrotic lesions, and whether blocking different immune checkpoints simultaneously has additive anti-fibrotic effects and is well tolerated (FIG. 6). We previously established a JUN-inducible mouse model, to develop fibrosis of the lung. Here, we compared our genetic model to the frequently used bleomycin-induced model of lung fibrosis and found that the fibrotic response in that chemical injury model was similar to our genetic lung fibrosis model, i.e., similar distinct cell lineages [CD45+ leukocytes, EpCAM+ bronchoepithelial cells, CD31+ blood vessel endothelial cells and lineage negative fibroblasts (CD45−EpCAM−CD31−)] clustered together by X-shift clustering (FIG. 6a), and both resulted in activation of phospho JUN (FIG. 14a).

Immune checkpoint inhibition and IL-6 signaling blockade stimulate T cells and macrophages to clear lung fibrosis in mice. PD-L1 ligand is upregulated in lung fibrosis in mice in a subset of pro-fibrotic fibroblasts (in both genetic and chemical injury model with bleomycin), which highly co-expressed CD47. In addition to expansion of macrophages, we also detected an immunosuppressive microenvironment as observed in human fibrotic lungs, including increased number of regulator T cells and exhausted T cells (FIG. 6b).

Figures 14A, 14B, 14C:
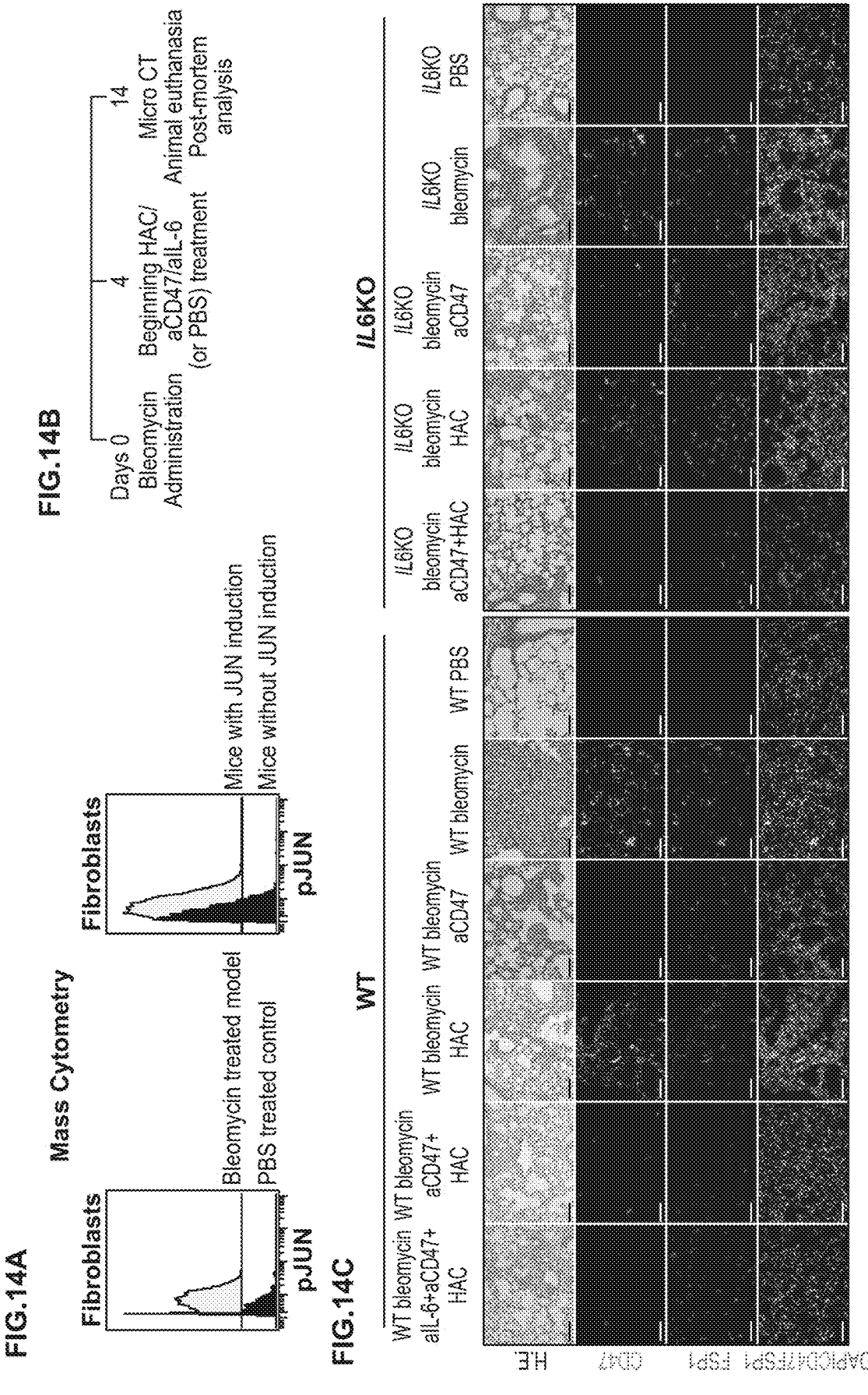
FIG. 14. (a) Histogram plots of mass cytometry data of phosphor p-JUN expression in lung fibroblasts comparing two different mouse models of lung fibrosis, the bleomycin induced lung fibrosis abundantly used by many labs, and the JUN induced lung fibrosis model, both demonstrated increased activation and phosphorylation of JUN after initiation of lung fibrosis in mice. (b) The time course of bleomycin induction in mice and in vivo treatment with blocking antibodies. (c, d) Morphological and molecular markers of representative histologic sections of wildtype and B6.129S2–//6$^{tm1Kopf}$/J (IL-6KO) mice lung tissues after fibrosis induction and treatment with blocking antibodies against immune checkpoint inhibitors and IL-6. Hematoxylin-Eosin (H.E.) stains and CD47, FSP1 counterstained with DAPI (c), Masson's Trichrome stains and PD-L1 and FSP1 with DAPI (d) demonstrating improved fibrosis along with decreased CD47 and PD-L1 immune checkpoint protein expression in fibroblasts (FSP1+). Scale bar, 100 μm. (e) Quantitation of PD-L1 and CD47 expression in fibroblasts and collagen fibrosis of 10 high power fields (40×) of trichrome-stained sections. Data are expressed as mean±SD, Ordinary one-way ANOVA (Dunnett's multiple comparisons test), non-significant; ****P<0.0001. The immune stains have been evaluated by a blinded pathologist, in addition to image J software. (f) Phagocytosis assays demonstrating that human PD-1+ expressing bone-marrow-derived macrophages eliminate pathogenic human fibrotic fibroblasts much more efficiently when treated with PD-L1 blocking protein (HAC), with synergistic effects when also treated with a blocking antibody against CD47. Data are expressed as mean±SD, and analyzed by using one-way ANOVA followed by Tukey's multiple comparisons test for multiple comparison, *P<0.05; **P<0.0001. (g) Flow cytometry studies demonstrating that PD-1 surface protein expression was upregulated in ~10% of peripheral blood macrophages (PBMCs) after stimulation (red histogram). (h) In vivo analysis of human fibrotic fibroblasts in kidney capsule adoptive transfer assay in NSG mice to study efficacy of PD-1/PD-L1 blockade with HAC protein. Representative bioluminescence imaging (BLI) image and quantification of luminescence intensity, trichrome and anti-GFP staining of kidney area with the xenograft demonstrate that PD-1/PD-L1 blockade with HAC increased fibrotic fibroblast clearance compared to placebo (PBS). Data are expressed as mean±SD, and analyzed by using two-way ANOVA followed by Tukey's multiple comparisons test for multiple comparison. P<0.01. Scale bar, 100 μm.
Figure 14D:
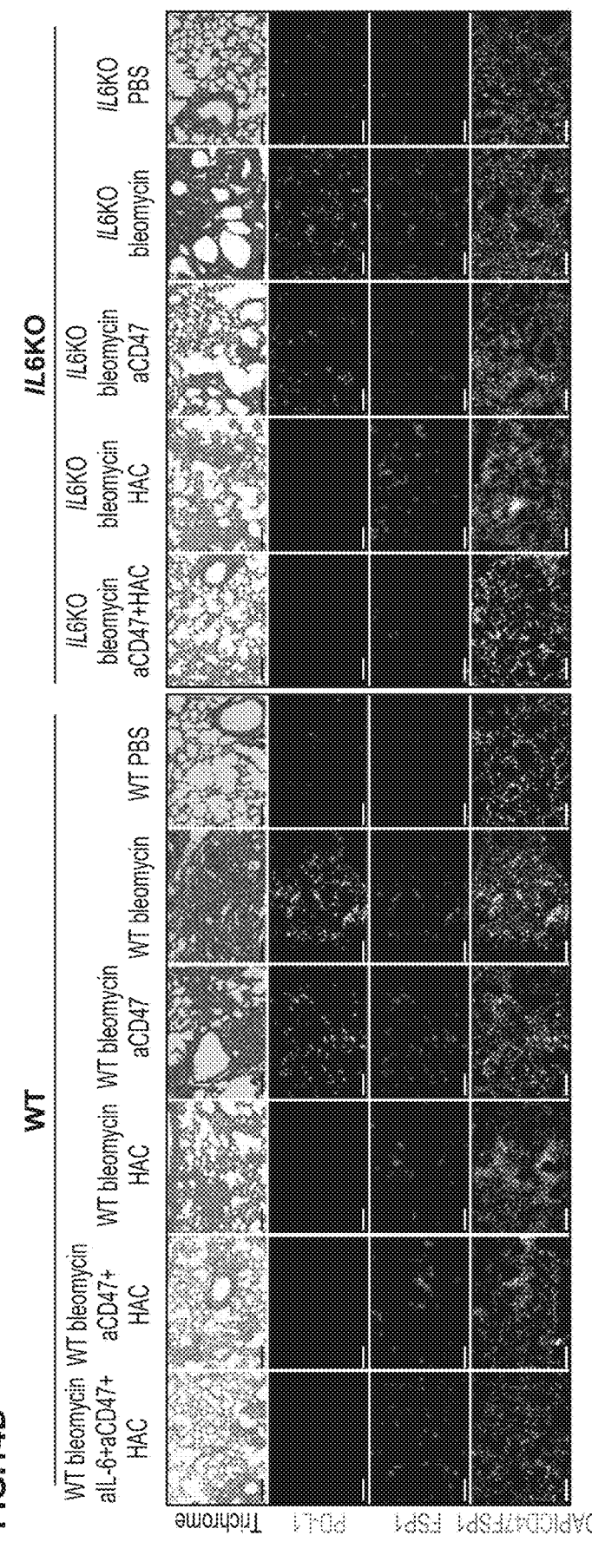

We tested blockade of PD-1/PD-L1 (single/combined with anti-CD47 antibody and IL-6 blockade) treatment in a mouse model of lung fibrosis mediated by bleomycin where treatment was initiated at day 4 after fibrosis induction (FIG. 14b). To assess and quantify the fibrotic response and the effects of immune checkpoint inhibition in vivo over time, we performed weekly serial high-resolution CT imaging of the lung, and found a striking reduction of the fibrosis in the lung highlighted by reduced radiodensities, most notable in lungs of mice treated with triple combined IL-6, PD-L1 and CD47 blockade (FIG. 6c, d).

In addition, we analyzed these mice using mass cytometry coupled with histopathological and immune stains of the lungs two weeks post-fibrosis initiation. Although there was increased PD-L1 co-expression with FSP1 in untreated mice with lung fibrosis, we found significantly decreased PD-L1+ CD47+ fibroblasts. FSP1 has been shown to be a highly specific marker for profibrotic lung fibroblasts. This finding correlates with decreased collagen content of lung sections of the mice which were treated with a triple combination of blocking antibodies against CD47 (Clone MIAP410) and IL-6 (Clone MP5-20F3), and an engineered non-antibody HAC protein which was reported as an effective anti-PD-L1 blockade in the treatment of mouse tumor models. B6.129S2–//6$^{tm1Kopf}$/J (IL-6 knock-out) mice treated with anti-CD47 antibody and the PD-1 blocking reagent HAC similarly resolved their lung fibrosis, confirming synergistic antifibrotic efficacy of IL-6 and immune checkpoint inhibition (FIG. 6e and FIG. 14c-e).

To evaluate the effects of immune checkpoint inhibition on innate immunity in the fibrotic lung, we performed phagocytosis assays and measured phagocytic uptake of fibrotic fibroblasts by macrophages after treating them in vitro with HAC protein, anti CD47 blocking antibody or a combination of both. We discovered that treatments with either HAC or anti CD47 significantly increased phagocytic uptake of fibrotic fibroblasts in vitro—we even found added efficacy when we blocked with both simultaneously. These data suggest that PD-L1 inhibition has anti-fibrotic efficacy through engaging PD-1 on macrophages, in addition to T cells, and provides an additive effect to CD47 in its anti-fibrotic properties (FIG. 14f). Further, we show that PD-1 is upregulated on a subset of macrophages, analogous to previously reported findings on TAMs (FIG. 14g).

In addition to these two syngeneic mouse models, we also used a humanized mouse model in which we have successfully engrafted primary human fibrotic lung fibroblasts in NOD-SCID gamma (NSG mice) underneath the kidney capsule. As key mediators of the innate immunity, macrophages are the only remaining leukocytes in this NSG xenograft model and have been shown to interact with human PD-L1 via their PD-1. Based on luciferase detection of the human fibrotic fibroblast graft, we effectively resolved pathogenic pulmonary fibrosis by targeting PD-L1 with HAC protein. This outcome is confirmed this outcome by loss of GFP-positive grafted cells and lack of fibrosis by trichrome staining by histology at study endpoint (FIG. 14h).

Figure 7:
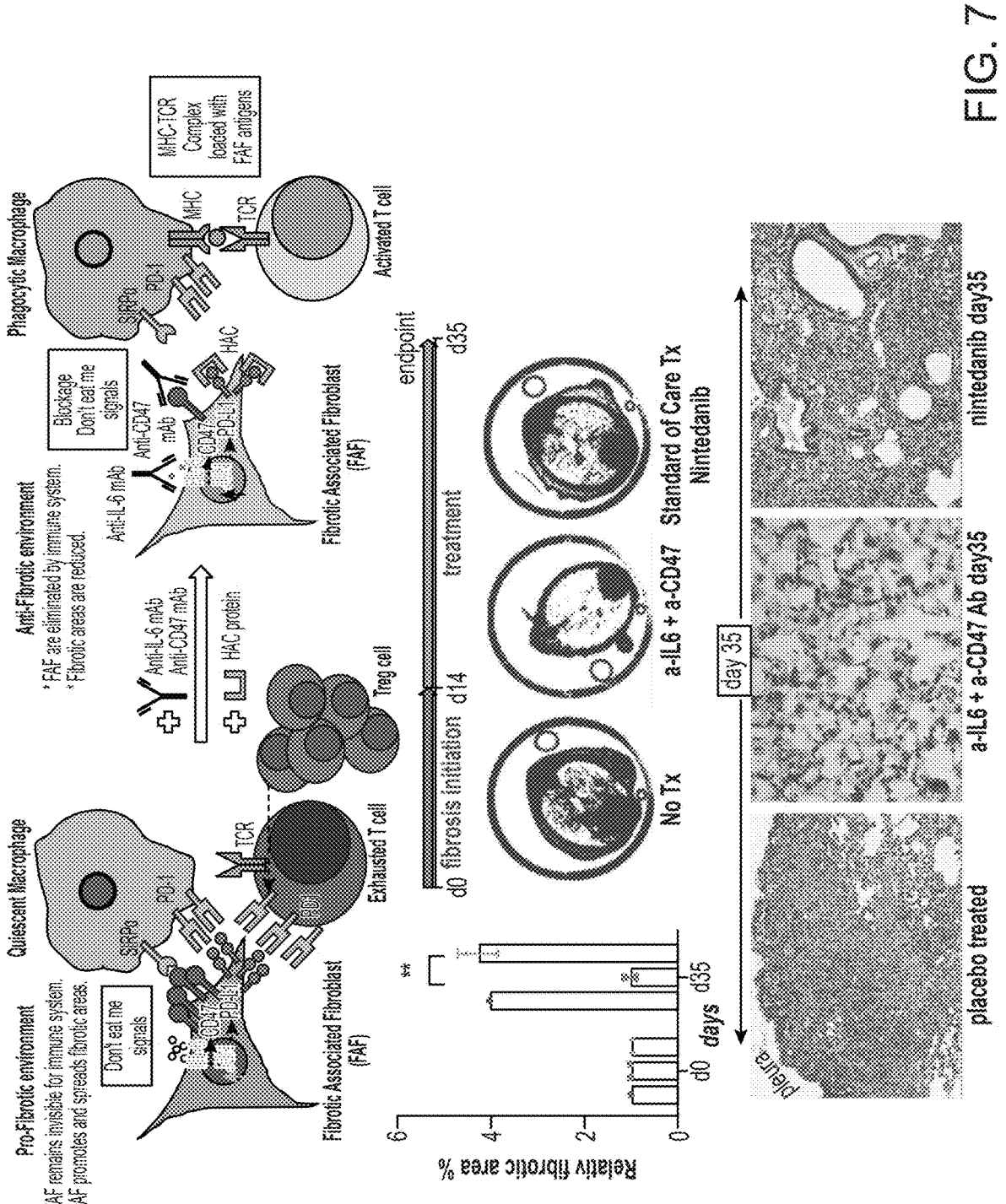
FIG. 7. Schematic diagram of the proposed mechanisms of fibrosis clearance. Left: in fibrotic lung, we find persistent myofibroblast activation in fibrotic plaques and JUN is upregulated at the transcriptional level in fibrosis-associated fibroblasts (FAFs) directly controlling the promoters and enhancers of CD47 and PD-L1 in FAFs amounting to an immune suppressive response of the innate immunity, dormant macrophage subsets which do not phagocytose, and continue to release chronic inflammatory cytokines to maintain the status. JUN also directly regulates IL-6 at the chromatin level resulting in increased expression and secretion of this potent cytokine by fibroblasts resulting in a suppressive adaptive immune response-chiefly T cell exhaustion and upregulation of regulatory T cells. Right: we disrupt the suppression of both the innate and adaptive immunity by blocking the immune checkpoint proteins CD47 and PD-L1 as well as the proinflammatory IL-6 cytokine pathway by stimulating phagocytic removal of profibrotic fibroblasts and T cell activation leading to clearance of the fibrosis in the lung.
Figure 8:
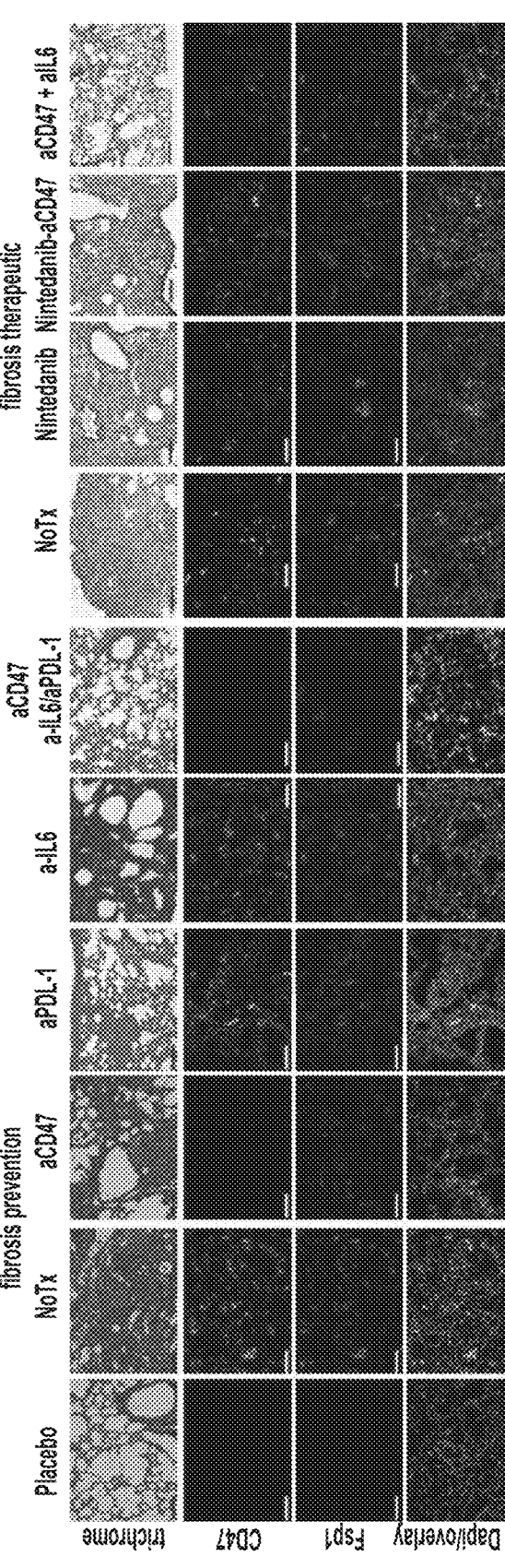
FIG. 8. Therapeutic treatment of lung fibrosis in mice with IL6 and CD47 proofs to be superior to standard of care treatment with nintedanib. Top Panel shows micro CT scans of lungs of mice after therapeutic treatment of lung fibrosis at study endpoint day 35 with no treatment (No Tx), combinational treatment of anti-IL6 and anti-CD47 (α-IL6+α-CD47), or nintedanib. The CT scans of the lungs show improved black densities compared to no treatment and nintedanib (some improvement). Middle panel shows representative image of Masson Trichrome stained sections of peripheral lung fibrosis after JUN induction treated with placebo (PBS), or a combination of α-IL6 and α-CD47 at day 35, or nintedanib monotherapy at day 35. The combination of α-IL6 and α-CD47 demonstrates increased macrophage recruitment, and many macrophages with ingested extracellular matrix components and much improved extracellular matrix and lung fibrosis compared to untreated and intermediate response for nintedanib. Bottom panel shows immune stains for fibroblasts (Fsp1, a fibroblast specific marker in pulmonary fibrosis) in conjunction with evaluation of immune checkpoint proteins after treatment comparing fibrosis prevention with a therapeutic treatment approach against lung fibrosis to the right supporting elimination of CD47+ fibroblasts with α-CD47 treatment and improvement of fibrosis, versus partial anti-fibrotic responses with single treatments for α-CD47, αPD-L1, α-IL6 and Nintedanib.

In summary, we demonstrate that immune checkpoints CD47, PD-L1 and IL-6 signaling are dramatically upregulated in a JUN-dependent fashion in pulmonary fibrosis patients and mouse lung fibrosis models. Fibroblasts, macrophages and T cells under pro-fibrotic environment were all phenotypically different than a normal control. Blockade of JUN-controlled, profibrotic and immune suppressive programs released immune suppression, and improved resolution of fibrosis in pulmonary fibrosis diseases (FIG. 7).

Fibrosis is a reactive process initiated by the stimulation of fibroblasts from leukocytes and the progression of fibrosis is determined by a dynamic balance between anti-fibrotic and pro-fibrotic mediators within the microenvironment composed of diverse cellular subtypes. As demonstrated in this study, we profiled millions of cells from the same cohort in a single multiplexed experiment and showed the heterogeneity of fibroblasts in pulmonary fibrosis patients. The up-regulation of PD-L1 and CD47 in fibroblast subpopulations together with the immunosuppressive phenotype in T cells and macrophages suggested that the interactions between fibroblasts and leukocytes create the microenvironment in fibrotic lungs to restrict the removal of fibroblasts.

The elevated activities of the JUN pathway in fibroblasts revealed by phospho-c-Jun specific antibodies showed the involvement of JUN pathways in the progression of pulmonary fibrosis. Indeed, by performing ATAC-seq, ChIP-seq and reporter assays, we demonstrated that JUN pathway induces profibrotic and immunosuppressive genes expression through a mechanism which forms a positive feedback loop to increase CD47 expression via IL-6. The reduction of pulmonary fibrosis in mouse fibrosis models by blocking combinations of IL-6, CD47, and PD-L1 validated the above mechanistic results and provides a therapeutic strategy to alleviate fibrosis in pulmonary fibrosis patients.

JUN is a transcription factor that coordinates the transcriptional regulation of genes that are essential for cellular growth and proliferation, such as cell cycle, self-renewal, metabolism and survival. We show that JUN expression in fibroblasts increases IL-6 expression and secretion, which has direct effects on both the adaptive and innate immune system. Furthermore, we discovered that JUN expression in fibroblasts upregulates the expression of the immune checkpoint genes PD-L1 and CD47.

Clinically, CD47 and PD-L1 are of interest because clinically relevant reagents have been developed by multiple pharmaceutical companies to target both immune checkpoint molecules. Antibody therapies against both are currently being tested in clinical trials for cancer. Further, blocking antibodies against IL-6 and IL-6 receptor are FDA approved or in clinical trials, e.g. to treat rheumatoid arthritis and acute cytokine release syndrome, a side effect of CAR-T cell therapy. Our work is the first to target immune checkpoint and immune regulatory proteins in combination with IL-6, to achieve synergy in disrupting pro-fibrotic pathways. In addition, the in vivo studies confirm our mechanistic studies—that JUN activation drives the expression of CD47 and PD-L1 in fibrotic lung fibroblasts, mediated by IL-6 signaling.

In conclusion, our data suggest that inhibition of each of these pathways (single/combined) and in particular a combination of CD47 and IL-6 blockade, is useful in treatment of pulmonary fibrosis diseases. These data provide a critical preclinical study and provide a basis for IND-enabling studies for halting or reversing the often-fatal course of pulmonary fibrosis diseases.

Methods

Isolation of fibroblasts from human tissue. Human fibroblasts were obtained from discarded fresh lung tissue from de-identified patients. The tissue was minced and filtered through 70 µm filters, centrifuged at 600 g for 5 min to remove non-homogenized pieces of tissue. Tissue homogenate was treated with ACK lysing buffer (Thermo Fisher) for 10-15 min, centrifuged for 600 g, washed twice in DMEM with 10% fetal bovine serum (Gibco) and plated at a density of approximately 500,000 cells/cm$^2$ in DMEM with 10% fetal bovine serum, 1% penicillin/streptomycin (Thermo Fisher Scientific) and Ciprofloxacin 10 µg/mL, Corning) and kept in an incubator at 37° C. 95% $O_2$/5% $CO_2$. Media was changed after 24 h and cells were cultured until 80-90% confluent before each passage.

Single Cell Mass Cytometry (CyTOF). Samples were processed as previously described. Briefly the cell samples were fixed with 2% paraformaldehyde at room temperature for 20 min followed by two washes with PBS containing 0.5% BSA. Formaldehyde-fixed cell samples were incubated with metal-conjugated antibodies against surface markers for 1 hr, washed once with PBS containing 0.5%

BSA, permeabilized with methanol on ice for 15 min, washed twice with PBS containing 0.5% BSA and then incubated with metal-conjugated antibodies against intracellular molecules for 1 hr. Cells were washed once with PBS containing 0.5% BSA, and then incubated at room temperature for 20 min with an iridium-containing DNA intercalator (Fluidigm) in PBS containing 2% paraformaldehyde. After intercalation/fixation, the cell samples were washed once with PBS containing 0.5% BSA and twice with water before measurement on a CyTOF mass cytometer (Fluidigm). Normalization for detector sensitivity was performed as previously described. After measurement and normalization, the individual files were analyzed by first gating out doublets, debris and dead cell based on cell length, DNA content and cisplatin staining. ViSNE maps were generated with publicly available software tools by considering all surface markers.

Immunostaining. Tissue sections (4 μm thickness) were cut from tissue blocks of archival deidentified human biopsies using a microtome for immunofluorescence staining. The sections were baked at 65° C. for 20 min, deparaffinized in xylene and rehydrated via a graded ethanol series. The sections were then immersed in epitope retrieval buffer (10 mM sodium citrate, pH 6) and placed in a pressure cooker for 45 min. The sections were subsequently rinsed twice with $dH_2O$ and once with wash buffer (TBS, 0.1% Tween, pH 7.2). Residual buffer was removed by gently touching the surface with a lint-free tissue before incubating with blocking buffer for 30 min. Blocking buffer was subsequently removed, and the sections were stained overnight at 4° C. in a humidified chamber. The following morning, the sections were rinsed twice in wash buffer, a secondary antibody (Invitrogen, Carlsbad, CA) was used for visualization of signal. Images of histological slides were obtained on a Leica Eclipse E400 microscope (Leica, Wetzlar, Germany) equipped with a SPOT RT color digital camera model 2.1.1 (Diagnostic Instruments, Sterling Heights, MI). For MIBI, slides were postfixed for 5 min (PBS, 2% glutaraldehyde), rinsed in dH2O and stained with Hematoxylin for 10 s, at the end, the sections were dehydrated via graded ethanol series, air dried using a vacuum desiccator for at least 24 h before imaging. MIBI imaging are performed by NanoSIMS 50 L spectroscopy (Cameca, France) at Stanford Nano Shared Facilities (SNSF) and analyzed by using Image with Plugin OpenMIMS (NRIMS).

ELISA. Bronchoalveolar lavage was harvested from patient lungs immediately (within 5 minutes) after explant, 5 mL were injected into the peripheral airspaces and at least 2 mL harvested for all specimens, which was subsequently snap frozen in liquid N2. All specimens were surgical specimens and no post-mortem specimens were included. The expression of PD-L1 and IL-6 from bronchoalveolar lavage was quantitated following the protocols of ELISA kits: Human IL-6 Quantikine ELISA Kit and Human/Cynomolgus Monkey B7-H1/PD-L1 Quantikine ELISA Kit from R&D Systems.

Lentivirus preparation. 80-90% confluent 293T cells were transfected with 4 μg Transfer plasmid (JUN tet-on overexpression plasmid, tetracycline-controllable transactivator plasmid, JUN CRISPR knock-out plasmid, TK control reporter plasmid, E7TK CD47 enhancer reporter plasmid and Luciferase-GFP plasmid), 2 μg pRRE Packing plasmid (GAG and Pol genes), 1 μg pRSV Packing plasmid (Rev gene), 1 μg pMD2.G enveloping plasmid and 24 μg PEI. The day after transfection, cell media was replaced, and cells were incubated for further 48 h, with media collection and replacement every 24 hr for twice. Cell media was centrifugated at 600 g for 10 min at 4° C. Then, supernatant was filtered through 0.22 μm strainer, ultra-centrifuged at 25,000 g for 2 h, aliquoted and flash frozen.

CRISPR-mediated genome engineering. Following the protocol from reported literature, the sequences of 2 site-specific guide RNAs (sgRNAs) that target exon 1 of the JUN gene were selected using the CRISPR Design Tool 43. Oligonucleotides with these sequences were cloned into the lentiCRISPRv2 vector (Addgene, Cambridge, MA) which uses Puromycin selection to enrich for cells with JUN knock out.

The sgRNA Sequence:

```
JUN sgRNA_1 F
CACCGTGAACCTGGCCGACCCAGTG (SEQ ID NO: 1)

JUN sgRNA_1 R
AAACCACTGGGTCGGCCAGGTTCAC (SEQ ID NO: 2)

JUN sgRNA_2 F
CACCGCCGTCCGAGAGCGGACCTTA (SEQ ID NO: 3)

JUN sgRNA_2 R
AAACTAAGGTCCGCTCTCGGACGGC (SEQ ID NO: 4)
```

Doxycycline (DOX) Inducible JUN overexpression. To generate JUN tet-on overexpression plasmid, we cloned JUN cDNA into IRES-Hygro-TetO-FUW vector (Addgene, Cambridge, MA). To introduce doxycycline (Dox) inducible JUN overexpression, the tetracycline controllable transactivator (rtTA) lentivirus was infected with JUN tet-on overexpression plasmid. Dox (2 mg/mL) was applied. Infection to turn on JUN overexpression, hygromycin selection started from the second day for 2 days.

ATAC-seq and ChIP-seq library preparation and sequencing library preparation. The primary fibrotic lung fibroblasts were infected with JUN knock-out lentiviruses, followed with 4 days puromycin selection; meanwhile the normal lung fibroblasts were infected with JUN overexpression lentiviruses, followed with 2 days hygromycin selection. A transposition reaction was initiated in each sample containing 50,000 nuclei as assessed by counting, subsequently a DNA library was prepared by using a Nextera DNA Library Preparation Kit (Illumina) and sequenced on the Illumina Nextseq 500 platform with 75-bp×2 paired-end reads. ChIPs and their respective inputs were generated as previously described. The libraries was prepared by using a TruSeq ChIP sample prepapration kit (Illumina) and sequenced by Nextseq500 pair end sequencing (75 bp).

Deep sequencing data analysis ATAC-seq and ChIP-seq data analysis used the Kundaje lab pipeline. Following tools and versions: Cutadapt v 1.9.1, Picard v1.126, Bowtie2 v2.2.8, MACS2 v2.1.0.20150731, and Bedtools v 2.26. First, Nextera adaptor sequences were trimmed from the reads by using cutadapt program v 1.9.1. These reads were aligned to human genome hg38 using bowtie2. The standard default settings were modified to allow mapped paired-end fragments up to 2 kb. Only the reads with mapping quality greater than 30 were kept, and the duplicated reads were removed using Picard tools v1.126. The reads from mitochondria were also removed, then convert PE BAM to tagAlign (BED 3+3 format) using Bedtools v 2.26 functions. Differential expression analysis were done by DESeq2. Differential peaks with p-val less than 0.01 and absolute log 2 fold change above 1.

Flow Cytometry. The analysis of IL-6 or surface molecules (CD47 and PD-1) was performed using monoclonal antibodies listed in the tables. Data were acquired by LSRII or LSRFortessa flow cytometers and analyzed using FlowJo software or Cytobank.

Protein expression and purification. Proteins blocking human or mouse PD-L1, (HACV or HACmb respectively) were produced as described previously.

Phagocytosis Assay. In vitro phagocytosis assays were performed by co-culture of $5\times10^4$ human macrophages with $1\times10^5$ CFSE-labeled fibroblasts for 2 hr in serum-free IMDM. Phagocytosis was analyzed by an LSRFortessa flow cytometer. The percentage of CFSE$^+$ macrophages was calculated and normalized to the maximal response by each independent donor against each cell line using FlowJo software (TreeStar).

Bleomycin induced mouse model and JUN induced lung fibrosis mouse model. For bleomycin administration, mice were anaesthetized with isoflurane followed by intratracheal instillation of bleomycin (4 U/kg per body weight) in 100 μl PBS as previously described. As published before, the reverse tetracycline transactivator (rtTA) ubiquitously inducible JUN from the Rosa26 promoter, and the inducible cassette is targeted the downstream of Col1a1 promotor. After crossing, the genotyping in inducible JUN mice was performed using primers for the transgene JUN and Rosa26. JUN was induced by adding doxycycline (2 mg/ml) (MilliporeSigma) to the drinking water, under the Col1a1 promotor.

In Vivo Antibody Blockade. For CD47 antibody blockade experiments, mice were injected intraperitoneally (IP) with a dosage of 500 μg CD47 antibody (Clone MP5-20F3, Bioxcell) diluted in 100 μl of PBS given on day 4. The same dosages were then given every other day up to two weeks. For PD-L1 blockade experiments, HAC protein (250 μg, IP) was given daily for entire treatment period. For IL-6 antibody blockade experiments, mice were injected intraperitoneally with 20 mg/kg dose of an anti-IL-6 monoclonal (Clone 43414, Bioxcell) antibodies twice a week for 2 weeks.

CT scan. Mice were anesthetized and CT Scans were performed using a Bruker Skycan 1276 (Bruker, Belgium). CT scans were then analyzed with the Bruker Skycan tools. To determine dense areas within the lungs, binary pictures were created using the heart as the cutoff value to split the tissue in dark (having at the least the same density as the heart) and white areas. Representative total lung and dense areas were measured in the upper and middle field. Finally, the fraction of the dense areas within the total lung areas was calculated.

Kidney capsule transplantation. After mice had been anesthetized, the areas over the right and/or left flank were shaved and disinfected. Thereafter, a flank cut was made.

The subcutaneous tissues were bluntly removed and an incision into the abdominal cavity was made. The kidney was luxate out of the abdominal cavity and a slight incision into the renal capsule was made. The renal capsule was bluntly detached from the renal tissue and $2\times10^5$ cells suspended in 10 μl of matrigel were injected under the kidney capsule. The kidney was pushed back into the abdominal cavity. The abdominal cavity and skin were closed using sutures.

Luciferase-based optimal imaging (BLI). 100 μl of luciferin substrate was intraperitoneally injected. Fifteen minutes later, optical imaging was performed using a Lago optical imaging system (Spectral imaging instruments, AZ, USA). Analysis was done with the Aura Software from the same manufacturer.

Statistics. Statistical analyses were performed using Prism software (GraphPad Software). Statistical significance was determined by the unpaired Student's t test for comparisons between two groups, one-way ANOVA with Tukey's post hoc test for multigroup comparisons (n.s., $P>0.05$; $*P<0.05$; $P<0.01$; $*P<0.001$; $****P<0.0001$). In statistical graphs, points indicate individual samples, and results represent the mean±SD unless indicated otherwise.

Data availability. Raw ATAC-seq and ChIP-seq data have been deposited in the Gene Expression Omnibus (GEO) database under accession code GSE115235. JUN ChIP-seq of HepG2 (GSM935364), MCF-7 (GSE91550), H1-hESC (GSM935614), A549 (GSE92221) and K562 (GSM1003609), Histone ChIP-seq data of H3K4me3 (GSM733723), H3K27ac (GSM733646), H3K9me3 (GSM1003531) and H3K27me3 (GSM733764) and RNA-seq data of fibrotic lungs (GSE52463) are from public GEO database.

Study approval. De-identified patient specimens in paraffin and discarded fresh patient tissues were used for our studies as approved in IRB-39881 and 18891. We received primary lung tissues exclusively from patients with end-stage pulmonary fibrosis undergoing transplantation. Therefore our cohort of patients represents severely fibrotic lung disease. It has been challenging to receive normal control lung tissues. While we have received lung tissues from normal lung resections from tumor resections from Stanford tissue bank as well as lungs from rapid autopsies, it appeared that only normal lung tissues harvested during surgery by tissue bank were of sufficient viability to include in our CyTOF studies; while other cell type fractions appeared representative we noted a bias towards less endothelial cells in the normal biopsies due to the relatively small amounts of lung tissue we received from tissue bank. Mice were maintained in Stanford University Laboratory Animal Facility in accordance with Stanford Animal Care and Use Committee and National Institutes of Health guidelines.

TABLE 1

| Patient # | Age (years) | Gender | Ethnicity | Smoking Status | IPF Stage | Pathology | Oxygen in LPM rest | DLCO % predicted | Comorbidities |
|---|---|---|---|---|---|---|---|---|---|
| 1 | 61 | Male | Asian | Non-smoker | endstage, fibrosing ILD | NSIP, PAR, BAC, honeycomb | 6-8 | 20 | GERD |
| 2 | 89 | Male | Caucasian | Former smoker | endstage, fibrosing ILD | UIP, honeycomb | 8 | 22 | GERD, DM type II |
| 3 | 72 | Male | Caucasian | Former smoker—quit 1976 | endstage, fibrosing ILD | UIP, honeycomb | 4-6 | <30 | none |
| 4 | 85 | Female | Caucasian | 2nd exposure, Non-smoker | endstage, fibrosing ILD | UIP, honeycomb | 4-6 | 25% | Hypercholesterolemia, DM type II |
| 5 | 69 | Male | Caucasian | Former smoker | endstage, fibrosing ILD | UIP, PAH, honeycomb | 8 | <20 | ILD, GERD, depression |
| 6 | 72 | Male | Caucasian | Never smoker | endstage, fibrosing ILD | UIP, honeycomb | 8 | 22 | GERD, HTN, Sleep aprise, ILD, skin cancer, BCC, SCC |
| 7 | 68 | Male | Caucasian | Former smoker—quit 1980 | endstage, fibrosing ILD | NSIP | 6 | 20 | SSC, psoriesis, OSA, HTN, obese |
| 8 | 88 | Male | Caucasian | Former smoker—quit 1990, 25 pack years | endstage, fibrosing ILD | UIP, honeycomb | 6 | 20 | GERD, HTN, CKD |
| 9 | 63 | Male | Caucasian | Former smoker—quit 1995, 25 pack years | endstage, fibrosing ILD | UIP, honeycomb | 10 | 18 | MCI, CAD, HTN, DM type II, hyperlipid, GERD, depression |
| 10 | 54 | Male | Hispanic | Former smoker | endstage, fibrosing ILD | chronic hypersens pneumonite | 4 | 19 | ILD, GERD, DM type II, TBC |
| 11 | 60 | Female | Asian | Non-smoker | endstage, fibrosing ILD | chronic hypersens pneumonite, PAH | 4 | 23 | GERD, HTN, hyperlipid, DM type II |
| 12 | 59 | Male | Caucasian | Former smoker | normal lung tissue, lobectomy# | normal lung tumor lung adenoCA | N/A | N/A | lung adenoCA |
| 13 | 86 | Male | Caucasian | Former smoker | normal lung tissue, lobectomy# | normal lung tumor lung adenoCA | N/A | N/A | lung adenoCA |
| 14 | 72 | Male | Caucasian | Former smoker | normal lung tissue, lobectomy# | normal lung tumor lung adenoCA | N/A | N/A | lung adenoCA |

*All the ILD patients included in the studies had histologic or radiographic evidence of end-stage fibrosing interstitial lung disease (ILD): UIP (8), fibrotic NSIP (2), fibrotic chronic interstitial pneumonitis (2), DLCO all severe decreased DLCO between <25% of predicted, FVC <80%, FVC 10% or greater decrement in FVC during 6-month follow-up, 6 minute walk pulse oximetry below 88% or 50 m decline in over 6 months, patients
**associated pulmonary hypertensive (PAH) features on histopathology.

Our healthy control lung specimens were derived from lung lobectomy specimens for lung cancer, we only received histologic healthy appearing lung distant from the tumor (lung specimen weights 150–200 g, tumor diameters ranging 0.8–2 cm, stage pT2pN0).

TABLE 2

| CYTOF | | | | | | | | | |
|---|---|---|---|---|---|---|---|---|---|
| Human Panel 1 | | | | | Human Panel 2 | | | | |
| Isotope | Protein | Clone | Manufacturer | Conc. (ug/mL) | Isotope | Protein | Clone | Manufacturer | Conc. (ug/mL) |
| Y | CD45 | HI30 | Fluidigm | 0.25 ul/100 ul | In | HLA-DR | L243 | Biolegend | 1.5 |
| In | CD61 | VI-PL2 | Bioleqend | 1 | Pr | CD235 | HIR2 | Fluidigm | 1 ul/100 ul |
| In | HLADR | L243 | Biolegend | 1.5 | Nd | Frat | sc-376148 | SANTA CRUZ | 2 |
| La | CD8 | RPA-T8 | Biolegend | 2 | Nd | Npm1 | H-106 | SANTA CRUZ | 6 |
| Pr | CD123 | 6H6 | Biolegend | 0.5 | Nd | CD47 | B6H12 | BD | 1.5 |
| Nd | CD19 | HIB19 | Fluidigm | 0.5 ul/100 ul | Sm | CK7 | OV-TL 12/30 | Millipore | 4 |
| Nd | Calreticulin | JM-3077-100J | MBL international | 3 | Nd | CD34 | 581 | Fluidigm | 1 ul/ 100 ul |
| Nd | CD11c | Bu15 | Biolegend | 0.5 | Sm | junB | sc-73 | SANTA CRUZ | 4 |
| Nd | CD4 | RPA-T4 | Fluidigm | 0.25 ul/100 ul | Nd | junD | ab28837 | Abcam | 4 |
| Nd | CD3 | UCHT1 | Biolegend | 1 | Eu | CD123 | 6H6 | Fluidigm | 1 ul/ 100 ul |
| Sm | CK7 | OV-TL 12/30 | Millipore | 4 | Sm | phospho AKT pS473 | D9E | Fluidigm | 1.5 ul/100 ul |
| Nd | CD16 | 3G8 | Fluidigm | 0.5 ul/100 ul | Eu | phospho MAPKAPK 2 pT334 | 27B7 | Cell Signaling | 4 |
| Sm | CD25 | 2A3 | Fluidigm | 0.5 ul/100 ul | Sm | phospho c-Jun pS73 | D47G9 | Cell Signaling | 4 |
| Nd | LAG3 | 11C3C65 | Fluidigm | 1 ul/100 ul | Gd | Dusp1 | C-19 | SANTA CRUZ | 0.75 |
| Eu | ICOS | C398.4A | Fluidigm | 0.5 ul/100 ul | Gd | CD7 | M-T701 | BD | 1 |
| Sm | phospho AKT pS473 | D9E | Fluidigm | 1.5 ul/100 ul | Gd | c-Fos | ab209794 | Abcam | 2 |
| Eu | CD45RA | HI100 | Fluidigm | 0.15 ul/100 ul | Tb | CD11c | Bu15 | Fluidigm | 1 ul/100 ul |
| Sm | phospho c-Jun pS73 | D47G9 | Cell Signaling | 4 | Gd | CD14 | M5E2 | Fluidigm | 1 ul/100 ul |
| Gd | IDO | D5J4E | Fluidigm | 0.25 ul/100 ul | Dy | Fra2 | sc-171 | SANTA CRUZ | 2 |
| Gd | CD86 | IT2.2 | Fluidigm | 0.5 ul/100 ul | Dy | CD3 | UCHT1 | Biolegend | 1.5 |
| Gd | CD28 | CD28.2 | Biolegend | 2 | Dy | FosB | sc-48 | SANTA CRUZ | 0.5 |
| Gd | CD169 | 7-239 | Fluidigm | 0.5 ul/100 ul | Ho | CD163 | GHI/61 | Fluidigm | 1 ul/100 ul |
| Tb | CCR7 | G043H7 | Fluidigm | 1 ul/100 ul | Er | phospho Rb pS807/pS811 | J112-906 | BD | 1.5 |
| Gd | PDGFRa | D13C6 | Fluidigm | 0.5 ul/100 ul | Er | phospho Erk1/2 pT202/pY204 | D13.14.4E | Fluidigm | 1.5 ul/100 ul |
| Dy | Tbet | 4B10 | Fluidigm | 0.5 ul/100 ul | Er | phospho HistoneH3 pS28 | HTA28 | Biolegend | 0.5 |
| Dy | Foxp3 | PCH101 | Fluidigm | 0.75 ul/100 ul | Tm | phospho p38 pT180/pY182 | 36/p38 | BD | 2 |
| Dy | PDL2 | 24F.10C12 | Fluidigm | 1 ul/100 ul | Er | CD68 | Y1/82A | Biolegend | 3 |
| Dy | podoplanin | ab10288 | Abcam | 2 | Yb | CD31 | WM59 | Biolegend | 1.5 |
| Ho | CD163 | GHI/61 | Fluidigm | 1 ul/100 ul | Yb | cleaved PARP | F21-852 | BD | 3 |
| Er | ARG1 | polyclonal | Fluidigm | 0.5 ul/100 ul | Yb | phospho JNK/SAPK pT183/pY185 | G9 | Cell Signaling | 3 |
| Er | GATA3 | TWAJ | Fluidigm | 0.75 ul/100 ul | Lu | phospho S6 S235/S236 | N7-548 | Fluidigm | 1 ul/100 ul |
| Er | CD206 | 15-2 | Fluidigm | 0.5 ul/100 ul | Yb | phospho CREB pS133 | 87G3 | CST | 1 |
| Tm | TIM3 | 344823 | R&D system | 2 | Ir | DNA | | | |
| Er | CD68 | Y1/82A | Biolegend | 1 | Pt | cisplatin | | | |
| Yb | PDL1 | 29E.2A3 | Biolegend | 1 | | | | | |
| Yb | CD31 | WM59 | Biolegend | 1 | | | | | |
| Yb | cPARP/CD235a | F21-852/HIR2 | BD/Biolegend | 0.5/0.125 | | | | | |
| Yb | eomes | WD1928 | eBioscience | 2 | | | | | |
| Lu | PD1 | EH12.2H7 | Fluidigm | 0.5 ul/100 ul | | | | | |

TABLE 2-continued

| | | | | | |
|---|---|---|---|---|---|
| Yb | | CD56 | NCAM16.2 | BD | 1 |
| Ir | | DNA | | | |
| Pt | | cisplatin | | | |
| Bi | | CD47 | CC2C6 | Fluidigm | 0.75 ul/100 ul |

Mouse Panel 1

| Metal Isotope | Mass | Protein | Clone | Manufacturer | Conc. (ug/mL) |
|---|---|---|---|---|---|
| Y | 89 | CD45 | 30-F11 | Fluidiqm | 0.25 ul/100 ul |
| In | 113 | TER119 | TER119 | Biolegend | 2 |
| In | 115 | Seal | E13-161.7 | Biolegend | 0.5 |
| La | 139 | Ly6G/C | 1A8 | Biolegend | 2 |
| Ce | 140 | CD11b | M1/70 | Biolegend | 2 |
| Pr | 141 | F4/80 | BM8 | Biolegend | 1 |
| Nd | 142 | CD47 | miap301 | Biolegend | 2 |
| Nd | 143 | calreticulin | JM-3077-100J | MBL international | 4 |
| Nd | 144 | CD16/32 | 93 | Fluidigm | 1 ul/100 ul |
| Nd | 145 | CD172a | P84 | BD Biosciences | 0.75 |
| Nd | 146 | CD80 | 16-10a1 | Biolegend | 4 |
| Sm | 147 | beta catenin | D10A8 | Fluidigm | 1 ul/100 ul |
| Nd | 148 | CD278 | C398.4A | Fluidigm | 1 ul/100 ul |
| Sm | 149 | KLRG1 | 2F1 | BD Biosciences | 8 |
| Nd | 150 | CD275 | HK5.3 | Biolegend | 2 |
| Eu | 151 | CD28 | 37.51 | Fluidigm | 2 ul/100 ul |
| Sm | 152 | CD3 | 145-2C11 | Fluidigm | 1 ul/100 ul |
| Eu | 153 | CD274 | 10F.9G2 | Fluidigm | 0.5 ul/100 ul |
| Sm | 154 | p-cJun | D47G9 | Cell Signaling Technology | 4 |
| Gd | 155 | CD4 | RM4-5 | Biolegend | 0.5 |
| Gd | 156 | CD90 | 30-H12 | Fluidigm | 0.25 ul/100 ul |
| Gd | 157 | CD41 | MWReg30 | Biolegend | 2 |
| Gd | 158 | Foxp3 | FJK-16S | Fluidigm | 4 ul/100 ul |
| Tb | 159 | PD-1 | RMP1-30 | Fluidigm | 2 ul/100 ul |
| Gd | 160 | tbet | 4B10 | Fluidigm | 4 ul/100 ul |
| Dy | 161 | EOMES | Dan11mag | eBioscience | 2 |
| Dy | 162 | CD115 | AFS98 | Biolegend | 1 |
| Dy | 164 | CD62L | MEL-14 | Fluidigm | 1 ul/100 ul |
| Ho | 165 | CD31 | 390 | Fluidigm | 2 ul/100 ul |
| Er | 166 | CD19 | 6D5 | Fluidigm | 1 ul/100 ul |
| Er | 167 | pErk | D13.14.4E | Fluidigm | 1 ul/100 ul |
| Er | 168 | CD8 | 53-6.7 | Fluidigm | 0.5 ul/100 ul |
| Tm | 169 | EpCAM | G8.8 | Biolegend | 2 |
| Er | 170 | CD49b | HMa2 | Fluidigm | 1 ul/100 ul |
| Yb | 171 | CD44 | IM7 | Fluidigm | 0.1 ul/100 ul |
| Yb | 172 | CD86 | GL1 | Fluidigm | 1 ul/100 ul |
| Yb | 173 | CTLA4 | UC10-4B9 | eBioscience | 4 |
| Yb | 174 | CD223 | C9B7W | Fluidigm | 2 ul/100 ul |
| Lu | 175 | CD273 | TY25 | Biolegend | 4 |
| Yb | 176 | B220 | RA3-6B2 | Biolegend | 1 |
| Ir | 191/193 | DNA | | | |
| Pt | 195 | Cisplatin | | | |
| Bi | 209 | MHCH | M5/114.15.2 | Fluidigm | 0.25 ul/100 ul |

MIBI

| Metal Isotope | Mass | Protein | Clone | Manufacturer |
|---|---|---|---|---|
| La | 139 | Collagen1 | ab34710 | Abeam |
| Nd | 142 | Fra1 | sc-376148 | SANTA CRUZ |
| Nd | 144 | eJun | ab31419 | Abeam |
| Nd | 145 | CD47 | B6H12 | BD |
| Sm | 149 | junB | sc-73 | SANTA CRUZ |
| Nd | 150 | junD | ab28837 | Abeam |
| Gd | 158 | cFos | ab209794 | Abeam |
| Dy | 162 | Fra2 | sc-171 | SANTA CRUZ |
| Dy | 164 | FosB | sc-48 | SANTA CRUZ |

FACS

| Antigen | Vendor | Clone | Staining Concentration |
|---|---|---|---|
| IL6 | Fluidigm | MQ213A5 | 1:50 |
| CD47 | Abcam | B6H12 | 1:100 |
| PD1 | Biolegend | EH12.2H7 | 1:100 |
| CD326 | Biolegend | 9C4 | 1:100 |

TABLE 2-continued

| | | | |
|---|---|---|---|
| CD45 | Biolegend | HI30 | 1:100 |
| CD31 | Biolegend | WM59 | 1:100 |

IHC

| Antigen | Vendor | Clone | Staining Concentration | fluorochromes |
|---|---|---|---|---|
| Collagen1 | Abcam | ab34710 | 1:100 | Alexa Fluor 594 |
| Actin, Smooth Muscle (SMA) | cell marque | 1A4 | 1:200 | Alexa Fluor 488 |
| CD47 | Abcam | B6H12.2 | 1:50 | Alexa Fluor 488 |
| PDL1 | CST | E1L3N | 1:100 | Alexa Fluor 594 |
| PD1 | Cell marque | NAT105 | 1:100 | Alexa Fluor 594 |
| PD1 | Abcam | EPR48772 | 1:100 | Alexa Fluor 488 |
| CD68 | Dako | KP1 | 1:200 | Alexa Fluor 488 |
| CD3 | Abcam | ab5690 | 1:100 | Alexa Fluor 594 |
| PDL1 | Abcam | MIH6 | 1:100 | Alexa Fluor 488 |
| FSP1 | EMD | 07-2274 | 1:200 | Alexa Fluor 594 |
| GFP | Abcam | ab13970 | 1:100 | Alexa Fluor 488 |

TABLE 3

CYTOF analysis of total numbers of live cells, fibroblasts and macrophages in human pulmonary fibrosis lungs and normal healthy non-fibrotic lungs.

| | Total live | Fibroblasts | Macrophage |
|---|---|---|---|
| PF-1 | 54734 | 26626 | 5209 |
| PF-2 | 204489 | 82094 | 11889 |
| PF-3 | 210786 | 19595 | 15715 |
| PF-4 | 16770 | 5104 | 1903 |
| PF-5 | 27951 | 1969 | 9563 |
| PF-6 | 79863 | 7778 | 17634 |
| PF-7 | 198291 | 149534 | 7322 |
| PF-8 | 21353 | 10575 | 2270 |

TABLE 3-continued

CYTOF analysis of total numbers of live cells, fibroblasts and macrophages in human pulmonary fibrosis lungs and normal healthy non-fibrotic lungs.

| | Total live | Fibroblasts | Macrophage |
|---|---|---|---|
| PF-9 | 86505 | 34367 | 17169 |
| PF-10 | 50439 | 31280 | 971 |
| PF-11 | 52805 | 11608 | 2409 |
| NC-1 | 175103 | 147576 | 2821 |
| NC-2 | 180465 | 58518 | 27427 |
| NC-3 | 215871 | 34424 | 34238 |

TABLE 4

| Results | Method | p-value | label | N | | t value/F value |
|---|---|---|---|---|---|---|
| FIG. 1i | unpaired t test (Two-tailed) | | | | mean with SD | |
| | JUN | 0.0097 | ** | IPF = 5; Normal = 3 | | t = 3.520 df = 7 |
| | PDL1 | 0.0204 | * | IPF = 5; Normal = 3 | | t = 2.983 df = 7 |
| | CD47 | 0.0351 | * | IPF = 5; Normal = 3 | | t = 2.607 df = 7 |
| FIG. 2f | unpaired t test (Two-tailed) | 0.0079 | ** | IPF = 11; Normal = 3 | mean with SD | t = 3.298 df = 10.09 |
| FIG. 3b | unpaired t test (Two-tailed) | | | | mean with SD | |
| | CD4 | <0.0001 | *** | IPF = 11; Normal = 3 | | t = 10.26 df = 13 |
| | CD8 | 0.0001 | *** | IPF = 11; Normal = 3 | | t = 5.300 df = 13 |
| FIG. 3d | unpaired t test with Welch's correction (Two-tailed) | <0.0001 | **** | IPF = 11; Normal = 3 | mean with SD | t = 6.138 df = 12.19 |
| FIG. 3f | unpaired t test with Welch's correction (Two-tailed) | 0.0102 | * | IPF = 11; Normal = 3 | mean with SD | t = 3.083 df = 11.23 |
| FIG. 4b | Ratio paired t test | | | | | |
| | JUN | 0.0032 | ** | 4 repeats | mean with SD | t = 8.740 df = 3 |
| | PDL1 | 0.0003 | *** | 4 repeats | mean with SD | t = 5.46 df = 3.307 |
| | CD47 | 0.0012 | ** | 4 repeats | mean with SD | t = 11.87 df = 3.026 |
| FIG. 4f | Ordinary one-way ANOVA (Tukey's multiple comparisons test) | | | | mean with SD | F (4, 10) = 33.18 |
| | D0 vs. D3 | 0.161 | ns | 3 repeats | | |
| | D0 vs. D6 | <0.0001 | **** | 3 repeats | | |
| | D6 vs. D6-7 | 0.0009 | *** | 3 repeats | | |
| | D6 vs. D6-10 | <0.0001 | **** | 3 repeats | | |
| FIG. 4g | Ordinary one-way ANOVA (Tukey's multiple comparisons test) | | | | mean with SD | F (2, 5) = 55.44 |
| | Baseline vs. cJUN-OE | 0.0013 | ** | 3 repeats | | |
| | Baseline vs. cJUN-KO | 0.0799 | ns | 3 repeats | | |
| | cJUN-OE vs. cJUN-KO | 0.0004 | *** | 3 repeats | | |

TABLE 4-continued

| Results | Method | p-value | label | N | | t value/F value |
|---------|--------|---------|-------|---|---|-----------------|
| FIG. 5d | Ratio paired t test | 0.0009 | *** | 4 repeats | mean with SD | t = 3.43 df = 3.009 |
| FIG. 5e | Ordinary one-way ANOVA (Bonferroni's multiple comparisons test) | | | | mean with SD | F (3, 8) = 1376 |
| | 0 ng/uL vs 1 ng/uL | <0.0001 | **** | 3 repeats | | |
| | 0 ng/uL vs 10 ng/uL | <0.0001 | **** | 3 repeats | | |
| | 0 ng/uL vs 100 ng/uL | <0.0001 | **** | 3 repeats | | |
| FIG. 5f | Ordinary one-way ANOVA (Tukey's multiple comparisons test) | | | | mean with SD | F (3, 4) = 63.00 |
| | 0 ng/uL vs 1 ng/uL | 0.7222 | ns | 3 repeats | | |
| | 0 ng/uL vs 10 ng/uL | 0.0062 | ** | 3 repeats | | |
| | 0 ng/uL vs 100 ng/uL | 0.0017 | ** | 3 repeats | | |
| FIG. 6d | Ordinary one-way ANOVA (Tukey's multiple comparisons test) | | | | mean with SD | F (8, 15) = 9.874 |
| | WT vs. IL6KO | 0.09816 | ns | 5 mice | | |
| | WT vs. WT + HAC | 0.4725 | ns | 5 mice | | |
| | WT vs. IL6KO + HAC | 0.0037 | ** | 5 mice | | |
| | WT vs. WT + HAC + aCD47 | 0.0196 | * | 5 mice | | |
| | WT vs. IL6KO + HAC + aCD47 | 0.0037 | ** | 5 mice | | |
| | WT vs. WT + aIL6 + HAC + CD47 | 0.0009 | *** | 5 mice | | |
| | WT vs. WT (PBS) | 0.0003 | | 5 mice | | |
| | WT. vs. IL6KO (PBS) | 0.0004 | *** | 5 mice | | |
| FIG. S1c | unpaired t test (Two-tailed) | | | | mean with SD | |
| | PDL1 (unpaired t test with Welch's correction) | 0.0032 | ** | 5 different fields | | t = 6.314 df = 4.007 |
| | CD47 | <0.0001 | **** | 5 different fields | | t = 15.45 df = 8 |
| FIG. S1f | unpaired t test (Two-tailed) | 0.0144 | * | IPF = 5; Normal = 3 | Min to Max | t = 2.621 df = 26 |
| FIG. S2d | unpaired t test (Two-tailed) | 0.0406 | * | IPF = 11; Normal = 3 | mean with SD | t = 2.273 df = 13 |
| FIG. S2e | unpaired t test with Welch's correction (Two-tailed) | 0.0054 | ** | 5 different fields | mean with SD | t = 5.190 df = 4.298 |
| FIG. S3c | unpaired t test (Two-tailed) | <0.0001 | * | IPF = 11; Normal = 3 | mean with SD | t = 5.973 df = 13 |
| FIG. S3d | unpaired t test with Welch's correction (Two-tailed) | 0.0003 | *** | 5 different fields | mean with SD | t = 10.11 df = 4.591 |
| FIG. S5b | unpaired t test with Welch's correction | 0.0005 | *** | IPF = 5; Normal = 3 | Min to Max | t = 4.887 df = 11.05 |
| FIG. S6e | Ordinary one-way ANOVA (Dunnett's) | | | | mean with SD | |
| PDL1 | WT PBS vs WT Bleo | <0.0001 | **** | 5 mice | | F (4, 20) = 132.1 |
| | WT PBS vs WT Bleo combo | 0.95 | ns | 5 mice | | |
| | WT PBS vs IL6KO bleo | <0.0001 | **** | 5 mice | | |
| | WT PBS vs IL6KO bleo combo | 0.9765 | ns | 5 mice | | |
| CD47 | WT PBS vs WT bleo | <0.0001 | **** | 5 mice | | F (4, 20) = 90.42 |
| | WT PBS vs WT bleo combo | 0.9999 | ns | 5 mice | | |
| | WT PBS vs IL6KO bleo | <0.0001 | **** | 5 mice | | |
| | WT PBS vs IL6KO bleo combo | 0.9999 | ns | 5 mice | | |
| Collage | WT PBS vs WT bleo | <0.0001 | **** | 5 mice | | F (4, 20) = 325.7 |
| | WT PBS vs WT bleo combo | 0.9962 | ns | 5 mice | | |
| | WT PBS vs IL6KO bleo | <0.0001 | **** | 5 mice | | |
| | WT PBS vs IL6KO bleo combo | 0.8716 | ns | 5 mice | | |
| FIG. S6f | Ordinary one-way ANOVA (Tukey's muliple comparisons test) | | | | mean with SD | F (3, 40) = 27.37 |
| | PBS vs. HAC | 0.0244 | * | 5 repeats | | |
| | PBS vs. anti-CD47 | <0.0001 | **** | 5 repeats | | |
| | PBS vs. anti-CD47, HAC | <0.0001 | **** | 5 repeats | | |
| FIG. S6h | Two-way ANOVA (Tukey's muliple comparisons test) | | | | mean with SD | F (3, 12) = 4.107 |
| | IPF HAC 0 d vs HAC 7 d | 0.0057 | | 3 mice | | |

Example 2

CD47 Prevents the Elimination of Diseased Fibroblasts in Scleroderma

Scleroderma is a devastating fibrotic autoimmune disease. Current treatments are partly effective in preventing disease progression, but do not remove fibrotic tissue. Here, we evaluated whether scleroderma fibroblasts take advantage of the "don't-eat-me-signal" CD47 and whether blocking CD47 enables the body's immune system to get rid of diseased fibroblasts. To test this approach, we used a Jun-inducible scleroderma model. We first demonstrated in patient samples that scleroderma upregulated JUN and increased promotor accessibilities of both JUN and the CD47. Next, we established our scleroderma model demonstrating that Jun mediated skin fibrosis through the hedgehog-dependent expansion of CD26+Sca1− fibroblasts in mice. In a niche-independent adaptive transfer model, JUN steered graft survival and conferred increased self-renewal to fibroblasts. In vivo, JUN enhanced the expression of CD47, and inhibiting CD47 eliminated an ectopic fibroblast graft and increased in vitro phagocytosis. In the syngeneic mouse, depleting macrophages ameliorated skin fibrosis. Therapeutically, combined CD47 and IL6 blockade reversed skin fibrosis in mice and led to the rapid elimination of ectopically transplanted scleroderma cells. Altogether, our study demonstrates the efficiency of combining different immunotherapies in treating scleroderma and provide a rationale for combining CD47 and IL6 inhibition in clinical trials.

Immune therapy has changed the therapeutic landscapes for several cancers within a few years, unleashing the body's own immune system in its fight against the tumor. PD1/PDL1 inhibition boosts T cell function and is approved as a first-line therapy for various cancers including NSCLC. CD47 prevents macrophages from eating their target cell and CD47 inhibition is currently investigated in advanced clinical trials. In contrast to immune checkpoint inhibitors and "don't-eat-me-signals", interleukin 6 blockade aims at reducing inflammatory responses that can worsen autoimmune diseases.

This study aimed at investigating whether the "don't-eat-me-signal" CD47 either alone or in combination with interleukin 6 blockade is able to prevent or reverse fibrotic skin changes in a Jun-driven mouse model. We hypothesized that this combination would allow the immune system to get rid of abnormal fibroblasts while preventing an ongoing inflammatory response through interleukin 6 blockade.

Results

Figures 16C, 16D:
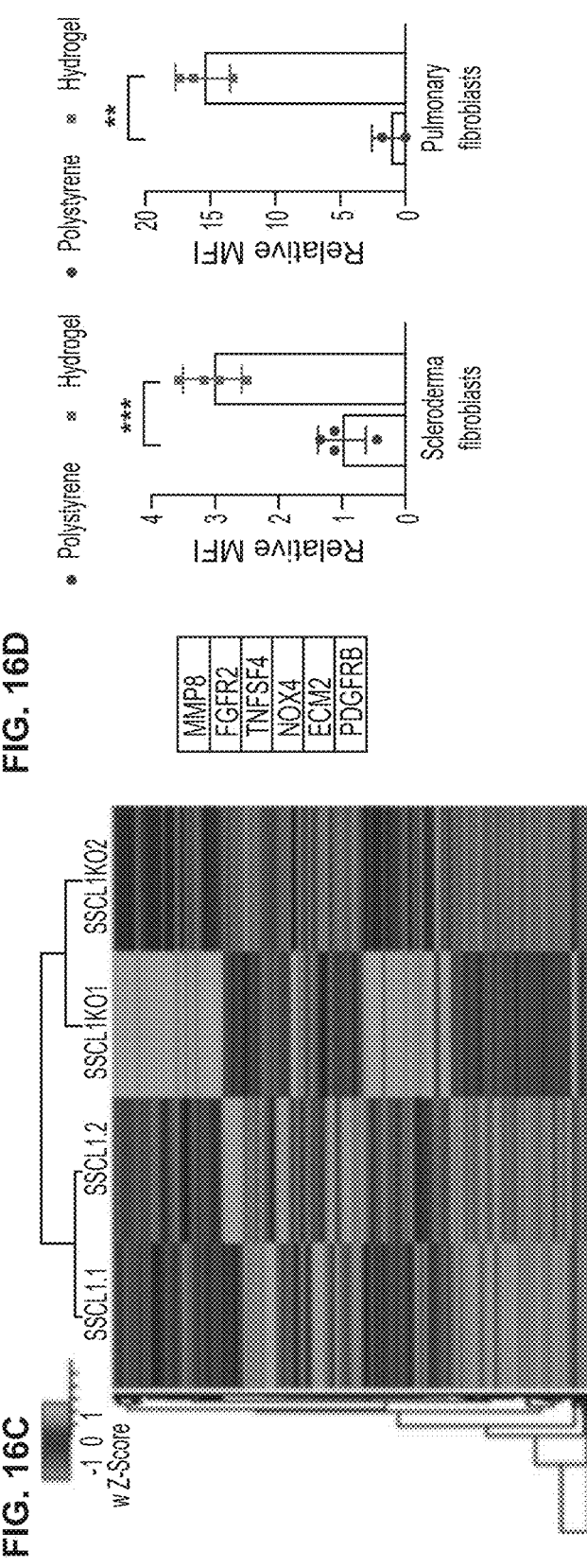
FIG. 16. Human scleroderma upregulates JUN. (A) IF pictures of human scleroderma and normal skin stained against pJUN and FSP1, counterstained with DAPI. Scale bar=25 μm. n=8-10. (B) Corresponding quantification of pJUN+ fibroblasts. Two-sided t-test. ***p<0.001. n=8-10. Bar graphs represent means with standard deviations.
Figure 23:
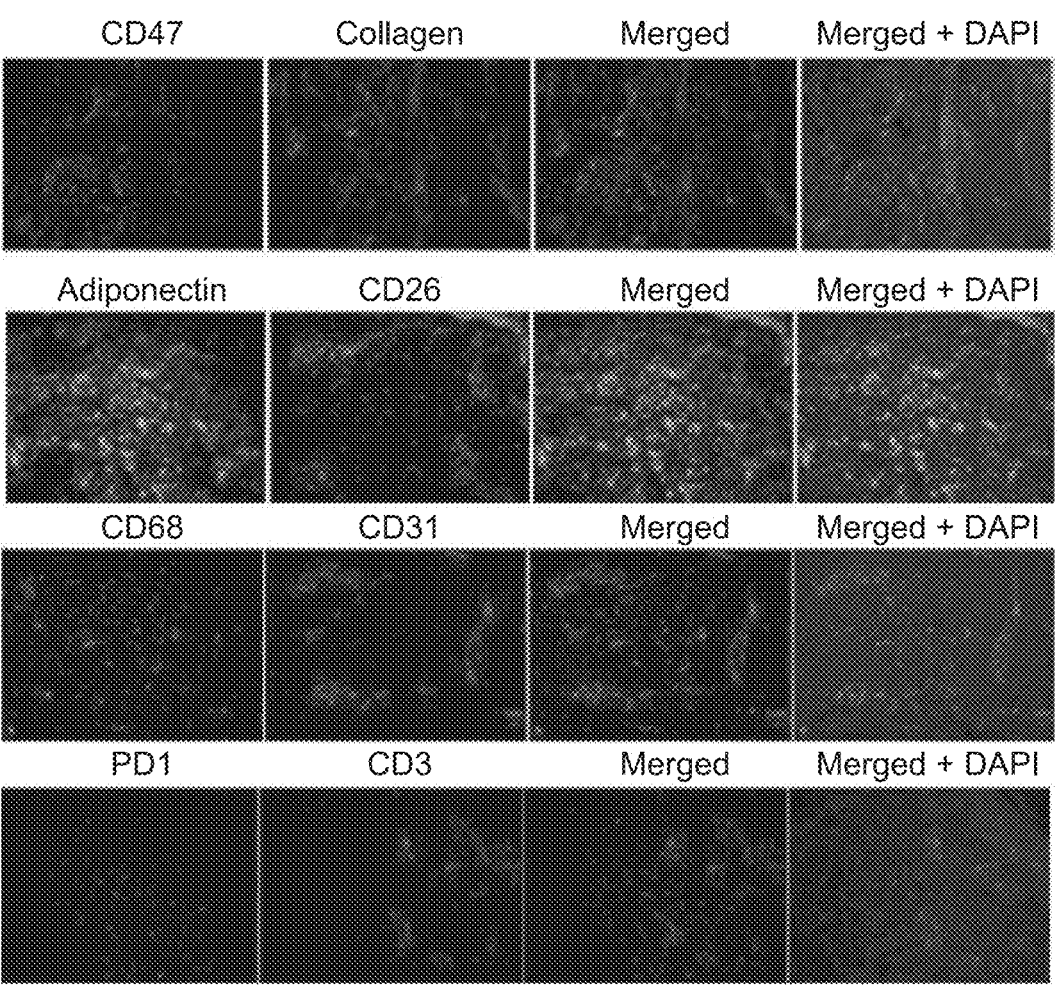
FIG. 23. Expression of different markers in human scleroderma samples. Chromatin accessibility changes in human scleroderma samples. Representative images of human scleroderma skin sections stained against different markers.

Human scleroderma activates JUN and CD47. At the beginning, we determined if JUN, CD47 and PDL1 are commonly upregulated in human scleroderma. Staining tissue sections, almost all FSP1+ fibroblasts in scleroderma but only a minority of FSP1+ fibroblasts in normal skin expressed pJUN (FIG. 16A, B). We then evaluated how primary dermal fibroblasts from scleroderma and normal skin regulate promotor accessibility of JUN and the hedgehog-associated genes GLI1 and PTCH1 through ATAC Seq studies (FIG. 17A). In addition, we ran these studies after JUN knockout and under vismodegib to study the effects of JUN and hedgehog inhibition in scleroderma fibroblasts (FIG. 17A). In accordance with our hypothesis, promotor accessibilities of JUN, GLI1 and PTCH were increased in scleroderma compared to normal skin (FIG. 17A). Vice versa, knocking JUN out decreased the promotor accessibility of GLI1 and PTCH1. As the focus of our study was to evaluate immune therapy, we analyzed the ATAC Seq data for CD47, PDL1 and IL6 as well (FIG. 17B). Promotor accessibility of all three genes was increased in scleroderma fibroblasts and JUN knockout led to decreased promotor accessibilities of CD47, PDL1 and IL6. Finally, ATAC Seq demonstrated distinct promotor accessibility clustering before and after JUN knockout in scleroderma fibroblasts and increased promotor accessibilities of several fibrosis-associated genes (FIG. 17C, D). Immunostainings of human scleroderma samples confirmed the expression of CD47, CD26 and PD1 (FIG. 23). The ATAC Seq studies did not answer which mechanism leads to the activation of JUN in scleroderma fibroblasts. One characteristic of the scleroderma skin, that it shares with all other fibrotic diseases, is its increased stiffness. To test if stiffer conditions themselves induce JUN activation, we plated primary scleroderma fibroblasts either on a stiff 70 kDa hydrogel or on a regular polystyrene dish. After two days, pJUN was significantly increased on the hydrogel, a result that we confirmed with primary pulmonary fibroblasts (FIG. 17E). In conclusion, our results with patient sections and human fibroblasts indicated that JUN was activated in human scleroderma both on the protein and the molecular level, that JUN interacts with the hedgehog pathway, and stiffer conditions on a hydrogel themselves induce JUN activation.

Figures 18A, 18B:
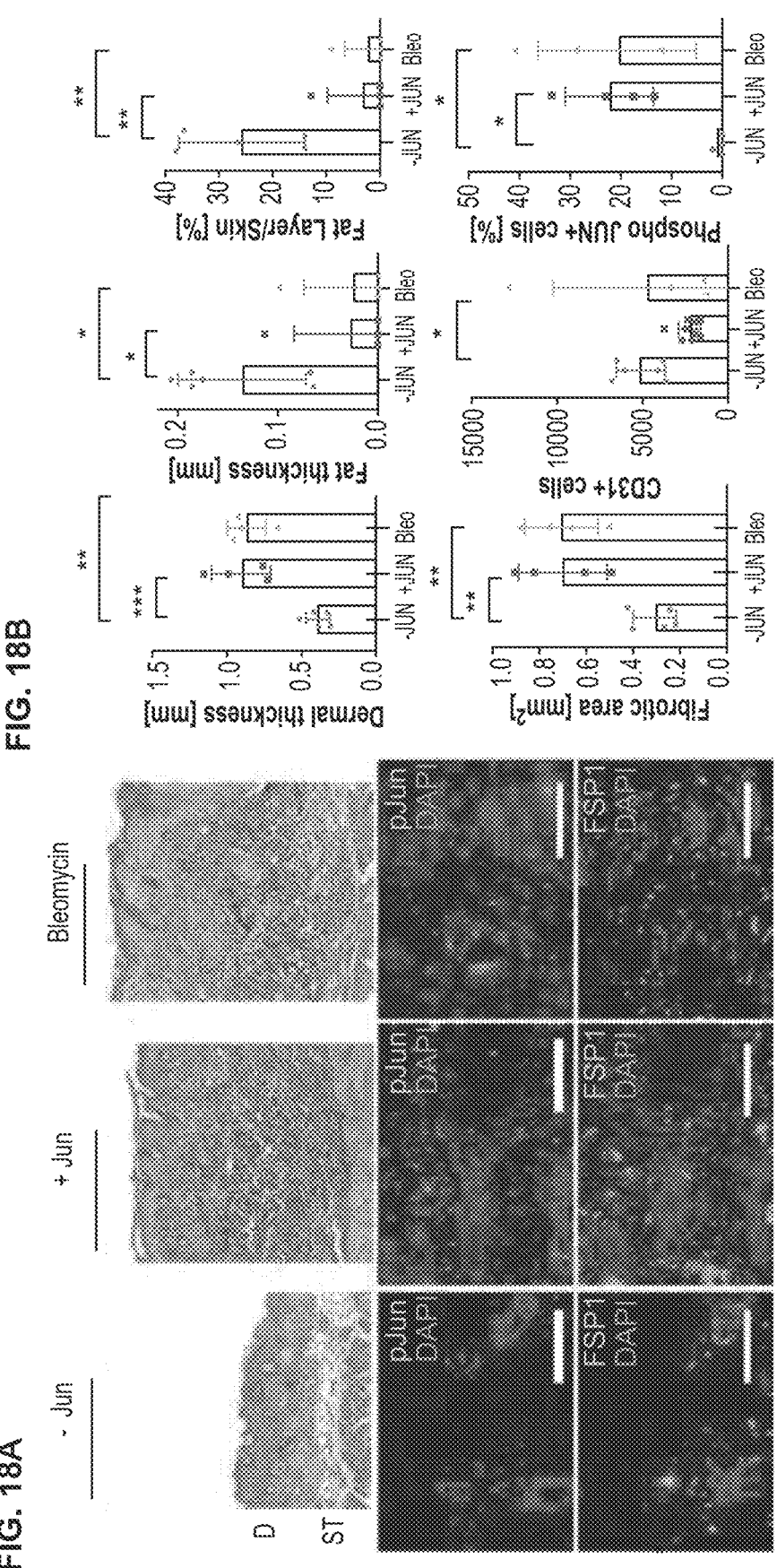
FIG. 18. JUN induces skin fibrosis in mice. (A) Representative trichrome stains and immunofluorescence stains against pJUN and FSP1 without JUN induction (−JUN), with JUN induction (+JUN) and after bleomycin injection. Black scale bar=500 μm. White scale bar=75 μm. (B) Corresponding quantification of dermal thickness, fat layer thickness, fat/skin thickness relationship, fibrotic areas, total CD31+ endothelial cells and dermal pJUN+ cells/Field of view. Turkey's multiple comparisons test. *p<0.05 p<0.01 *p<0.001. n=4-8. Bar graphs represent means with standard deviations.
Figure 24:
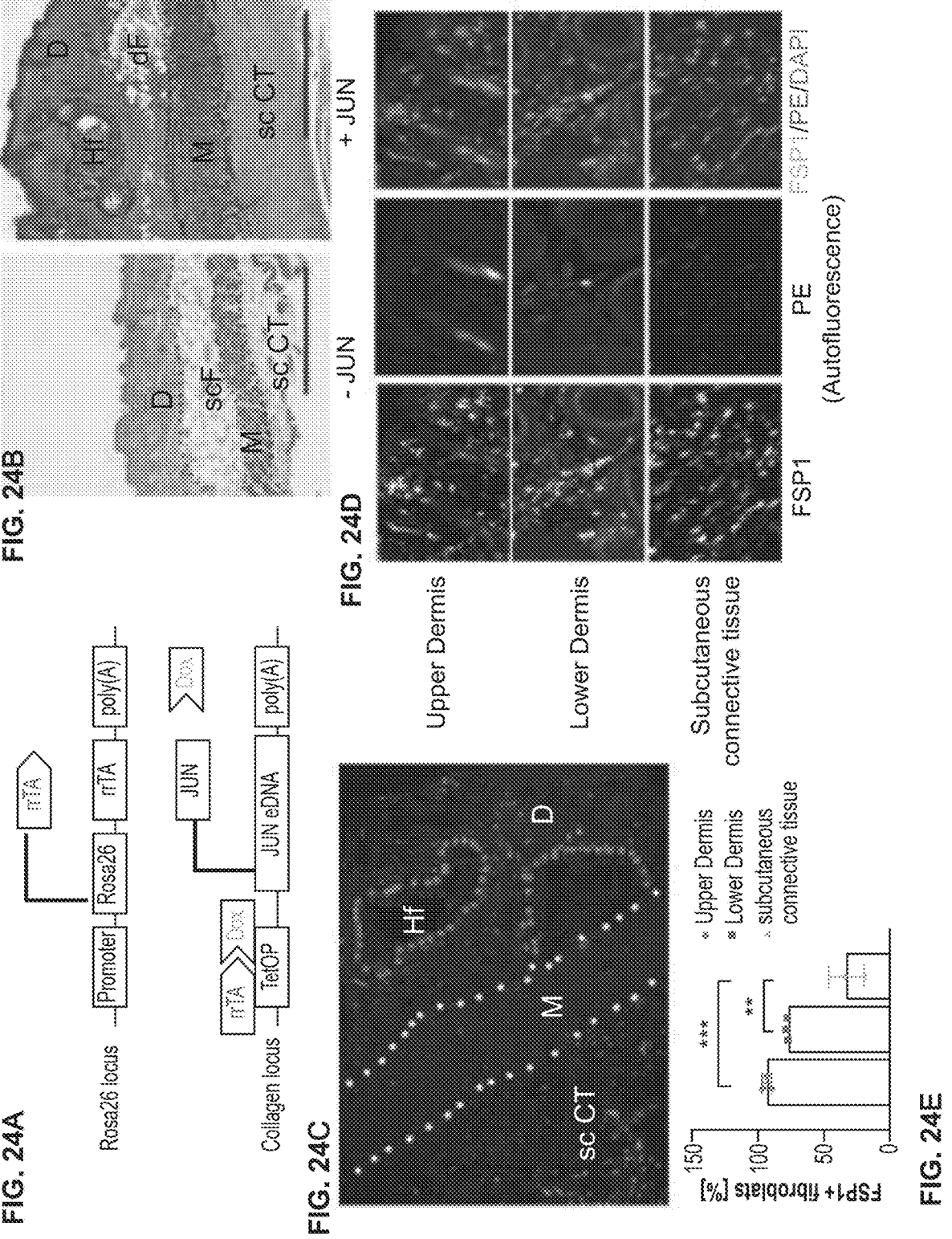
FIG. 24. Jun expands FSP1+ fibroblasts throughout the skin and the underlying tissue. (A) Genetic modifications of the JUN-inducible mouse. rrTA=reverse tetracycline transactivator, TetOP=Tetracycline/doxycycline-responsive operator (B) Representative Trichrome-stained whole skin sections without (−JUN) and with JUN induction (+JUN). D=Dermis, scF=subcutaneous fat, M=subcutaneous muscle, sc CT=subcutaneous connective tissue, dF=dermal fat, Hf=Hairfollicle. Scale bar=500 μm. (C) Whole skin section after Jun induction (corresponding to the section B). Green=FSP1+, blue=DAPI. D=Dermis, M=subcutaneous muscle, sc CT=subcutaneous connective tissue, dF=dermal fat, Hf=Hair follicle (D) Quantification of FSP1+ fibroblasts in the upper dermis, the lower dermis and the subcutaneous connective tissue. Indicated are the percentages of FSP1+ cells among all spindle-shaped fibroblasts. Turkey's multiple comparisons test. p<0.01 *p<0.001. Scale=500 μm. n=3. Bar graphs represent means with standard deviations. (E) Representative stains against FSP1 in the upper and lower dermis and the subcutaneous connective tissue after Jun induction.
Figure 25:
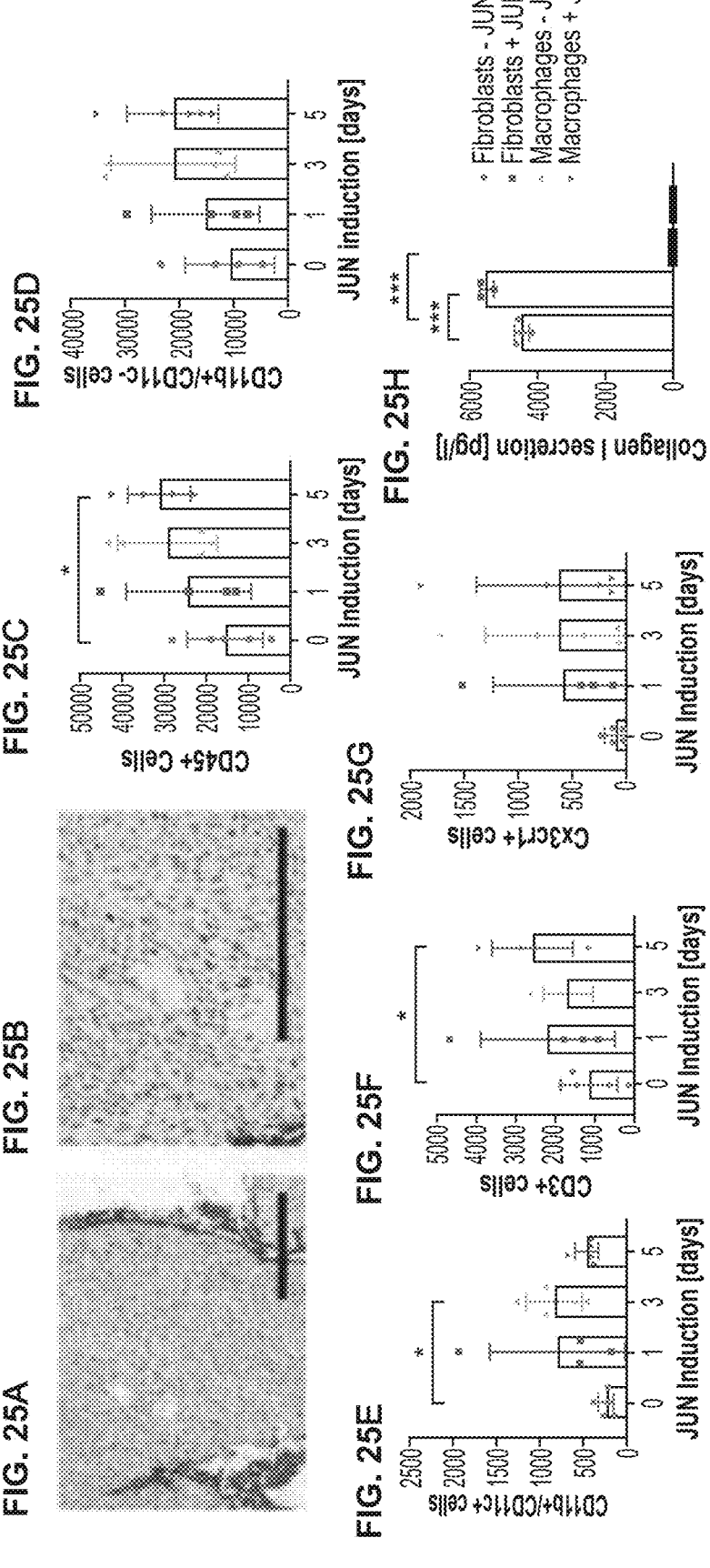
FIG. 25. Skin immune filtration under JUN induction. (A) Representative IHC stain against pJUN. Scale bar=200 μm. (B) Representative IHC stain against pJUN. Scale bar=200

Jun expands distinct fibroblast populations in a scleroderma model. Before studying the efficiency of CD47, we characterized the mechanisms of our Jun-driven mouse model, and how it compared to the widely used bleomycin model (FIG. 24A). We either induced Jun through intradermal doxycycline administrations every other day or administered intradermal bleomycin once at the beginning. After two weeks, both treatments led to significant fibrotic changes and a loss of fat tissue in the skin (FIG. 18A, B). Fibrotic changes included the whole dermis and the tissue below the subcutaneous muscle tissue (FIG. 24B-D). Interestingly, both Jun induction and bleomycin administration induced JUN activation to the same extent (FIG. 18B, FIG. 25A, B). JUN additionally led to an increased inflammatory infiltrate (FIG. 25) We then evaluated how Jun and bleomycin affect distinct fibroblast populations. For this purpose, we divided CD45−CD31−CD326− dermal fibroblasts into four groups, dependent on their expression of CD26 and SCA1 (FIG. 19A, FIG. 26). Both Jun induction and bleomycin expanded CD26+/SCA1− fibroblasts (CD26+ fibroblasts) and decreased CD26+/Sca1+ (double-positive, DP) fibroblasts (FIG. 19B, C. In a time-course study over five days, Jun increased CD26+ fibroblasts gradually while it decreased DP fibroblasts directly at the beginning (FIG. 27A-C). When Jun is induced longer than five days, CD26+ fibroblasts started to decrease while CD26−/SCA1− (double-negative, DN) fibroblasts expanded (FIG. 27D). As proliferation did not specifically affect CD26+ and CD26− fibroblasts this did suggest that immature CD26+ fibroblasts differentiate into mature DN fibroblasts (FIG. 27E, F).

Figures 19D, 19E, 19F, 19G, 19H:
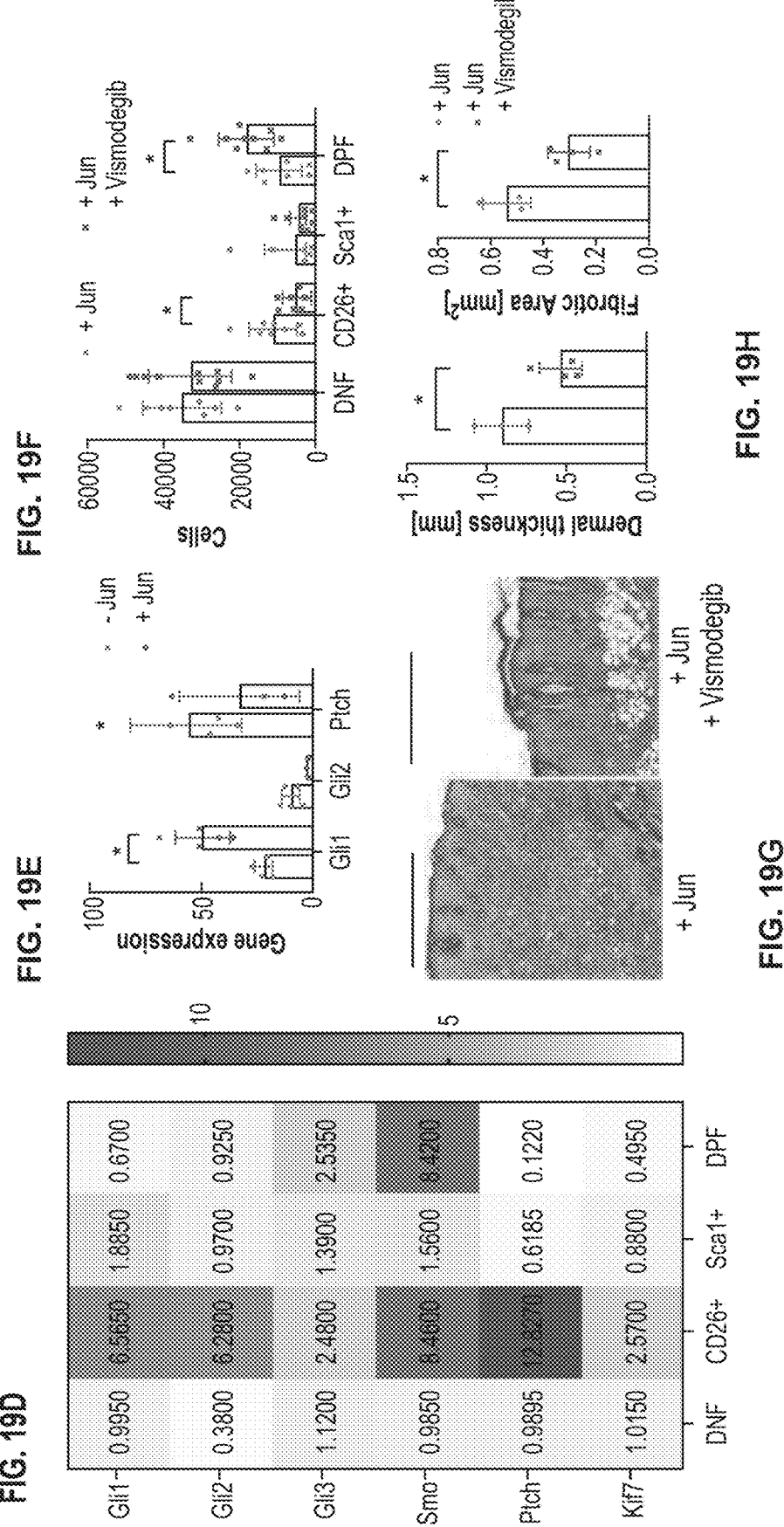
FIG. 19. JUN expands distinct fibroblast populations in a hedgehog dependent manner. (A) Schematic drawing of the localization of double-positive fibroblasts (DPF), CD26+ fibroblasts, Sca1+ fibroblasts and double-negative fibroblasts (DNF). (B) Representative fibroblast FACS plots without JUN induction, with JUN induction and after bleomycin injection (C) Corresponding quantification of total CD26+ fibroblasts, Sca1+ fibroblasts and DPF. Turkey's multiple comparisons test. ***p<0.001. n=4. Bar graphs represent means with standard deviations. (D) Heatmap of the expression of different hedgehog-associated genes in the different fibroblast populations. Values are normalized to the expression in DNF. n=3-6. (E) Expression of Gli1, GI2 and Ptch after JUN induction. All values are compared to the same standard value. Two-sided t-test. *p<0.05. n=3-6. Bar graphs represent means with standard deviations. (F) Fibroblast populations after three days of Jun induction+/−hedgehog inhibition. Indicated are total cells/100,000 live cells. Fisher's multiple comparisons test. *p<0.05 **p<0.01. n=8-11. Bar graphs represent means with standard deviations. (G) Representative trichrome stainings after intradermal JUN induction+/−hedgehog inhibition. Scale=500 μm. (H) Corresponding quantification of dermal thickness and fibrotic area. Two-sided t-test. *p<0.05. n=3. Bar graphs represent means with standard deviations.

CD26+ fibroblast expansion and skin fibrosis is hedgehog-dependent. After demonstrating that JUN causes dermal fibrosis and expands distinct CD26+ fibroblasts, we evaluated whether JUN distinctively influences hedgehog signaling in dermal fibroblast populations. Comparing the expression of several hedgehog-associated genes in FACS purified dermal fibroblasts, we observed increased hedgehog activation in CD26+ fibroblasts and inducing Jun even further increased the expression of the main hedgehog effector Gli1 (FIG. 19D, E, FIG. 28). To test if the hedgehog activation is mandatory for the expansion of CD26+ fibroblasts and the fibrotic skin changes under JUN, we blocked the hedgehog pathway with the smoothened inhibitor vismodegib. Hedgehog inhibition did not only reduce the expansion of CD26+ fibroblasts but also almost completely prevented skin fibrosis after two weeks (FIG. 19F, G, H). In conclusion, these results suggested that Jun drives skin fibrosis through the distinct activation of hedgehog signaling in CD26+ fibroblasts.

Figures 20H, 20I, 20J, 20K:
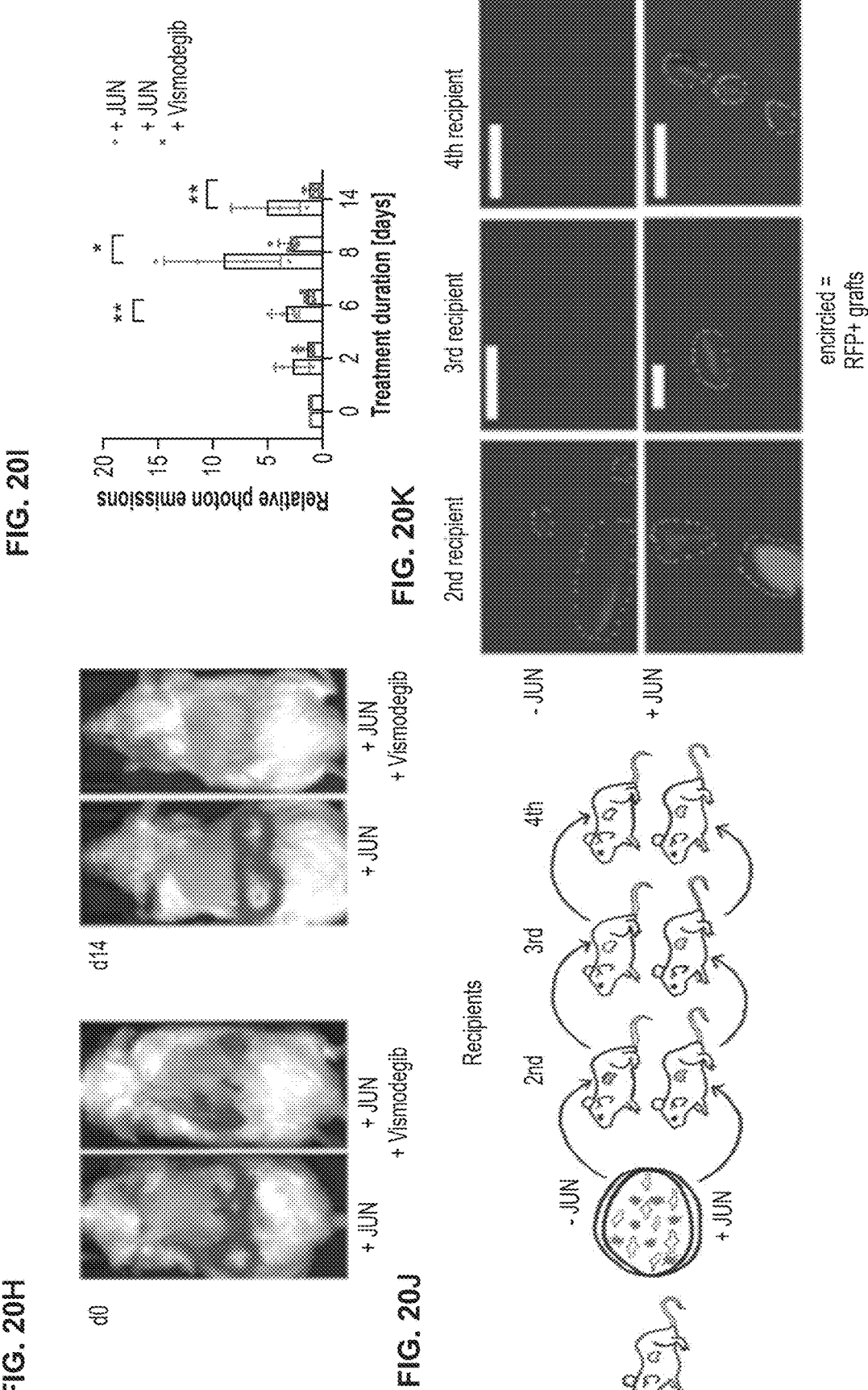
FIG. 20. JUN mediates increased self-renewal to fibroblasts. (A) Mean Fluorescence Intensity for pJUN after JUN knockout (ko JUN). Turkey's multiple comparisons test *p<0.05. n=2. Bar graphs represent means with standard deviations. (B) Mean fluorescence intensity for incorporated EdU (AF594) after JUN knockout (ko JUN), without JUN induction (−JUN) and under JUN induction (+JUN). Turkey's multiple comparisons test. **p<0.01. n=6. Bar graphs represent means with standard deviations. (C) Western blot bands for pJUN, pStat3, FSP1 and GAPDH without and with JUN induction in primary mouse dermal fibroblasts. (D) Kaplan Meier Curve of adaptive transfer graft survivals with JUN induction (+JUN), without JUN induction (−JUN) and after JUN knockout (ko JUN). Photon emissions below 100,000 were considered as a lost graft. n=5-8. (E) Representative optical images of an adaptive transfer model with JUN inducible fibroblasts. n=4-6. (F) Quantification of absolute photon emissions with and without JUN induction. Fisher's multiple comparisons test. *p<0.01. n=4-6. Bar graphs represent means with standard deviations. (G) Corresponding trichrome (10×) and pJUN stains of grafts. Black scale bar=200 μm. Red scale bar=25 μm. n=4-6. (H) Representative optical images of a JUN inducible adaptive transfer model+/−vismodegib. n=4-6. (I) Corresponding quantification of photon emissions. Values were normalized to the expression at day 0. Fisher's multiple comparisons test. *p<0.05 **p<0.01. n=4-6. Bar graphs represent means with standard deviations. (J) Schema of the adaptive serial transplantation model. (K) Corresponding pictures of RFP+ cells in the 2nd, 3rd and 4th recipient with and without JUN induction. Scale bar=500 μm. n=2.

Jun mediates increased self-renewal to fibroblasts. As a last step before evaluating CD47, we evaluated the effect of Jun on dermal fibroblasts outside their dermal niche. For this purpose, we first isolated fibroblasts from neonatal mouse skin. In vitro, an EdU uptake and subsequent flow cytometry demonstrated increased cell proliferation under Jun induction and in accordance with increased cell proliferation, JUN increased pStat3 signaling (FIG. 20A, B, C). To investigate how JUN effects cell survival and proliferation in an niche-independent in vivo environment, we used an adaptive transfer model in which we transplanted GFP/Luciferase-labeled primary mouse dermal fibroblasts under the kidney capsule of immunocompromised NOD.Scid.Gamma (NSG) mice. Tracking transplanted cells through luciferase-based optical imaging, knocking Jun out decreased graft survival (FIG. 20D). When comparing non-Jun induced cells to Jun-induced cells, Jun increased cell proliferation both in optical imaging and histology (FIG. 20E, F, G). Based on these and our previous results, we hypothesized that Jun increases self-renewal in fibroblasts. Supporting this hypothesis, blocking the stem cell-associated hedgehog pathway eliminated the fibroblast graft (FIG. 20H, I). We additionally explored a serial transplantation model in which we transplanted RFP-labeled fibroblasts directly from one mouse to the next (FIG. 20J). While we could no longer detect any RFP-labeled cells after the second recipient without Jun induction, we observed RFP-labeled cells even in the fourth recipient with Jun induction (FIG. 20K). This result strongly supports that Jun mediates increased self-renewal to fibroblasts.

JUN upregulates CD47 in mouse dermal fibroblasts. Having established and characterized our Jun-driven mouse model, we turned to immune therapy. While Jun induced CD47 expression in all fibroblast subpopulations, it increased PDL1 expression only in CD26+ and DP fibroblasts in vivo (FIG. 21 A, B, C, FIG. 29A, B). We then explored if immune therapy could eliminate primary mouse dermal fibroblasts in an adaptive transfer model. For this purpose, we treated immunocompromised mice with either a CD47 or a PDL1 inhibitor after transplanting primary mouse dermal fibroblasts under their kidney capsule. Both inhibitors eliminated the graft (FIG. 21 D, E, F, FIG. 29C, D). Regarding CD47, we observed in vitro that JUN decreases and CD47 inhibition increases phagocytosis (FIG. 21 G, H, FIG. 30). In regard of PD1/PDL1, we determined PD1 expression on mouse macrophages, suggesting a mechanism through which PDL1 blockade is also effective in a T cell-deficient environment such as the immunocompromised NSG mouse (FIG. 29E, F). Investigating the contribution of macrophages to skin fibrosis initiation, macrophage depletion through a CSFR1 inhibitor ameliorated skin fibrosis (FIG. 21 I, J, K).

Combining CD47 and IL6 inhibition prevents loss in subcutaneous fat tissue. We then investigated if immune therapy targeting either the immune checkpoint PD1/PDL1 or the "don't-eat-me-signal" CD47 also allows prevention of fibrosis in our Jun-induced mouse. As our results had shown that both hedgehog signaling and IL6 contribute to scleroderma, we combined both immune therapies either with vismodegib (CD47/PDL1 inhibition+vismodegib) or with the IL6 inhibitor tocilizumab (CD47/IL6 inhibition). For this purpose, we concomitantly administered these treatment schedules and induced Jun intradermally for two weeks (FIG. 31 A). Compared to the control group, neither treatments reduced the thickness of the skin or its fibrotic area (FIG. 31 B, C, D). However, the percentage of dermal fat tissue and the fatty area overall was increased with CD47/IL6 inhibition (FIG. 31 E, F). Additionally, both treatment groups demonstrated a decreased cellular dermal infiltrate When examining the cellular infiltrate more closely, both treatments reduced the number of CD3+ cells in the dermis (FIG. 31 G, H). Additionally, both treatments decreased the dermal number of K167+ cells and prevented the agglomeration of macrophages (FIG. 31 G, H, I, J).

Figures 22A, 22B, 22C, 22D, 22E, 22F, 22G, 22H, 22I:
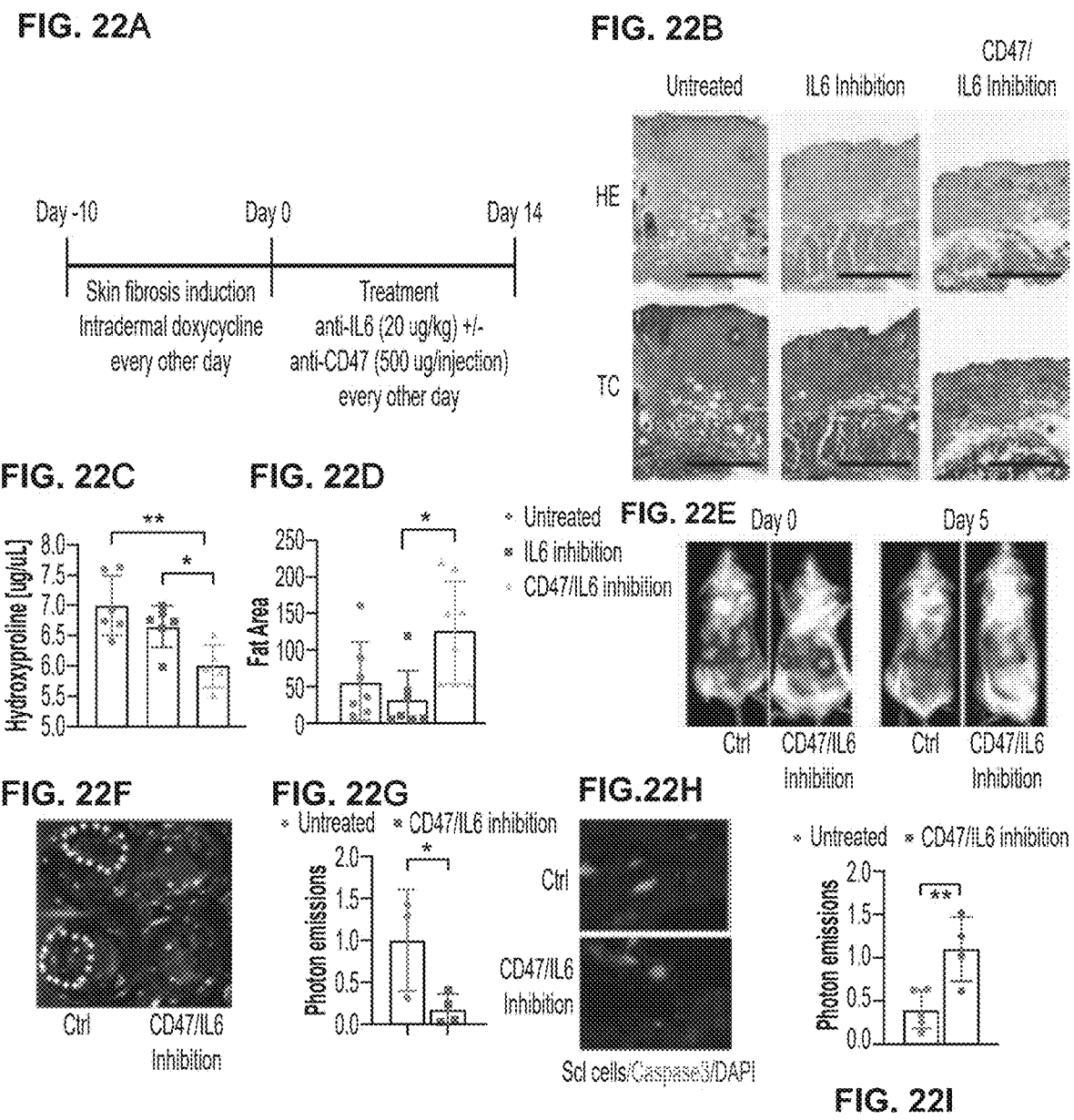
FIG. 22. Combined CD47/IL6 inhibition reverses skin fibrosis. (A) Schematic outline of the therapeutic trial. (B) Representative H&E and Trichrome stains of the different groups. Scale bar=500 μm. n=4. (C) Hydroxyproline content of the skin. Turkey's multiple comparisons test. *p<0.05 **p<0.01. n=6. Graph bars represent means with standard deviations. (D) Amount of fat tissue. Values indicate μm2/μm skin width. Turkey's multiple comparisons test. *p<0.05. n=8. Graph bars represent means with standard deviations. (E) Representative optical images of ectopically transplanted GFP/Luciferase-labeled human scleroderma fibroblasts+/−CD47/IL6 inhibition. (F) Optical imaging of explanted kidneys on day 5. (G) Quantification of photon emissions of explanted kidney grafts normalized to the values of the untreated mice. Two-sided t-test. *p<0.05. n=3-4. Bar graphs represent means with standard deviations. (H) Corresponding Caspase3 staining of kidney grafts. Scale bar=25 μm. (I) Corresponding percentage of Caspase3+ GFP+ fibroblasts. Two-sided t-test. **p<0.01. n=4-5. Bar graphs represent means with standard deviations.

Therapeutic CD47/IL6 inhibition reverses skin fibrosis. Having evaluated immune therapies in disease initiation, we then tested whether CD47 inhibition reverses skin fibrosis in mice. To study this, we induced skin fibrosis over two weeks before starting treatment with combined CD47/IL6 blockade or IL6 blockade alone (FIG. 22 A, B). Encouragingly, two weeks after treatment initiation, the skin hydroxyproline content in the treated mice was lower than in the control groups (FIG. 22 B, C). Additionally, the fat area was increased under CD47/IL6 inhibition, reversing the skin to an almost normal state (FIG. 22 B, D). Otherwise, the overall infiltrate with immune cells did show no differences between the individual treatment groups (FIG. 32 A-D). Looking for side effects, we additionally harvested other organs. Only the bone marrow demonstrated anemic changes, while the other organs all appeared normal (FIG. 32 E).

CD47/IL6 inhibition eliminates scleroderma fibroblasts in an adaptive-transfer model. Finally, we evaluated if CD47/IL6 inhibition accelerates the elimination of transplanted human scleroderma fibroblasts in an adaptive transfer model. Two days after transplantation, we started the treatment with CD47/IL6 inhibition and tracked the GFP/Luciferase-labeled cells through optical imaging (FIG. 22 E). Five days after treatment start. Performing optical imaging on the explanted kidneys confirmed decreased optical signals in the treatment group (FIG. 22 F, G). In accordance with the accelerated elimination of the grafts, we additionally observed significantly more apoptotic GFP+ fibroblasts under CD47/IL6 (FIG. 22 H, I). In summary, we were able to demonstrate that blocking CD47 and IL6 prevented the loss in fat tissue during disease initiation, reversed fibrotic skin changes thereafter, and eliminated human scleroderma fibroblasts in an adaptive transfer model.

In this study, we evaluated the efficiency of the "don't-eat-me-signal" CD47 either alone or in combination with an IL6 inhibitor in a scleroderma mouse model. Systemic sclerosis and its skin manifestation scleroderma are autoimmune diseases and current treatments mainly aim at stopping the progression of the diseases. A true cure with a significant reduction of fibrosis can rarely be achieved. Therefore, a therapy that allows to remove abnormal fibrosis and fibroblasts would represent a breakthrough.

Regarding the role of JUN in human scleroderma, we demonstrate that scleroderma fibroblasts activate JUN on the protein level. In accordance with that, the promotor accessibility of JUN is increased in primary human scleroderma fibroblasts compared to normal skin fibroblasts. We additionally demonstrate that the promotors of the hedgehog-associated genes GLI1 and PTCH1 are more readily accessible in scleroderma fibroblasts. JUN knockout reduced the promotor accessibility of PTCH1 and GLI1, and vice versa, the hedgehog inhibitor vismodegib reduced the promotor accessibility of JUN. This points towards the interconnection between JUN and hedgehog signaling. Importantly, the promotors of CD47 and PDL1 were more easily accessible in scleroderma, suggesting that the abnormal fibroblasts use "don't-eat-me-signals" and immune checkpoints as a protective mechanism against the host's immune system. Additionally, the interleukin 6 promoter was more readily accessible, a finding that corresponds with a recent study in which IL6 activated profibrotic pathways in explanted scleroderma samples. At the end of this part, we demonstrate that stiffer conditions on a hydrogel induce JUN activation, both in scleroderma and pulmonary fibroblasts.

Intradermal Jun induction caused dermal fibrosis and a loss in subcutaneous fat tissue. Additionally, it reduced CD31+ endothelial cells and increased the infiltration with CD3+ cells, hence exhibiting fibrosis, vasculopathy and inflammation—three of four hallmarks of scleroderma.

Except the decrease in CD31+ cells, Jun induction mimicked the changes after bleomycin injection. Interestingly, both Jun induction and bleomycin led to the same extent of JUN activation. According to the Jun-driven mouse model JUN activation alone is enough to cause dermal fibrosis. Once activated JUN could then maintain and worsen skin fibrosis through IL6/pStat3 signaling.

We show that JUN expands CD26+ fibroblasts and decreases DP fibroblasts in the beginning. When induced over a longer time course, CD26+ fibroblasts then start to decrease and DN fibroblasts expand significantly. These results suggest that during fibrosis initiate CD26+ fibroblasts first increase and then finally differentiate into CD26-fibroblasts. In the following experiments, we demonstrate that CD26+ fibroblast activate hedgehog signaling and that Jun induction even further increases this activation. Importantly, inhibiting the hedgehog pathway with vismodegib reverses two previous findings-both the expansion of CD26+ fibroblasts and the dermal fibrosis. In conclusion, these data demonstrate that JUN leads to dermal fibrosis through the distinct activation of hedgehog signaling in CD26+ fibroblasts.

In an adaptive transfer model, we show that Jun expands dermal fibroblasts and supports graft survival independent of their dermal niche. Additionally, Jun induction allowed to detect transplanted fibroblasts up to the fourth recipient in a serial transplantation model, strongly indicating that JUN mediates increased self-renewal to fibroblasts. A clonal expansion of fibroblasts can be the source of fibrotic changes in scleroderma.

We assessed if immune therapy, targeting either CD47 or PDL1, either in combination with vismodegib or in combination with IL6 blockade allows to prevent or reverse skin fibrosis. Jun induction increased CD47 in all and PDL1 in two of the fibroblast populations. Blocking either CD47 or PDL1 in the adaptive transfer model led to the elimination of the graft while the graft continued to grow without immune therapy. In accordance with its role as a "don't-eat-me-signal" CD47 inhibition increased phagocytosis in vitro. Regarding the PD1/PDL1 axis, we demonstrated in accordance with recent publications that mouse macrophages in our models express PD1 as well, suggesting that PDL1-inhibition in the T-cell deficient NSG mouse works through its interaction with PD1 on macrophages. In this study, we observed that the depletion of macrophages through a CSFR1 inhibitor ameliorated skin fibrosis.

We then determined the efficiency of CD47 inhibition in the syngeneic mouse. We first demonstrated that CD47/IL6 inhibition did not decrease the content of connective tissue in the skin in a prospective study. However, the loss of fat tissue with stiffening of the skin is a hallmark of scleroderma and CD47/IL6 increased the dermal fat content. Importantly, we then moved to a therapeutic study in which we first induced Jun over two weeks before starting treatment. To determine to which extent IL6 blockade contributes to changes in skin fibrosis in our mouse model, we added a IL6 blockade only group. Strikingly, CD47/IL6 significantly decreased skin fibrosis and increased dermal fat, in comparison both to the untreated and the IL6 blockade only group. Exempt anemic changes, we did not observe any histological side effects under CD47/IL6 inhibition. In accordance with these findings, CD47/IL6 blockade accelerated the elimination of human scleroderma fibroblasts and increased apoptosis in an adaptive transfer model.

Our macrophage depletion study and our therapeutic study point demonstrate that macrophages can act as a double-edged sword. On one hand they worsen fibrosis initiation, on the other hand they can remove fibrotic tissue. To protect themselves from phagocytosis, fibroblasts upregulate CD47 during disease initiation and progression, thereby enhancing their survival. Through CD47 blockade, fibroblasts become more accessible to macrophages, and can finally be eliminated through phagocytosis.

Retrospective studies suggest that these patients can be treated safely and effectively with immune therapies. Both CD47 and IL6 inhibition are normally well tolerated. CD47 inhibition can cause anemia and infections are more common in patients treated with the IL6 antibody tocilizumab. However, these adverse events are rarely high-grade. In accordance with that, exempt anemic changes in the bone marrow, CD47/IL6 treated mice did not show any other histologic side effects under CD47 and IL6 inhibition.

Our study demonstrates that combined immunotherapy can reverse fibrotic skin conditions. The pathogenesis leading to fibrosis in different conditions may vary, however, they share an end stage with abnormal and persistent fibroblasts leading to significant morbidity and even death. Current therapies mainly stop disease progression but do not reverse fibrosis. Combining CD47 inhibition to enhance phagocytosis and IL6 blockade to suppress underlying detrimental inflammatory processes, in contrast, can lead to a true healing of fibrosis. Regarding the good safety profiles of currently available CD47 and IL6 blocking agents, we believe that our study gives enough evidence to safely try combined immunotherapy with CD47 and IL6 inhibition in patients with highly fibrotic and stable, non-progressive scleroderma.

Materials and Methods

Husbandry. JUN mice were kept on a regular diet in the facilities of the Veterinary Service Center at Stanford University and had a B6/129 background. Nod.Scid.Gamma mice were purchased from the Jackson Laboratory. Mice were kept on a standard diet. Female and male mice were used. When different sexes were used for individual experiments, groups were sex-matched. Mice were not backcrossed and between 6 and 12 weeks of age during experiments.

Genotyping. To determine the genotype, we harvested tissue from the tail of newborn mice on day 10. We digested the DNA with Quickextract (Lucigen Corporation) at 68° C. for 90 minutes, followed by heat inactivation at 98° C. for five minutes. We ran the genotyping PCR for the Rosa26 and the collagen status with the Phusion® High Fidelity DNA Polymerase (New England Biolabs) and the same primers as described previously.

Adaptive transfer under the kidney capsule. After anesthetizing mice, we areas over both flanks were shaved. After creating a flank cut the subcutaneous tissue was bluntly removed from the underlying soft tissue. The abdominal wall was incised and the kidney luxated out of the abdominal cavity. After piercing the kidney and detaching the renal capsule from the renal tissue, 50,000 to 200,000 cells suspended in matrigel were injected under the kidney capsule. Afterwards, the kidney was replaced into the abdominal cavity and the abdominal wall and the skin were separately sutured.

Administration of vismodegib, PDL1 inhibitor, CD47 antibody and CSFR1 antibody. We administered vismodegib (30 mg/kg bodyweight) (Selleckchem) intraperitoneally two times daily. The CD47 antibody (Bio X Cell) was given every other day. The first dosage was 100 μg, followed by 500 μg. For PDL1 inhibition, we injected 100 μl (2.5 mg/ml)

of HAC anti-PD1 daily. To deplete macrophages, we injected 400 µg of the CSFR1 antibody (Bio X Cell) every other.

Intradermal and systemic JUN induction. To induce JUN locally, we injected 20 µl of doxycycline (MilliporeSigma) (2 mg/ml) intradermally on the back. For systemic JUN induction, we injected doxycycline intraperitoneally (20 µg/g body weight). In both systems, we performed the injections every other day.

Luciferase-based optimal imaging. We intraperitoneally injected 100 µl of luciferin substrate (15 mg/ml) (Biosynth). 15 minutes later, we performed optical imaging with the Lago optical imaging system (Spectral imaging instruments) and analyzed the images with the Aura Software from the same manufacturer.

Harvesting of mouse skin for subsequent cell cultures or flow cytometry. Mice were euthanized with $CO_2$. Their backs were shaved, washed and disinfected with 70% EtOH. After excising the back skin, tissue was minced with scissors, followed by a digestion step in DMEM+10% PS, supplemented with 40 µl/ml of Liberase (Roche), for 30 minutes at 37° in the cell incubator on a shaker. The digestion reaction was quenched with DMEM+10% FCS. The medium and tissue specimens were filtered through a 70 µm cell strainer (Falcon). Cells were then either used for flow cytometry or cell culture.

Isolation and maintenance of primary mouse dermal fibroblast cultures. After filtering cells and tissue as described previously, cells were washed two times with PBS. The supernatant was removed and cell pellets and tissue parts were transferred into a culture dish. Cells were kept in DMEM+5% HPL supplemented with Ciprofloxacin over five days. Medium was changed on the first and third day. When being 50% confluent, cells were split.

Isolation of primary human scleroderma and pulmonary fibroblast cultures. Human fibroblasts were obtained discarded fresh lungs tissues from de-identified patients. The tissue was minced and filtered through 70 µm filters, centrifuged at 600 g for 5 min to remove non-homogenized pieces of tissue. Tissue homogenate was treated with ACK lysing buffer (Thermo Fisher) for 10-15 min, centrifuged for 600 g, washed twice in DMEM with 10% fetal bovine serum (Gibco) and plated at a density of approximately 500,000 cells/$cm^2$ in DMEM with 10% fetal bovine serum, 1% penicillin/streptomycin (Thermo Fisher Scientific) and Ciprofloxacin 10 µg/mL, Corning) and kept in an incubator at 37° C. 95% $O_2$/5% $CO_2$. Media was changed after 24 h and cells were cultured until 80-90% confluent before each passage.

Cell culture maintenance. All cell cultures were kept in DMEM supplemented with HPL. Cells were regularly checked for signs for infection and splitted once being more than 80% confluent. For splitting, cell cultures were washed with PBS and incubated with Trypsin (Gibco) for 5 minutes. The reaction was then quenched with DMEM+HPL. Cell suspensions were spun down and reapplied on cell dishes.

Lentivirus preparation. Around 80-90% confluent 293T cells were transfected with 4 µg transfer plasmid (JUN CRISPR knockout plasmid, Luciferase-GFP plasmid, or RFP plasmid), 2 µg pRRE Packing plasmid (GAG and Pol genes), 1 µg pRSV Packing plasmid (Rev gene), 1 µg pMD2.G enveloping plasmid and 24 µg PEI. The day after transfection, cell media was replaced, and cells were incubated for further 48 h, with media collection and replacement every 24 h twice. Cell media was centrifugated at 600×g for 10 min at 4° C. Then, the supernatant was filtered through a 0.22-µm strainer, ultra-centrifuged at 25,000×g for 2 h, aliquoted and flash-frozen.

```
Sequences for JUN sgRNA:
For:
CACCGCCGTCCGAGAGCGGACCTTA (SEQ ID NO: 3)

Rev:
AAACTAAGGTCCGCTCTCGGACGGC (SEQ ID NO: 4)
```

Phagocytosis assay. Peritoneal macrophages were harvested from non-JUN inducible B6 mice. After euthanizing the mice, the skin above the abdomen was cut to expose the peritoneum. The abdominal cavity was then flushed with 5 ml of cold 50 mM EDTA without disrupting vessels. The injected fluid was then aspirated. After adding 10 ml of PBS, the cell suspension was centrifuged for 5 minutes at 300 g, followed by another washing step with PBS and a centrifugation step. The harvested cells were then plated into a 10 ml dish in regular medium. After two hours, the medium was exchanged and M-CSF (20 µg/ml) (MilliporeSigma) was added. After two days, the medium was exchanged with fresh M-CSF. In the meantime, JUN inducible fibroblasts were prepared and labeled with a RFP plasmid. On day 2, JUN was induced in one group by adding doxycycline (1 µg/ml) to the cell culture medium. On day 3, macrophages and fibroblasts with and without JUN induction were harvested and counted. The fibroblast populations were then split again, one group with CD47 inhibition and one group without CD47 inhibition. Cells with CD47 inhibition were then incubated for one hour with the CD47 antibody (Bio X cell) on ice in FACS buffer while the cells were kept on ice in FACS buffer as well. For measuring phagocytosis through flow cytometry, 25,000 macrophages and fibroblasts were mixed in individual wells of a 96-well plate. After a two hour incubation period on a shaker in a regular cell incubator, wells were washed with cold PBS, followed by trypsinization for 10 minutes. FACS buffer added, the plate was centrifuged, followed by another washing step with FACS buffer. After spinning down the plate, cells were incubated with a CD11b and CD45 antibody (BioLegend) for 45 minutes on ice. Afterward, cells were washed and resuspended in FACS buffer, followed by flow analysis in a CytoFlex Flow cytometer (Beckman Coulter). For analysis, CD45+CD11b+ cells were gated and the percentage of RFP/PE+ cells determined. For immunofluorescence, macrophages were plated on fibronectin (MilliporeSigma) coated glass slides (VWR). After 45 minutes, fibroblasts were added and incubated with macrophages for one hour. After that, slides were vigorously washed three times with cold PBS, followed by a regular stain of cells plated on glass slides as described elsewhere in the method section.

Hydrogel preparation. The wells of a 24-well glass bottom plates (Mattek) were incubated with 2 M NaOH for one hour. After a washing step with $ddH_2O$, the wells were incubated with 500 µl of 2% Aminopropyltriethoxysilane (MilliporeSigma) (diluted in 95% EtOH). The wells were rinsed with $ddH_2O$, followed by incubating the wells with 500 µl of 0.5% Glutaraldehyd (MilliporeSigma) for 30 minutes. The wells were then rinsed with $ddH_2O$ and dried at 60° C. For a stiffness of 70 kPa, 46.25 µl of 40% Acrylamid (MilliporeSigma) were mixed with 55.5 µl of 2% bis-acrylamid (MilliporeSigma) and 83.25 µl of $ddH_2O$. Then, 1.2 µl of 10% Ammonium persulfate (MilliporeSigma) and 0.8 µl of TEMED (MilliporeSigma) were added to the mixture before. Each well of the plate was coated with 4 µl of the mixture and a coverslip (Glaswarenfabrik Karl Hecht GmbH). After 20 minutes, the coverslip was removed with tweezers. 500 µl of 50 mM HEPES (MilliporeSigma) were added to the wells. After sterilizing the plate for 1 hour under UV light, 200 µl of 0.5% SANPAH crosslinker (ProteoChem) were added to each well. After activating the crosslinker on UV light for ten minutes, wells were washed with 50 mM HEPES two times. A $\frac{1}{15}$ solution of Matrigel (MilliporeSigma) diluted in 50 mM HEPES were added to the plate. The plate was incubated overnight at room temperature. Before being used, the plate was rinsed with 50 mM HEPES and incubated with regular cell culture medium for 30 minutes at 37° C. in the incubator.

Hydroxyproline assay. We determined the hydroxyproline content with a Hydroxyproline assay kit (MilliporeSigma) according to the manufacturer's specifications. 10 mg of tissue was minced with scissors and homogenized in 100 µL of deionized water. 100 µL of 12 M HCL was added to each sample and incubated at 120° C. for 3 hours. Samples were centrifuged at 10,000 g for 3 minutes and 25 µL of the supernatant was plated into a 96-well and subsequently incubated at 60° C. until all liquid was evaporated. Standards and reagents were prepared as instructed in the manufacturer's protocol. 100 µL of the chloramine T oxidation buffer mixture was added to each sample and standard and incubated for 5 minutes at room temperature. 100 µL of diluted DMAB reagent was added to each sample and standard and incubated in a 60° C. water bath for 90 minutes. Absorbance was read at 560 nm. All samples and standards were performed in technical duplicates.

Preparation of human platelet lysate (HPL) and HPL-containing medium. Expired human platelets were obtained from the Stanford Blood Bank. Then, platelets were lysed through five quick freeze-thaw cycles. Platelet lysates were then spun down at 4,000 g for 10 minutes, aliquoted into 15 ml tubes and stored at –80° C. For preparing cell mediums, platelet lysates were warmed up, then spun down at 4,000 g for 10 minutes, and sequentially filtered through 0.80, 0.45 and 0.22 µm filters. The final medium, containing DMEM, 5% HPL, 1% Penicillin/Streptomycin and 2 Units of Heparin/ml, was then filtered through a 0.22 µm filter and stored at 4° C.

Flow cytometry and sorting. For live cells, we washed single cell suspensions with FACS buffer (PBS+2% FBS+ 1% Penicillin/Streptomycin+1 mM EDTA+25 mM HEPES) and then stained the cells with the primary antibodies for 45 minutes. Cells were washed and subsequently resuspended with FACS buffer. For intracellular stainings, cells were fixed with BD Wash/Perm (Becton, Dickinson and Company), followed by the same steps used for the live cells, with the exception of using BD Wash/Perm (Becton Dickinson and Company) instead of the FACS buffer. For flow cytometry, we either used the CytoFlex Flow Cytometer (Beckman Coulter) for analysis only, or the BD FACS Aria III (Becton, Dickinson and Company) for analysis and sorting. We performed the data analysis with the newest version of FlowJo (FlowJo, LLC).

Tissue fixation and hematoxylin staining. We kept harvested tissue in 10% formalin overnight. Tissue was then submitted to the Stanford Human Pathology/Histology Service Center for paraffin-embedding and cutting. We deparaffinized and rehydrated the tissue slides with xylene and a descending ethanol row. After washing the slides in PBS, we incubated them in hematoxylin (American MasterTech) for 4 minutes, then in bluing reagent (ThermoFisher Scientific) for 2 minutes and in Harleco® (MilliporeSigma) for 2 minutes, Slides were dehydrated with ethanol and xylene (MilliporeSigma) and mounted with Permount® (ThermoFisher Scientific).

Trichrome Staining. We used a One Step Trichrome Stain Kit (American MasterTech). After deparaffinization and rehydration, the tissue was incubated in Bouin's Fluid overnight, followed by Modified Mayer's Hematoxylin for seven minutes and One Step Trichrome Stain for five minutes. Slides were dehydrated with ethanol and xylene and covered with Permount® (ThermoFisher Scientific).

Immunofluorescence Staining of paraffin-embedded sections. When using paraffin-embedded tissue, we first deparaffinized and rehydrated the tissue. Then, we performed antigen retrieval with a citric acid buffer in a pressure cooker for 15 minutes, followed by blocking with 5% serum. Sections were incubated with the primary antibody over night at 4° C. After washing in PBST, we incubated the sections with the secondary antibody at room temperature for 30 minutes under agitation. Sections were washed, counterstained with DAPI and mounted with fluoromount (SouthernBiotech). Images of histological slides were obtained on a Leica Eclipse E400 microscope (Leica) equipped with a SPOT RT color digital camera model 2.1.1 (Diagnostic Instruments).

Immunofluorescence Staining of OCT-embedded sections. For OCT sections, harvested tissue was fixed in 4% PFA for at least two hours, followed by an incubation in 30% sucrose overnight. Tissue was then embedded in OCT and stored at –80° C. Thereafter, the OCT block was cut into 10 µm sections. Sections were stored at –20° C. Before staining, sections were dried for at least 15 minutes at room temperature. Sections were rehydrated in PBS. For intranuclear stains, sections were incubated for 10 minutes in TritonX at room temperature. Otherwise, cells were blocked with 5% for one hour. The remaining steps were the same as for the immunofluorescence stains of paraffine-embedded tissue.

Immunofluorescence Staining of cells plated on glass slides. For plating cells on glass slides (VWR), areas were encircled on glass slides with a fat pen (Vector Laboratories), followed by sterilization for at least one hour under UV light. Then, fibronectin (20 µg/ml PBS) was added. After incubating the slides for one hour in a cell incubator at 37° C., the fibronectin solution was aspirated and the slides were dried in the cell culture cabinet. Cells were added onto the glass slides, and incubated for different amount of times in regular cell culture medium. Thereafter, the glass slides were washed in PBS, followed by fixing the cells with 4% PFA at room temperature for ten minutes. The slides were washed again in PBS, followed by permeabilization in TritonX for ten minutes for intranuclear stainings. Otherwise, cells were blocked with 5% serum for one hour. Afterwards, the staining procedure equaled the staining protocol of the paraffin-embedded slides.

Immunohistochemistry. When using paraffin-embedded tissue, we first deparaffinized and rehydrated the tissue. Then, we performed antigen retrieval with a citric acid buffer in a pressure cooker for 15 minutes, followed by blocking with 5% serum. Sections were incubated with the primary antibody over night at 4° C. After washing in PBST, we incubated the sections with the secondary HRP-antibody at room temperature for one 30 minutes under agitation. Sections were washed in PBST and ddH$_2$O followed by incubation for 15-20 minutes in AEC Peroxidase Substrate (Vector Laboratories). Sections were washed in ddH$_2$O and incubated in Modified Mayer's Hematoxylin for 4 Minutes. After washing in ddH$_2$O, slides were mounted with fluoromount (SouthernBiotech).

RNA extraction, cDNA and quantitative polymerase chain reaction. FACS purified cells were sorted into trizol (ThermoFisher Scientific). For RNA extraction, we added chloroform and centrifuged the tubes. We transferred the upper phase to a new tube and added 70% EtOH. Afterwards, the complete volume was added to the columns of the RNEasy MiniElute Cleanup Kit (Qiagen). Between the next three centrifugation steps, we washed the columns with 80% EtOH (+H$_2$O), 80% EtOH (+RPE) and 70% EtOH. After letting the membranes slightly dry, we added water onto the membranes, centrifuged the columns and measured the RNA quantity and quality of the flow through with a NanoDrop 2000 (ThermoFisher Scientific). For cDNA creation, we used the iScript™ Advanced cDNA Synthesis Kit (Bio-Rad) according to the manufacturer's specifications. Up to 1 μg of RNA was transformed into cDNA. We then ran qPCR on a 7900 HT Fast-Time PCR System (Applied Biosystems). Reactions contained 2.5 μl of H$_2$O, 5 μl of PowerUp™ SYBR™ Green Master Mix (Applied Biosystems), 1 μM of Primers (0.5 μl) and 2 μl of cDNA.

Western Blotting. Cells in a well of a 6-well-plate were lysed with 150-200 μl of urea buffer. Cell lysates were sonicated and centrifuged. Protein concentrations were determined with the Pierce BSA Protein Assay (ThermoFisher Scientific). 10 μg of protein were mixed with loading dye and heated up to 99° C. for five minutes. Protein lysates were added to a Bolt 4-12% Bis-Tris-Plus Gel (Invitrogen). After 30 minutes, proteins were transferred to a nitrocellulose membrane for 90 minutes. Membranes were blocked with 5% milk powder in PBST for 30 minutes, followed by incubating the membranes with the primary antibody diluted in the blocking buffer for 1 hour at room temperature. Membranes were washed three times with PBST for five minutes each. Membranes were incubated with the secondary antibody diluted in the blocking buffer at room temperature, followed by three washing steps in PBST. Membranes were incubated with Luminata Forte Western HRP Substrate (MilliporeSigma) for five minutes and developed on UltraCruz® Autoradiography films (Santa Cruz Biotechnology). Membranes were stripped with Restore™ Western Blot Stripping Buffer (ThermoFisher Scientific) for five minutes. Membranes were then blocked, incubated with primary and secondary antibodies and developed as described in this section.

Primary antibodies. Flow cytometry: CD3 (Biolegend, #100209, Clone 17A2), CD4 (Biolegend, #100422, Clone GK1.5), CD11b (BD, #554411, Clone M1/70), CD11c (Biolegend, #117324, Clone N418), CD25 (Biolegend #102035, Clone PC61), CD26 (Biolegend, #137805, Clone H194-112), CD31 (BD, #553373, Clone MEC 13.3), CD45 (Biolegend, #103110, Clone 30-F11), CD47 (Biolegend, #127527, Clone Miap301), CD326 (Biolegend, #118218, Clone G8.8), F4/80 (Biolegend, #123116, Clone BM8), PDL1 (Biolegend, #124312, Clone 10F.9G2), Sca1 (Biolegend, #108114), phospho c-Jun (Ser73) (CST, #32705, Clone D47G9)

Immunohistochemistry/Immunofluorescence: Adiponectin (abcam, #ab22554), CD3 (abcam, #ab5690), CD11b (Novus, #NB110-89474), CD26 (abcam, #ab28340), CD26 (R&D, #AF954), CD31 (Dako, #m0823), CD47 (FisherScientific, #14-0479-82, Clone B6H12), CD47 (R&D, #AF1866), CD68 (Agilent, #GA60691-2, Clone KP1), Cleaved Caspase 3 (CST, #96645, Clone 5A1E), FSP1 (MilliporeSigma, #07-2274), FSP1 (Abcam, #ab58597), Collagen 1 (Abcam, #ab34710), FSP1 (MilliporeSigma, #07-2274), Ki67 (abcam, #ab15580), PD1 (Cell marque, #315M-96, Clone NAT105), PD1 (R&D, #AF1021), PDL1 (R&D, #AF1019), phospho c-Jun (Ser73) (CST, #32705, Clone D47G9).

Western: c-Jun (CST, #9165S, Clone 60A8), FSP1 (MilliporeSigma, #07-2274), GAPDH (GeneTex, #627408, Clone GT239), phospho c-Jun (Ser73) (CST, #32705, Clone D47G9), phospho Stat3 (CST, #9131S).

Secondary antibodies. AF488 Goat anti-rabbit (CST, #44125), AF594 Goat anti-rabbit (Invitrogen, #A-11012), AF594 Donkey anti-goat (Novus, #NBP1-75607), AF594 Goat anti-mouse (Invitrogen, #A-11032), HRP Goat anti-rabbit (abcam, #205718).

ATAC-Seq Library preparation, sequencing, and data preprocessing. The ATAC-seq was performed as discribed before. Briefly, 50000 cells were collected and washed with cold PBS and lysed using 0.1% NP40 in resuspension buffer. Tn5 transposition of nuclei pellets was carried out at 37° C. for 30 min, using the DNA sample preparation kit from Nextera (Illumina). The reaction was purified using QIAGEN MinElute columns and then amplified for 8-15 cycles to produce libraries for sequencing. ATAC-seq libraries were sequenced on Illumina HiSeq 4000. ATAC-seq pair-end reads were trimmed for Illumina adaptor sequences and transposase sequences using Kundaje ATAC_pipelines. The libraries were initially sequenced on a Miseq sequencer and analyzed using a custom script to determine the enrichment score, only libraries that had the highest score above the threshold (>5) were chosen for deeper sequencing. Two independent, biological replicates were sequenced per sample. The data have been uploaded to the Gene Expression Omnibus (GEO) under the accession number GSE151943.

Deep sequencing data analysis. Differentially accessible peaks from the merged union peak list were selected with the DESeq2 package from bioconductor using raw read counts of each samples using log 2 fold change >1, and p value <0.05. The read counts of the differential peaks in each sample were further normalized by Z-score transformation. Peak genomic annotation was performed by HOMER package. Hierarchical clustering was used to cluster the peaks and samples. The results was presented as heatmap by Morpheus from Broad Institute.

Statistics. We used the newest version of Graphpad prism (Graphpad Software Inc) for creating graphs and running statistical analyses. When two values were compared, a two-sided student's t-test was used, if more than two values were analyzed. When more than two values were directly compared to each other, we used the Turkey's multiple comparisons test. When two values were compared over different time points, without comparing the time points to each other, we used Fisher's multiple comparisons test. Generally, experiments included at least three independent values from two independent experiments. P values below 0.05 were considered as statistically significant. Regarding naturally occurring higher variation in animal trials, we determined before the experiment to exclude the highest and lowest values (when n was at least 8) or the two highest and two lowest values (when n of 16 was reached).

Study approval. Animal trials were approved by the Stanford Administrative Panel on Laboratory Animal Care (#30911). Tissue for human primary cultures was obtained from discarded fresh skin specimens from de-identified patients.

Example 3

CD47 and IL6 Targeted Therapy for the Treatment of Fibrosis and Inflammation in Sclerodermatous Graft-Vs-Host Disease in Mice and Humans To determine whether c-Jun is a driver of the fibrosis in cGVHD, we analyzed a new mouse model of cGVHD (by MHC-matched, minor H mismatched HCT), which developed cGVHD. We found that these sclerodermatous skin lesions were composed of c-Jun/CD47/Fsp1 positive fibroblasts in these mice but also patient biopsies of cGVHD, and similar, to skin fibrosis in the c-Jun model. IL6 was highly increased both in the mouse and patient tissues. Non-alcoholic liver cirrhosis and NASH is a chronic inflammatory and fibrotic condition in the liver. We were able to demonstrate that pathogenic fibroblasts in patient samples (50 liver biopsies) with liver cirrhosis express increased JUN, CD47 and mesothelin, a pathologic fibroblast precursor marker and increased levels of IL6.

Chronic graft-vs-host disease (cGVHD) is a major obstacle to the success of allogeneic hematopoietic stem cell transplantation (HCT) in patients. Sclerodermatous GVHD (sclGVHD) is a more severe form of cGVHD associated with poor prognosis and low sensitivity to immune suppressive therapy. Our studies demonstrate the underlying pathophysiology of sclGVHD using novel mouse models and patient specimens. The results described show that JUN and CD47 are key players modulating the genetic and epigenetic landscape of sclGVHD pathogenesis in the context of dermal fibrosis and inflammation, underscoring the potential of JUN and CD47 targeted therapeutics for the treatment of sclGVHD.

Sclerodermatous GVHD (sclGVHD) is one of the more severe forms of cGVHD and resembles systemic sclerosis (sS), a disease where Hedgehog (Hh) signaling modulates fibrogenesis. Several clinical trials are underway investigating the effect of Hh inhibitors for the treatment of sclGVHD. Graft-versus-host disease (GVHD) occurs in 30-70% of patients and contributes to 50% of non-relapse mortalities. Historically, the acute and chronic forms of GVHD have been distinguished by their onset pre and post days (d+100) after-HCT, but currently clinical features are more commonly used to delineate the two syndromes.

Preclinical animal models have been critical to study acute cGVHD and elucidate its molecular pathophysiology to guide the development of effective therapeutic modalities in clinic. Allogeneic hematopoietic cell transplantation (allo-HCT) is currently the only curative treatment modality for many hematologic malignancies and immune disorders. The preparative or conditioning regimen is critical to the HCT procedure. The pro-inflammatory environment generated by preparative conditioning together with infiltration of alloreactive donor T cells results in tissue damage, primarily affecting the intestines, skin, and liver. Suppression of T-cell activity by classical drugs including calcineurin inhibitors, steroids, STAT signaling modulators have been previously effective for treating acute GVHD.

In contrast, the clinical spectrum and phenotypes of cGVHDs are much broader, typically involving fibrotic tissue transformation, often resembling autoimmune disorders. There is no current consensus about the underlying molecular pathogenesis of cGVHD. However, some studies demonstrate a range of immunological events in the post-HCT period that lead to different states of chronic inflammation ultimately causing tissue dysfunction and fibrosis. Acute inflammation and tissue injury in the earlier phase may converge into chronic inflammation with deregulated immunity, followed by aberrant tissue repair that often results in tissue fibrosis.

The underlying determinants driving fibrogenesis in fibrotic diseases, including sS, and cGVHD are not yet defined, and involve—but are not limited to—transforming growth factor B (TGF-β), platelet-derived growth factor (PDGF), connective-tissue growth factor (CTGF), vasoactive peptide, and integrin signaling. Previous studies have implicated the Hedgehog Signaling pathway to play a role in regulating scl-GVHD, a more severe form of cGVHD.

Owing to the current dearth in knowledge pertaining to scl-GVHD induction, we hypothesize that there exist a range of inflammatory cells delivering profibrotic signals. Such signals while initially performing tissue repair following transplant-related injury of the skin, can eventually perpetuate uncontrolled pathologic fibrosis. Therefore, we aimed at identifying downstream fibrotic gene expression signatures in fibroblasts associated with chronic inflammation. Our prior studies have demonstrated that many end-stage fibrotic diseases converge in the activation of the AP1 transcription factor JUN in pathologic fibroblasts. JUN induction resulted in the upregulation of CD47 in fibroblasts. CD47 is a key anti-phagocytic molecule known to render cells resistant to programmed cell removal. To validate our hypothesis, we examined JUN expression in skin from mice and humans with scl-GVHD. In this study we describe (a) a new MHC-matched, minor antigen mismatched model of scl-GVHD, in which the male (but not female) BALB.K recipients of female AKR/J grafts (both H2$^k$) develop severe scl-GVHD following non-myeloablative allo-HCT. Findings from our studies have been validated in primary human patient samples. (b) Moreover, we use primary fibroblasts of scl-GVHD patients to study transcriptional reprogramming at the chromatin level in scl-GVHD and identify genomic alterations in response to the blockade of immune regulatory proteins CD47 and IL6.

In summary, we describe a novel mechanism through which chronic inflammation perpetuates fibrosis via activation of JUN, CD47, IL6, and the Hh pathway, which result in a profibrotic signature in scl-GVHD. Our findings are of particular interest, as these pathways have been implicated in tissue fibrogenesis in other contexts and indicate potential targets for therapeutic intervention using Hh inhibitors, anti-CD47 and IL6R antibodies.

RESULTS

Upregulation of JUN and CD47 in fibroblasts from patients with scl-GVHD. JUN and CD47 have been previously implicated in regulating vital pathomechanisms of fibrotic disease. Fibroblasts strongly expressed JUN, which is a part of the activator protein 1 (AP-1), a transcription factor involved in acute phase responses to cytokines, growth factors, infections, and other stimuli. To first analyze the expression patterns of JUN and CD47 in patient samples we used skin biopsies from 45 sclGVHD patients. Skin samples from patients with clinically severe scl-GVHD that had undergone myeloablative, reduced intensity, non-myeloablative conditioning and mobilized peripheral blood or bone marrow grafts from related or unrelated donors were selected for the study. A schematic describing patient characteristics and a table with consolidated clinical characteristics is shown (FIG. 34A). Using tissue microarray analysis and immunofluorescence staining, our data shows a strong expression and activation of JUN and CD47 in the dermal fibroblasts of sclGVHD patients, relative to their respective controls (FIG. 34B, C).

JUN knockout alters chromatin accessibility and nucleosome positioning of fibrosis genes and immune regulatory proteins. While we did see an enrichment of JUN in patient samples of sclGVHD, we further sought to understand JUN's regulatory function in modulating genome wide chromatin accessibility both in vitro and in patients. We performed ATAC-seq (Assay for Transposase-Accessible Chromatin using sequencing) on isolated primary fibroblasts from fresh human sclGVHD skin biopsies. Our results reveal open chromatin conformations in the JUN KO samples relative to the control samples (FIG. 35A). To further validate the impact of JUN in determining the epigenomic landscape of fibrotic specimens, we knocked down JUN using CRISPR-Cas9 in sclGVHD fibroblasts and show that JUN deletion correlated with a significant decrease in promoter binding accessibility to IL6 and CD47 (FIG. 35B). This chromatin remodeling was found to increase accessibility to the JUN promoter, IL-6 promoter and CD47 enhancer/promoter (FIG. 35 B). In contrast, normal fibroblasts display minimal accessibility to the JUN promoter (FIG. 35 A, FIG. 35 B). These findings validated our hypothesis that JUN is a main regulator affecting the transcription of IL6 and CD47. Of note, JUN deletion also decreased the chromatin accessibility of key members of the Hh pathway (GLI1, PTCH1, PTCH2). We further confirmed our findings by performing ChIPseq on JUN KO samples relative to control and show the relative promoter occupancies for JUN, IL6 and CD47 (FIG. 35 B).

JUN, CD47 and FSP1 are upregulated in a novel mouse model of sclGVHD. While we describe the expression of JUN and CD47 in human patient skins of cGVHD and isolate a plausible mechanism through which JUN potentiates its function in promoting fibrogenesis in cGHVD, we further sought to recapitulate this effect in a novel mouse model. The strategy for generating this model is displayed (FIG. 36A). In this model male (not female) recipients of female grafts developed severe scleroderma with massive skin thickening and collagen deposition (FIG. 36B).

We have previously reported that lethally irradiated BALB.K mice (H2$^k$) given T-cell replete AKR/J grafts (H2$^k$) succumb to fulminant acute GVHD which has been validated by other groups as well. Additionally, we have previously shown engraftment failure of AKR/J HSC grafts supplemented with CD4$^+$ cells when transplanted into sublethally irradiated BALB.K mice. In contrast, in our present study we show that when recipients were infused with 3000 purified female AKR/J KTLS-HSCs, or HSCs plus 1×10$^6$ CD8$^+$ T cells—but no CD4$^+$ cells (FIG. 36A, B) all recipients survived, had mild transient weight loss but no signs of acute GVHD. Mixed donor/host chimerism was found in all blood lineages. Between day +80 and day +180 post allo-HCT a substantial proportion of male mice (17/27 (63%)) began to display sclerodermatous skin lesions ("scl-GVHD") that were tightly fixed to the fascia, particularly affecting the flank areas, while none of the female recipients displayed any clinical or histological skin pathology ("healthy controls") (FIGS. 36A and B). This late-onset scl-GVHD was not associated with significant weight loss or death. Examination of isolated tissues revealed extensive dermal fibrosis with mixed inflammatory infiltrates of predominantly macrophages (Mϕ), neutrophils and few T cells (FIG. 36 C). Also, Histological analysis revealed that scleroderma with massive thickening of the dermis and collagen deposition was only observed in male and not female recipients of female grafts (FIG. 36 C).

Thickening and homogenization of collagen bundles throughout the reticular dermis or pandermal sclerosis was observed with overlying interface changes like thickening and homogenization of subcutaneous septa. Further, immunostaining was performed on tissue sections obtained from our scl-GVHD models and staining was compared to healthy controls and aged BALB mice. Here we show that JUN, CD47 and FSP1 are significantly (p<0.01) overexpressed in mouse tissue from the sclGVHD model relative to the controls (FIG. 36 D). We also used immunohistochemistry on the specimens to show that diseased tissue infiltrates comprised mainly of granulocytes and CD3$^+$ T cells and some CD11b$^+$ macrophages (FIG. 36 E). Interestingly there were no B cells with little or no dendritic cells (FIG. 36 E).

Examination of the inflammatory skin infiltrates by FACS revealed that they contained mostly macrophages and neutrophils, while there were few CD4$^+$ T cells, and rarely CD8$^+$ T cells or B cells. In contrast, in the skin of unmanipulated wildtype (WT) controls or healthy female recipients very few hematopoietic cells could be isolated, as displayed on the SSc/FSc plots (FIG. 39).

Serum of scl-GVHD mice and controls was analyzed by a multiplex assay for quantification of 38 different mouse cytokines/chemokines. Consistent with the cellular infiltrate's serum levels of MCP-3 (macrophage chemo-attractant protein-3, CCL7) were significantly higher in male mice with scl-GVHD compared with both wildtype and healthy female controls (FIG. 33G). Moreover, IL-13, MIP1A, and RANTES were significantly increased in some scl-GVHD mice, but not in wildtype or healthy female controls. In contrast, IL-15 and IL-3 were increased in a higher proportion of transplanted healthy female controls, compared with scl-GVHD mice. The proportion of mice per experimental group that had elevated cytokine levels. There was no additional increase in cytokine levels in the serum for MIP2, Eotaxin, GM-CSF, IL-12, IL-17, IL-2, IL-31, IP10, LIF, LIX, MCP1, MIP1b, TNFα, and VEGF.

Chronic graft-versus-host disease (cGVHD) continues to be a debilitating disease inflicting tissue injury and putting patients at a high risk for death from infections. Even so, there are limited advances made in the treatment of cGVHD, with no drugs currently approved by the Food and Drug Administration (FDA) for treating glucocorticoid-dependent patients or those with glucocorticoid-refractory disease. However, recent new therapeutic approaches have emerged that are being tested in preclinical models and clinical trials. Treatment strategies are still scarce owing to limited understanding of the pathophysiology of cGVHD because of its complex heterogeneity and manifestation of multiple phenotypes associated with fibrotic signatures relative to acute GVHD. Problems associated with the lack of good preclinical mouse models and patient data analyses pose a challenge to understand the pathophysiological and immunological evolution of the disease. The early onset of cGVHD is associated with activation of the innate immune system and non-hematopoietic stem cells like fibroblasts. Many of the animal models do not display manifestations of cGVHD, and therefore, attempts to model a more protracted disease with less inflammatory but more fibrotic changes have been mostly futile. A common model used to study chronic scl-GVHD is the MHC-matched B10.D2 into BALB/C combination, which gives transient signs of skin GVHD around d+40 to d+50. Also frequently used is the MHC-mismatched C57BL/6 into B10.BR model in which aberrant germinal center formation results in pathologic IgG-antibody deposition in the lung and a murine form of bronchiolitis obliterans. In this study we describe an allo-HCT constellation that can reproduce most features of chronic GVHD seen in humans. Our animal models generated with male recipients of female grafts are affected following nonmyeloablative conditioning and MHC-matched transplantation and display a protracted course of scleroderma. We have validated the genetic and epigenetic landscape observed in our animal models using human patient specimens thus demonstrating that both our preclinical models can recapitulate the genetic signatures of cGVHD.

The skin is one of the largest organs of the human body and provides a protective interface between the body and the external environment. The dermis forms the skin scaffold consisting of a dense extracellular matrix meshwork and different cell populations, including fibroblasts, sensory neurons and endothelial and immune cells. Postnatally, fibroblasts stop proliferating and enter a quiescent state for efficient ECM deposition and remodeling. Upon tissue damage dermal fibroblasts become activated, start proliferating and deposit/remodel ECM (Rognoni). As wounds heal, the plasticity in the dermis and epidermis typically resolves. Intriguingly, it was shown that the coordinated switch in fibroblast behavior from being highly proliferative in embryonic development to quiescence postnatally in order to allow efficient EMC deposition/remodeling is balanced by a negative feedback loop which is necessary and sufficient to define dermal architecture during development. So far, the cell intrinsic and extrinsic regulatory mechanisms controlling dermal fibroblast lineage identity, behavior and fate, are not fully elucidated. In the epidermis and dermis, the Hippo signaling pathway and its downstream effectors, the transcriptional coactivators Yes-associated protein (YAP) and transcriptional coactivator with PDZ-binding motif (TAZ, also called WW Domain Containing Transcription Regulator 1 (WWTR1) regulate diverse tissue-specific functions during development, homeostasis and regeneration. During skin morphogenesis and hair follicle development the production of sonic hedgehog (SHH) by WNThi cells induces maturation of HD. The dermis is highly vascularized and innervated, and cells of the immune system traffic through both the dermis and the epidermis.

Similarly, in physiologic health a delicate balance exists in tissues that heal from an inflammatory insult. This balance is significantly affected by endogenous anti-inflammatory mediators, which block additional inflammatory cell infiltration and activation, but also promote resolution and repair of the inflamed tissue, thereby preventing fibrogenesis and scar formation. Resolution of inflammation is tightly orchestrated by cells, proteins, and mediators. Tissues are cleared from inflammatory leukocytes and their products, and return to homeostatic architecture and function. Fibrosis, in contrast, is a pathological condition that originates from chronic non-resolving inflammation that allows simultaneous production and action of inflammatory, reparative, and angiogenic factors in an unbalanced fashion with excessive deposition of extracellular matrix that impairs tissue architecture and function. Activated, proliferating fibroblasts produce large amounts of collagen I and fibronectin. Macrophages are a significant balancing element in both fibrosis and tissue repair as they are a major source of TGFβ. During physiologic resolution of inflammation neutrophils undergo apoptosis and get cleared by macrophages, which in turn undergo reprogramming. Macrophage reprogramming leads to the production of cytokines and growth factors that promote wound healing, immune regulation and angiogenesis. TGFβ is a key cytokine in the resolution of inflammation, immune regulation, wound healing and fibrosis.

We recently demonstrated that many end-stage fibrotic diseases, including idiopathic pulmonary fibrosis; sS; myelofibrosis; kidney-, pancreas-, and heart-fibrosis; and nonalcoholic steatohepatosis converge in the activation of the AP1 transcription factor JUN in pathologic fibroblasts, and our findings suggested, that JUN may be a central node controlling these essential pathways. JUN is widely expressed in skin epithelium and many other epithelial cells, but not at high levels in stromal cells. JUN is also part of the acute phase response cascade, has a role in bone formation, and has a reputation as an oncogene, and its up-regulation has been shown in various cancers. One striking observation we made in our prior studies but also in the context of scl-GVHD that JUN induction results in upregulation of CD47 in fibroblasts. CD47 is a self-protective don't-eat-me epitope, that has been shown to be expressed by various solid cancers and hematopoietic malignancies, and most recently in atherosclerosis. Its blockade by antibodies or artificial, high-affinity Sirpa analogs prevents this repressive signal in macrophages, leading to their activation and active phagocytosis. Here, we show that this property is not limited to cancer cells because fibrosis was effectively reversed with anti-CD47 treatment by elimination of fibroblasts by macrophages.

Our findings suggest that also in scl-GVHD fibrosis is the end result of inflammatory responses to various immunological events that merge in upregulation of JUN. JUN activates the immune checkpoint CD47, and thereby induces excessive tissue repair and fibrosis by preventing the halting and resolution of the immune-triggered process but rather perpetuating fibrogenesis. Our data suggest the possibility to develop therapeutic strategies interfering with the activity of JUN directly, CD47, or the Hh pathway. A small molecule inhibitor against JUN is available but has systemic side effects. CD47 antibodies are currently studied in clinical trials for different types of cancer. In the urgent need of identifying more effective, targeted treatments for patients with scl-GVHD recently few clinical trials in the US and Spain have been initiated to test the efficacy of the Hh inhibitors vismodegib and glasdegib in patients with scl-GVHD. In our own limited experience responses can be remarkable—but are not observed in all patients.

In our own studies on the effect of different agents on the resolution of established scl-GVHD the combination of an anti-CD47 antibody together with IL-6 blockade was the most effective therapeutic intervention. Also, we observed an effect of the Hh inhibitor vismodegip on scl-GVHD skin lesions. Less effective was Pirfenidone.

A number of cell-based studies have shown that pirfenidone reduces fibroblast proliferation, inhibits transforming growth factor beta stimulated collagen production and reduces the production of fibrogenic mediators such as transforming growth factor beta. Pirfenidone has also been shown to reduce production of inflammatory mediators such as tumor necrosis factor alpha and IL-1B in both cultured cells and isolated human peripheral blood mononuclear cells. These activities are consistent with the broader anti-fibrotic and anti-inflammatory activities observed in animal models of fibrosis.

Materials and Methods

Animal studies and mice: Female AKR/J mice (H2$^k$; Thy1.1, CD45.2) served as donors for male and female BALB.K hosts (H2$^k$, Thy1.2, CD45.2). HSC donors were 6-10 weeks old, recipients ≥8 weeks at transplant. All mice were bred and maintained under pathogen-free conditions at the Stanford University Research Animal Facility, or purchased from Jackson Laboratories (AKR/J). Animal studies were approved by the Stanford University Administrative Panel on Laboratory Animal Care (APLAC).

Human Samples: De-identified patient specimens in paraffin and fresh patient tissues were used for our studies as approved in IRB11177 and in concordance with the declaration of Helsinki.

Isolation and transplantation of HSC and T lymphocytes: Bone marrow was flushed from tibiae and femurs into HBSS/2% FBS, enriched for c-Kit (3C11) cells by magnetic column separation (CD117 MicroBeads, MACS Separation Columns LS; Miltenyi Biotec, Auburn, CA), and 'KTLS-HSC' were purified by FACS-sorting, selecting for c-Kit$^+$ Thy1.1$^{lo\text{-}int}$ Sca-1$^+$ Lin$^{neg}$ (CD3e, CD4, CD5, CD8a, B220, Gr1, Mac1 and Ter119). For co-transfer of CD8$^+$ cells these were extracted from spleens by magnetic column separation to a purity of >90% (CD8a MicroBeads; Miltenyi Biotec). BALB.K recipients received a sublethal 400 cGy dose total body gamma irradiation 3-5 h prior to tail-vein injection of a radioprotective dose of 3,000 KTLS-HSC. In co-transfer experiments 1×10$^6$ CD8$^+$ T cells were injected simultaneously with the HSC. Following hematopoietic cell transplantation (HCT) mice were monitored for survival, weight loss, and clinical signs of GVHD.

Cell harvest, antibody staining and flow cytometry: Antibody stainings were performed according to standard protocols. Samples were analyzed and sorted on the Stanford Shared FACS facility FACS-instruments (LSRII, FACSAria).

For blood samples red blood cell lysis was performed with ammonium chloride NaAcetate. For analysis of skin infiltrating leukocytes skin was cut into small pieces, digested with dispase and DNAse at 37° C. for 1 hour, and manually processed into a single cell suspension. Mononucleated cells were then isolated by density gradient (Ficoll-Paque Plus; GE Healthcare). Cells were washed in PBS/2% FBS, blocked for 10 min with Fcg-block (BD PharMingen), and antibody-stained for 30 min on ice. Propidium iodide staining, ethidium monoazide, or a viability kit (LIVE/DEAD® Fixable Aqua Dead Cell Stain Kit, Invitrogen) were used to exclude dead cells. Samples were analyzed and sorted on the Stanford shared FACS facility Hi-Dimensional FACS instruments (LSR II; FACSAria with DiVa electronics; Becton Dickinson, Mountain View, CA).

Antibodies used for FACS were specific for c-Kit (2B8), Thy1.1 (OX-7), Sca-1 (D7), lineage markers CD3e (145-2C11 or 17A2), CD4 (GK1.5), CD5 (53-7.3), CD8a (53-6.7), B220 (RA3-6B2), Gr1 (RB6-8C5), Mac1 (M1/70) and TER-119 (TER-119), in addition, Thy1.2 (53-2.1). Antibodies were from eBioscience, Biolegend, Invitrogen, or BD Biosciences.

Engraftment and chimerism: Blood multilineage hematopoietic reconstitution and chimerism were assessed by flow cytometry at 4, 6, and 12 weeks post-HCT. For the AKR/J into BALB.K model donor/host T cells were distinguished using Thy1.1$^+$ (donor) and Thy1.2$^+$ (host) markers. Chimerism analysis of B cells and granulocytes/monocytes required PCR for D6mit3, a microsatellite marker with informative polymorphism for AKR/J and BALB.K. Genomic DNA was isolated from FACS-sorted populations using the DNeasy Kit according to the manufacturer's instructions (Qiagen, Valencia, CA). Standard PCR conditions were used. PCR amplicons were stained with ethidium bromide for allele determination on 2% agarose gels.

Cytokine/Chemokine Multiplex Assay. The following 38 mouse cytokines/chemokines were quantified by cytokine/chemokine multiplex assay at the Stanford core facility: G-SCF/CSF-3, IL10, IL-3 LIF IL-1B, IL-2, M-CSF, IP-10, VEGF-A, IL4, IL-5, IL-6, TGFB, IFN-a, IL-22, IL-9, IL-13, IL-27, IL-23, IFN-g, IL-12P70, GM-CSF, GRO-a, RANTES, TNF-a, MIP-1a, MCP-3, MCP-1, IL-17A, IL-15/IL-15R, MIP-2, IL-1a, LIX, EOTAXIN, IL-28, IL-18, MIP-1b, IL-31; mean fluorescent intensity was measured and the concentrations of each cytokine/chemokine has been quantified by the standard curve method in pg/mL; experimental details can be found at iti.stanford.edu/himc.html, the Stanford Human Immune Monitoring Center.

Histology and imaging: Mice: Skin and other target organs of GVHD (liver, lung, intestines) were collected from affected mice with scleroderma and from controls, fixed in 10% neutral buffered formalin, embedded in paraffin, sectioned, and stained with hematoxylin and eosin or, to assess for fibrosis, stained with reticulin, trichrome, anti-SMA, anti FSP-1, and c-Jun. Embedding and H&E-staining were performed by the Histo-Tec Laboratory, Hayward, CA. Images of histological slides were obtained on a Nikon Eclipse E400 microscope (Nikon) equipped with a SPOT RT color digital camera (model 2.1.1; Diagnostic Instruments). Images were analyzed in Adobe Photoshop (Adobe Systems).

Human: Tissue sections (4 μm thickness) were cut from tissue blocks of archival de-identified human biopsies using a microtome for immunofluorescence staining. The sections were baked at 65° C. for 20 min, de-paraffinized in xylene, and rehydrated via a graded ethanol series. The sections were then immersed in epitope retrieval buffer (10 mM sodium citrate, pH 6) and placed in a pressure cooker for 45 min. The sections were subsequently rinsed twice with dH2O and once with wash buffer (TBS, 0.1% Tween, pH 7.2). Residual buffer was removed by gently touching the surface with a lint-free tissue before incubating with blocking buffer for 30 min. Blocking buffer was subsequently removed, and the sections were stained overnight at 4° C. in a humidified chamber. The following morning, the sections were rinsed twice in wash buffer, and secondary antibody (Invitrogen) was used for visualization of signal. Images of histological slides were obtained on a Leica Eclipse E400 microscope (Leica) equipped with a SPOT RT color digital camera (model 2.1.1; Diagnostic Instruments).

We validated all of the antibodies we used for immunostaining first by staining positive and negative controls of healthy human and mouse tissues, but also lung cancer, breast cancer, adrenal, placenta, tonsils, peripheral blood mononuclear cells, and spleen. To find the optimal antibody concentration and decrease nonspecific staining, we subsequently titrated the respective antibodies by serial dilution from 1:50, 1:100, and 1:200 to 1:500. We included positive and negative control tissues and sections stained with isotype control with each subsequent immunostain.

Statistical Methods: The results are expressed as the mean±SEM for n given samples. Data were analyzed using the two-tailed Student's t test or ANOVA with any p value less than or equal to 0.05 being considered significant. Survival was monitored and analyzed by Kaplan-Meyer analysis. Numbers of recipient mice are indicated, and the p value was derived by log-rank test. Microsoft Excel Software was used to create weight curves and to assess p-values for groups by 2-tailed student t-test. GraphPad-Prism 7.0 software was used to create Kaplan-Meier survival curves and column-bar diagrams, displaying the mean and SEM, were created using GraphPad-Prism 7.0 software.

In Vivo Drug Application. Six- to 12-wk-old Jun transgenic and control mice were either maintained on doxycycline containing water or induced intratracheally and concomitantly systemically treated with anti-CD47 antibody (100 μL i.p.), VEGF inhibitor PD173074 (2 mg/kg once per day i.p.), and a PI3K inhibitor wortmannin (2 mg/kg 3×/wk i.p.).

ATAC-Seq Library preparation, sequencing, and data preprocessing. The ATAC-seq was performed as discribed before. Briefly, 50000 cells were collected and washed with cold PBS and lysed using 0.1% NP40 in resuspension buffer. Tn5 transposition of nuclei pellets was carried out at 37° C. for 30 min, using the DNA sample preparation kit from Nextera (Illumina). The reaction was purified using QIA-GEN MinElute columns and then amplified for 8-15 cycles to produce libraries for sequencing. ATAC-seq libraries were sequenced on Illumina HiSeq 4000. ATAC-seq pair-end reads were trimmed for Illumina adaptor sequences and transposase sequences using Kundaje ATAC_pipelines. The libraries were initially sequenced on a Miseq sequencer and analyzed using a custom script to determine the enrichment score, only libraries that had the highest score above the threshold (>5) were chosen for deeper sequencing. Two independent, biological replicates were sequenced per sample.

Deep sequencing data analysis. Differentially accessible peaks from the merged union peak list were selected with the DESeq2 package from bioconductor using raw read counts of each samples using log 2 fold change >1, and p value <0.05. The read counts of the differential peaks in each sample were further normalized by Z-score transformation. Peak genomic annotation was performed by HOMER package. Hierarchical clustering was used to cluster the peaks and samples. The results were presented as heatmap by Morpheus from Broad Institute.

Example 4

Human pathogenic liver fibroblasts coexpress CD47, mesothelin and IL6. Slides are shown in FIG. 40, with representative sections of patients with liver cirrhosis and liver cancer.

---

What is claimed is:

1. A method for treatment of fibrosis in a mammalian patient, the method comprising:

administering a synergistic combination of (i) an effective dose of an agent that blocks the CD47/SIRPα pathway; and (ii) an effective dose of an IL-6 blocking agent to the mammalian patient effective to reduce fibrosis.

2. The method of claim 1, wherein the fibrosis is pulmonary fibrosis.

3. The method of claim 1, wherein the fibrosis is interstitial lung disease.

4. The method of claim 1, wherein the fibrosis is skin fibrosis.

5. The method of claim 1, wherein the fibrosis is scleroderma.

6. The method of claim 1 wherein the fibrosis is liver fibrosis.

7. The method of claim 1, wherein the fibrosis is non-alcoholic steatohepatitis (NASH) or liver cirrhosis.

8. The method of claim 1, wherein the patient is human.

9. A method for treatment of fibrosis in a mammalian patient, the method comprising:

administering a synergistic combination of (i) an effective dose of an agent that blocks the PD-1/PD-L1 pathway and (ii) an effective dose of an IL-6 blocking agent to the mammalian patient effective to reduce fibrosis.

10. The method of claim 1, wherein the agent that blocks the CD47/SIRPα pathway is an antibody or variant thereof that binds to CD47 and inhibits the interaction between CD47 and SIRPα.

11. The method of claim 1, wherein agent that blocks the CD47/SIRPα pathway is an antibody or variant thereof that binds to SIRPα and inhibits the interaction between CD47 and SIRPα.

12. The method of claim 1, wherein the agent that blocks the CD47/SIRPα pathway is a soluble SIRPα polypeptide.

13. The method of claim 1, wherein the IL-6 blocking agent is administered concomitantly with the agent that blocks the CD47/SIRPα pathway.

14. The method of claim 1, wherein the IL-6 blocking agent binds to IL-6.

15. The method of claim 1, wherein the IL-6 blocking agent binds to IL-6R.

16. The method of claim 14, wherein the IL-6 blocking agent is an antibody or variant thereof.

17. The method of claim 1, further comprising monitoring efficacy of treatment by detection of deposition of extracellular matrix proteins in an imaging system or by determining an improvement or stabilization in one or more of forced vital capacity (FVC), single breath diffusing capacity for carbon monoxide, transfer coefficient for carbon monoxide, 6-min walk test or pulse rate recovery.

18. The method of claim 17, wherein the imaging system is high-resolution computed tomography or radiography.

19. A method for treatment of fibrosis in a mammalian patient, the method comprising:

administering a synergistic combination of (i) an effective dose of an agent that blocks the CD47/SIRPα pathway; (ii) an effective dose of an IL-6 blocking agent to the mammalian patient effective to reduce fibrosis; and (iii) an effective dose of an agent that blocks the PD-1/PD-L1 pathway to the mammalian patient effective to reduce fibrosis.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 1
caccgtgaac ctggccgacc cagtg                                      25

<210> SEQ ID NO 2
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 2
aaaccactgg gtcggccagg ttcac                                      25

<210> SEQ ID NO 3
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 3
caccgccgtc cgagagcgga cctta                                      25

<210> SEQ ID NO 4
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 4
aaactaaggt ccgctctcgg acggc                                      25